(12) United States Patent
Shoshtaev

(10) Patent No.: US 11,684,484 B2
(45) Date of Patent: Jun. 27, 2023

(54) EXPANDABLE FUSION DEVICE WITH INTERDIGITATING FINGERS

(71) Applicant: INTEGRITY IMPLANTS INC., Palm Beach Gardens, FL (US)

(72) Inventor: Eugene Shoshtaev, Del Mar, CA (US)

(73) Assignee: INTEGRITY IMPLANTS INC., Palm Beach Gardens, FL (US)

( * ) Notice: Subject to any disclaimer, the term of this patent is extended or adjusted under 35 U.S.C. 154(b) by 297 days.

(21) Appl. No.: 17/149,325

(22) Filed: Jan. 14, 2021

(65) Prior Publication Data
US 2021/0196470 A1 Jul. 1, 2021

Related U.S. Application Data

(63) Continuation of application No. 16/290,428, filed on Mar. 1, 2019, now Pat. No. 11,285,018.
(Continued)

(51) Int. Cl.
*A61F 2/44* (2006.01)
*A61F 2/30* (2006.01)

(52) U.S. Cl.
CPC ............ *A61F 2/447* (2013.01); *A61F 2/4425* (2013.01); *A61F 2002/30579* (2013.01); *A61F 2002/443* (2013.01); *A61F 2250/0009* (2013.01)

(58) Field of Classification Search
CPC ...................................................... A61F 2/447
See application file for complete search history.

(56) References Cited

U.S. PATENT DOCUMENTS

| 4,309,777 A | 1/1982 | Patil |
| 4,733,665 A | 3/1988 | Palmaz |

(Continued)

FOREIGN PATENT DOCUMENTS

| CN | 101909548 | 7/2014 |
| DE | 10 2018 206693 | 2/2019 |

(Continued)

OTHER PUBLICATIONS

U.S. Appl. No. 17/317,825, filed Jan. 10, 2017, Shoshtaev—owned by Applicant.
(Continued)

*Primary Examiner* — Christian A Sevilla
(74) *Attorney, Agent, or Firm* — McNees Wallace & Nurick LLC

(57) ABSTRACT

Expandable spinal fusion devices, systems, and methods of using them are provided, and they can be inserted in a subject in a collapsed state through a small surgical corridor, and the expand cephalocaudal only, transverse only, or in both directions, in which direction of expansion can also be obtained independently, if desired, after the insertion. These inventions are valuable in reducing risk and surgical complexity, allowing for an on-the-fly selection of a desirable width footprint, a desired control of height expansion through a gradual cephalocaudal expansion, and a desired control of the alignment of the adjacent vertebral bodies. Devices, systems, and methods are also offered to provide a desired control of the contact area desired between the device and the upper and lower vertebral endplates achieved, for example, using an interdigitated endplate system.

18 Claims, 41 Drawing Sheets

Related U.S. Application Data

(60) Provisional application No. 62/637,306, filed on Mar. 1, 2018.

(56) References Cited

U.S. PATENT DOCUMENTS

| | | |
|---|---|---|
| 4,759,766 A | 7/1988 | Buettner-Janz et al. |
| 4,820,305 A | 4/1989 | Harms et al. |
| 4,997,432 A | 3/1991 | Keller |
| 5,192,327 A | 3/1993 | Brantigan |
| 5,221,261 A | 6/1993 | Termin et al. |
| 5,609,635 A | 3/1997 | Michelson |
| 5,658,336 A | 8/1997 | Pisharodi |
| 5,976,187 A | 11/1999 | Richelsoph |
| 5,980,522 A | 11/1999 | Koros |
| 5,980,552 A | 11/1999 | Pinchasik et al. |
| 6,039,761 A | 3/2000 | Li et al. |
| 6,102,950 A | 8/2000 | Vaccaro |
| 6,126,689 A | 10/2000 | Brett |
| 6,176,882 B1 | 1/2001 | Biedermann |
| 6,193,757 B1 | 2/2001 | Foley et al. |
| 6,368,351 B1 | 4/2002 | Glenn et al. |
| 6,375,682 B1 | 4/2002 | Fleischmann et al. |
| 6,395,031 B1 | 5/2002 | Foley et al. |
| 6,409,766 B1 | 6/2002 | Brett |
| 6,419,705 B1 | 7/2002 | Erickson |
| 6,425,919 B1 | 7/2002 | Lambrecht et al. |
| 6,432,107 B1 | 8/2002 | Ferree |
| 6,436,119 B1 | 8/2002 | Erb et al. |
| 6,443,989 B1 | 9/2002 | Jackson |
| 6,482,235 B1 | 11/2002 | Lambrecht et al. |
| 6,488,710 B2 | 12/2002 | Besselink |
| 6,491,724 B1 | 12/2002 | Ferree |
| 6,575,899 B1 | 6/2003 | Foley et al. |
| 6,582,439 B1 | 6/2003 | Sproul |
| 6,582,441 B1 | 6/2003 | He et al. |
| 6,582,467 B1 | 6/2003 | Teitelbaum |
| 6,595,998 B2 | 7/2003 | Johnson et al. |
| 6,666,891 B2 | 12/2003 | Boehm, Jr et al. |
| 6,821,276 B2 | 11/2004 | Lambrecht et al. |
| 6,821,298 B1 | 11/2004 | Jackson |
| 6,893,464 B2 | 5/2005 | Kiester |
| 7,018,415 B1 | 3/2006 | McKay |
| 7,083,650 B2 | 8/2006 | Moskowitz et al. |
| 7,087,055 B2 | 8/2006 | Lim et al. |
| 7,204,853 B2 | 4/2007 | Gordon et al. |
| 7,214,243 B2 | 5/2007 | Taylor |
| 7,217,293 B2 | 5/2007 | Branch, Jr. |
| 7,316,686 B2 | 1/2008 | Dorchak et al. |
| 7,544,208 B1 | 6/2009 | Mueller et al. |
| 7,621,950 B1 | 11/2009 | Globerman et al. |
| 7,643,884 B2 | 1/2010 | Pond, Jr et al. |
| 7,655,046 B2 | 2/2010 | Dryer et al. |
| 7,678,148 B2 | 3/2010 | Peterman |
| 7,731,751 B2 | 6/2010 | Butler et al. |
| 7,771,473 B2 | 8/2010 | Thramann |
| 7,819,921 B2 | 10/2010 | Grotz |
| 7,828,845 B2 | 11/2010 | Estes et al. |
| 7,828,849 B2 | 11/2010 | Lim |
| 7,846,206 B2 | 12/2010 | Oglaza et al. |
| 7,850,733 B2 | 12/2010 | Baynham et al. |
| 7,862,618 B2 | 1/2011 | White et al. |
| 7,879,098 B1 | 2/2011 | Simmons, Jr. |
| 7,909,872 B2 | 3/2011 | Zipnick |
| 7,918,888 B2 | 4/2011 | Hamada |
| 7,951,202 B2 | 5/2011 | Ralph et al. |
| 8,062,375 B2 | 11/2011 | Glerum et al. |
| 8,070,754 B2 | 12/2011 | Fabian et al. |
| 8,070,813 B2 | 12/2011 | Grotz et al. |
| 8,083,744 B2 | 12/2011 | Dorchak |
| 8,088,163 B1 | 1/2012 | Kleiner |
| 8,105,382 B2 | 1/2012 | Olmos et al. |
| 8,110,004 B2 | 2/2012 | Valdevit et al. |
| 8,118,870 B2 | 2/2012 | Gordon et al. |
| 8,123,810 B2 | 2/2012 | Gordon et al. |
| 8,167,950 B2 | 5/2012 | Aferzon et al. |
| 8,182,538 B2 | 5/2012 | O'Neil et al. |
| 8,187,332 B2 | 5/2012 | McLuen |
| 8,236,058 B2 | 8/2012 | Fabian et al. |
| 8,241,363 B2 | 8/2012 | Sommerich et al. |
| 8,267,939 B2 | 9/2012 | Cipoletti et al. |
| 8,273,129 B2 | 9/2012 | Baynham et al. |
| 8,353,961 B2 | 1/2013 | McClintock |
| 8,353,963 B2 | 1/2013 | Glerum |
| 8,398,713 B2 | 3/2013 | Weiman |
| 8,435,298 B2 | 5/2013 | Weiman |
| 8,491,659 B2 | 7/2013 | Weiman et al. |
| 8,518,120 B2 | 8/2013 | Glerum et al. |
| 8,523,944 B2 | 9/2013 | Jimenez et al. |
| 8,551,173 B2 | 10/2013 | Lechmann et al. |
| 8,556,979 B2 | 10/2013 | Glerum et al. |
| 8,628,578 B2 | 1/2014 | Miller et al. |
| 8,632,595 B2 | 1/2014 | Weiman |
| 8,663,332 B1 | 3/2014 | To |
| 8,685,098 B2 | 4/2014 | Glerum et al. |
| 8,777,993 B2 | 7/2014 | Siegal et al. |
| 8,845,731 B2 | 9/2014 | Weiman |
| 8,852,279 B2 | 10/2014 | Weiman et al. |
| 8,882,840 B2 | 11/2014 | McClintock et al. |
| 8,894,712 B2 | 11/2014 | Varela |
| 8,900,307 B2 | 12/2014 | Hawkins et al. |
| 8,906,099 B2 | 12/2014 | Poulos |
| 8,926,704 B2 | 1/2015 | Glerum et al. |
| 8,936,641 B2 | 1/2015 | Cain |
| 8,940,048 B2 | 1/2015 | Butler |
| 8,940,052 B2 | 1/2015 | Lechmann et al. |
| 9,060,876 B1 | 1/2015 | To |
| 8,986,387 B1 | 3/2015 | To |
| 9,034,041 B2 | 5/2015 | Wolters |
| 9,039,771 B2 | 5/2015 | Glerum et al. |
| 9,044,342 B2 | 6/2015 | Perloff et al. |
| 9,066,813 B2 | 6/2015 | Farris et al. |
| 9,138,328 B2 | 9/2015 | Butler et al. |
| 9,155,628 B2 | 10/2015 | Glerum et al. |
| 9,186,259 B2 | 11/2015 | To |
| 9,216,095 B2 | 12/2015 | Glerum et al. |
| 9,241,806 B2 | 1/2016 | Suh |
| 9,278,008 B2 | 3/2016 | Perloff et al. |
| 9,320,610 B2 | 4/2016 | Alheidt et al. |
| 9,333,092 B2 | 5/2016 | To |
| 9,351,848 B2 | 5/2016 | Glerum et al. |
| 9,402,733 B1 | 8/2016 | To |
| 9,402,739 B2 | 8/2016 | Weiman et al. |
| 9,421,110 B2 | 8/2016 | Masson |
| 9,439,782 B2 | 9/2016 | Kleiner |
| 9,445,918 B1 | 9/2016 | Lin et al. |
| 9,463,052 B2 | 10/2016 | Geist |
| 9,474,625 B2 | 10/2016 | Weiman |
| 9,480,574 B2 | 11/2016 | Lee et al. |
| 9,480,576 B2 | 11/2016 | Pepper et al. |
| 9,545,316 B2 | 1/2017 | Ashley et al. |
| 9,561,116 B2 | 2/2017 | Weiman et al. |
| 9,566,168 B2 | 2/2017 | Glerum et al. |
| 9,597,200 B2 | 3/2017 | Glerum et al. |
| 9,636,154 B2 | 5/2017 | Overes et al. |
| 9,655,744 B1 | 5/2017 | Pimenta |
| 9,662,224 B2 | 5/2017 | Weiman et al. |
| 9,675,466 B2 | 6/2017 | Overes et al. |
| 9,675,469 B2 | 6/2017 | Landry et al. |
| 9,717,601 B2 | 8/2017 | Miller |
| 9,730,803 B2 | 8/2017 | Dimauro et al. |
| 9,737,411 B2 | 8/2017 | Loebl et al. |
| 9,795,493 B1 | 10/2017 | Bannigan |
| 9,801,640 B2 | 10/2017 | O'Neil et al. |
| 9,801,733 B2 | 10/2017 | Wolters et al. |
| 9,801,734 B1 | 10/2017 | Stein et al. |
| 9,839,528 B2 | 12/2017 | Weiman et al. |
| 9,883,953 B1 | 2/2018 | To |
| 9,889,019 B2 | 2/2018 | Rogers et al. |
| 9,907,673 B2 | 3/2018 | Weiman et al. |
| 9,913,727 B2 | 3/2018 | Thommen et al. |
| 9,913,736 B2 | 3/2018 | To |
| 9,974,662 B2 | 5/2018 | Hessler et al. |
| 9,987,143 B2 | 6/2018 | Robinson et al. |
| 9,999,517 B2 | 6/2018 | To |

(56) References Cited

U.S. PATENT DOCUMENTS

| | | |
|---|---|---|
| 10,052,215 B2 | 8/2018 | Hessler et al. |
| 10,058,350 B2 | 8/2018 | Geist |
| 10,080,592 B2 | 9/2018 | Geist |
| 10,085,849 B2 | 10/2018 | Weiman et al. |
| 10,098,757 B2 | 10/2018 | Logan et al. |
| 10,105,238 B2 | 10/2018 | Koch et al. |
| 10,137,007 B2 | 11/2018 | Dewey et al. |
| 10,143,565 B2 | 12/2018 | Farris et al. |
| 10,143,569 B2 | 12/2018 | Weiman et al. |
| 10,149,773 B2 | 12/2018 | To |
| 10,154,911 B2 | 12/2018 | Predick et al. |
| 10,182,851 B2 | 1/2019 | Robie et al. |
| 10,206,788 B2 | 2/2019 | Field et al. |
| 10,426,634 B1 | 2/2019 | Al-Jazaeri et al. |
| 10,226,356 B2 | 3/2019 | Grotz |
| 10,226,360 B2 | 3/2019 | Baynham |
| 10,238,503 B2 | 3/2019 | Branch et al. |
| 10,251,759 B2 | 4/2019 | Butler et al. |
| 10,265,192 B2 | 4/2019 | Eastlack et al. |
| 10,322,014 B2 | 6/2019 | To |
| 10,342,675 B2 | 7/2019 | Alheidt |
| 10,383,743 B2 | 8/2019 | To |
| 10,413,419 B2 | 9/2019 | Thibodeau |
| 10,441,430 B2 | 10/2019 | Ludwig et al. |
| 10,470,891 B2 | 11/2019 | Sharifi-Mehr et al. |
| 10,470,894 B2 | 11/2019 | Foley et al. |
| 10,485,675 B2 | 11/2019 | Sharifi-Mehr et al. |
| 10,492,918 B2 | 12/2019 | DiMauro |
| 10,531,964 B2 | 1/2020 | Miller et al. |
| 10,624,756 B2 | 4/2020 | Bernard et al. |
| 10,631,996 B2 | 4/2020 | Bernard et al. |
| 10,682,239 B2 | 6/2020 | Hsu et al. |
| 10,687,876 B2 | 6/2020 | Vrionis et al. |
| 10,869,769 B2 | 12/2020 | Eisen et al. |
| 10,898,340 B2 | 1/2021 | Koch et al. |
| 11,076,968 B2 | 8/2021 | To |
| 2002/0035400 A1 | 3/2002 | Bryan et al. |
| 2002/0040243 A1 | 4/2002 | Attali |
| 2002/0068977 A1* | 6/2002 | Jackson ............ A61F 2/4455 606/247 |
| 2003/0074075 A1 | 4/2003 | Thomas et al. |
| 2003/0083746 A1 | 5/2003 | Kuslich |
| 2004/0010315 A1 | 1/2004 | Song |
| 2004/0024463 A1 | 2/2004 | Thomas et al. |
| 2005/0256576 A1 | 11/2005 | Moskowitz et al. |
| 2006/0100706 A1 | 5/2006 | Shadduck |
| 2006/0122701 A1 | 6/2006 | Kiester |
| 2006/0167547 A1 | 7/2006 | Suddaby |
| 2006/0287729 A1 | 12/2006 | Segal et al. |
| 2007/0118222 A1 | 5/2007 | Lang |
| 2007/0173939 A1 | 7/2007 | Kim et al. |
| 2007/0219634 A1 | 9/2007 | Greenhalgh |
| 2008/0009876 A1 | 1/2008 | Sankaran et al. |
| 2008/0021556 A1 | 1/2008 | Edie |
| 2008/0021559 A1 | 1/2008 | Thramann |
| 2008/0147193 A1 | 6/2008 | Matthis |
| 2008/0234687 A1 | 9/2008 | Schaller |
| 2008/0281346 A1 | 11/2008 | Greenhalgh |
| 2008/0281424 A1 | 11/2008 | Parry et al. |
| 2009/0018524 A1 | 1/2009 | Greenhalgh |
| 2009/0076607 A1 | 3/2009 | Aalsma et al. |
| 2009/0138083 A1 | 5/2009 | Biyani |
| 2009/0281551 A1 | 5/2009 | Frey |
| 2009/0222043 A1 | 9/2009 | Altarac |
| 2009/0234389 A1 | 9/2009 | Chuang |
| 2010/0010542 A1 | 1/2010 | Jackson |
| 2010/0010633 A1 | 1/2010 | Kohm |
| 2010/0042218 A1 | 2/2010 | Nebosky et al. |
| 2010/0082109 A1 | 4/2010 | Greenhalgh et al. |
| 2010/0198352 A1 | 8/2010 | Edie |
| 2010/0217325 A1 | 8/2010 | Hochschuler |
| 2010/0222884 A1 | 9/2010 | Greenhalgh |
| 2010/0234956 A1 | 9/2010 | Attia |
| 2010/0286783 A1 | 11/2010 | Lechmann et al. |
| 2010/0292796 A1 | 11/2010 | Greenhalgh |
| 2011/0022090 A1 | 1/2011 | Gordon |
| 2011/0029082 A1 | 2/2011 | Hall |
| 2011/0046748 A1 | 2/2011 | Martin |
| 2011/0130835 A1 | 6/2011 | Ashley |
| 2011/0172774 A1 | 7/2011 | Varela |
| 2011/0190816 A1 | 8/2011 | Sheffer |
| 2011/0282453 A1 | 11/2011 | Greenhalgh |
| 2011/0301712 A1 | 12/2011 | Palmatier |
| 2011/0319997 A1 | 12/2011 | Glerum |
| 2012/0029636 A1 | 2/2012 | Ragab |
| 2012/0029645 A1 | 2/2012 | Fabian et al. |
| 2012/0035729 A1 | 2/2012 | Glerum et al. |
| 2012/0046748 A1 | 2/2012 | Weiman |
| 2012/0083889 A1 | 4/2012 | Purcell |
| 2012/0089185 A1 | 4/2012 | Gabelberger |
| 2012/0109319 A1 | 5/2012 | Perisic |
| 2014/0039625 A1 | 7/2012 | To |
| 2012/0209386 A1 | 8/2012 | Triplett et al. |
| 2012/0271396 A1 | 10/2012 | Zheng |
| 2012/0290090 A1 | 11/2012 | Glerum et al. |
| 2012/0303126 A1 | 11/2012 | Kirschman |
| 2013/0023996 A1 | 1/2013 | McCormack |
| 2013/0184822 A1 | 7/2013 | Kleiner |
| 2014/0243981 A1 | 8/2014 | Davenport et al. |
| 2015/0100128 A1 | 4/2015 | Glerum et al. |
| 2015/0148908 A1 | 5/2015 | Marino et al. |
| 2015/0190242 A1 | 7/2015 | Blain et al. |
| 2015/0374508 A1 | 12/2015 | Sandul |
| 2016/0015530 A1 | 1/2016 | To |
| 2016/0256291 A1 | 9/2016 | Miller |
| 2016/0317315 A1 | 11/2016 | Weiman |
| 2016/0338854 A1 | 11/2016 | Serhan et al. |
| 2017/0000622 A1* | 1/2017 | Thommen ............ A61F 2/4425 |
| 2017/0119540 A1 | 5/2017 | Greenhalgh |
| 2017/0128226 A1* | 5/2017 | Faulhaber ........... A61F 2/30767 |
| 2017/0209282 A1 | 7/2017 | Aghayev et al. |
| 2017/0224504 A1 | 8/2017 | Butler et al. |
| 2017/0224505 A1 | 8/2017 | Butler et al. |
| 2017/0231780 A1 | 8/2017 | D'urso |
| 2017/0239063 A1 | 8/2017 | Predick |
| 2017/0281358 A1 | 10/2017 | Wagner et al. |
| 2017/0333198 A1 | 11/2017 | Robinson |
| 2017/0333203 A1 | 11/2017 | Glerum |
| 2017/0354512 A1 | 12/2017 | Weiman et al. |
| 2018/0042735 A1 | 2/2018 | Schell et al. |
| 2018/0214221 A1 | 3/2018 | Crawford et al. |
| 2018/0185163 A1 | 7/2018 | Weiman et al. |
| 2018/0193164 A1 | 7/2018 | Shoshtaev |
| 2018/0256357 A1 | 9/2018 | To |
| 2018/0296361 A1 | 10/2018 | Butler et al. |
| 2018/0303626 A1 | 10/2018 | Rogers et al. |
| 2018/0360489 A1 | 12/2018 | Geist |
| 2018/0360617 A1 | 12/2018 | Fabian et al. |
| 2019/0053913 A1 | 2/2019 | To |
| 2019/0060085 A1 | 2/2019 | Geist |
| 2019/0076263 A1 | 3/2019 | Emstad |
| 2019/0091033 A1 | 3/2019 | Dewey et al. |
| 2019/0201209 A1 | 3/2019 | Branch et al. |
| 2019/0099278 A1 | 4/2019 | Farris et al. |
| 2019/0110900 A1 | 4/2019 | Suddaby |
| 2019/0110902 A1 | 4/2019 | Vigliotti et al. |
| 2019/0117409 A1 | 4/2019 | Shoshtaev |
| 2019/0117827 A1 | 4/2019 | Roth |
| 2019/0290448 A1 | 6/2019 | Predick et al. |
| 2019/0209339 A1 | 7/2019 | To |
| 2019/0240039 A1 | 8/2019 | Walker et al. |
| 2019/0254836 A1 | 8/2019 | Cowan et al. |
| 2019/0254841 A1 | 8/2019 | To |
| 2019/0269521 A1 | 9/2019 | Shoshtaev |
| 2019/0307573 A1 | 10/2019 | Sicotte et al. |
| 2019/0328544 A1 | 10/2019 | Ashley et al. |
| 2019/0336299 A1 | 11/2019 | Bernard et al. |
| 2020/0000607 A1 | 1/2020 | To |
| 2020/0015985 A1 | 1/2020 | Rogers et al. |
| 2020/0030110 A1 | 1/2020 | Sharabani et al. |
| 2020/0093609 A1 | 3/2020 | Shoshtaev |
| 2020/0113706 A1 | 4/2020 | Robinson |
| 2020/0129307 A1 | 4/2020 | Hunziker et al. |
| 2020/0229939 A1 | 7/2020 | To |

(56) References Cited

U.S. PATENT DOCUMENTS

| | | | |
|---|---|---|---|
| 2020/0352732 A1 | 11/2020 | To | |
| 2021/0045893 A1 | 2/2021 | To | |
| 2021/0228373 A1* | 7/2021 | Rieger | A61F 2/442 |

FOREIGN PATENT DOCUMENTS

| | | | | |
|---|---|---|---|---|
| DE | 102018206693 B3 * | 2/2019 | | A61F 2/4455 |
| EP | 1011503 | 2/1998 | | |
| EP | 1233732 | 2/2001 | | |
| EP | 2327377 | 3/2002 | | |
| EP | 1532949 | 11/2003 | | |
| EP | 2237748 | 1/2009 | | |
| EP | 13862126 | 12/2013 | | |
| EP | 19162909.6 | 12/2013 | | |
| EP | 14842880 | 6/2016 | | |
| EP | 16740662 | 11/2017 | | |
| EP | 18738659.4 | 1/2018 | | |
| EP | 17853887.2 | 7/2019 | | |
| EP | 19760773.2 | 12/2020 | | |
| JP | 2009/505686 | 7/2005 | | |
| WO | WO 1996/040015 | 6/1996 | | |
| WO | WO 2000/044319 | 1/2000 | | |
| WO | WO 2001/066047 | 7/2001 | | |
| WO | WO 2005/112834 | 12/2005 | | |
| WO | WO 2008/005627 | 5/2007 | | |
| WO | WO 2007/076374 | 7/2007 | | |
| WO | WO 2008/035849 | 7/2007 | | |
| WO | WO 2008/033457 | 3/2008 | | |
| WO | WO 2008/089252 | 7/2008 | | |
| WO | WO 2008/121162 | 10/2008 | | |
| WO | WO 2010/077359 | 7/2010 | | |
| WO | WO 2012/135764 | 10/2012 | | |
| WO | WO 2013/148176 | 10/2013 | | |
| WO | WO 2014/164625 | 10/2014 | | |
| WO | WO 2016/019241 | 2/2016 | | |
| WO | WO-2016019241 A1 * | 2/2016 | | A61F 2/4455 |
| WO | WO 2017/004503 | 1/2017 | | |
| WO | WO 2017/035155 | 3/2017 | | |

OTHER PUBLICATIONS

U.S. Appl. No. 17/380,897, filed Jul. 20, 2020, Shoshtaev—owned by Applicant.
U.S. Appl. No. 60/666,945 (priority for U.S. Pat. No. 7,731,751, cited herein), filed Mar. 31, 2005, Butler, et al.
U.S. Appl. No. 61/585,724 (priority for U.S. Pat. No. 9,463,052, cited herein), filed Jan. 12, 2012, Geist—owned by Applicant.
U.S. Appl. No. 61/737,054, filed Dec. 15, 2013, To—owned by Applicant.
U.S. Appl. No. 61/875,688, filed Oct. 4, 2013, To—owned by Applicant.
U.S. Appl. No. 62/232,021 (priority for U.S. Pat. No. 10,058,350, cited herein), filed Sep. 24, 2015, Geist—owned by Applicant.
U.S. Appl. No. 62/444,663 (priority for U.S. 2018/0193164, cited herein), filed Jan. 10, 2017, Shoshtaev—owned by Applicant.
U.S. Appl. No. 62/471,206 (priority for U.S. 2018/0193164, cited herein), filed Jan. 10, 2017, Shoshtaev—owned by Applicant.
U.S. Appl. No. 62/481,565 (priority for U.S. 2018/0193164, cited herein), filed Jan. 10, 2017, Shoshtaev—owned by Applicant.
U.S. Appl. No. 62/536,335 (priority for PCT/US2018/43517, cited herein), filed Jul. 24, 2017, To—owned by Applicant.
U.S. Appl. No. 62/550,557 (priority for U.S. Appl. No. 16/113,040, cited herein), filed Aug. 25, 2017, Geist—owned by Applicant.
PCT/US2013/052799, To—owned by Applicant, Jul. 31, 2012.
Written opinion and search report for PCT/US2013/052799, To—owned by Applicant, dated Dec. 2, 2012.
PCT/US2013/073435 Published as WO 2014/093136, To—owned by Applicant, Dec. 5, 2013.
Written opinion and search report for PCT/US2013/073435, To—owned by Applicant, dated Apr. 30, 2012.
PCT/US2014/054437, To—owned by Applicant, Feb. 26, 2014.
Written opinion and search report for PCT/US2014/054437, To—owned by Applicant, dated Jan. 6, 2015.
PCT/US2016/014100, To—owned by Applicant, Dec. 17, 2015.
Written opinion and search report for PCT/US2016/014100, To—owned by Applicant, dated Jan. 6, 2015.
PCT/US2017/52708, To—owned by Applicant, Sep. 21, 2017.
Written opinion and search report for PCT/US2017/52708, To—owned by Applicant, Sep. 21, 2017.
PCT/US2016/053467 Published as WO 2017/053813, Geist—owned by Applicant, Sep. 24, 2015.
Written opinion and search report for PCT/US2016/053467, Geist—owned by Applicant, dated Sep. 24, 2015.
PCT/US2018/13207 Published as WO 2018/132502, Shoshtaev—owned by Applicant, Jan. 10, 2018.
Written opinion and search report for PCT/US2018/13207, Shoshtaev—owned by Applicant, dated Jan. 10, 2018.
PCT/US2018/43517, To—owned by Applicant, Jul. 24, 2018.
Written opinion and search report for PCT/US2018/43517, To—owned by Applicant, dated Jul. 24, 2018.
PCT/US2019/20354, Shoshtaev—owned by Applicant, Mar. 1, 2018.
Written opinion and search report for PCT/US2019/20354, Shoshtaev—owned by Applicant, dated Mar. 1, 2018.
PCT/US2021/42392, Shoshtaev—owned by Applicant, Jul. 20, 2020.
Basho, R. et al. Lateral interbody fusion: Indications and techniques. Operative techniques in orthopaedics 21(3): 204-207 (Sep. 2011).
Caliber, www.globusmedical.com [online] URL: http://www.globusmedical.com/mis/166-caliber [retrieved on Jul. 27, 2012].
Cole, D. et al. Comparison of low back fusion techniques: transforaminal lumbar interbody fusio (TLIF) or posterior lumbar interbody fusion (PLIF) approaches. Curr rev Musculoskelet med 2(2): 118-126 published online Apr. 29, 2009 Doi: 1007/s12178-009-9053-B10 [retrieved Jun. 2009].
CAPSTONE® PEEK spinal system PLIF anf TLIF surgical technique. Medtronic Sofamor Danek 1-36 (2009).
Coalign. Introducing AccuLIF expandable lumbar interbody fusion technology, [online] URL: http://www.coalign.com [retrieved on Jul. 27, 2012].
Chapman, C. A. Design of an expandable intervertebral cage utilizing shape memory alloys. University of Toledo and OhioLINK, 2011. [online] URL: http://etd.ohiolink.edu/view.cgi?acc_num=toledo1302226375 [retrieved Feb. 13, 2013].
Dorso-Lumbar Vertebral Body Cages DSC, Sintea Plustek. [online] URL: http://www.sinteaplustek.com/spine_dsc_eng.html [retrieved on Feb. 13, 2013].
"Integrity Implants" (Integrity Implants) URL: http://www.integrityimplants.com/ [retrieved from internet Sep. 17, 2018].
"Integrity Implants v3" (Integrity Implants) URL: https://vimeo.com/232697959 ; [retrieved from the internet Nov. 16, 2017].
Interbody Fusion Cage (Neo IC) Source, www.tradekorea.com [online] URL: http://www.tradekorea.com/product-detail/P00015150/Interbody_Fusion_Cage_Neo_IC_.html [retrieved Feb. 13, 2013].
Kaech, D.L et al. Spinal restabilization procedures, diagnostic and therapeutic aspects of intervertebral fusion cages, artificial discs and mobile implants. Elsevier Science B.V. Part II: 121-204(2002).
Kiapour, A et al. A biomechanical finite element study of subsidence and migration tendencies in stand-alone fusion procedures—comparison of an in situ expandable device with a rigid device. J Spine 1(4): 5 pages (2012).
Le Huec, J.C. et al. Endoscope surgery of the spine, a review of 4 years? Practice, maltrise orthopaedique. Jan. 1999 [online] URL: http://www.maitrise-orthop.com/viewPage_us.do?id=435 [retrieved on Feb. 5, 2013].
PowerBuilt. Powerbuilt 940378 medium tailpipe expander set. [online] URL: http://www.amazon.com/Powerbuilt-940377-Tailpipi-Expander-Series/dp/B004KED6A [retrieved on Feb. 17, 2013].
PR Newswire. Benvenue Medical starts enrolling patients in the post-market lift study on the luna interbody spacer system for degenerative disc disease. Mar. 20, 2012, [online] URL: http://www.prnewswire.com/news-releases/benvenue-medical-starts-enrolling-patients-in-the-post-market-lift-study-on-the-luna-interbody-spacer-system-for-degenerative-disc-disease-143441246.html [retrieved on Jan. 27, 2013].

(56) References Cited

OTHER PUBLICATIONS

Sasani, M. et al. Single-stage posterior corpectomy and expandable cage placement for treatment of thoracic or lumbar burst fractures. Spine 34(1): E33-E40 (Jan. 1, 2009).
Spineology. OptiMesh 1500E deploying grafting system, [online] URL: http://www.spineology.com/fb/intl/products/products/optimesh 1500e.html (retrieved Jun. 3, 2013).
STAXX XD, www.spinewave.com. [online] URL: http://www.spinewave.com/products/xd_us.html [retrieved on Jan. 27, 2013].
SYNFIX-LR System. Instruments and implants for stand-alone anterior lumbar interbody fusion (ALIF). Synthes SynFix-LR system technique guide 52 pages (2010).
Transforaminal Lumbar Interbody Fusion (TLIF). Virgina spine institute, Reston Virgina. [online] URL: http://www.spinemd.com/operative-treatments/tlif-transforaminal-lumbat-interbody-fusion.com 1-6 (2013). [retrieved on Jun. 16, 2013].
Uchida, K. et al. Anterior expandable strut cage replacement for osteoporotic thoracolumbar vertebral collapse. J Neurosurg Spine 4(6): 454-462 (Jun. 2006).
XENOS. Cage mesh system for spine. Biotek Chetan Meditech Pvt. Ltd. [online] URL: http://www.biotekortho.net/spine-treatment.html [retrieved on Feb. 13, 2013].
ZEUS-O, [online] URL: http://www.amendia.com/zeuso.html [retrieved on Jan. 27, 2013].
U.S. Appl. No. 17/546,816, filed Jul. 24, 2017, To—owned by Applicant.
U.S. Appl. No. 17/553,136, filed Dec. 13, 2012, To—owned by Applicant.
Written opinion and search report for PCT/US2021/42392, Shoshtaev—owned by Applicant, Jul. 20, 2020.

\* cited by examiner

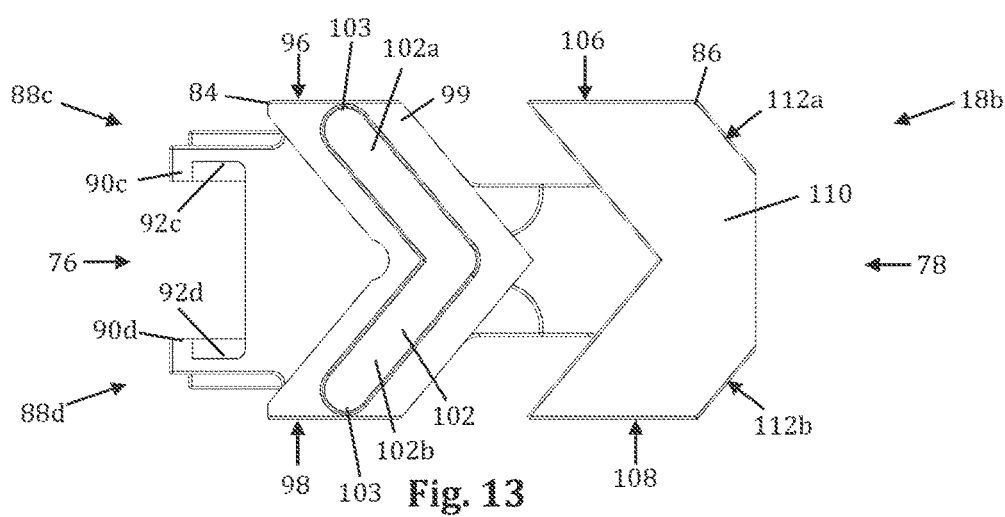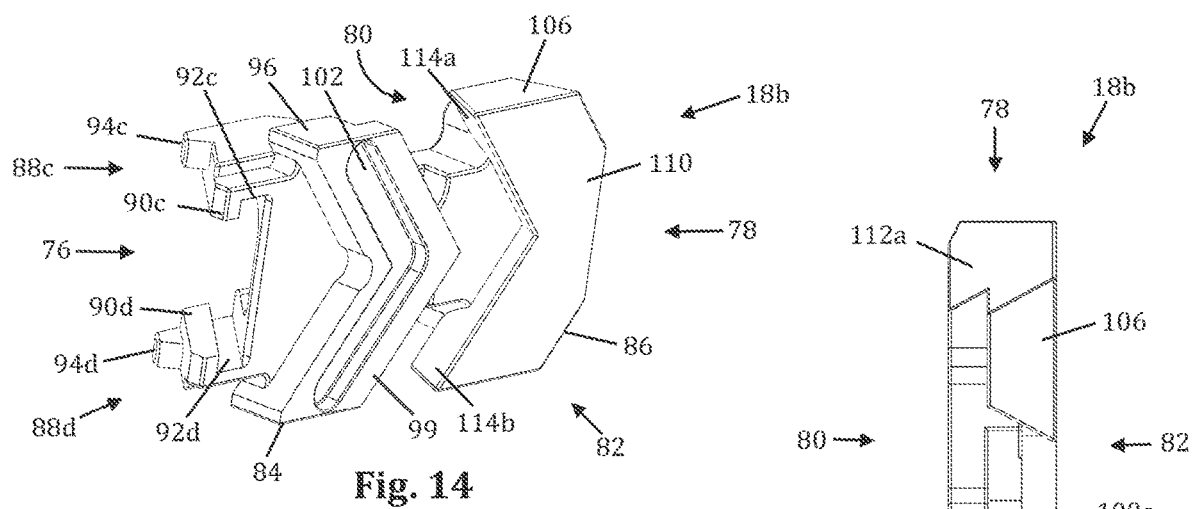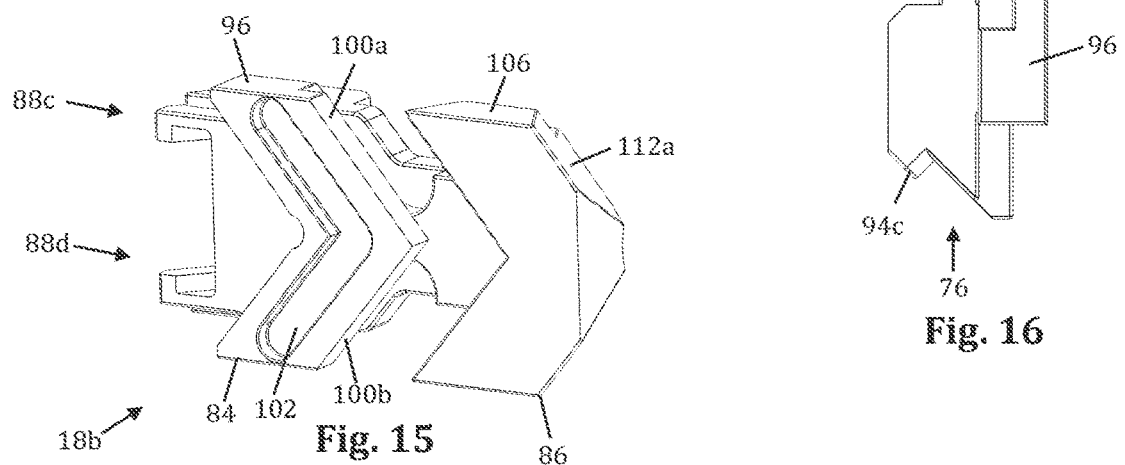

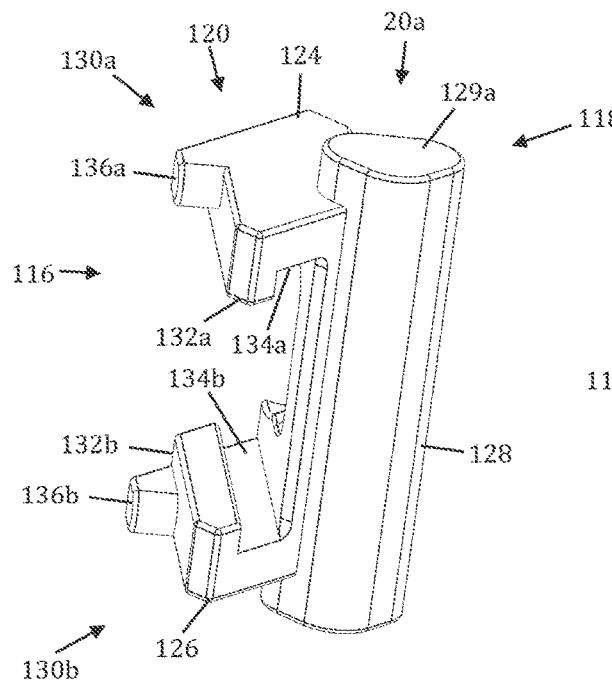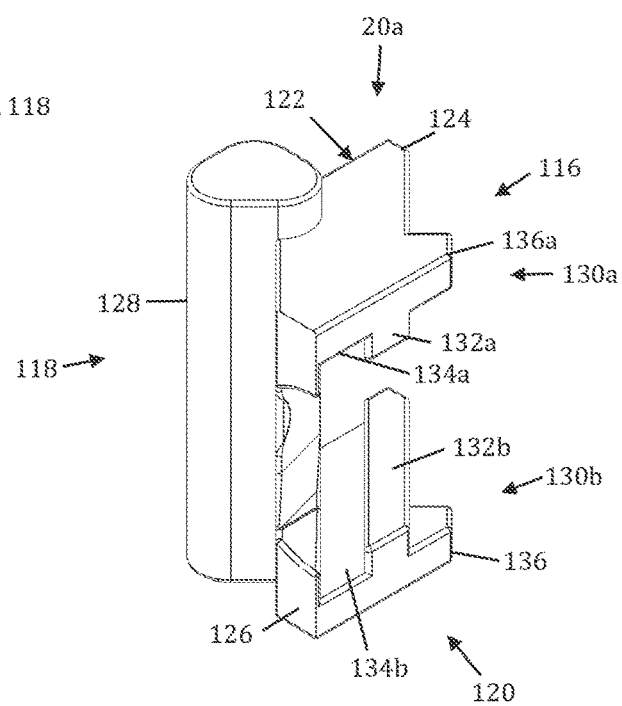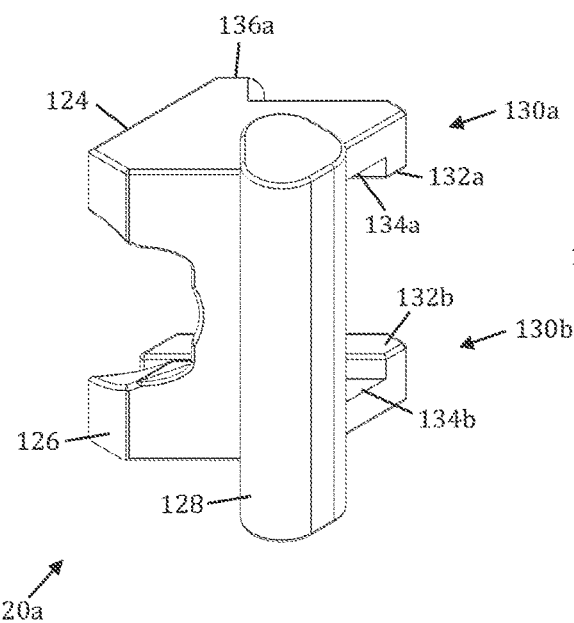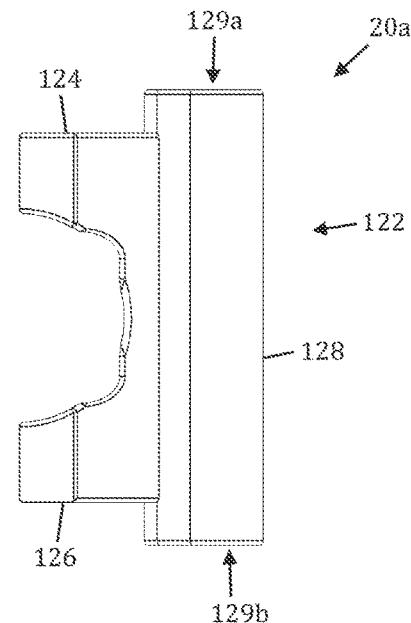

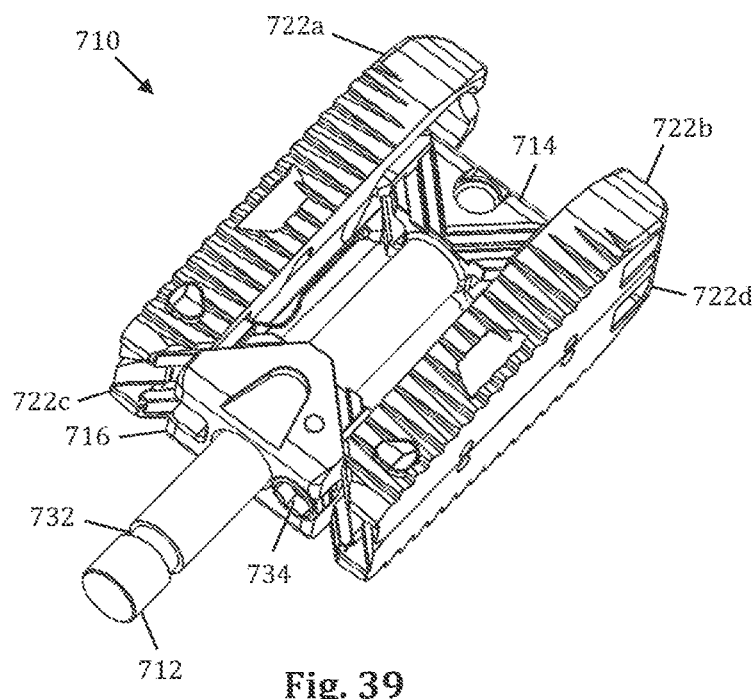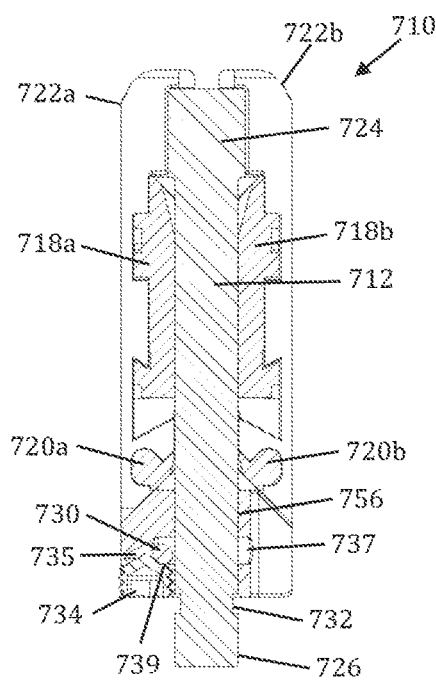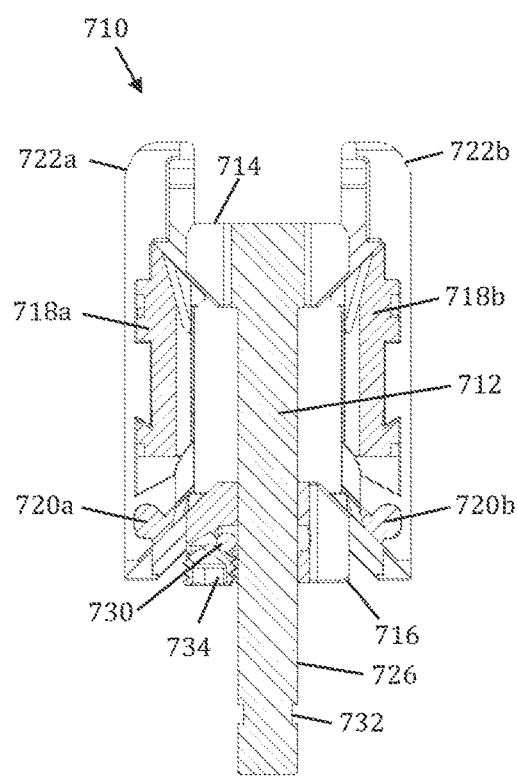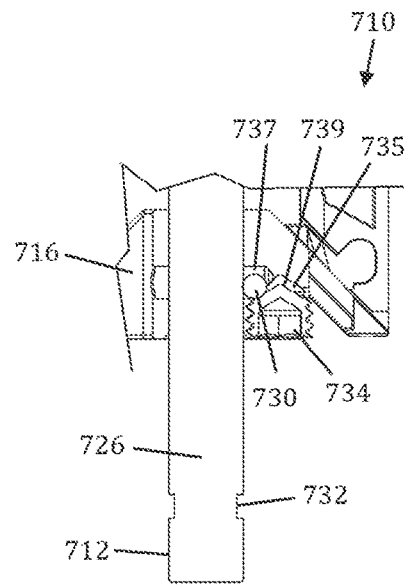
Fig. 39
Fig. 40
Fig. 41
Fig. 42

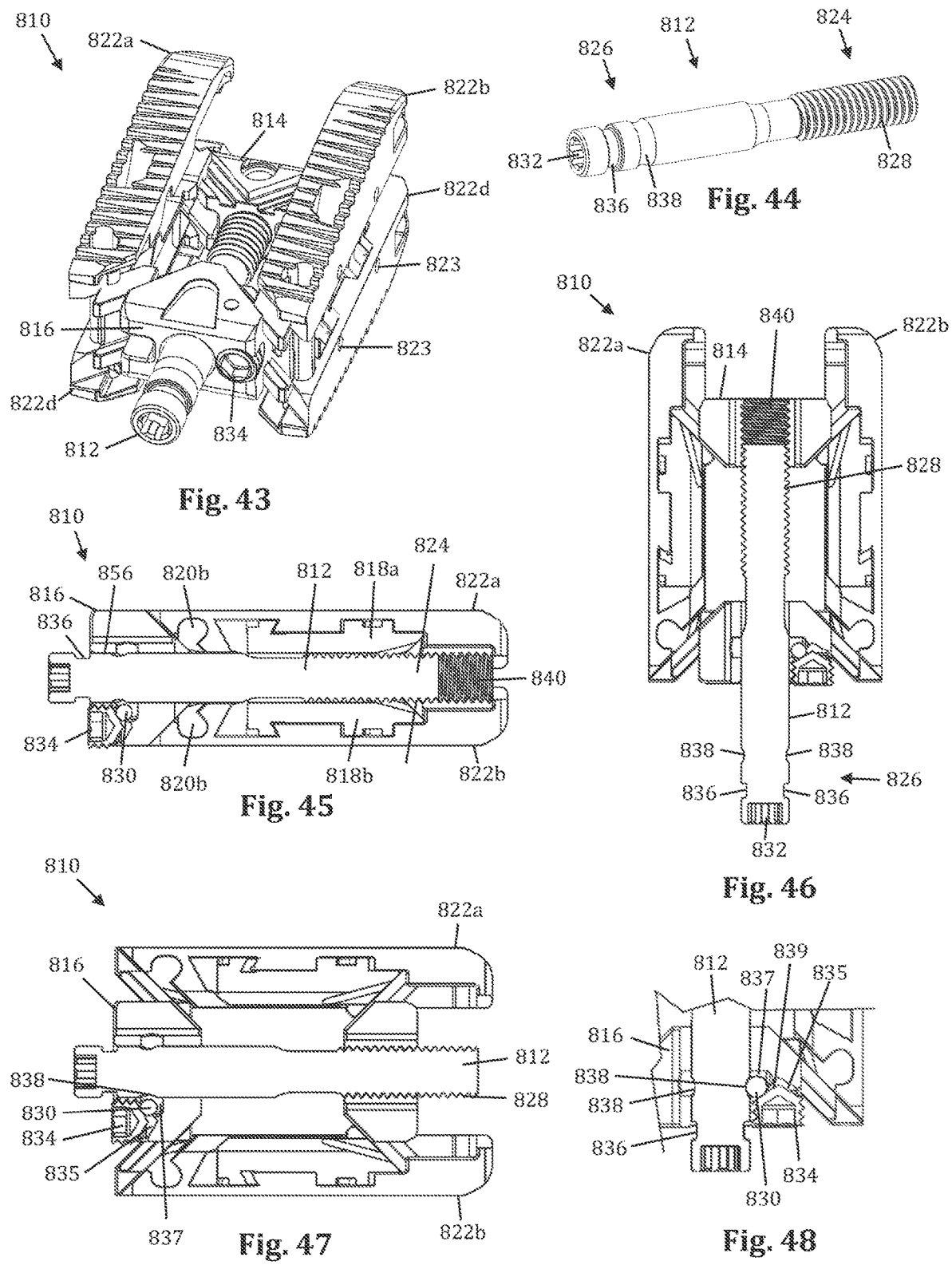

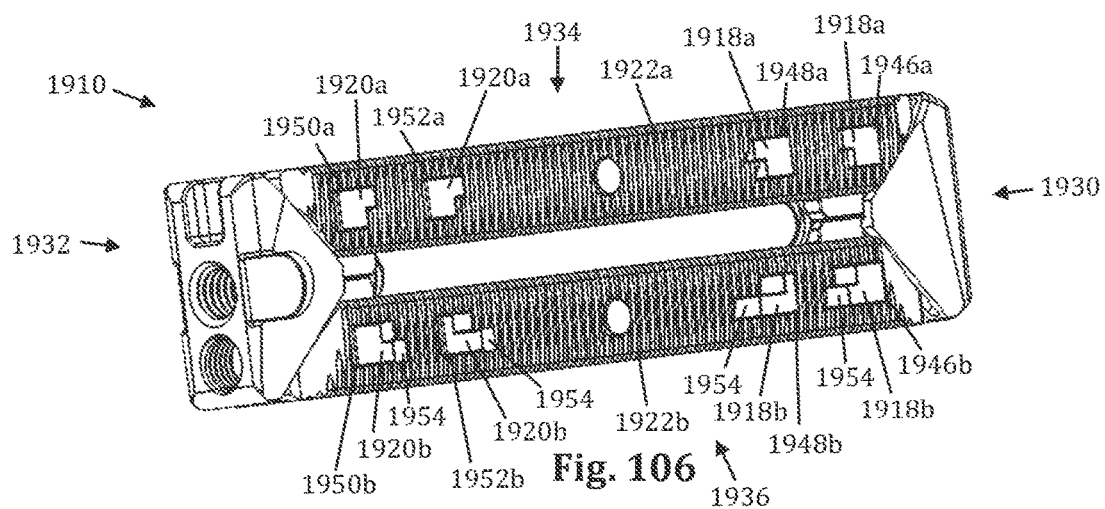
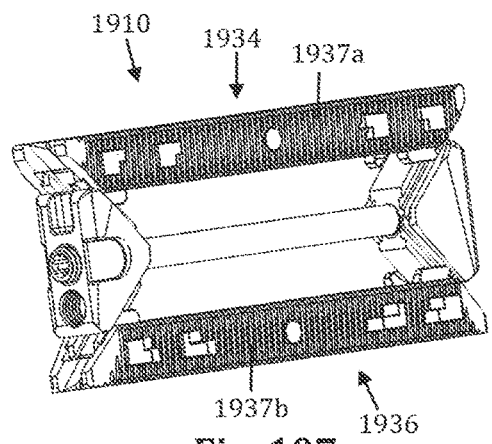
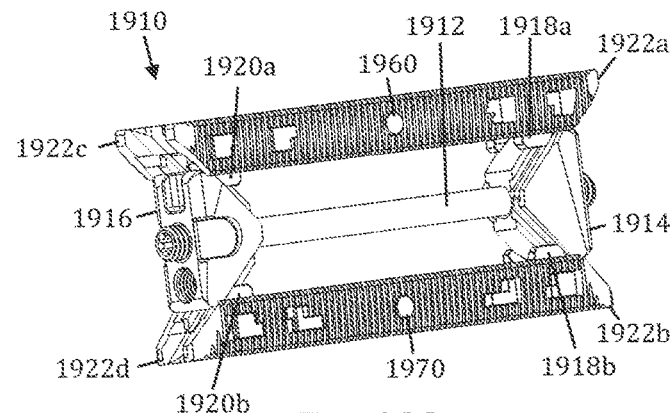
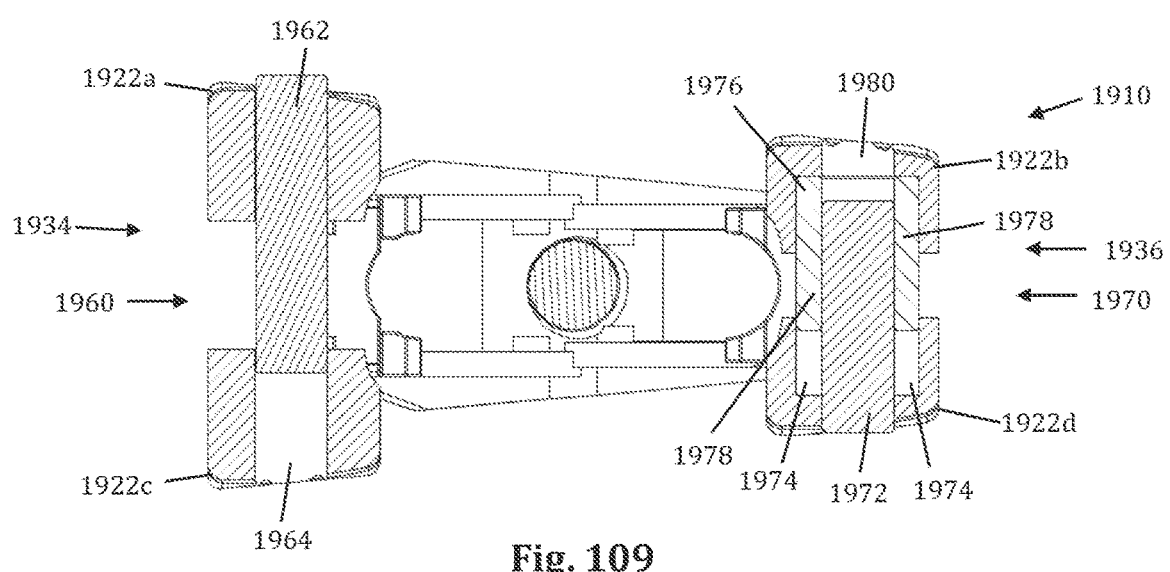

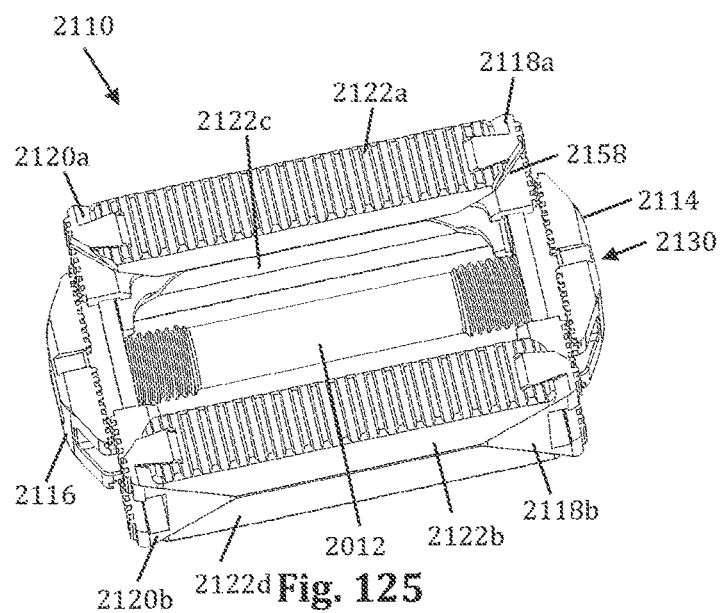
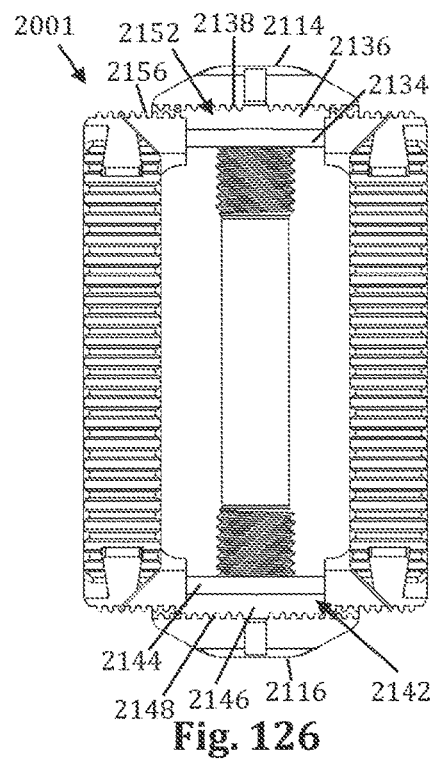
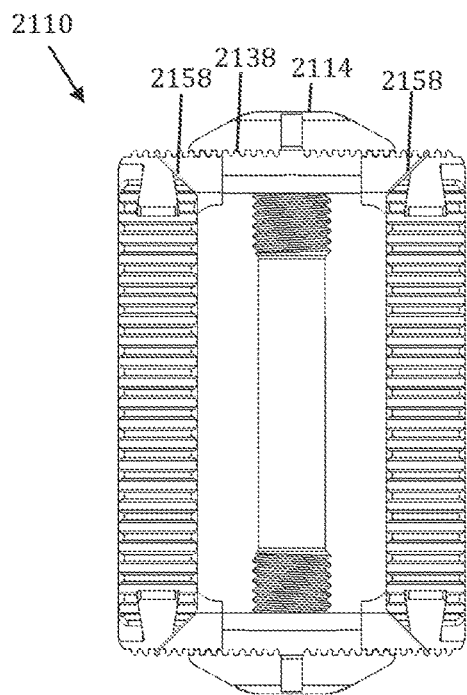
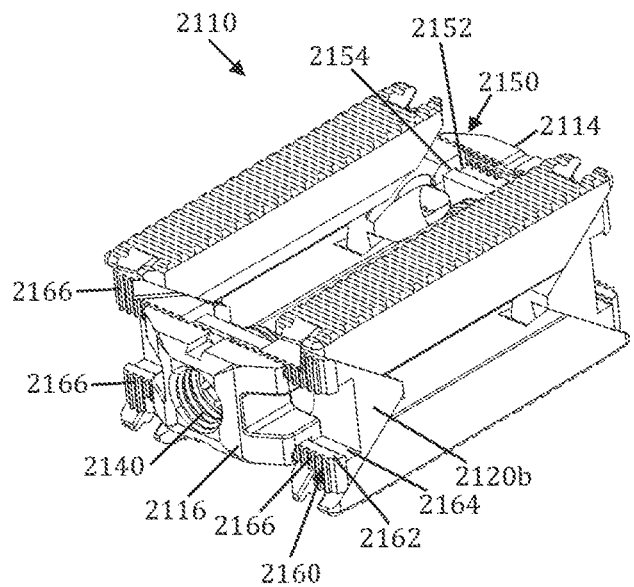
Fig. 125
Fig. 126
Fig. 127
Fig. 128

EXPANDABLE FUSION DEVICE WITH INTERDIGITATING FINGERS

CROSS REFERENCES TO RELATED APPLICATIONS

This is a continuation application of U.S. application Ser. No. 16/290,428, filed Mar. 1, 2019, which claims priority to U.S. Provisional Application No. 62/637,306, filed Mar. 1, 2018, each of which is hereby incorporated herein by reference in its entirety.

BACKGROUND

Field of the Invention

The teachings herein are directed generally to medical devices and methods, including devices and methods for promoting an intervertebral fusion, such as devices that can be inserted in a subject in a collapsed state through a small surgical corridor, and the expand cephalocaudal only, transverse only, or in both directions, in which direction of expansion can also be obtained independently, if desired, after the insertion.

Description of the Related Art

The teachings provided herein include methods, devices, and systems for performing a spinal implant procedure on a subject. A spinal fusion is typically employed to eliminate pain caused by the motion of degenerated disk material. Upon successful fusion, a fusion device becomes permanently fixed within the intervertebral disc space. A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are challenges associated with the known conventional fusion devices and methodologies. For example, present methods for installing a conventional fusion device may require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height may make it difficult for a surgeon to install the fusion device in the distracted intervertebral space.

As such, there exists a need for a fusion device capable of being installed inside an intervertebral disc space at a minimum to no distraction height and for a fusion device capable of maintaining a normal distance between adjacent vertebral bodies when implanted.

One of the most common post-operative complications of intervertebral fusion surgery is intervertebral graft or cage subsidence which are minimized or mitigated by using an intervertebral cage or graft of a larger footprint. This is often difficult because to minimize the trauma and morbidity associated with spine surgery, it is often advantageous to utilize the smallest surgical access corridor possible to achieve the goals of surgery. As such there exists a need for a fusion device capable of being inserted through a relatively small surgical corridor and capable to then be expanded to a larger footprint suitable to resist subsidence.

It should be appreciated that a spinal fusion, for example, is a procedure that can be used to eliminate pain. This pain, for example, can be caused by the motion of degenerated disk material. Upon a successful fusion, a fusion device becomes permanently fixed within the intervertebral disc space. Unfortunately, the devices and procedures used in the art still suffer several problems, including those discussed above. One of skill will understand that the inventions described herein, however, address several of these problems including at least, for example, (i) a reduced surgical complexity and risk in an insertion of the device through the use of a minimum to minimal, or perhaps no, intervertebral distraction; (ii) a reduced surgical complexity and risk in an insertion of the device through a small surgical corridor; (iii) a desired width control in the expansion of the device through a variable transverse expansion system in a single device which provides for an on-the-fly selection of a desirable footprint, which can be a larger, or perhaps biased, footprint for achieving a desired alignment, or perhaps for avoiding subsidence of the device during use; (iv) a desired control of height expansion through a gradual cephalocaudal expansion of the device, gradually increased at a desired amount and speed via a drive system, to obtain a desirable intervertebral height and/or pressure, for controllably decompressing the neural elements and reaching the desired the intervertebral height with increased safety due to the incremental control of the speed, amount, and pressure of expansion applied to the surrounding tissue; (v) a desired control of the alignment of the adjacent vertebral bodies through a control that is provided by a design that provides freedom to choose any expansion width desired, and obtaining that desired width independent of the gradual height control; and, (vi) a desired control of the contact area desired between the device and the upper and lower vertebral endplates achieved, for example, using an interdigitated endplate system.

SUMMARY

Expandable spinal fusion devices, systems, and methods of using them are provided, and they can be inserted in a subject in a collapsed state through a small surgical corridor, and the expand cephalocaudal only, transverse only, or in both directions, in which direction of expansion can also be obtained independently, if desired, after the insertion. These inventions are valuable in reducing risk and surgical complexity, allowing for an on-the-fly selection of a desirable width footprint, a desired control of height expansion through a gradual cephalocaudal expansion, and a desired control of the alignment of the adjacent vertebral bodies. Devices, systems, and methods are also offered to provide a desired control of the contact area desired between the device and the upper and lower vertebral endplates achieved, for example, using an interdigitated endplate system.

In some embodiments, the expandable fusion device includes a first endplate, a second endplate, a third endplate, and a fourth endplate, two endplates of which form an upper endplate assembly, and the remaining two of which form a lower endplate assembly. The device can also include a cephalocaudal expansion assembly configured to cause a cephalocaudal expansion between the upper endplate assembly and the lower endplate assembly. Moreover, the device can also include a transverse expansion assembly configured to cause a transverse expansion within the upper endplate assembly and the lower endplate assembly. In some embodiments, the cephalocaudal expansion assembly can be selected from one of, and the transverse expansion assembly is selected from the other of, (a) a drive system having an actuator including a drive feature and a longitudinal axis; a wedge assembly coupled to the actuator; and, a ramp assembly slidably coupled with the wedge assembly; wherein, each of the first endplate, second endplate, third endplate, and fourth endplate is slidably coupled with the ramp assembly; and, (b) a spacer system having at least a first spacer configured for insertion between a first pair of adjacent endplates selected from group consisting of the first endplate, the second endplate, the third endplate, and the fourth endplate.

It should be appreciated that the spacer system can have a single spacer, or a plurality of spacers. In some embodiments, for example, the spacer system can have any configuration desired, for example, as it can have a pair of spacer of equal or different width and/or length. In some embodiments, a pair of spacers can be inserted independently or as part of a combined spacer unit. Such a combined spacer unit can be forked, for example, and it can be removable as a tool after establishing the desired spacing in vivo, or it can be left in place in the subject during the procedure as an implant. One of skill will appreciate the versatility in selecting a spacer size on-the-fly, to obtain a desired width, for example, as the desired amount of expansion can vary, and can change during a procedure. Moreover, the skilled artisan will also highly appreciate that the expansion of the device using the drive system operates independent of the expansion of the device using the spacer system, offering an improved versatility in the operating room.

In some embodiments, a pair of spacers are used. As such, after insertion of a first spacer between the first pair of adjacent endplates, the spacer system can include a second spacer configured for insertion between the remaining pair of adjacent endplates, the remaining pair selected from group consisting of the first endplate, the second endplate, the third endplate, and the fourth endplate; wherein, the second spacer is selected for a desired amount of expansion. The insertion of the second spacer can be independent of the insertion of the first spacer, or it can be inserted concurrently.

In some embodiments, the upper endplate assembly includes the first endplate and the second endplate; and, the lower endplate assembly includes the third endplate and the fourth endplate. In such embodiments, the cephalocaudal expansion assembly can include the drive system; wherein, the upper endplate assembly is slidably coupled with the ramp assembly; the lower endplate assembly is slidably coupled with the ramp assembly; and, the cephalocaudal expansion assembly is configured to cause a cephalocaudal expansion between the upper endplate assembly and the lower endplate assembly upon an activation of the actuator. And, in some embodiments, the transverse expansion assembly includes the spacer system for the transverse expansion, the first spacer is configured for insertion between the third endplate and the fourth endplate, and the second spacer is configured for insertion between the third endplate and the fourth endplate.

It should be appreciated that the endplates are a structural component of the devices, and the devices are designed to support significant forces present in the intervertebral space of a subject. A such, in some embodiments, the first endplate, the second endplate, the third endplate, and the fourth endplate are each a beam having a longitudinal axis and selected for it's rigidity. However, it should be appreciated that, in some embodiments, perhaps the design is selected to provide some flexibility, such that the first endplate, the second endplate, the third endplate, and the fourth endplate are each selected for a desired amount of flexibility to, perhaps, conform to the vertebral endplates and provide a limited compliance that, for example, may reduce point pressure on the vertebral endplates to reduce the risk of subsidence. In some embodiments, it should be appreciated that the the first endplate, the second endplate, the third endplate, and the fourth endplate can each be designed to be rigid, flexible, or a combination of rigid and flexible. In some embodiments, for example, each of the first endplate, the second endplate, the third endplate, and the fourth endplate can be formed from a combination of materials, perhaps each designed with a first rigid material to impart a rigid characteristic to maintain the straight conformation of the longitudinal axis of each beam, and a second flexible material that is compliant enough for the beam surface contacting the vertebral endplate is a second material conform to the vertebral endplates and provide a limited compliance that, for example, may reduce point pressure on the vertebral endplates to reduce the risk of subsidence. The endplates can each be designed to have any one or any combination of these features, such that any set of endplates can have a great deal of flexibility in design. For example, the top endplate assembly can have a surface that is flexible in contact with its respective vertebral endplate, and the bottom endplate assembly can have a surface that is rigid in contact with the its respective vertebral endplate, and the like. On the contrary, all endplates can have a flexible contact surface, and all can have a rigid contact surface. Moreover the sizes of the endplates can vary alone and in combination. In some embodiments, at least one of the second endplate and the fourth endplate is larger than at least one of the first endplate and the third endplate.

The drive system can be used in the device for either vertical or lateral expansion, either alone or in combination with the spacer system which can also be used in the device for either vertical or lateral expansion. The actuator of the drive system can be configured to have a distal end and a proximal end, wherein at least a portion of the distal end comprises a first thread feature, at least a portion of the proximal end comprises a second thread feature, and the proximal end comprises the drive feature which can be configured to attach to a corresponding drive element of a driving instrument. The wedge assembly of the drive system provides the forces to expand the device and, in some embodiments, the wedge assembly comprises a distal wedge and a proximal wedge. The ramp assembly redirects the force from the wedge assembly to the endplates and, in some embodiments, the ramp assembly comprises a first distal ramp, a second distal ramp, a first proximal ramp, and a second proximal ramp.

Since those of skill may want to inhibit or prevent the device from regressing from it's expanded state in vivo, an expansion lock can be provided in the drive system and/or the spacer system. In some embodiments, the expansion lock includes a friction lock configured to lock with contact between the wedge assembly and the ramp assembly. And, in some embodiments, the expansion lock includes a snap lock between the first spacer and the first pair of adjacent endplates, the second spacer and the remaining pair of adjacent endplates, or both depending on whether a single spacer, or a plurality of spacers, is used. In some embodiments, the actuator has a "neutral" position, wherein the spacer system is free to expand the device, and an "engaged" position, wherein the spacer system is locked and can no longer expand or collapse. The engaged position can be a friction lock, for example, or it can be an engagement of complementary teeth, a key in a slot, or the like. In view of the means set-forth herein, the expansion lock can also include any means for locking into place the expansion of first pair of adjacent endplates, the remaining pair of adjacent endplates, or both.

Methods of fusing intervertebral spaces are also provided. In some embodiments, a method of fusing an intervertebral space of a subject can include inserting any device taught herein into an intervertebral space of the subject with an inserter tool and performing a cephalocaudal expansion and a transverse expansion of the device by (i) actuating the drive system and (ii) inserting the spacer system into the device, the actuating and inserting performed independently and in separate steps. One of skill will appreciate that the performing of the expansion using the drive system operates can be independent of the expansion using the spacer system, which provides a great deal of needed versatility and control in the operating room.

In some embodiments, the methods include attaching an inserter tool to the device for the inserting; and, driving the actuator with the drive element of a driving instrument, the drive element configured for engaging with the drive feature of the actuator. In some embodiments, the actuator has a distal end and a proximal end, at least a portion of the distal end comprises a first thread feature, at least a portion of the proximal end comprises a second thread feature, and the proximal end comprises the drive feature, and the drive feature is configured to attach to a corresponding drive element of a driving instrument. In some embodiments, the method can further comprise attaching an inserter tool to the device for the inserting; and, driving the actuator with the drive element of a driving instrument, the drive element configured for engaging with the drive feature of the actuator and rotating the actuator with the driving instrument.

In some embodiments, the method of fusing an intervertebral space of a subject includes inserting any device taught herein into an intervertebral space of the subject and performing the transverse expansion using the spacer system, the performing including inserting a first spacer into the device for a desired amount of expansion. In some embodiments, the insertion of the first spacer can be accompanied by the insertion of a second spacer in the device, and this can occur in series or concurrently. The method can also include performing a cephalocaudal expansion using the drive system, the performing including actuating the drive system in the device; wherein, the actuating and inserting of the spacer(s) are performed independently and in separate steps, in some embodiments. Likewise, such methods can further include attaching an inserter tool to the device for the inserting; and, driving the actuator with the drive element of a driving instrument, the drive element configured for engaging with the drive feature of the actuator. In some embodiments, the actuator has a distal end and a proximal end, at least a portion of the distal end comprises a first thread feature, at least a portion of the proximal end comprises a second thread feature, and the proximal end comprises the drive feature, and the drive feature is configured to attach to a corresponding drive element of a driving instrument. In such embodiments, the method further comprises attaching an inserter tool to the device for the inserting; and, driving the actuator with the drive element of a driving instrument, the drive element configured for engaging with the drive feature of the actuator and rotating the actuator with the driving instrument.

Devices that are expandable in length are also provided. In some embodiments, an expandable fusion device that is expandable in length can include a first expandable device coupled to a second expandable device; a first actuator for expanding the first expandable device and the second expandable device; and, a second actuator configured for coupling the first expandable device to the second expandable device. In some embodiments, the first actuator is part of a drive system having a first wedge assembly for the first expandable device coupled to the first actuator; and, a first ramp assembly slidably coupled with the first wedge assembly; and, a second wedge assembly for the second expandable device coupled to the first actuator; and, a second ramp assembly slidably coupled with the second wedge assembly. In some embodiments, each of the first expandable device and the second expandable device include a first endplate, a second endplate, a third endplate, and a fourth endplate, each endplate of which is slidably coupled with the ramp assembly.

Likewise, devices that expand laterally while providing a substantial increase in the area that contacts vertebral endplates are provided. In some embodiments, a laterally expandable fusion device can include an upper endplate assembly having a first endplate with a first plurality of protrusions and a second endplate with a second plurality of protrusions; and a lower endplate assembly having a third endplate with a third plurality of protrusions and a fourth endplate with a fourth plurality of protrusions. In some embodiments, the first plurality of protrusions are interdigitated with the second plurality of protrusions to telescope upon the lateral expansion and provide a substantially increased surface area for contact with an upper vertebral endplate in an intervertebral space; the third plurality of protrusions are interdigitated with the fourth plurality of protrusions to telescope upon the lateral expansion and provide a substantially increased surface area for contact with an lower vertebral endplate in an intervertebral space; and, each of the first endplate, second endplate, third endplate, and fourth endplate have a plurality of receptacles for (i) receiving each of the respective plurality of protrusions upon a collapse of the device; and, (ii) releasing each of the respective plurality of protrusions upon a collapse of the device. In such embodiments, each protrusion on one endplate can have a mating surface, on the opposing endplate, such as recess, groove, channel, or port, for example, to mate with, or be received, on the opposing or adjacent end-plate. In some embodiments, the first plurality of protrusions and the second plurality of protrusions slidably translate with a tongue-in-groove configuration to provide additional rigidity to the upper endplate assembly upon the lateral expansion; and, the third plurality of protrusions and the fourth plurality of protrusions slidably translate with a tongue-in-groove configuration to provide additional rigidity to the lower endplate assembly upon the lateral expansion.

Further areas of applicability of the present disclosure will become apparent from the detailed description provided hereinafter. It should be understood that the detailed description and specific examples, while indicating the preferred or exemplary embodiments of the disclosure, are intended for purposes of illustration only and are not intended to limit the scope of the disclosure.

BRIEF DESCRIPTION OF THE DRAWINGS

Novel features of the disclosure are set forth with particularity in the appended claims. A better understanding of the features and advantages of the inventions taught herein, however, can be obtained by reference to the following detailed description that sets forth illustrative embodiments, in which the principles of the disclosure are utilized, and the accompanying drawings of which:

FIG. 13 is side plan view of an example of a distal ramp forming part of the expandable fusion device of FIG. 3, according to some embodiments;

FIGS. 14-15 are perspective views of the distal ramp of FIG. 13, according to some embodiments;

FIG. 16 is a top plan view of the distal ramp of FIG. 13, according to some embodiments;

FIGS. 17-19 are perspective views of an example of a proximal ramp forming part of the expandable fusion device of FIG. 3, according to some embodiments;

FIG. 20 is a plan view of the proximal ramp of FIG. 17, according to some embodiments;

FIG. 39 is a perspective view of another example of an expandable fusion device in a width-expanded state, according to some embodiments;

FIGS. 40-41 are sectional views of the expandable fusion device of FIG. 39 in various states of expansion, according to some embodiments;

FIG. 42 is a sectional view of a proximal portion of the expandable fusion device of FIG. 39, according to some embodiments;

FIG. 43 is a perspective view of another example of an expandable fusion device in a fully expanded state, according to some embodiments;

FIG. 44 is a perspective view of an example of an actuator forming part of the expandable fusion device of FIG. 43, according to some embodiments;

FIGS. 45-47 are sectional views of the expandable fusion device of FIG. 43 in various states of expansion, according to some embodiments;

FIG. 48 is a sectional view of a proximal portion of the expandable fusion device of FIG. 43, according to some embodiments;

FIG. 106 is a perspective view of another example of an expandable fusion device in a fully collapsed state, according to some embodiments;

FIG. 107 is a perspective view of the expandable fusion device of FIG. 106 in a width-expanded state, according to some embodiments;

FIG. 108 is a perspective view of the expandable fusion device of FIG. 106 in a fully expanded state, according to some embodiments;

FIG. 109 is a sectional view of the expandable fusion device of FIG. 108, according to some embodiments;

FIGS. 123-125 are perspective views of the expandable fusion device of FIG. 122 in various states of expansion, according to some embodiments;

FIGS. 126-127 are top plan views of the expandable fusion device of FIG. 122, according to some embodiments;

FIG. 128 is a perspective view of the expandable fusion device of FIG. 122 in a fully expanded state, according to some embodiments;

DETAILED DESCRIPTION

Figure 1:
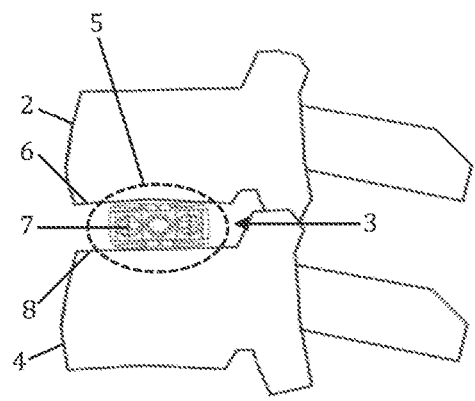
FIG. 1 depicts an example of an expandable fusion device implanted between two vertebral bodies in an initial collapsed state, according to some embodiments.

Expandable spinal fusion devices, systems, and methods of using them are provided and reduce surgical complexity and risk through the use of a minimum to minimal, or perhaps no, intervertebral distraction and use of a small surgical corridor. The devices, systems, and methods allow for a desired width control in the expansion of the device through a variable transverse expansion system in a single device which provides for an on-the-fly selection of a desirable footprint, which can be a larger, or perhaps biased, footprint for achieving a desired alignment, or perhaps for avoiding subsidence of the device during use. They also allow for a desired control of height expansion through a gradual cephalocaudal expansion of the device, gradually increased at a desired amount and speed via a drive system, to obtain a desirable intervertebral height and/or pressure, for controllably decompressing the neural elements and reaching the desired the intervertebral height with increased safety due to the incremental control of the speed, amount, and pressure of expansion applied to the surrounding tissue. A desired control of the alignment of the adjacent vertebral bodies is offered through a design that gives a surgeon the freedom to choose any expansion width desired, and obtaining that desired width independent of the gradual height control. Devices, systems, and methods are also offered that allow for a desired control of the contact area desired between the device and the upper and lower vertebral endplates achieved, for example, using an interdigitated endplate system.

The fusion devices taught herein can include a proximal wedge, a distal wedge, a first ramp, a second ramp, a third ramp, a forth ramp, a first endplate, a second endplate, a third endplate, a fourth endplate, an actuator, and a retention member designed to constrain the linear motion of the actuator relative to the proximal wedge. The actuator capable of drawing the proximal wedge and the distal wedge together or apart from each other, forcing the first ramp away from the fourth ramp and forcing the second ramp away from the third ramp and also forcing the first ramp away from or toward the second ramp and forcing the third ramp away from or toward the fourth ramp, to result in moving the first endplate, the second endplate, the third endplate and the fourth endplate outwardly from each other and into an expanded configuration.

Optionally, in any embodiment, the device can have a width comprising an external width of at least one of the upper endplate assembly and the lower endplate assembly. Optionally, in any embodiment, the device can have a height comprising an external distance between the upper endplate assembly and the lower endplate assembly. Optionally, in any embodiment, actuation of the drive feature by a first number of actuations in a first actuation direction can increase the width without increasing the height. Optionally, in any embodiment, actuation of the drive feature by a second number of actuations beyond the first number of actuations in the first actuation direction can increase at least one of the height and the width.

One of skill will appreciate the range of expansions available, as well as the improved, and independent, control of both cephalocaudal and transverse expansions that is offered to the art by the devices presented herein. In some embodiments, the width (dimension in which the device expands in the transverse direction in vivo) of the device can range from about 5 mm to about 30 mm in the collapsed state, and any amount or range therein in increments of 1 mm; and, from about 10 mm to about 60 mm in the expanded state, and any amount or range therein in increments of 1 mm. In some embodiments, the height (dimension in which the device expands in the cephalocaudal direction in vivo) of the device can range from about 5 mm to about 20 mm in the collapsed state, and from about 10 mm to about 40 mm in the expanded state. The percent expansion in either direction can range from about 1% to about 100%, and any percent therein in increments of 1%, in some embodiments. As such, in the collapsed state, the width of the device can be about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, or any amount or range therein in increments of 0.1 mm; and, the height can be about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, or any amount or range therein in increments of 0.1 mm. Likewise, in the expanded state, the width of the device can be about 10 mm, about 12 mm, about 14 mm, about 16 mm, about 18 mm, about 20 mm, about 24 mm, about 24 mm, about 26 mm, about 28 mm, about 30 mm, about 32 mm, about 34 mm, about 36 mm, about 38 mm, about 40 mm, about 42 mm, about 44 mm, about 46 mm, about 48 mm, about 50 mm, about 52 mm, about 54 mm, about 56 mm, about 58 mm, about 60 mm, or any amount or range therein in increments of 0.1 mm; and, the height can be about 10 mm, about 12 mm, about 14 mm, about 16 mm, about 18 mm, about 20 mm, about 22 mm, about 24 mm, about 26 mm, about 28 mm, about 30 mm, about 32 mm, about 34 mm, about 36 mm, about 38 mm, about 40 mm, or any amount or range therein in increments of 0.1 mm. Any combination, or combination of ranges, of the above height and width dimensions can be used together, in some embodiments. In some embodiments, for example, a device can have a height ranging from about 7-8 mm when collapsed, whereas the height ranges from about 12-14 mm when expanded in vivo; and, it can have a width a ranging from about 7-20 mm when collapsed, whereas the width ranges from about 14-40 mm when expanded in vivo. In some embodiments, for example, a device can have a height ranging from about 6-10 mm when collapsed, whereas the height ranges from about 12-20 mm when expanded in vivo; and, it can have a width a ranging from about 6-24 mm when collapsed, whereas the width ranges from about 12-48 mm when expanded in vivo.

Figure 2:
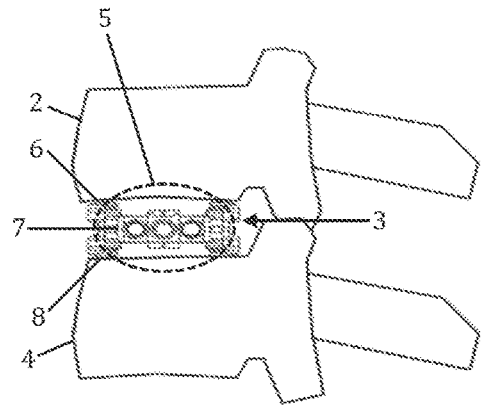
FIG. 2 depicts the expandable fusion device of FIG. 1 implanted between two vertebral bodies in a fully expanded state, according to some embodiments.
Figure 3:
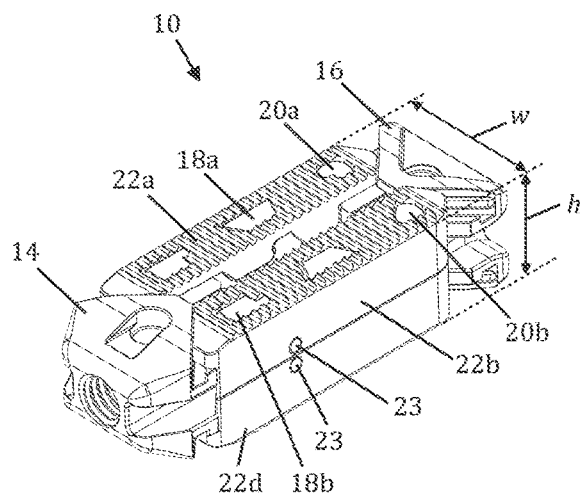
FIG. 3 is a perspective view of an example of an expandable fusion device in a collapsed state, according to some embodiments.
Figure 4:
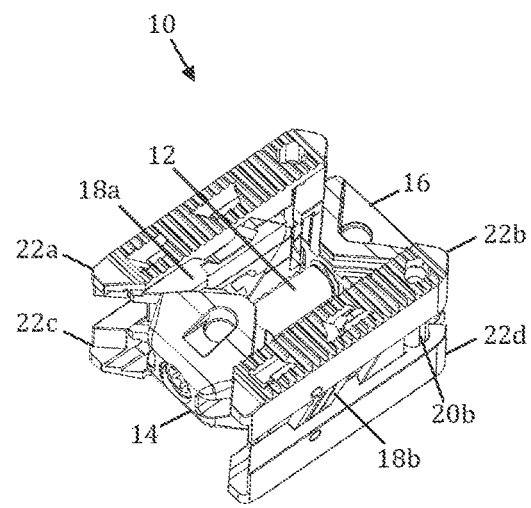
FIG. 4 is a perspective view of the expandable fusion device of FIG. 3 in a fully expanded state, according to some embodiments.
Figure 5:
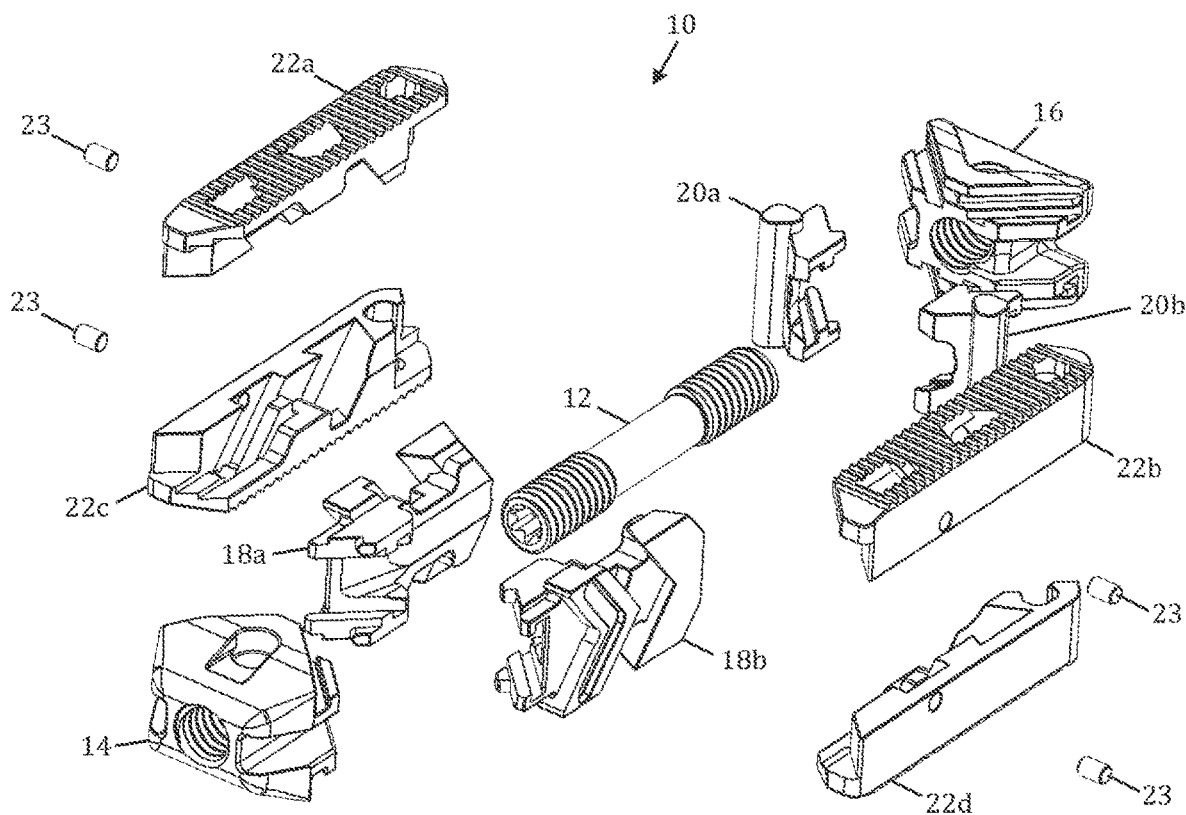
FIG. 5 is an exploded perspective view of the expandable fusion device of FIG. 3, according to some embodiments.

FIGS. 1-2 illustrate an example of one embodiment of an expandable fusion device 7 of the type disclosed herein, and is a representative example of the type of expansion common to each embodiment described by way of example below. By way of example, FIG. 1 illustrates the expandable fusion device 7 in an initial collapsed state positioned within an intervertebral space 3 between adjacent vertebral bodies 2, 4 having endplates 6, 8, respectively, by way of surgical access corridor 5. Implanting the expandable fusion device 7 in an initial collapsed state reduces the impaction force and the size of the surgical corridor 5 required for implantation. FIG. 2 illustrates the expandable fusion device 7 in an expanded state (expanded in both width and height) engaging vertebral endplates 6, 8 of adjacent vertebral bodies 2, 4, respectively. The expandable fusion device 7 may be longer than it is wide in its initial collapsed state and the endplates may also be longer than they are wide. Expanding the fusion device 7 while positioned between the vertebral bodies 2, 4 (e.g. "intraoperative expansion") allows an increase in the width of the fusion device 7 and correspondingly the spacing or contact area (or foot-print) between the fusion device 7 and the endplates 6, 8 beyond that which would otherwise be allowed by the surgical corridor 5. Additionally, intraoperative expansion of the expandable fusion device 7 facilitates the application of distraction forces to the endplates 6, 8 in order to increase and maintain the distance and/or angle between the vertebral bodies 2, 4, by increasing and maintaining the height of the implant and/or the angular orientation of its components.

Preferably, the various components of the fusion device 7 (and further embodiments) described herein are manufactured out of a Titanium alloy (including but not limited to Ti-6Al-4V alloys) or a Cobalt alloy including but not limited to CoCrMo alloys. Moreover, manufacturing some of the threaded components of the fusion device 7 out of a CoCr-based alloy allows for increased strength, reduced size, and other performance considerations. However, it should be understood that the various components of the expandable fusion device 7 (and/or any embodiment described herein) may be made out of a variety of materials including but not limited to metals and alloys (e.g. Commercially Pure Titanium, Titanium alloys including Ti-6Al-4V based alloys, Cobalt alloys including CoCrMo alloys, Stainless steel, Tantalum and its alloys, Platinum and its alloys, etc.), polymers (e.g. PEEK, PEKK, PEKEK, PEI, PET, PETG, UHMWPE, PPSU, Acetal, Polyacetal, etc. including carbon fiber reinforced varieties and other varieties filled, for example, with Carbon Fiber, Carbon nano-tubes, Graphene, Barium Sulfate or Hydroxyapatite), ceramics (e.g. Aluminum Oxide, Zirconium oxide, Silicon nitride, diamond-like carbon, etc. as well as various metalized ceramics an metal-ceramic composites).

As such, in any embodiments, at least one of the actuator, the wedge assembly, the ramp assembly, the upper endplate assembly, and the lower endplate assembly can comprise titanium, cobalt, stainless steel, tantalum, platinum, PEEK, PEKK, carbon fiber, barium sulfate, hydroxyapatite, a ceramic, zirconium oxide, silicon nitride, carbon, bone graft, demineralized bone matrix product, synthetic bone substitute, a bone morphogenic agent, a bone growth inducing material, or any combination thereof.

Optionally, in any embodiment, bone allograft, bone autograft, xenogaft, demineralized bone matrix product, synthetic bone substitute, bone morphogenic agents, or other bone growth inducing material are introduced within and/or around the fusion device 7 to further promote and facilitate the intervertebral fusion. In one embodiment, the fusion device 7 may be preferably packed or injected with bone graft, demineralized bone matrix product, synthetic bone substitute, bone morphogenic agents, or other bone growth inducing material after it has been expanded, but in other embodiments, the graft material may also be introduced into the intervertebral space 3 within or around the fusion device 7 prior to implantation or after the implantation but prior to expansion.

Optionally, in any embodiment, the device can further comprise one or more pins. Optionally, in any embodiment, at least one of the first endplate, the second endplate, the third endplate, and the fourth endplate, can comprise a bone-facing surface that does not contain any through-holes. Optionally, in any embodiment, at least two of the first endplate, the second endplate, the third endplate, and the fourth endplate can be equivalent. Optionally, in any embodiment, at least two of the first endplate, the second endplate, the third endplate, and the fourth endplate can have mirrored symmetry.

FIGS. 3-23 illustrate an example of an expandable fusion device 10 for implantation between two adjacent vertebrae according to some embodiments. Referring first to FIGS.

3-5, and by way of example only, the expandable fusion device 10 of the present embodiment includes an actuator 12, a distal wedge 14, a proximal wedge 16, a pair of distal ramps 18a, 18b, a pair of proximal ramps 20a, 20b, a plurality of endplates 22a-22d, and a plurality of guide pins 23. As will be described in greater detail below, the distal and proximal wedges 14, 16 are coupled with the actuator 12. The distal ramps 18a, 18b are slideably coupled with the distal wedge 14. The proximal ramps 20a, 20b are slideably coupled with the proximal wedge 16. The plurality of endplates 22a-22d are slideably coupled with the ramps 18a, 18b, 20a. 20b. More specifically, the first endplate 22a comprises a first upper endplate slideably associated with the first distal ramp 18a and the first proximal ramp 20a, the second endplate 22b comprises a second upper endplate slideably associated with the second distal ramp 18b and the second proximal ramp 20b, the third endplate 22c comprises a first lower endplate slideably associated with the first distal ramp 18a and the first proximal ramp 20a, and the fourth endplate 22d comprises a second lower endplate slideably associated with the second distal ramp 18b and the second proximal ramp 20b. In the exemplary embodiment, the endplates 22a-22d may also be in sliding contact with the wedges 14 and 16 when the device is in an initial collapsed state.

Figure 6:
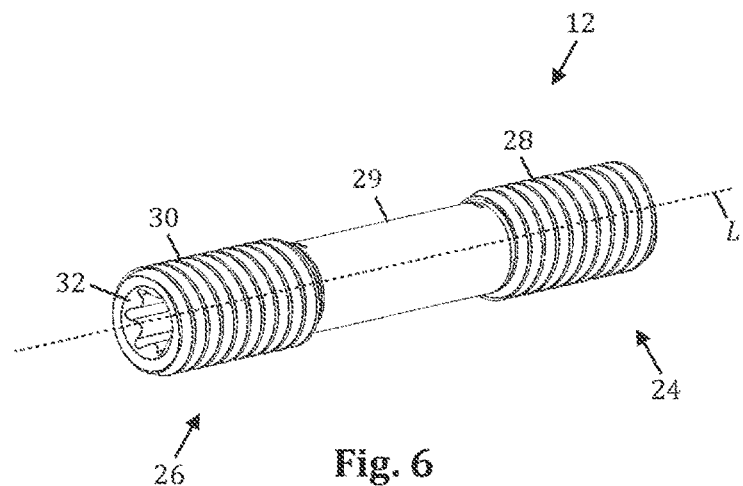
FIG. 6 is a perspective view of an example of an actuator forming part of the expandable fusion device of FIG. 3, according to some embodiments.

FIG. 6 illustrates an example of an actuator 12 forming part of the expandable fusion device 10 of the present embodiment. By way of example only, the actuator 12 comprises a cylindrically shaped elongate shaft having a distal end 24, a proximal end 26, and a longitudinal axis L. At least a portion of the distal end 24 includes a first thread feature 28. Similarly, at least a portion of the proximal end 26 includes a second thread feature 30. The first and second thread features 28, 30 may be separated by a non-threaded segment 29 disposed between the first thread feature 289 and the second thread feature 30. At least one of the distal and proximal ends 24, 26 includes a drive feature 32 coincident with the longitudinal axis L and configured to engage with a driver instrument (not shown) to operate the actuator. The first and second thread features 28, 30 each comprise a thread disposed externally around the shaft of the actuator 12. By way of example, the first thread feature 28 and the second thread feature 30 may have opposing threading directions. Alternatively, the first and second thread features 28, 30 may have the same threading direction. For example, at least one of the first and second thread features 28, 30 may comprise a right-handed threading. Alternatively (or additionally), at least one of the first and second thread features 28, 30 may comprise a left-handed threading. The drive feature 32 comprises a recessed region configured to receive a driving instrument. The recessed region may comprise any shape capable of engaging a corresponding drive element of driving instrument, including but not limited to (and by way of example only) a slot, Phillips, pozidrive, frearson, robertson, 12-point flange, hex socket, security hex socket, star drive, security torx, ta, tri-point, tri-wing, spanner head, clutch, one-way, double-square, triple-square, polydrive, spline drive, double hex, bristol, or a pentalobe recess or any other shaped recess. Alternatively, the drive feature 32 may comprise a protuberance (for example a hex, a hexalobular, or a square protuberance or any other shaped protuberance) extending longitudinally from the proximal and/or distal end and configured to be coupled to a driving instrument.

Optionally, in any embodiment, the actuator can have a distal end and a proximal end. Optionally, in any embodiment, at least a portion of the distal end can comprise a first thread feature. Optionally, in any embodiment, at least a portion of the proximal end can comprise a second thread feature. Optionally, in any embodiment, the proximal end can comprise the drive feature. Optionally, in any embodiment, at least one of the first thread feature and the second thread feature can comprise a thread disposed externally around the actuator. Optionally, in any embodiment, at least one of the first thread feature and the second thread feature can have an opposite threading direction.

Optionally, in any embodiment, the wedge assembly can comprise a distal wedge and a proximal wedge. Optionally, in any embodiment, actuation of the drive feature in the first direction can converge the distal wedge and the proximal wedge toward one another. Optionally, in any embodiment, the distal wedge can comprise a third thread feature, wherein the third thread feature can be threadably coupled to the first thread feature. Optionally, in any embodiment, the proximal wedge can comprise a fourth thread feature, wherein the fourth thread feature can be threadably coupled to the second thread feature. Optionally, in any embodiment, the third thread feature can comprise a thread disposed internally within the distal wedge. Optionally, in any embodiment, the fourth thread feature can comprise a thread disposed internally within the proximal wedge.

Figure 7:
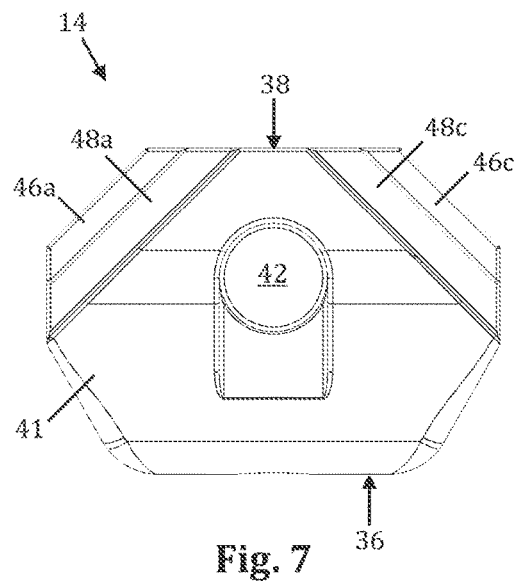
FIG. 7 is a top plan view of an example of a distal wedge forming part of the expandable fusion device of FIG. 3, according to some embodiments.
Figure 8:
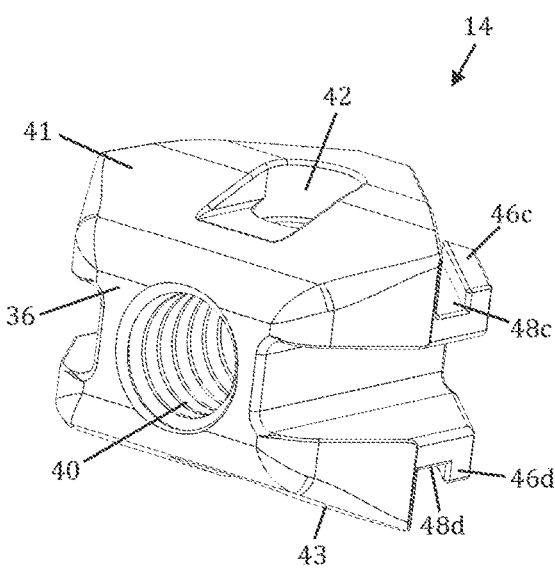
FIG. 8 is a perspective view of the distal wedge of FIG. 7, according to some embodiments.
Figure 9:
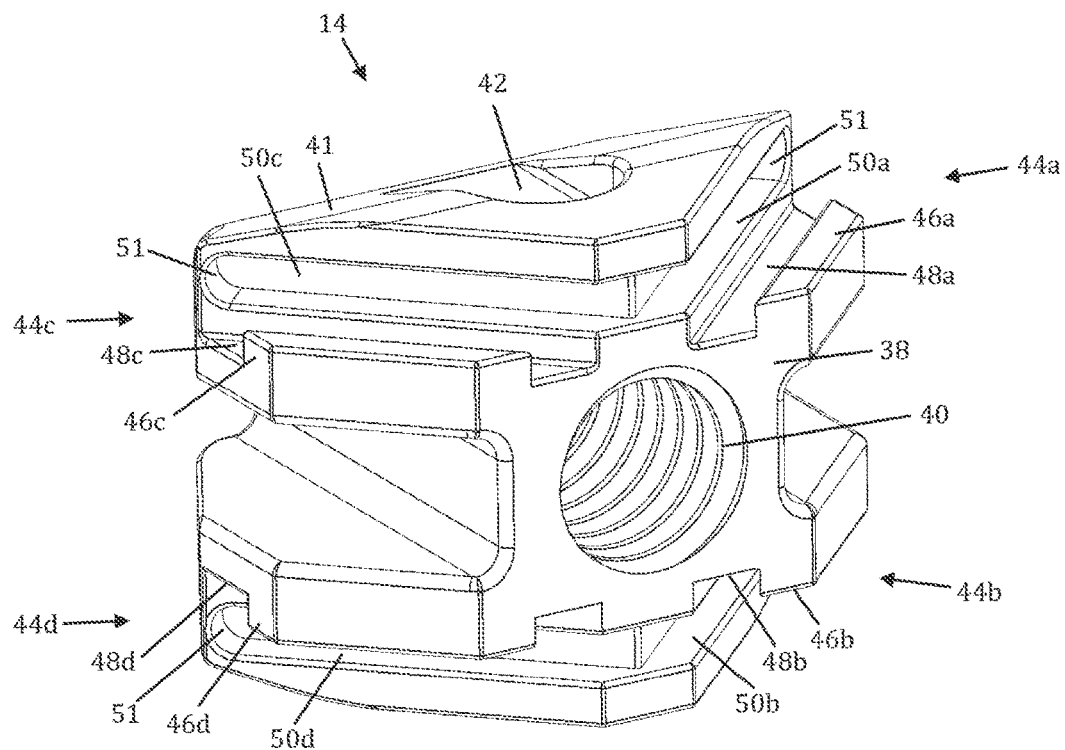
FIG. 9 is another perspective view of the distal wedge of FIG. 7, according to some embodiments.

FIGS. 7-9 illustrate an example of a distal wedge 14 according to the current embodiment. By way of example, the distal wedge 14 may have an isosceles trapezoid prism shape comprising a distal face 36, a proximal face 38, and a thread feature 40 extending axially therethrough between the distal and proximal faces 36, 38. The distal wedge 14 includes distally tapered top and bottom surfaces 41, 43 that aid in the insertion process. The distal wedge 14 further comprises one or more engagement features 42 configured for temporary attachment to an inserter tool, for example one or more recesses 42 on the top and/or bottom surfaces 41, 43 of the distal wedge 14. The thread feature 40 comprises an internal thread configured for threaded coupling with the first thread feature 28 of the actuator 12. The distal wedge 14 may be configured for slideable coupling with the first and second distal ramps 18a, 18b and/or the endplates 22a, 22b, 22c, 22d. To facilitate slideable coupling with the first and second distal ramps 18a, 18b, the distal wedge 14 comprises a plurality of tongue and groove connectors 44a-44d, each comprising a ridge or tongue (e.g. ridge 46a-46d) and a slot or groove (e.g. slot 48a-48d), and a plurality of control slots 50a-50d. By way of example only, the tongue and groove connectors 44a-44d slideably mate with tongue and groove connectors 88a-88d on the distal ramps 18a, 18b, and the control slots 50a-50d slideably receive the protrusions 94a-94d on the distal ramps 18a, 18b. By way of example, the tongue and groove connector 44a comprises an upper right tongue and groove connector 44a (when viewing the proximal face 38 of the distal wedge 14 (as shown in FIG. 9)), the tongue and groove connector 44b comprises a lower right tongue and groove connector 44b, the tongue and groove connector 44c comprises an upper left tongue and groove connector 44c, and the tongue and groove connector 44d comprises a lower left tongue and groove connector 44d. By way of example, the upper right tongue and groove connector 44a and the upper left tongue and groove connector 44c, and the lower right tongue and groove connector 44b and the lower left tongue and groove connector 44d have mirrored symmetry about a sagittal plane of the distal wedge 14. Similarly, the upper right tongue and groove connector 44a and the lower right tongue and groove connector 44b, and the upper left tongue and groove connector 44c and a lower left tongue and groove connector 44d have mirrored symmetry about a transverse plane of the distal wedge 14. By way of example, the medial plane of each of the tongue and groove connectors 44a-44d are oriented at a transverse angle from the sagittal plane of the distal wedge 14.

Optionally, in any embodiment, the ramp assembly can comprise a first distal ramp, a second distal ramp, a first proximal ramp, and a second proximal ramp. Optionally, in any embodiment, the slideable coupling between at least one of the wedge assembly and the ramp assembly, the ramp assembly and the upper endplate, assembly, and the ramp assembly and the lower endplate assembly can be at a transverse angle from the longitudinal axis. The transverse angle can be, for example, in a range that includes about 0 degrees to about 90 degrees. Accordingly, in any embodiment, the transverse angle can be at least about 0 degrees.

Optionally, in any embodiment, the slideable coupling between at least one of the wedge assembly and the ramp assembly, the ramp assembly and the upper endplate, assembly, and the ramp assembly and the lower endplate assembly can comprise a protrusion and a slot. Optionally, in any embodiment, the protrusion can extend from at least one of the wedge assembly, the ramp assembly, the upper endplate assembly, and the lower endplate assembly, wherein the slot is disposed in at least one of the upper endplate assembly, and the lower endplate assembly. Optionally, in any embodiment, the protrusion can comprise a pin, a ridge, a dimple, a bolt, a screw, a bearing, or any combination thereof. Optionally, in any embodiment, the slot can comprise a through slot, a blind slot, a t-slot, a v-slot, a groove, or any combination thereof.

By way of example only, the control slot 50a comprises an upper right control slot 50a (when viewing the proximal face 38 of the distal wedge 14 (as shown in FIG. 9)), the control slot 50b comprises a lower right control slot 50b, the control slot 50c comprises an upper left control slot 50c, and the control slot 50d comprises a lower left control slot 50d. By way of example, the upper right control slot 50a and the upper left control slot 50c, and the lower right control slot 50b and the lower left control slot 50d have mirrored symmetry about a sagittal plane of the distal wedge 14. Similarly, the upper right control slot 50a and the lower right control slot 50b, and the upper left control slot 50c and a lower left control slot 50d have mirrored symmetry about a transverse plane of the distal wedge 14. By way of example, the medial plane of each of the control slots 50a-50d are oriented at a transverse angle from the sagittal plane of the distal wedge 14. Each of the control slots 50a-50d includes a translation stop 51 at the distal-lateral terminus of the respective control slot. The translation stop 51 blocks further distal-lateral translation of the protrusions 94a-94d on the distal ramps 18a, 18b, which stops outward movement of the distal ramps 18a, 18b and thus stops width expansion of the expandable fusion device 10.

Figure 10:
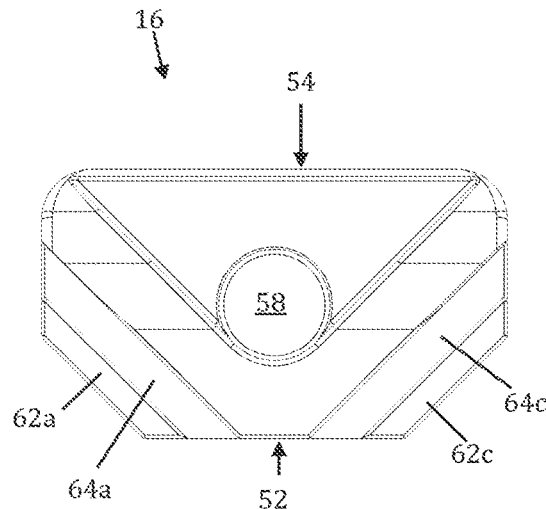
FIG. 10 is a top plan view of an example of a proximal wedge forming part of the expandable fusion device of FIG. 3, according to some embodiments.
Figure 11:
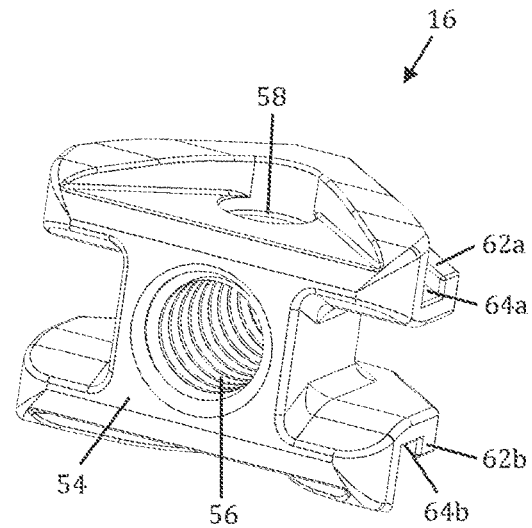
FIG. 11 is a perspective view of the proximal wedge of FIG. 10, according to some embodiments.
Figure 12:
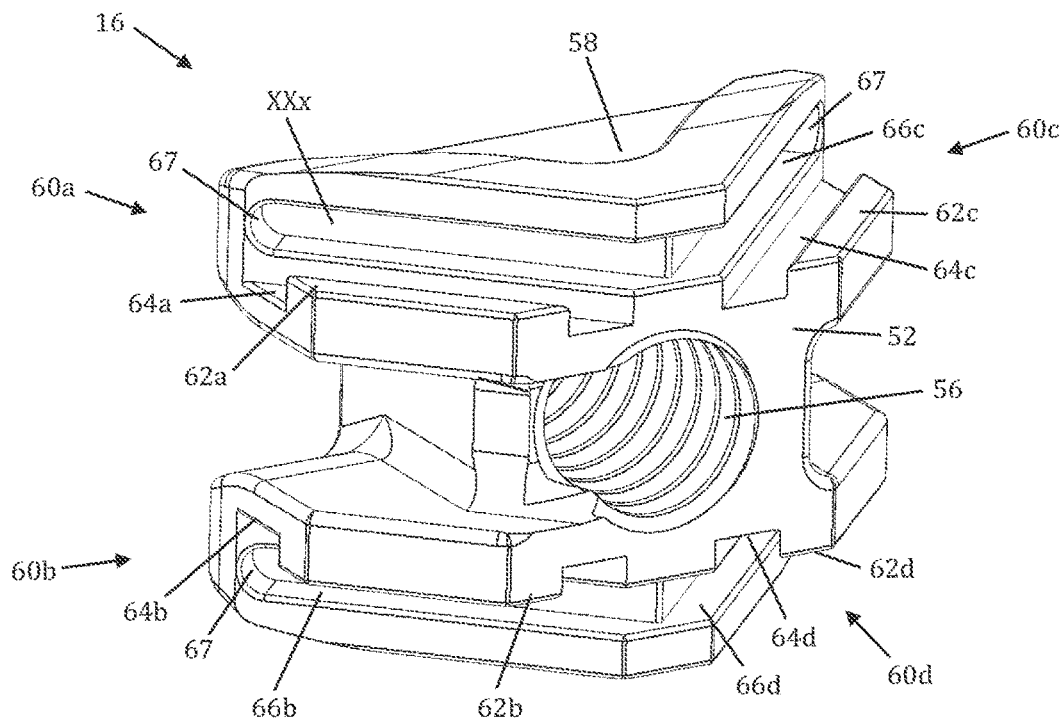
FIG. 12 is another perspective view of the proximal wedge of FIG. 10, according to some embodiments.

FIGS. 10-12 illustrate an example of a proximal wedge 16 according to the current embodiment. By way of example, the proximal wedge 16 has an isosceles trapezoid prism shape comprising a distal face 52, a proximal face 54, and a thread feature 56 extending axially therethrough between the distal and proximal faces 52, 54. The proximal wedge 34 further comprises one or more engagement features 58 configured for temporary attachment to an inserter tool, for example one or more recesses 58 on the top and/or bottom sides of the distal wedge 16. The thread feature 56 comprises an internal thread configured for threaded coupling with the second thread feature 30 of the actuator 12. The proximal wedge 16 may be configured for slideable coupling with the first and second proximal ramps 20a, 20b and/or the endplates 22a, 22b, 22c, 22d. To facilitate slideable coupling, the proximal wedge 16 comprises a plurality of tongue and groove connectors 60a-60d, each comprising a ridge or tongue (e.g. ridge 62a-62d) and a slot or groove (e.g. slot 64a-64d), and a plurality of control slots 66a-66d. By way of example, the tongue and groove connectors 60a-60d slideably mate with tongue and groove connectors 130a-130d on the proximal ramps 20a, 20b, and the control slots 66a-66d slideably receive the protrusions 136a-136d on the proximal ramps 20a, 20b. By way of example, the tongue and groove connector 60a comprises an upper left tongue and groove connector 60a (when viewing the distal face 52 of the proximal wedge 16 (as shown in FIG. 12), the tongue and groove connector 60b comprises a lower left tongue and groove connector 60b, the tongue and groove connector 60c comprises an upper right tongue and groove connector 60c, and the tongue and groove connector 60d comprises a lower right tongue and groove connector 60d. By way of example, the upper left tongue and groove connector 60a and the upper right tongue and groove connector 60c, and the lower left tongue and groove connector 60b and the lower right tongue and groove connector 60d have mirrored symmetry about a sagittal plane of the proximal wedge 16. Similarly, the upper left tongue and groove connector 60a and the lower left tongue and groove connector 60b, and the upper right tongue and groove connector 60c and the lower right tongue and groove connector 60d have mirrored symmetry about a transverse plane of the proximal wedge 16. By way of example, the medial plane of each of the tongue and groove connectors 60a-60d are oriented at a transverse angle from the sagittal plane of the proximal wedge 16.

By way of example only, the control slot 66a comprises an upper left control slot 66a (when viewing the distal face 52 of the proximal wedge 16 (as shown in FIG. 12)), the control slot 66b comprises a lower left control slot 66b, the control slot 66c comprises an upper right control slot 66c, and the control slot 66d comprises a lower right control slot 66d. By way of example, the upper left control slot 66a and the upper right control slot 66c, and the lower left control slot 66b and the lower right control slot 66d have mirrored symmetry about a sagittal plane of the proximal wedge 16. Similarly, the upper left control slot 66a and the lower left control slot 66b, and the upper right control slot 66c and a lower right control slot 66d have mirrored symmetry about a transverse plane of the proximal wedge 16. By way of example, the medial plane of each of the control slots 66a-66d are oriented at a transverse angle from the sagittal plane of the proximal wedge 16. Each of the control slots 66a-66d includes a translation stop 67 at the proximal-lateral terminus of the respective control slot. The translation stop 67 blocks further proximal-lateral translation of the protrusions 136a-136d on the proximal ramps 20a, 20b, which stops outward movement of the proximal ramps 20a, 20b and thus stops width expansion of the expandable fusion device 10.

By way of example, the first and second distal ramps 18a, 18b are identical mirror images of one another, and thus only the second distal ramp 18b is described in detail herein, however it should be understood that the features described with respect to the second distal ramp 18b also apply to the first distal ramp 18a without reservation. Similarly, the first and second proximal ramps 20a, 20b are identical mirror images of one another, and thus only the first proximal ramp 20a will be described in detail herein, however it should be understood that the features described with respect to the first proximal ramp 20a also apply to the second proximal ramp 20b without reservation.

FIGS. 13-16 illustrate an example of a second distal ramp 18*b* according to the present embodiment. By way of example, the second distal ramp 18*b* has a distal end 76, a proximal end 78, a medial side 80 (e.g. oriented toward the actuator 12 in the assembled expandable fusion device 10), and a lateral side 82 (e.g. oriented away from the actuator 12 in the assembled expandable fusion device 10). Generally, the second distal ramp 18*b* comprises a rectangular prism divided into two lobes, a first lobe 84 and a second lobe 86, that facilitate height expansion of the expandable fusion device 10.

The second distal ramp 18*b* may be configured for slideable coupling with the distal wedge 14 and/or the endplates 22*b*, 22*d*. To facilitate slideable coupling, the distal end 76 comprises a pair of tongue and groove connectors 88*c*, 88*d*, each comprising a ridge or tongue (e.g. ridge 90*c*, 90*d*) and a slot or groove (e.g. slot 92*c*, 92*d*), and a pair of protrusions 94*c*, 94*d*. The tongue and groove connectors 88*c*, 88*d* slideably mate with tongue and groove connectors 44*c*, 44*d* on the distal wedge 14, and the protrusions 94*c*, 94*d* slideably mate with the control slots 50*c*, 50*d* on the distal wedge 14. Although not shown, similar features on the first distal ramp 18*a* (e.g. tongue and groove connectors and protrusions) mate with corresponding features on the distal wedge 14 (e.g. tongue and groove connectors 44*a*, 44*b* and control slots 50*a*, 50*b*). By way of example, the tongue and groove connector 44*c* comprises an upper tongue and groove connector 44*c* (e.g., FIG. 14), the tongue and groove connector 44*d* comprises a lower tongue and groove connector 44*d*, the protrusion 50*c* comprises an upper protrusion 50*c*, and the protrusion 50*d* comprises a lower protrusion 50*d*. The upper and lower protrusions 50*c*, 50*d* are positioned on the respective medial distal corners of the second distal ramp 18*b*. The tongue and groove connectors 88*c*, 88*d* are angled in a medial-lateral direction to correspond with the angle of the tongue and groove connectors 44*c*, 44*d* of the distal wedge 14.

The first lobe 84 comprises a chevron shape having an apex oriented in the proximal direction. The first lobe 84 includes a top surface 96, a bottom surface 98, a lateral surface 99, and angled proximal surfaces 100*a*, 100*b*. By way of example, the first lobe 84 has a generally L-shaped cross-sectional shape, however it should be noted that the first lobe 84 may have any suitable cross-sectional shape including but not limited to (and by way of example only a circle, an oval, an ellipse, a triangle, a square, a T-shape, a V-shape, a regular polygon, an irregular polygon, or an irregular shape, or any combination thereof). The angled proximal surface 100*a* slideably engages inclined surface 152 of the second upper endplate 22*b* and angled proximal surface 100*b* slideably engages the angled surface 152 of the second lower endplate 22*d* to facilitate height expansion. The first lobe 84 further includes a V-shaped recessed ramp slot 102 formed within the lateral surface 99 and configured to slideably receive one or more guide pins 23 (see FIG. 5) therein to help stabilize the construct during height expansion, as well as provide a hard stop 103 for height expansion.

By way of example, the V-shaped ramp slot 102 comprises an upper ramp slot 102*a* and a lower ramp slot 102*b*. As shown by way of example in FIG. 13, upper and lower ramp slots 102*a*, 102*b* may have equivalent slopes. The equivalent slopes of the ramp slots 102*a*, 102*b* enable the upper endplate assembly and the lower endplate assembly to translate upwards and downwards, respectively, away from the actuator 12, at the same rate with respect to a rotation of the actuator 12. Alternatively, the ramp slots 102*a*, 102*b* may have inequivalent slopes. In such an arrangement, the inequivalent slopes of the ramp slots 102*a*, 102*b* enable the upper endplate assembly and the lower endplate assembly to translate upwards and downwards, respectively, away from the actuator 12, at different rates with respect to a rotation of the actuator 12. Furthermore, as shown by way of example in FIG. 13, upper and lower ramp slots 102*a*, 102*b* converge and intersect. In some embodiments, the ramp slots 102*a*, 102*b* converge and do not intersect.

The second lobe 86 comprises a truncated chevron shape having a truncated apex oriented in the proximal direction. The proximal lobe 86 includes a top surface 106, a bottom surface 108, a lateral surface 110, and angled proximal surfaces 112*a*, 112*b*, and angled distal surfaces 114*a*, 114*b*. By way of example, the second lobe 86 has a generally trapezoidal cross-sectional shape (see, e.g., FIG. 16). The trapezoidal cross-section of the second lobe 86 is advantageous because having nonparallel leading contact surfaces of the dual chevron shape (e.g. angled surfaces 100*a*, 100*b* and angled surfaces 112*a*, 112*b*) increases the stability of the construct during height expansion. Furthermore, the trapezoidal shape of the second lobe 86 increases the surface area of the proximal angled surfaces 112*a*, 112*b* and the distal angled surfaces 114*a*, 114*b*, which increases the strength of the construct to resist compressive forces after height expansion has been completed. The angled proximal surface 112*a* slideably engages angled surface 156 of the second upper endplate 22*b* and angled proximal surface 112*b* slideably engages the angled surface 156 of the second lower endplate 22*d* to facilitate height expansion.

FIGS. 17-20 illustrate an example of a first proximal ramp 20*a* according to the present embodiment. By way of example, the first proximal ramp 20*a* has a proximal side 116, a distal side 118, a medial side 120 (e.g. oriented toward the actuator 12 in the assembled expandable fusion device 10), and a lateral side 122 (e.g. oriented away from the actuator 12 in the assembled expandable fusion device 10). The first proximal ramp 20*a* comprises an upper portion 124, a lower portion 126, and a vertical post 128 connecting the upper and lower portions 124, 126. By way of example, the vertical post 128 is positioned on the lateral side 122 of the ramp 20*a*.

The first proximal ramp 20*a* may be configured for slideable coupling with the proximal wedge 16 and/or the endplates 22*a*, 22*c*. To facilitate slideable coupling, the proximal side 116 comprises a pair of tongue and groove connectors 130*a*, 130*b*, each comprising a ridge or tongue (e.g. ridge 132*a*, 132*b*) and a slot or groove (e.g. slot 134*a*, 134*b*), and a pair of protrusions 136*a*, 136*b*. The tongue and groove connectors 130*a*, 130*b* slideably mate with tongue and groove connectors 60*a*, 60*b* on the proximal wedge 16, and the protrusions 136*a*, 136*b* slideably mate with the control slots 66*a*, 66*b* on the proximal wedge 16. Although not shown, similar features on the second proximal ramp 20*b* (e.g. tongue and groove connectors and protrusions) mate with corresponding features on the proximal wedge 16 (e.g. tongue and groove connectors 60*c*, 60*d* and control slots 66*c*, 66*d*). By way of example, the tongue and groove connector 130*a* and the protrusion 136*a* are located on the upper portion 124 and comprises an upper tongue and groove connector 130*a* and upper protrusion 136*a*, respectively, and the tongue and groove connector 130*b* and protrusion 136*b* are located on the lower portion 126 and comprise a lower tongue and groove connector 130*b* and lower protrusion 136*b*, respectively. The upper and lower protrusions 136*a*, 136*b* are positioned on the respective medial-proximal corners of the first proximal ramp 20*a*. The tongue and groove connectors 130*a*, 130*b* are angled in a medial-lateral direction to correspond with the angle of the tongue and groove connectors 60*a*, 60*b* of the proximal wedge 16.

The vertical post 128 has a top surface 129*a*, a bottom surface 129*b*, and is sized and configured to extend vertically between the first upper endplate 22*a* and the first lower endplate 22*c*, and is configured to slidingly mate with the vertical channels 150 of the first upper endplate 22*a* and first lower endplate 22*c*. Because the post 128 is vertically oriented, when the first proximal ramp 20*a* (and second proximal ramp 20*b*) is caused to axially translate by the proximal wedge 16, the endplates 22*a*, 22*c* can only translate vertically relative to the first proximal ramp 20*a*.

Optionally, in any embodiment, the upper endplate assembly can comprise a first endplate and a second endplate, and wherein the lower endplate assembly can comprise a third endplate and a fourth endplate. Optionally, in any embodiment, at least one of the first endplate and the second endplate, the third endplate and the fourth endplate, the first proximal ramp and the second proximal ramp, and the first distal ramp and the second distal ramp can have mirrored equivalence. Optionally, in any embodiment, at least one of the second endplate and the fourth endplate can be larger than at least one of the first endplate and the third endplate. Optionally, in any embodiment, at least one of the exterior faces of the first end plate, the second endplate, the third endplate, and the fourth endplate can comprise a texture configured to grip the vertebrae.

Figure 21:
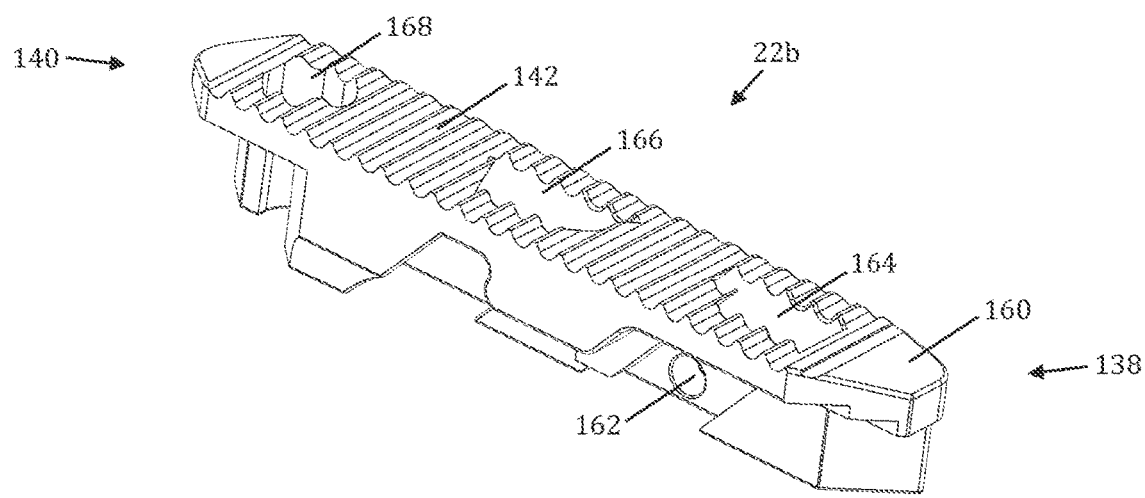
FIGS. 21-22 are perspective views of an example of an endplate forming part of the expandable fusion device of FIG. 3, according to some embodiments.
Figure 22:
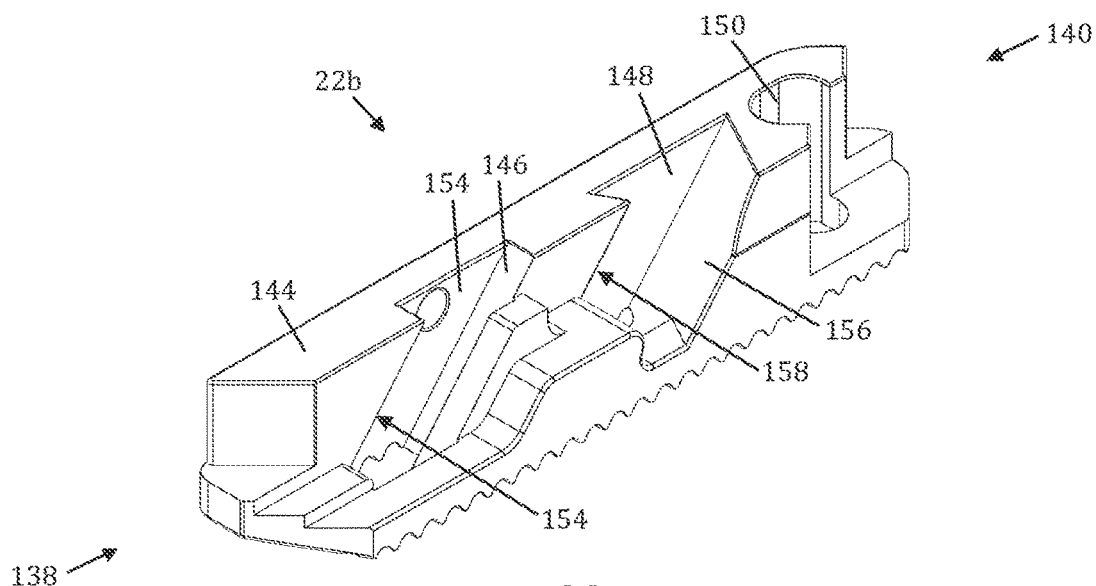
Figure 23:
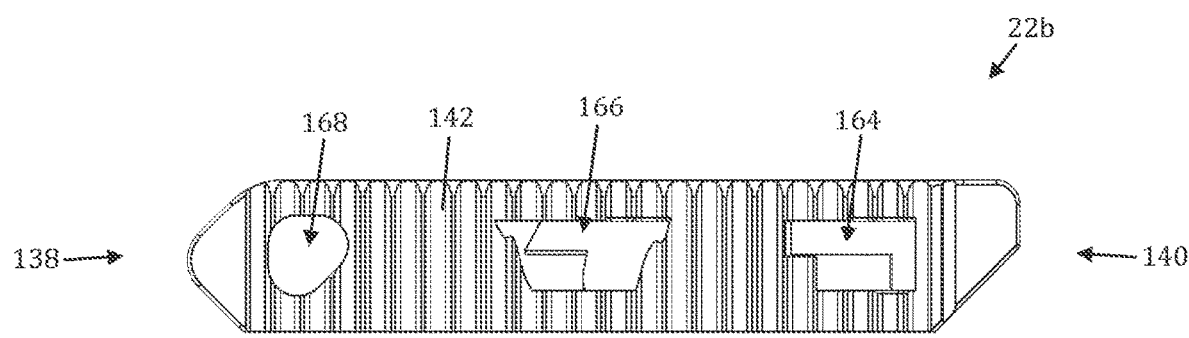
FIG. 23 is a top plan view of the endplate of FIG. 21, according to some embodiments.

By way of example, the various endplates 22*a*-22*d* are either identical or identical mirror images of one another, and thus only one of the endplates needs to be described in further detail. By way of example only, endplate 22*b* (e.g. second upper endplate) is described in detail herein, however it should be understood that the features described with respect to the endplate 22*b* also apply to the other endplates 22*a*, 22*c*, 22*d* without reservation. FIGS. 21-23 illustrate one example of an endplate 22*b* according to the present disclosure. By way of example only, the endplate 22*b* has a first (e.g. distal) end 138 and a second (e.g. proximal) end 140. In the illustrated embodiment, the endplate 22*b* further comprises an outer vertebral contacting surface 142 connecting the first end 138 and the second end 140, and an inner-facing surface 144 connecting the first end 138 and the second end 140. The outer vertebral contacting surface 142 may comprise a texture configured to grip the vertebrae.

By way of example, the texturing may comprise at least one tooth, ridge, roughened area, metallic coating, ceramic coating, keel, spike, projection, groove, or any combination thereof. The inner-facing surface 144 is generally planar and smooth and may flushly abut a corresponding inner-facing surface on another endplate (e.g. endplate 22*d*) when the fusion device 10 is fully contracted.

The endplate 22*b* further comprises a first inclined slot 146 proximate the first end 138, extending from the inner-facing surface 144 to the outer surface 142, a second inclined slot 148 positioned proximally of the first inclined slot 146 the second inclined slot 148 extending from the inner-facing surface 144 to the outer surface 142, and a vertical channel 150 positioned proximate the second end 140 extending from the inner-facing surface 144 to the outer surface 142. Optionally, in any embodiment, the slopes or shapes of the inclined slots 146 and 148 are equal or differ from each other.

The first inclined slot 146 has a generally L-shaped cross section, a inclined surface 152 generally transverse to the longitudinal axis of the implant, and a inclined surface 154 opposite of the inclined surface 152 and generally transverse to the longitudinal axis, wherein the inclined surfaces 152, 154 are parallel. The first inclined slot 146 is sized and configured to slideably receive a portion (e.g. upper portion) of the first lobe 84 of the second distal ramp 18*b* such that the distal surface 100*a* of the first lobe 84 is slideably associated with the inclined surface 152. Thus, after width expansion has completed, as the distal wedge 14 advances the distal ramp 18*a* toward the proximal wedge 16 (and proximal ramp 20*a*), the endplate 22*b* is vertically displaced in part due to the angular translation along the inclined surface 152 (resulting in height expansion).

The inclined slot 148 has a generally trapezoidal cross section, an angled surface 156 generally transverse to the longitudinal axis of the implant, and an angled surface 158 opposite of the angled surface 156 and generally transverse to the longitudinal axis, wherein the angled surfaces 156 and 158 taper toward each other. The second inclined slot 148 is sized and configured to slideably receive a portion (e.g. upper portion) of the second lobe 86 of the second distal ramp 18*b* such that the distal surface 112*a* of the second lobe 86 is slideably associated with the angled surface 156. Thus, after width expansion has completed, as the distal wedge 14 advances the distal ramp 18*a* toward the proximal wedge 16 (and proximal ramp 20*a*), the endplate 22*b* is vertically displaced in part due to the angular translation along the angled surface 156 (resulting in height expansion).

The vertical channel 150 has a size and shape corresponding to the size and shape of the vertical post 128 of the proximal ramp 20*b*, and is configured to facilitate vertical translation of the endplate 22*b* relative to the proximal ramp 22*b*.

By way of example, the endplate 22*b* may further include a chamfer 160 proximate the first end 138 to help facilitate introduction of fusion device 10 between the adjacent vertebral bodies 2 and 4 by reducing the height of the endplate 22*b* at first end 138 thereby providing a tapered leading edge. The endplate 22*b* may further include a pin aperture 162 configured to hold the guide pin 23. The outer contact surface 142 further includes a plurality of apertures corresponding to the inclined slots 146, 148 and vertical channel 150. By way of example, a first aperture 164 is positioned proximate the first end 138 and corresponds to the first inclined slot 146. As such, the first aperture 164 has a generally L-shaped cross-section. The first aperture 164 is sized and dimensioned to receive a portion of the first lobe 84 therethrough so that the top surface 96 of the first lobe 84 is generally level with the outer surface 142 when the expandable fusion device 10 is fully contracted. The second aperture 166 is located proximally of the first aperture 164 and corresponds to the second inclined slot 148. As such, the second aperture 166 has a generally trapezoidal cross-section. The second aperture 166 is sized and dimensioned to receive a portion of the second lobe 86 therethrough so that the top surface 106 of the second lobe 86 is generally level with the outer surface 142 when the expandable fusion device 10 is fully contracted. The third aperture 168 is located near the proximal end and corresponds to the vertical channel 150. As such, the third aperture 168 has a cross-sectional shape matching the cross-sectional shape of the vertical channel 150. The third aperture 168 is sized and dimensioned to receive a portion of the vertical post 128 therethrough so that the top surface 129*a* of the vertical post is generally level with the outer surface 142 when the expandable fusion device 10 is fully contracted. This feature is beneficial in that allowing portions of the ramps 18*b*, 20*b* to extend through the endplate 22*b* to be level with the outer surface 142 thereof enables the expandable fusion device 10 to have a lower height h when in the fully contracted position.

As illustrated in FIGS. 21-23, the outer contact surface 142 of the endplate 22b is generally planar to enable the outer contact surface 142 to engage with the adjacent vertebral body (e.g. vertebral body 2 in FIG. 1). Alternatively, outer contact surface 142 may be curved in one or more planes to allow for a greater degree of engagement with the adjacent vertebral body 2. In another embodiment, the outer contact surface 142 may be generally planar but include a generally straight ramped surface or a curved ramped surface. The ramped surface allows for engagement with the adjacent vertebral body 2 in a lordotic fashion and/or for example in a coronally tapered fashion. Optionally, in any embodiment, an arrangement of non-ramped endplates of different heights as well as ramped and non-ramped endplates of different heights also results in a geometry suitable for lordotic engagement with the endplates. It is further contemplated that although in one embodiment, all endplates in the fusion device 10 have the same length, in other embodiments, some or all of the endplates may have different lengths to better accommodate the target anatomy. Optionally, one or more of the endplates may be shorter, longer, narrower, or wider than others. It should be understood that although the various alternative geometries of the endplates are presented here as discrete embodiments, these alternative embodiments have optional features which may be substituted or mixed/matched with any other embodiment in the specification. It should also be understood that substituting any of the aforementioned optional alternative features in the endplate component may or will necessitate the mating components (e.g. the endplates, the ramps and the wedges) to use the inverse and/or complementary geometry of/to those features for proper contemplated engagement between the various components of the fusion device 10 and between those components and the surrounding anatomy and that the shape of that inverse and/or complementary geometry would follow inevitably from the optional alternative feature geometry described above.

Varying the slopes of the slots 146 and 148 or limiting the allowable travel between the ramps and the slots 146 and 148 within each of the endplates may result, but is not limited to the first ends 138 and the second ends 140 expanding evenly on both top and bottom of the fusion device 10, expanding unevenly on both top and bottom, expanding evenly on top and unevenly on bottom or expanding evenly on bottom and unevenly on top of the fusion device 10.

Optionally, in any embodiment, the first endplate 22a, the second endplate 22b, the third endplate 22c, and the fourth endplate 22d are substantially identical, but although all four have the same set of features, the specific size and angular orientation of these features do not have to be identical in all embodiments or within any particular embodiment. Similarly, the first distal ramp 18a and the second distal ramp 18b are substantially identical to one another, and the first proximal ramp 20a and second proximal ramp 20b are substantially identical to one another, but although each pair has the same set of features, the specific size and angular orientation of these features do not have to be identical in all embodiments or within any particular embodiment. It should be noted that the ramps, even while identical in an embodiment, may or need to be suitably rotated or mirrored to be assembled into arrangements shown by way of example herein.

In use, the actuator 12 functions to pull the distal wedge 14 and proximal wedge 16 together forcing the endplates 22a and 22c away from the endplates 22b and 22d which in turn forces the first distal ramp 18a away from the second distal ramp 18b and also forces the first proximal ramp 20a away from the second proximal ramp 20b (resulting in width expansion of the fusion device 10). It should be mentioned that in other embodiments the actuator 12 may function to pull the distal wedge 14 and proximal wedge 16 together, forcing the first distal ramp 18a away from the second distal ramp 18b and also forcing the first proximal ramp 20a away from the second proximal ramp 20b, which ramps further force the endplates 22a and 22c away from the endplates 22b and 22d (resulting in width expansion of the fusion device 10). Then, only after the width expansion is at least partially complete, the first distal ramp 18a and the first proximal ramp 20a are pulled toward each other and the second distal ramp 18b and the second proximal ramp 20b are pulled toward each other. The movement of the first distal ramp 18a and the first proximal ramp 18b toward each other forces the first upper endplate 22a away from the first lower endplate 22c and the movement of the second distal ramp 18b toward the second proximal ramp 20b forces the second upper endplate 22b away from the second lower endplate 22d (resulting in height expansion).

Optionally, in any embodiment, the ramps 18a and 20a and the ramps 18b and 20b only start moving toward each other after the width expansion has completely or substantially or at least partially taken place and the ramps 18a and 18b have substantially reached the limit of their travel relative to the distal wedge 14 and the ramps 20a and 20b have substantially reached the limit of their travel relative to the proximal wedge 16. Optionally, in any embodiment, this delay in height expansion is achieved through the endplates 22a, 22b, 22c, 22d being slidably engaged with the distal wedge 14 and, optionally in some embodiments, the proximal wedge 16 through an initial portion of width expansion process (in some embodiments, said engagement between endplates and wedges may prevent or inhibit the distal and the proximal ramps from moving toward each other thus inhibiting height expansion). During the width expansion process, as the wedges 14 and 16 move toward each other, they eventually disengage from endplates 22a, 22b, 22c, 22d and allow them to expand in height. Optionally, the delay in height expansion may be further accomplished by means of an inserter instrument constraining the height expansion until the width expansion has substantially taken place.

Optionally, in any embodiment, a small gap may exist between the endplates and the wedges in the initial collapsed state. This results in the first number of actuations in a first actuation direction increasing both height and width, but not necessarily at the same time. For example, the device may first start expanding in height or in width depending on external loading conditions and/or inserter instrument configuration (e.g. an inserter may be configured to initially restrict height expansion, width expansion or neither). Actuation of the drive feature by a second number of actuations beyond the first number of actuations in the first actuation direction then increases at least one of the height and the width. In some embodiments, the first number of actuations of the actuator 12 may result in at least some height expansion (and in some embodiments—exclusively height expansion), whereas further rotation of the actuator 12 then increases at least one of width and height.

When fully assembled, the first expandable fusion device 10 is a stable assembly of components that are all detained within the assembly throughout its full range of motion by means of "tongue and groove" articulations, the use of fasteners such as, for example, pins, balls, screws, and set screws. Optionally, in any embodiment, the fasteners are affixed in one component and travel in a mating feature (such as a track) of another component thereby limiting the range of motion of the first component to the amount permissible by the track feature thereby preventing the components from disassembly.

By way of example, at least one of the first endplate 22a, the second endplate 22b, the third endplate 22c, and the fourth endplate 22d contacts at least one of the distal wedge 18a and the proximal wedge 18b when the expandable fusion device 10 is in its collapsed state. Alternatively, at least one of the first endplate 22a, the second endplate 22b, the third endplate 22c, and the fourth endplate 22d does not contact at least one of the distal wedge 18a and the proximal wedge 18b when the expandable fusion device 10 is in its collapsed state. The contact between at least one of the first endplate 22a, the second endplate 22b, the third endplate 22c, and the fourth endplate 22d and at least one of the distal wedge 18a and the proximal wedge 18b affects the expansion of the expandable fusion device 10.

The expandable fusion device 10 has a width w comprising an external width of at least one of the upper endplate assembly (e.g. endplates 22a, 22b) and the lower endplate assembly (e.g. endplates 22c, 22d). Optionally, in any embodiment, the device has a height h comprising an external distance between the upper endplate assembly and the lower endplate assembly (e.g. between endplates 22a, 22c and/or 22b, 22d).

Optionally, in any embodiment, actuation of the drive feature 32 by a first number of actuations in a first actuation direction increases the width w without increasing the height h. Optionally, in any embodiment, actuation of the drive feature 32 by a second number of actuations beyond the first number of actuations in the first actuation direction increases at least one of the height h and the width w. Optionally, in any embodiment, actuation of the drive feature 32 by a second number of actuations beyond the first number of actuations in the first actuation direction increases both the height h and the width w, wherein actuation of the drive feature 32 by a third number of actuations beyond the second number of actuations in the first actuation direction increases the height h without increasing the width w. Optionally, in any embodiment, actuation of the drive feature 32 by a second number of actuations beyond the first number of actuations in the first actuation direction increases neither the height h nor the width w, wherein actuation of the drive feature 32 by a third number of actuations beyond the second number of actuations in the first actuation direction increases the height h without increasing the width w. Optionally, in any embodiment, the width w of the device 10 reaches an apex once the drive feature 32 is actuated by at least the first number of actuations. Optionally, in any embodiment, the height h of the device 10 reaches an apex once the drive feature 32 is actuated by at least the first and second number of actuations.

Optionally, in any embodiment, actuation of the drive feature 32 by a second number of actuations beyond the first number of actuations in the first actuation direction increases both the height h and the width w. Optionally, in any embodiment, actuation of the drive feature 32 by a second number of actuations beyond the first number of actuations in the first actuation direction increases the height h without increasing the width w.

Optionally, in any embodiment, actuation of the drive feature 32 in the first actuation direction by at least the first number of actuations increases the height h of the device 10 by about 30% to about 400%. Optionally, in any embodiment, actuation of the drive feature 32 in the first actuation direction by at least the first and the second number of actuations increases the width w of the device by about 14% to about 150%.

Figure 24:
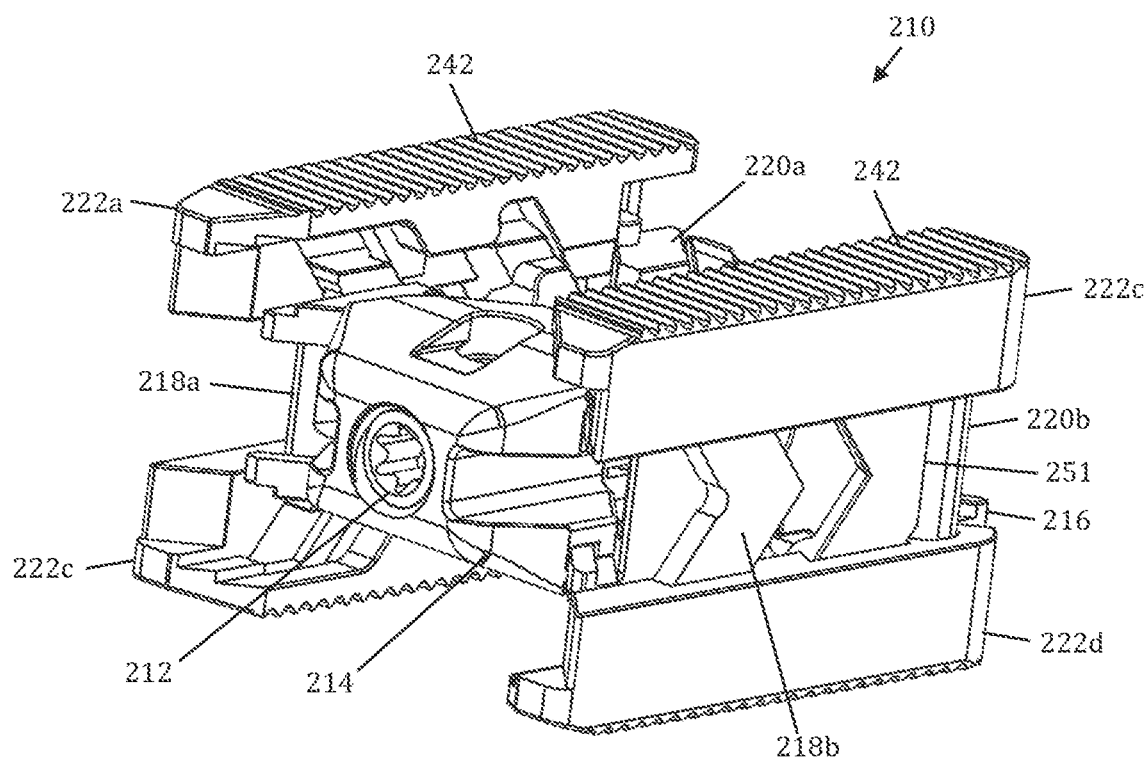
FIG. 24 is a perspective view of another example of an expandable fusion device in a fully expanded state, according to some embodiments.

FIG. 24 illustrates an example of an expandable fusion device 210 for implantation between two adjacent vertebrae according to another embodiment of the disclosure. By way of example only, the expandable fusion device 210 of the present embodiment includes an actuator 212, a distal wedge 214, a proximal wedge 216, a pair of distal ramps 218a, 218b, a pair of proximal ramps 220a, 220b, and a plurality of endplates 222a-222d. As with previously-described embodiments, the distal and proximal wedges 214, 216 are coupled with the actuator 212. The distal ramps 218a, 218b are slideably coupled with the distal wedge 214. The proximal ramps 220a, 220b are slideably coupled with the proximal wedge 216. The plurality of endplates 222a-222d are slideably coupled with the ramps 218a, 218b, 220a. 220b. Generally, the expandable fusion device 210 is substantially similar to expandable fusion device 10 described above, and any/all of the features described above with respect to fusion device 10 (and any other expandable fusion device described herein) may apply to fusion device 210 unless otherwise noted.

By way of example only, in the current embodiment, the device 210 does not comprise guide pins (e.g. pins 23 of device 10), and as a result the endplates 222a, 222b, 222c, 222d do not comprise a hole (e.g. aperture 162 of device 10) configured to accept the pin and the distal ramps 218a, 218b do not include corresponding ramp slots (e.g. ramp slots 102 of device 10). Thus in the present embodiment (and any embodiment that does not have ramp slots and/or guide pins), height expansion may be stopped by a physical interface 251 between the distal and proximal wedges 218a, 220a, and the distal and proximal wedges 218b, 220b, as shown by way of example in FIG. 24. Furthermore, by way of example only, one or more of the endplates 222a, 222b, 222c, 222d comprises a continuous uninterrupted outer bone contacting surface 242. That is, the one or more endplates 222a, 222b, 222c, 222d do not comprise apertures corresponding to the first slot, second slot, and/or vertical channel (e.g. apertures 164, 166, 168 of device 10).

The expandable fusion device 210 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 210.

Figure 25:
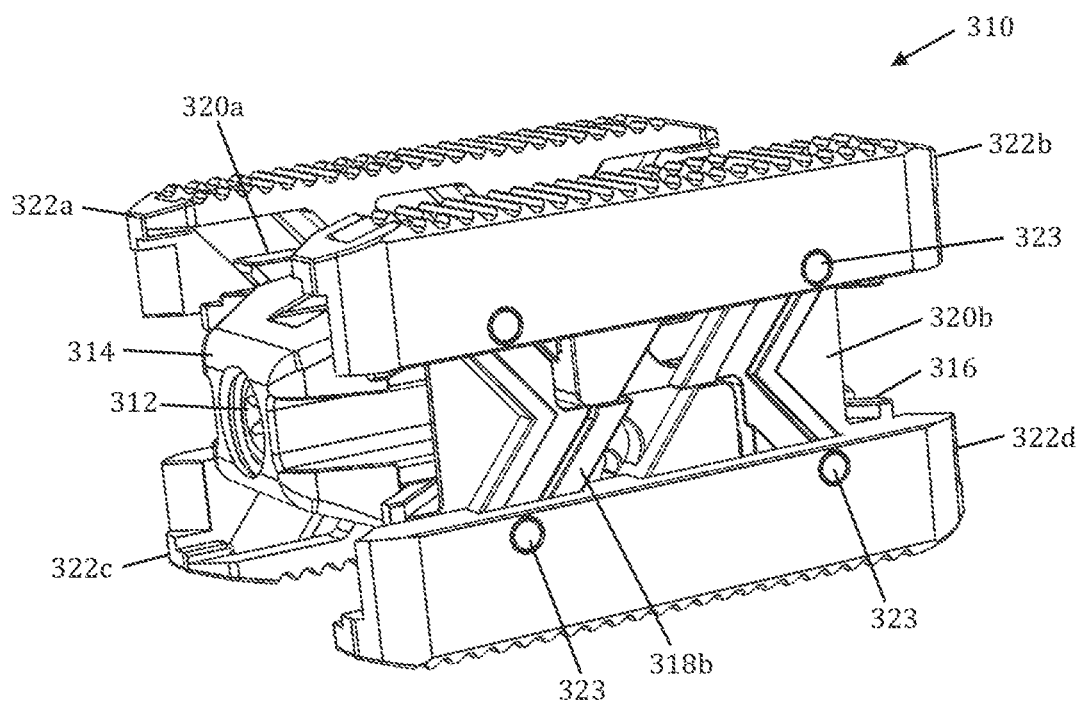
FIG. 25 is a perspective view of another example of an expandable fusion device in a fully expanded state, according to some embodiments.
Figure 26:
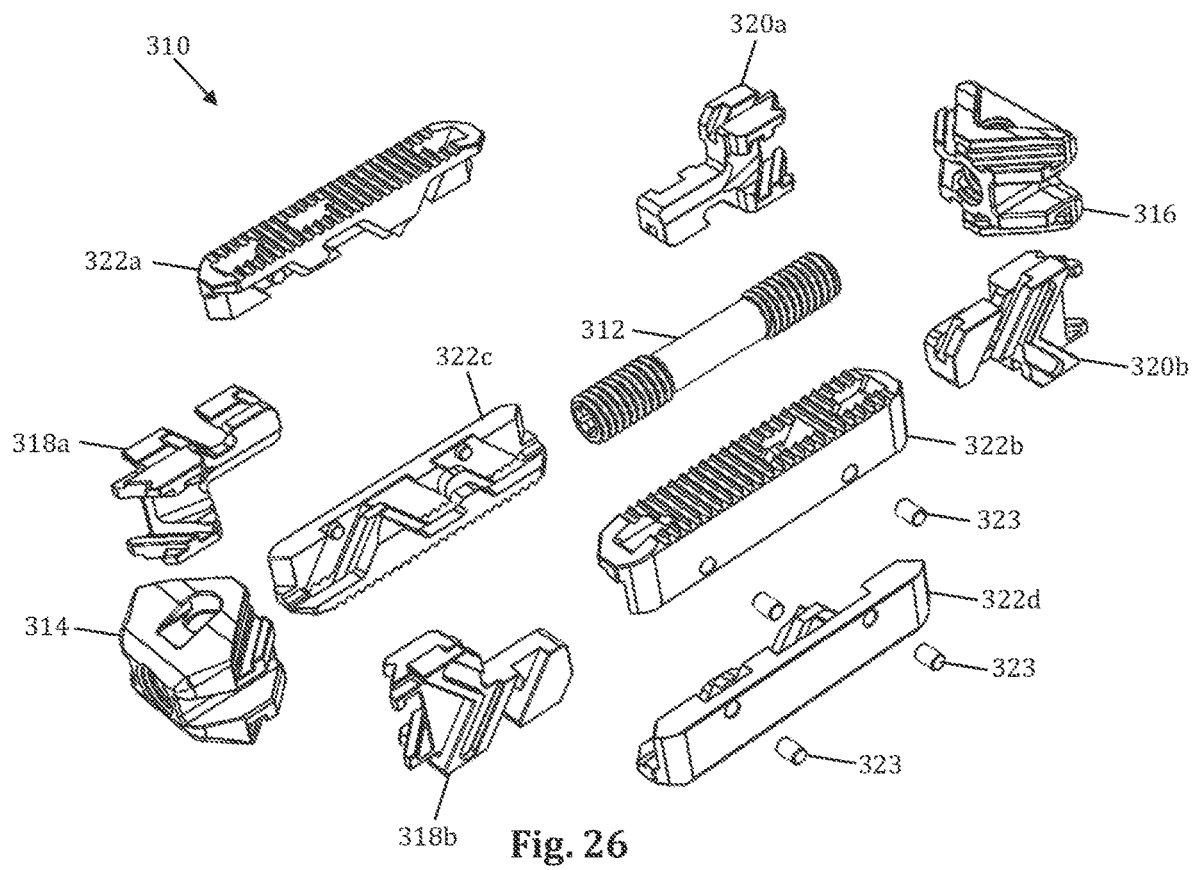
FIG. 26 is an exploded perspective view of the expandable fusion device of FIG. 25, according to some embodiments.
Figure 27:
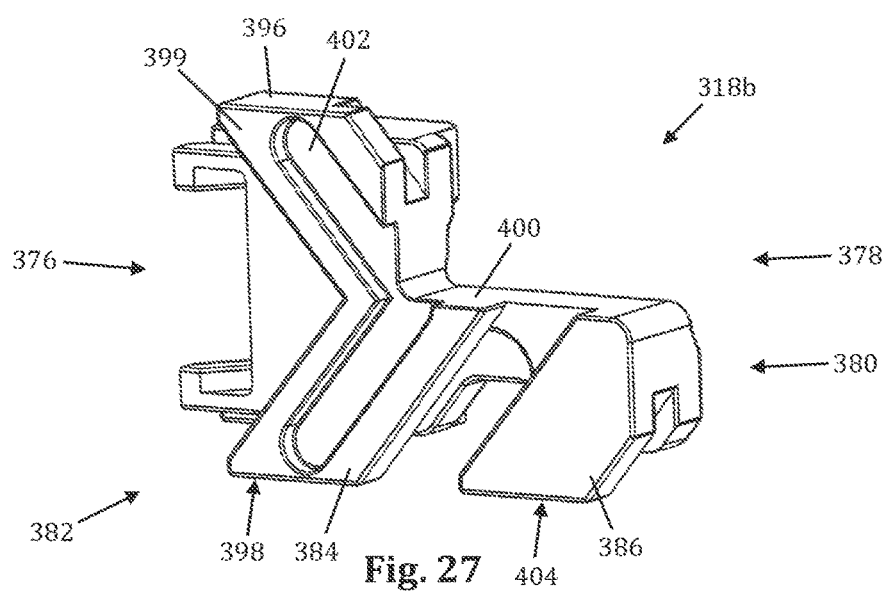
FIG. 27 is a perspective view of an example of a distal ramp forming part of the expandable fusion device of FIG. 25, according to some embodiments.
Figure 28:
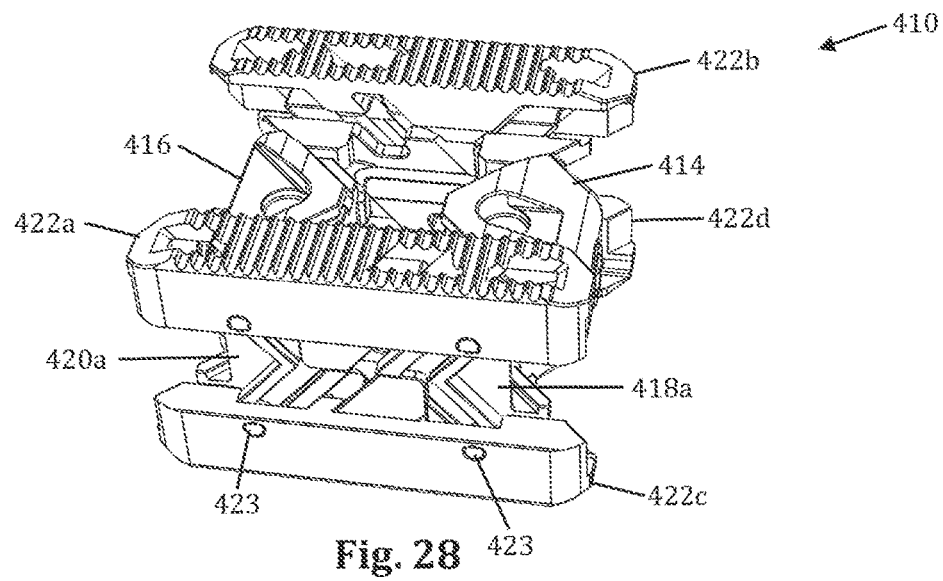
FIG. 28 is a perspective view of another example of an expandable fusion device in a fully expanded state, according to some embodiments.
Figure 29:
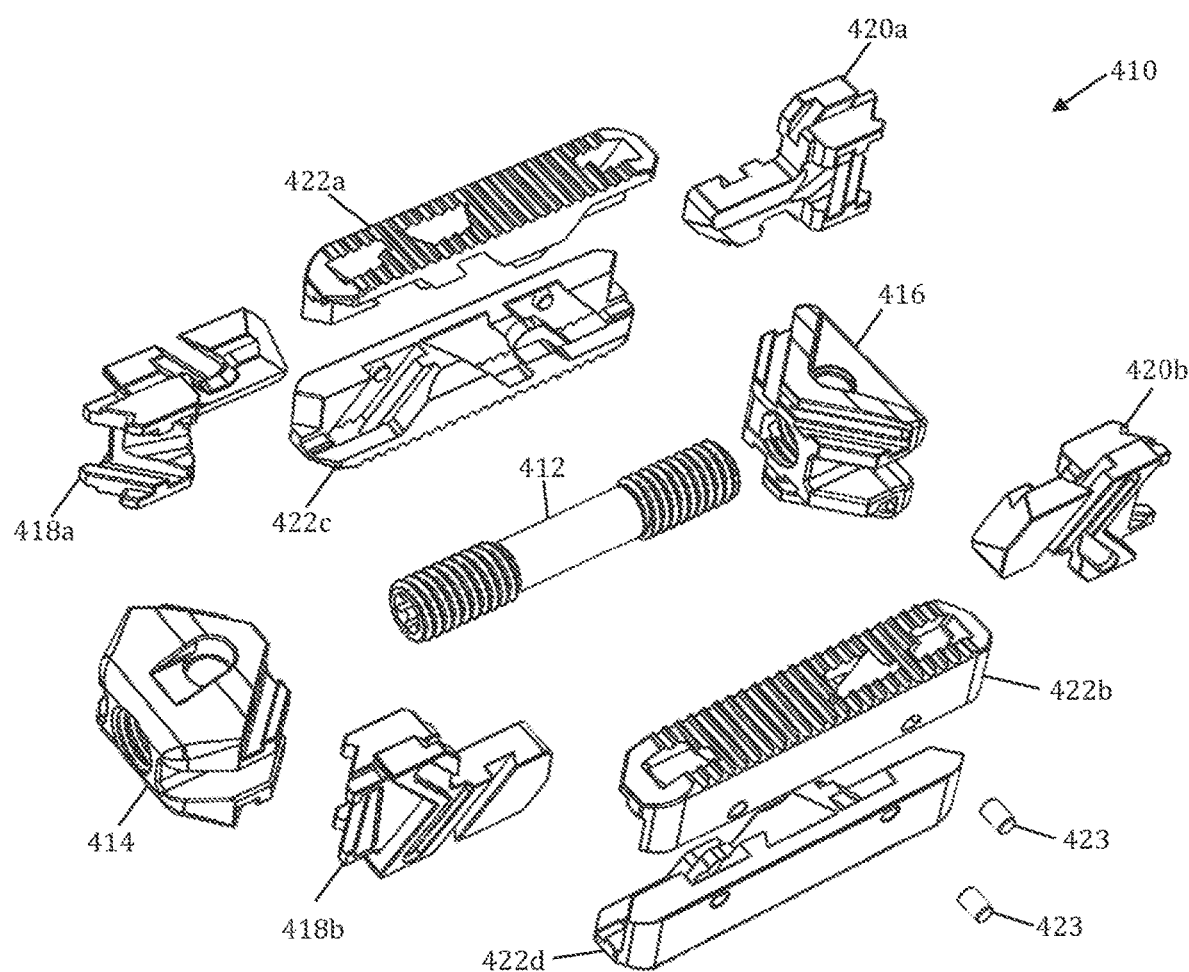
FIG. 29 is an exploded perspective view of the expandable fusion device of FIG. 28, according to some embodiments.

FIGS. 25-27 illustrate an example of an expandable fusion device 310 for implantation between two adjacent vertebrae according to another embodiment of the disclosure. By way of example only, the expandable fusion device 310 of the present embodiment includes an actuator 312, a distal wedge 314, a proximal wedge 316, a pair of distal ramps 318a, 318b, a pair of proximal ramps 320a, 320b, a plurality of endplates 322a-322d, and a plurality of guide pins 323. As with previously-described embodiments, the distal and proximal wedges 314, 316 are coupled with the actuator 312. The distal ramps 318a, 318b are slideably coupled with the distal wedge 314. The proximal ramps 320a, 320b are slideably coupled with the proximal wedge 316. The plurality of endplates 322a-322d are slideably coupled with the ramps 318a, 318b, 320a. 320b. Generally, the expandable fusion device 310 is substantially similar to expandable fusion device 10 described above, and any/all of the features described above with respect to fusion device 10 (and any other expandable fusion device described herein) may apply to fusion device 310 unless otherwise noted.

FIG. 27 illustrates an example of a second distal ramp 318*b* according to the present embodiment. By way of example, the second distal ramp 318*b* has a distal end 376, a proximal end 378, a medial side 380 (e.g. oriented toward the actuator 312 in the assembled expandable fusion device 310), and a lateral side 382 (e.g. oriented away from the actuator 312 in the assembled expandable fusion device 310). Generally, the second distal ramp 318*b* comprises a rectangular prism divided into two lobes, a first lobe 384 and a second lobe 386, that facilitate height expansion of the expandable fusion device 310. The second distal ramp 318*b* may be configured for slideable coupling with the distal wedge 314 and/or the endplates 322*b*, 322*d*. The slideable coupling with the wedge 314 is identical to that described above with respect to fusion device 10.

The first lobe 384 comprises a general chevron shape having an apex oriented in the proximal direction. The first lobe 384 includes a top surface 396, a bottom surface 398, and a lateral surface 399. By way of example, the first lobe 384 has a generally L-shaped cross-sectional shape, however it should be noted that the first lobe 384 may have any suitable cross-sectional shape including but not limited to (and by way of example only a circle, an oval, an ellipse, a triangle, a square, a T-shape, a V-shape, a regular polygon, an irregular polygon, or an irregular shape, or any combination thereof). The first lobe 384 further includes a V-shaped recessed ramp slot 402 formed within the lateral surface 399 and configured to slideably receive the one or more guide pins 323 therein to help stabilize the construct during height expansion, as well as provide a hard stop for height expansion.

The second lobe 386 comprises a half chevron shape having a truncated apex oriented in the proximal direction. The second lobe 386 a bottom surface 404 and a generally L-shaped cross-sectional shape, however it should be noted that the second lobe 386 may have any suitable cross-sectional shape including but not limited to (and by way of example only a circle, an oval, an ellipse, a triangle, a square, a T-shape, a V-shape, a regular polygon, an irregular polygon, or an irregular shape, or any combination thereof).

By way of example, the second distal ramp 318*b* further includes an L-shaped cutaway surface 400 configured to slideably mate with a corresponding L-shaped cutaway surface on the second proximal ramp 320*b*. The L-shaped cutaway is advantageous in that it enables the distal ramps 318*a*, 318*b* and proximal ramps 320*a*, 320*b* to be identical to one another. Furthermore, since the ramps 318*a*, 318*b*, 320*a*, 320*b* are identical, the endplates 322*a*, 322*b*, 322*c*, 322*d* are also identical. This reduces the number of different parts needed during assembly.

The expandable fusion device 310 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 310.

FIGS. 28-31 illustrate an example of an expandable fusion device 410 for implantation between two adjacent vertebrae according to another embodiment of the disclosure. By way of example only, the expandable fusion device 410 of the present embodiment includes an actuator 412, a distal wedge 414, a proximal wedge 416, a pair of distal ramps 418*a*, 418*b*, a pair of proximal ramps 420*a*, 420*b*, a plurality of endplates 422*a*-422*d*, and a plurality of guide pins 423. As with previously-described embodiments, the distal and proximal wedges 414, 416 are coupled with the actuator 412. The distal ramps 418*a*, 418*b* are slideably coupled with the distal wedge 414. The proximal ramps 420*a*, 420*b* are slideably coupled with the proximal wedge 416. The plurality of endplates 422*a*-422*d* are slideably coupled with the ramps 418*a*, 418*b*, 420*a*. 420*b*. Generally, the expandable fusion device 410 is substantially similar to expandable fusion device 310 described above, and any/all of the features described above with respect to fusion device 310 (and any other expandable fusion device described herein, including in particular expandable fusion device 10) may apply to fusion device 410 unless otherwise noted.

Figure 30:
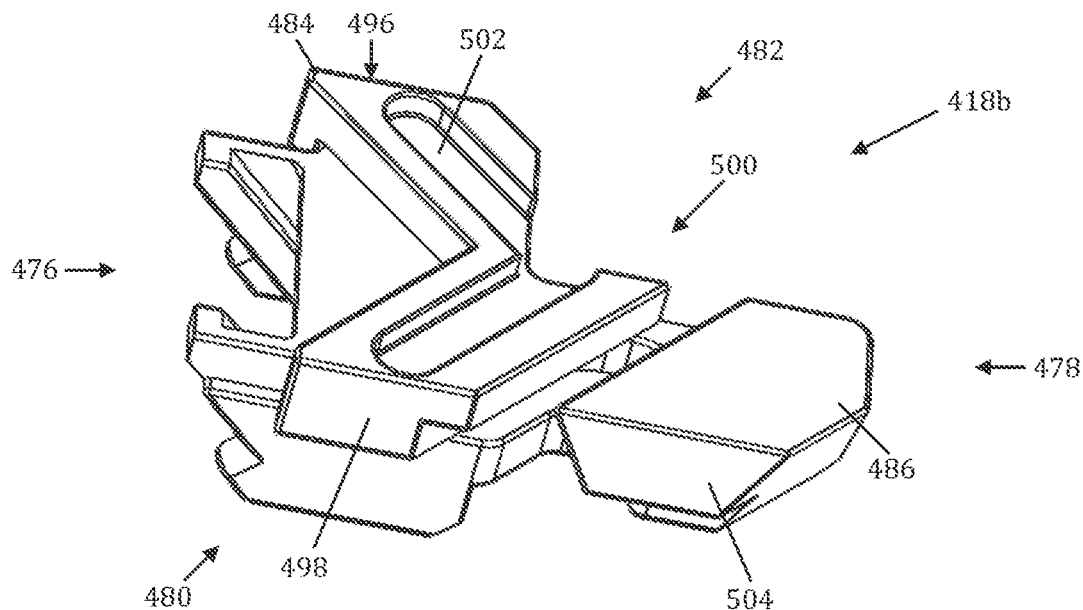
FIG. 30 is a perspective view of an example of a distal ramp forming part of the expandable fusion device of FIG. 28, according to some embodiments.

FIG. 30 illustrates an example of a second distal ramp 418*b* according to the present embodiment. By way of example, the second distal ramp 418*b* has a distal end 476, a proximal end 478, a medial side 480 (e.g. oriented toward the actuator 412 in the assembled expandable fusion device 410), and a lateral side 482 (e.g. oriented away from the actuator 412 in the assembled expandable fusion device 410). Generally, the second distal ramp 418*b* comprises a rectangular prism divided into two lobes, a first lobe 484 and a second lobe 486, that facilitate height expansion of the expandable fusion device 410. The second distal ramp 418*b* may be configured for slideable coupling with the distal wedge 414 and/or the endplates 422*b*, 422*d*. The slideable coupling with the wedge 414 is identical to that described above with respect to fusion device 10.

The first lobe 484 comprises a general chevron shape having an apex oriented in the proximal direction. The first lobe 484 includes a top surface 496, a bottom surface 498, and a lateral surface 499. By way of example, the first lobe 484 has a generally L-shaped cross-sectional shape, however it should be noted that the first lobe 484 may have any suitable cross-sectional shape including but not limited to (and by way of example only a circle, an oval, an ellipse, a triangle, a square, a T-shape, a V-shape, a regular polygon, an irregular polygon, or an irregular shape, or any combination thereof). The first lobe 484 is configured for slideable mating a first inclined slot 446 of the endplate 422*b*, the first inclined slot 446 having a complementary cross-sectional shape. The first lobe 484 further includes a V-shaped recessed ramp slot 502 formed within the lateral surface 499 and configured to slideably receive the one or more guide pins 423 therein to help stabilize the construct during height expansion, as well as provide a hard stop for height expansion. The second lobe 486 comprises a half chevron shape having a truncated apex oriented in the proximal direction. The second lobe 486 has a bottom surface 504 and a generally trapezoidal cross-sectional shape. The second lobe 486 is configured for slideable mating a second inclined slot 448 of the endplate 422*b*, the second inclined slot 448 having a complementary trapezoidal cross-sectional shape.

By way of example, the second distal ramp 418*b* further includes an L-shaped cutaway surface 500 configured to slideably mate with a corresponding L-shaped cutaway surface on the second proximal ramp 420*b*. The L-shaped cutaway is advantageous in that it enables the distal ramps 418*a*, 418*b* and proximal ramps 420*a*, 420*b* to be identical to one another. Furthermore, since the ramps 418*a*, 418*b*, 420*a*, 420*b* are identical, the endplates 422*a*, 422*b*, 422*c*, 422*d* are also identical. This reduces the number of different parts needed during assembly.

The expandable fusion device 410 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 410.

Figure 31:
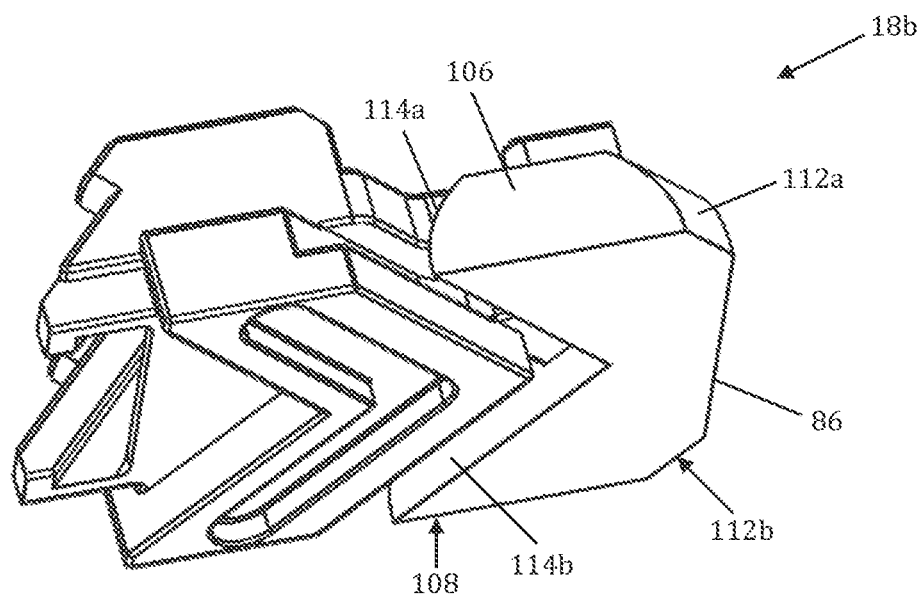
FIG. 31 is a perspective view of another example of a distal ramp forming part of the expandable fusion device of FIG. 3, according to some embodiments.

FIG. 31 illustrates an example of an alternative embodiment of a dual chevron ramp according to some embodiments. For example, the dual chevron ramp may comprise an alternate example embodiment the proximal ramp 18b described above in relation to expandable fusion device 10, however the proximal ramp 18b of the present embodiment may be used with any expandable fusion device described herein that comprises a dual chevron ramp.

In the present embodiment shown in FIG. 31, the second lobe 86 comprises a truncated chevron shape having a truncated apex oriented in the proximal direction. The proximal lobe 86 includes a top surface 106, a bottom surface 108, a lateral surface 110, and curved proximal surfaces 112a, 112b, and curved distal surfaces 114a, 114b. By way of example, the second lobe 86 has a generally truncated elliptical cross-sectional shape (see, e.g., FIG. 16). The truncated elliptical cross-sectional shape of the second lobe 86 of the instant example is similar to the trapezoidal cross-section of the second lobe 86 described above. The truncated elliptical cross-section shape is advantageous because having nonparallel leading contact surfaces of the dual chevron shape (e.g. angled surfaces 100a, 100b and curved surfaces 112a, 112b) increases the stability of the construct during height expansion. Furthermore, the truncated elliptical shape of the second lobe 86 increases the surface area of the proximal curved surfaces 112a, 112b and the distal curved surfaces 114a, 114b (even compared with the trapezoidal cross-sectional shape), which increases the strength of the construct to resist compressive forces after height expansion has been completed. The curved proximal surface 112a slideably engages a corresponding curved surface of the second upper endplate 22b and curved proximal surface 112b slideably engages a corresponding curved surface of the second lower endplate 22d to facilitate height expansion.

Figure 32:
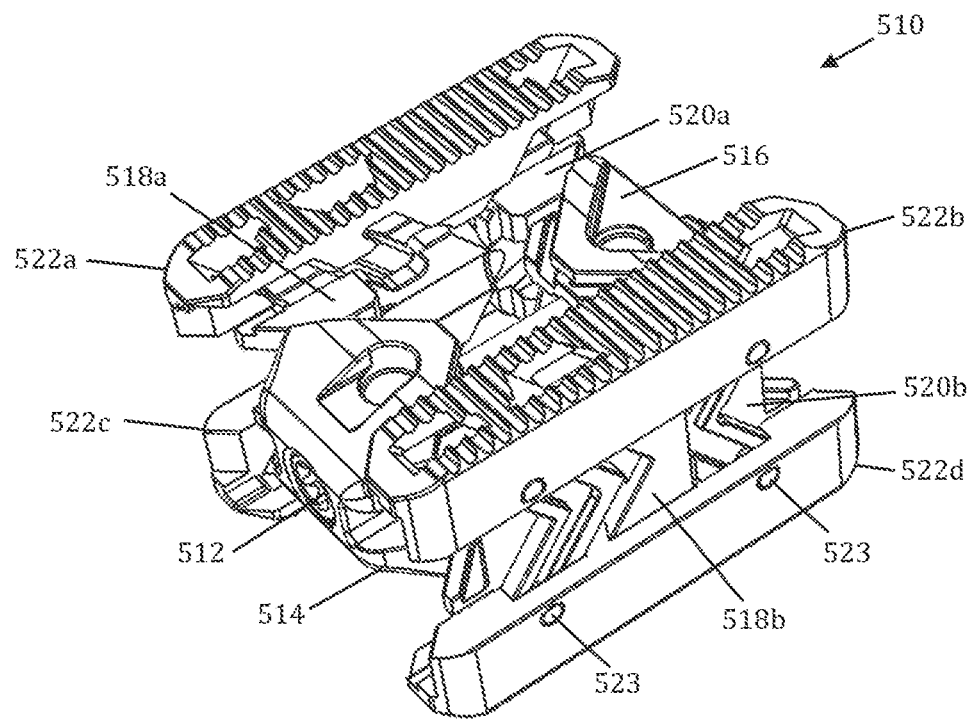
FIG. 32 is a perspective view of another example of an expandable fusion device in a fully expanded state, according to some embodiments.
Figure 33:
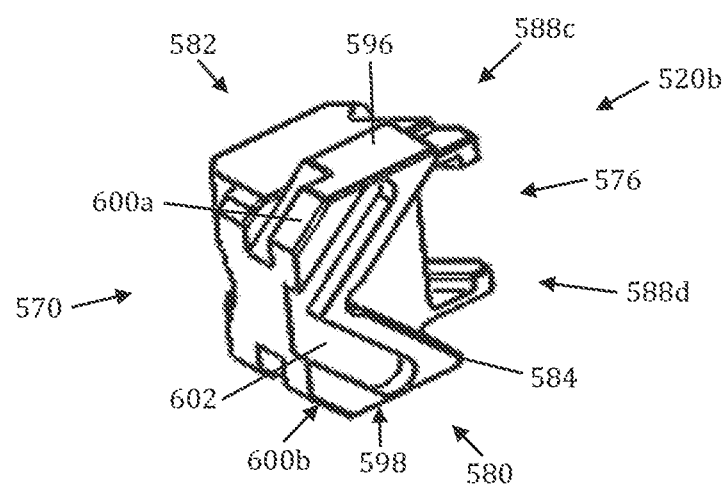
FIG. 33 is a perspective view of an example of a proximal ramp forming part of the expandable fusion device of FIG. 32, according to some embodiments.
Figure 34:
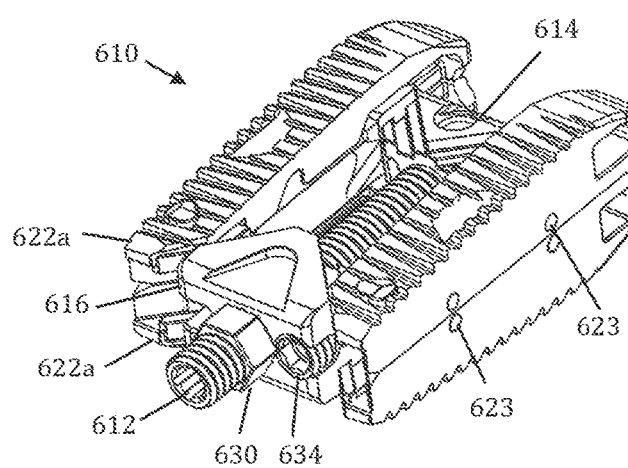
FIG. 34 is a perspective view of another example of an expandable fusion device in a width-expanded state, according to some embodiments.

FIGS. 32-33 illustrate an example of an expandable fusion device 510 for implantation between two adjacent vertebrae according to another embodiment of the disclosure. By way of example only, the expandable fusion device 510 of the present embodiment includes an actuator 512, a distal wedge 514, a proximal wedge 516, a pair of distal ramps 518a, 518b, a pair of proximal ramps 520a, 520b, a plurality of endplates 522a-522d, and a plurality of guide pins 523. As with previously-described embodiments, the distal and proximal wedges 514, 516 are coupled with the actuator 512. The distal ramps 518a, 518b are slideably coupled with the distal wedge 514. The proximal ramps 520a, 520b are slideably coupled with the proximal wedge 516. The plurality of endplates 522a-522d are slideably coupled with the ramps 518a, 518b, 520a. 520b. Generally, the expandable fusion device 510 is substantially similar to expandable fusion device 10 described above, and any/all of the features described above with respect to fusion device 10 (and any other expandable fusion device described herein) may apply to fusion device 510 unless otherwise noted.

FIG. 33 illustrates an example of a proximal ramp 520b forming part of the expandable fusion device 510 according to some embodiments. Generally, the proximal ramp 520b resembles a distal half of a distal ramp (e.g. distal ramp 18a or 18b) described herein above. By way of example only, the proximal ramp 520b has a proximal end 576, a distal end 578, a medial side 580 (e.g. oriented toward the actuator 512 in the assembled expandable fusion device 510), and a lateral side 582 (e.g. oriented away from the actuator 512 in the assembled expandable fusion device 510).

The proximal ramp 520b may be configured for slideable coupling with the proximal wedge 516 and/or the endplates 522b, 522d. To facilitate slideable coupling, the proximal end 576 comprises a pair of tongue and groove connectors 588c, 588d like tongue and groove connectors previously described that slideably mate with corresponding tongue and groove connectors on the proximal wedge 516. The proximal ramp 520b further comprises a single lobe 584 comprising a chevron shape having a truncated apex oriented in the distal direction. The lobe 584 includes a top surface 596, a bottom surface 598, a lateral surface 599, and angled distal surfaces 600a, 600b. By way of example, the lobe 584 has a generally L-shaped cross-sectional shape, however it should be noted that the lobe 584 may have any suitable cross-sectional shape including but not limited to (and by way of example only a circle, an oval, an ellipse, a triangle, a square, a T-shape, a V-shape, a regular polygon, an irregular polygon, or an irregular shape, or any combination thereof). The angled distal surfaces 600a, 600b slideably engage corresponding inclined surfaces of the endplates 522b, 522d to facilitate height expansion in a similar fashion as described above with respect to previous embodiments. The lobe 584 further includes a V-shaped recessed ramp slot 602 formed within the lateral surface 599 and configured to slideably receive one or more guide pins 523 therein to help stabilize the construct during height expansion, as well as provide a hard stop for height expansion. According to the present example embodiment, proximal ramp 520a is a mirrored equivalence proximal ramp 520b.

The expandable fusion device 510 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 510.

FIGS. 34-38 illustrate an example of an expandable fusion device 610 for implantation between two adjacent vertebrae according to another embodiment of the disclosure. By way of example only, the expandable fusion device 610 of the present embodiment includes an actuator 612, a distal wedge 614, a proximal wedge 616, a pair of distal ramps 618a, 618b, a pair of proximal ramps 620a, 620b, a plurality of endplates 622a-622d, a plurality of guide pins 623, a nut 630, and a lock screw 634. As with previously-described embodiments, the distal and proximal wedges 614, 616 are coupled with the actuator 612. The distal ramps 618a, 618b are slideably coupled with the distal wedge 614. The proximal ramps 620a, 620b are slideably coupled with the proximal wedge 616. The plurality of endplates 622a-622d are slideably coupled with the ramps 618a, 618b, 620a. 620b. Generally, the expandable fusion device 610 is substantially similar to expandable fusion device 10 described above, and any/all of the features described above with respect to fusion device 10 (and any other expandable fusion device described herein) may apply to fusion device 610 unless otherwise noted. By way of example only, the expandable fusion device 610 is illustrative of an alternative actuator mechanism that may be applied to any expandable fusion device examples described herein, according to some embodiments.

Figure 35:
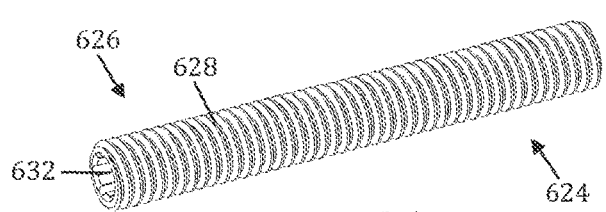
FIG. 35 is a perspective view of an example of an actuator forming part of the expandable fusion device of FIG. 34, according to some embodiments.

FIG. 35 illustrates an example of an actuator 612 forming part of the expandable fusion device 610 of the present embodiment. By way of example only, the actuator 612 comprises a cylindrically shaped elongate shaft having a distal end 624, a proximal end 626, and a longitudinal axis extending therethrough. Unlike the actuator 12 described above, the actuator 612 of the present example has a single thread feature 628 extending substantially along the entire length of the elongate shaft. At least one of the distal and proximal ends 624, 626 includes a drive feature 632 coincident with the longitudinal axis and configured to engage with an instrument (not shown) to immobilize the actuator 612 while a driver mechanism turns the nut 630. The thread feature 628 comprises a thread disposed externally around the shaft of the actuator 612. By way example, the thread feature 628 may comprise a right-handed threading. Alternatively, the thread feature 628 may comprise a left-handed threading. The drive feature 632 comprises a recessed region configured to receive a driving/holding instrument.

The recessed region may comprise any shape capable of engaging a corresponding element of an appropriate instrument, including but not limited to (and by way of example only) a slot, Phillips, pozidrive, frearson, robertson, 12-point flange, hex socket, security hex socket, star drive, security torx, ta, tri-point, tri-wing, spanner head, clutch, one-way, double-square, triple-square, polydrive, spline drive, double hex, bristol, or a pentalobe recess or any other shaped recess. Alternatively, the drive feature 632 may comprise a protuberance (for example a hex, a hexalobular, or a square protuberance or any other shaped protuberance) extending longitudinally from the proximal and/or distal end and configured to be coupled to a driving/holding instrument.

Figure 36:
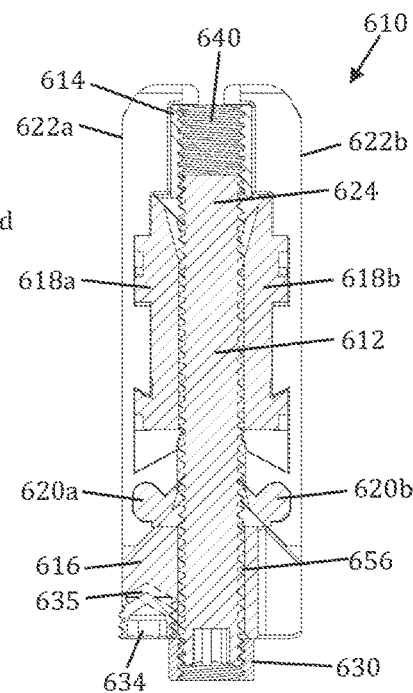
FIGS. 36-38 are sectional views of the expandable fusion device of FIG. 34 in various states of expansion, according to some embodiments.

FIG. 36 illustrates the expandable fusion implant 610 (in cross-section) in fully collapsed form. The actuator 612 is positioned such that the distal end 624 is partially threaded into the threaded aperture 640 of the distal wedge 614. The proximal end 626 extends proximally from the proximal wedge 616 and is associated with a nut 630. The shaft of the actuator 612 extends through an unthreaded aperture 656 of the proximal wedge 616 to the distal wedge 614. To effectuate width expansion of the expandable fusion device 610, an instrument (not shown) is used to engage and immobilize the actuator 612. The same or different instrument is then used to rotate the nut 630 (e.g. in a clockwise direction for right-handed threading, counterclockwise for left-handed threading). This rotation will cause the nut 630 to advance distally along the actuator 612, which pushes the proximal wedge 616 into the construct toward the distal wedge 614. The proximal wedge 616 also causes the ramps to move, thereby effectuating expansion (e.g. width only, first width then height, width and height, etc.) of the expandable fusion implant 610 without any movement of the actuator or the distal wedge 614.

Figure 37:
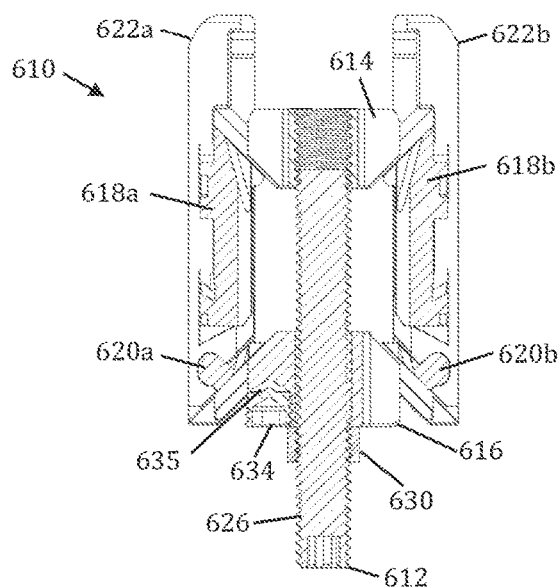
Figure 38:
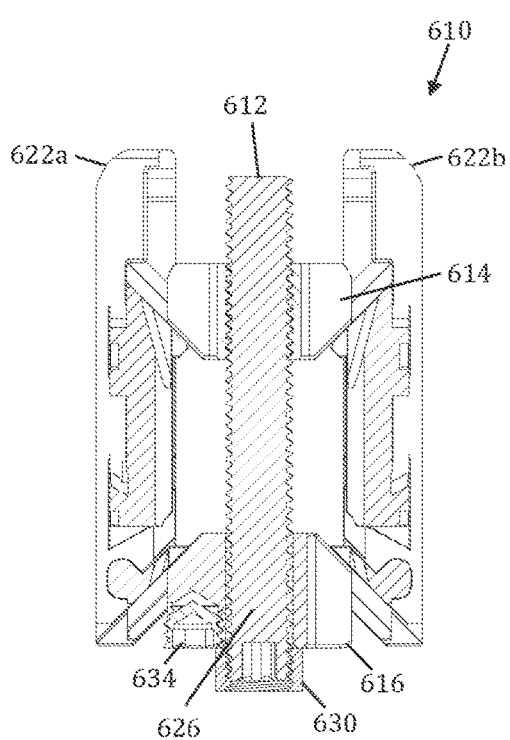
Figure 49:
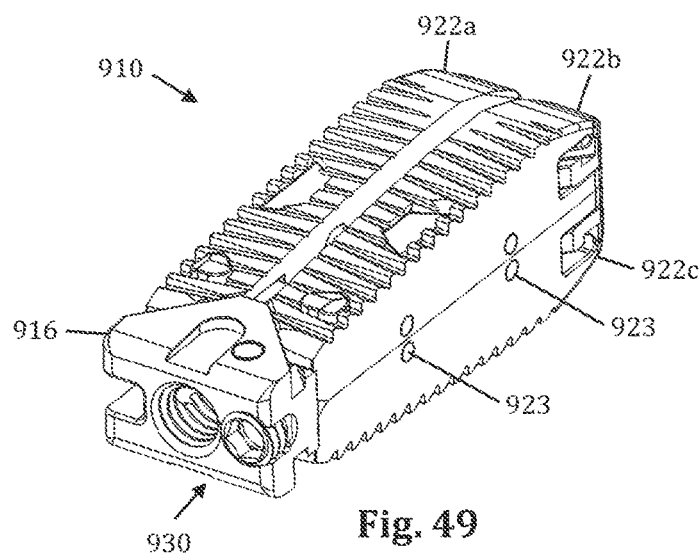
FIG. 49 is a perspective view of another example of an expandable fusion device in a fully collapsed state, according to some embodiments.

Upon completion of the desired expansion, at least a portion of the proximal portion 626 of the actuator 612 will be protruding proximally from the proximal wedge 616 (e.g. proximal overhang), as shown in FIG. 37. If so desired, the actuator 612 may be advanced into the expanded fusion device 610 by using an instrument (not shown) to hold the nut 630 in place while the same or different instrument is used to rotate the actuator (e.g. in a clockwise direction for right-handed threading, counterclockwise for left-handed threading) thereby threading the actuator 612 into the distal wedge 614 to a desirable distance (e.g. FIG. 38 illustrates a fully advanced actuator 612). Once the actuator 612 has been advanced as desired to minimize the proximal overhang, the lock screw 634 may be advanced into a threaded lock screw aperture 635 formed in wedge 616 adjacent to the unthreaded aperture 656 so that that lock screw 634 engages with the actuator 612 to prevent the proximal wedge 616 from moving relative to the actuator 612, thereby "locking" the wedge 616 (and the expansion) in place.

The expandable fusion device 610 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 610.

FIGS. 39-42 illustrate an example of an expandable fusion device 710 for implantation between two adjacent vertebrae according to another embodiment of the disclosure. By way of example only, the expandable fusion device 710 of the present embodiment includes an actuator 712, a distal wedge 714, a proximal wedge 716, a pair of distal ramps 718a, 718b, a pair of proximal ramps 720a, 720b, a plurality of endplates 722a-722d, a plurality of guide pins 723, a locking element 730, and a lock screw 734. As with previously-described embodiments, the distal and proximal wedges 714, 716 are coupled with the actuator 712. The distal ramps 718a, 718b are slideably coupled with the distal wedge 714. The proximal ramps 720a, 720b are slideably coupled with the proximal wedge 716. The plurality of endplates 722a-722d are slideably coupled with the ramps 718a, 718b, 720a. 720b. Generally, the expandable fusion device 710 is substantially similar to expandable fusion device 10 described above, and any/all of the features described above with respect to fusion device 10 (and any other expandable fusion device described herein) may apply to fusion device 710 unless otherwise noted. By way of example only, the expandable fusion device 710 is illustrative of an alternative actuator mechanism that may be applied to any expandable fusion device examples described herein, according to some embodiments.

By way of example only, the actuator 712 comprises a cylindrically shaped elongate shaft having a distal end 724 and a proximal end 726. The distal end 724 is attached to or is integrally formed with the distal wedge 714 such that the actuator 712 comprises a proximal protrusion from the distal wedge 714. The actuator 712 of the present example has no thread feature but instead is a smooth elongate shaft. The proximal end 726 may include an engagement feature 732 (e.g. groove, ridge, and the like) configured to securely engage with an instrument (not shown).

FIG. 40 illustrates the expandable fusion implant 710 (in cross-section) in fully collapsed form. The proximal end 726 of the actuator 712 extends proximally from the proximal wedge 716 at least so far as to ensure that the engagement feature 732 is proximal of the unthreaded aperture 756 of the proximal wedge 716 (and therefore accessible by an engagement instrument). The shaft of the actuator 612 extends through the unthreaded aperture 756 of the proximal wedge 716 to the distal wedge 714. To effectuate width expansion of the expandable fusion device 710, an engagement instrument (not shown) is used to securely engage the actuator 712 at the engagement feature 732. The same or different instrument is then used to brace against the proximal wedge 716 to ensure the proximal wedge 716 does not move during expansion. The instrument is then used to pull the actuator 712, and by extension the distal wedge 714 into the construct toward the proximal wedge 716. The distal wedge 714 also causes the ramps to move, thereby effectuating expansion (e.g. width only, first width then height, width and height, etc.) of the expandable fusion implant 710 without any movement of the proximal wedge 716.

When the desired expansion has been achieved (e.g. FIG. 41), the actuator 712 must be secured by a locking element 730. To facilitate this, the proximal wedge 716 includes a locking element 730 at least partially retained within a cross-bore 737. The cross-bore 737 is configured to retain the locking element 730 (e.g. ball detent, pin detent, or other suitable feature capable of exerting immobilizing force upon the actuator shaft) therein while also enabling exposure to the non-threaded aperture 756 (for contacting the actuator 712) and the lock screw aperture 735 (for contacting the lock screw 734)(see, e.g. FIG. 42). Upon completion of the desired expansion, the lock screw 734 is tightened within the lock screw aperture 735, which in turn deflects the locking element 730 medially such that the locking element 730 forcibly contacts the actuator 712 to prevent translation of the actuator 712. The lock screw 734 has a tapered nose 739 that enables the application of off-axis lateral force to the locking element 730, deflecting or biasing the locking element 730 in a medial direction. By way of example, the actuator 712 may have a corresponding locking feature (e.g., groove, series of grooves, serrations, friction surface, etc.) configured to interact with the locking element 730 to improve resistance to slippage. Furthermore, at least a portion of the proximal portion 726 of the actuator 712 will be protruding proximally from the proximal wedge 716, as shown in FIG. 41. If so desired, the exposed proximal portion of the actuator 712 may be sheared off and removed.

The expandable fusion device 710 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 710.

FIGS. 43-48 illustrate an example of an expandable fusion device 810 for implantation between two adjacent vertebrae according to another embodiment of the disclosure. By way of example only, the expandable fusion device 810 of the present embodiment includes an actuator 812, a distal wedge 814, a proximal wedge 816, a pair of distal ramps 818a, 818b, a pair of proximal ramps 820a, 820b, a plurality of endplates 822a-822d, a plurality of guide pins 823, a locking element 830, and a lock screw 834. As with previously-described embodiments, the distal and proximal wedges 814, 816 are coupled with the actuator 812. The distal ramps 818a, 818b are slideably coupled with the distal wedge 814. The proximal ramps 820a, 820b are slideably coupled with the proximal wedge 816. The plurality of endplates 822a-822d are slideably coupled with the ramps 818a, 818b, 820a, 820b. Generally, the expandable fusion device 810 is substantially similar to expandable fusion device 10 described above, and any/all of the features described above with respect to fusion device 10 (and any other expandable fusion device described herein) may apply to fusion device 810 unless otherwise noted. By way of example only, the expandable fusion device 810 is illustrative of an alternative actuator mechanism that may be applied to any expandable fusion device examples described herein, according to some embodiments.

FIG. 44 illustrates an example of an actuator 812 forming part of the expandable fusion device 810 of the present embodiment. By way of example only, the actuator 812 comprises a cylindrically shaped elongate shaft having a distal end 824, a proximal end 826, and a longitudinal axis. The actuator 812 of the present example has a single thread feature 828 positioned near/at the distal end 824. The proximal end 826 includes a drive feature 832 coincident with the longitudinal axis and configured to engage with an instrument (not shown) to rotate the actuator 812 to reduce proximal overhang after expansion, and an engagement feature 838 (e.g. groove, ridge, and the like) configured to securely engage with an instrument (not shown). The thread feature 828 comprises a thread disposed externally around the shaft of the actuator 812. By way example, the thread feature 828 may comprise a right-handed threading. Alternatively, the thread feature 828 may comprise a left-handed threading. The drive feature 832 comprises a recessed region configured to receive a driving/holding instrument. Alternatively, the drive feature 832 may comprise a protuberance (for example a hex, a hexalobular, or a square protuberance or any other shaped protuberance) extending longitudinally from the proximal and/or distal end and configured to be coupled to a driving/holding instrument.

FIG. 45 illustrates the expandable fusion implant 810 (in cross-section) in fully collapsed form. The actuator 812 is positioned such that the distal end 824 is partially threaded into the threaded aperture 840 of the distal wedge 814. The proximal end 826 of the actuator 812 extends proximally from the proximal wedge 816 at least so far as to ensure that the engagement feature 736 is proximal of the unthreaded aperture 856 of the proximal wedge 816 (and therefore accessible by an engagement instrument). The shaft of the actuator 812 extends through the unthreaded aperture 856 of the proximal wedge 816 to the distal wedge 814, to which the actuator 812 is threadedly engaged. To effectuate width expansion of the expandable fusion device 810, an engagement instrument (not shown) is used to securely engage the actuator 812 at the engagement feature 836. The same or different instrument is then used to brace against the proximal wedge 816 to ensure the proximal wedge 816 does not move during expansion. The instrument is then used to pull the actuator 812, and by extension the distal wedge 814 into the construct toward the proximal wedge 816. The distal wedge 814 also causes the ramps to move, thereby effectuating expansion (e.g. width only, first width then height, width and height, etc.) of the expandable fusion implant 810 without any movement of the proximal wedge 816.

Upon completion of the desired expansion, at least a portion of the proximal portion 826 of the actuator 812 will be protruding proximally from the proximal wedge 816 (e.g. proximal overhang), as shown in FIG. 46. If so desired, the actuator 812 may be advanced into the expanded fusion device 810 by using a driver instrument (not shown) to rotate the actuator 812 (e.g. in a clockwise direction for right-handed threading, counterclockwise for left-handed threading) thereby threading the actuator 812 into the distal wedge 814 to a desirable distance (e.g. FIG. 47 illustrates a fully advanced actuator 812). Once the actuator 812 has been advanced as desired to reduce or minimize proximal overhang, the actuator 812 must be secured by a locking element 830. To facilitate this, the proximal wedge 816 includes a locking element 830 at least partially retained within a cross-bore 837. The cross-bore 837 is configured to retain the locking element 830 (e.g. ball detent, pin detent, or other suitable feature capable of exerting immobilizing force upon the actuator shaft) therein while also enabling exposure to the non-threaded aperture 856 (for contacting the actuator 812) and the lock screw aperture 835 (for contacting the lock screw 834)(see, e.g. FIG. 48). Upon completion of the desired expansion, the lock screw 834 is tightened within the lock screw aperture 835, which in turn deflects the locking element 830 medially such that the locking element 830 forcibly contacts the actuator 812 to prevent translation of the actuator 812. By way of example, the lock screw 834 has a tapered nose 839 that enables the application of off-axis lateral force to the locking element 830, deflecting or biasing the locking element 830 in a medial direction. By way of example, the actuator 812 may have a corresponding locking feature 838 (e.g., groove, series of grooves, serrations, friction surface, etc.) configured to interact with the locking element 830 to improve resistance to slippage.

The expandable fusion device 810 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 810.

FIGS. 49-53 illustrate an example of an expandable fusion device 910 for implantation between two adjacent vertebrae according to another embodiment of the disclosure. By way of example only, the expandable fusion device 910 of the present embodiment includes an actuator 912, a distal wedge 914, a proximal wedge 916, a pair of distal ramps 918a, 918b, a pair of proximal ramps 920a, 920b, a plurality of endplates 922a-922d, and a plurality of guide pins 923. As with previously-described embodiments, the distal and proximal wedges 914, 916 are coupled with the actuator 912. The distal ramps 918a, 918b are slideably coupled with the distal wedge 914. The proximal ramps 920a, 920b are slideably coupled with the proximal wedge 916. The plurality of endplates 922a-922d are slideably coupled with the ramps 918a, 918b, 920a. 920b. Generally, the expandable fusion device 910 is substantially similar to expandable fusion device 10 described above, and any/all of the features described above with respect to fusion device 10 (and any other expandable fusion device described herein) may apply to fusion device 910 unless otherwise noted. By way of example only, the expandable fusion device 910 is illustrative of a pin detent locking mechanism that may be applied to any expandable fusion device examples described herein, according to some embodiments.

By way of example, the actuator 912 shown in FIGS. 49-53 is substantially identical to the actuator 10 described above, and comprises a distal end 924, proximal end 926, and a longitudinal axis, however the locking mechanism described herein may be applied to any other actuator examples described herein. By way of example, the at least one of the distal end 924 and proximal end 926 may be threaded.

Figure 50:
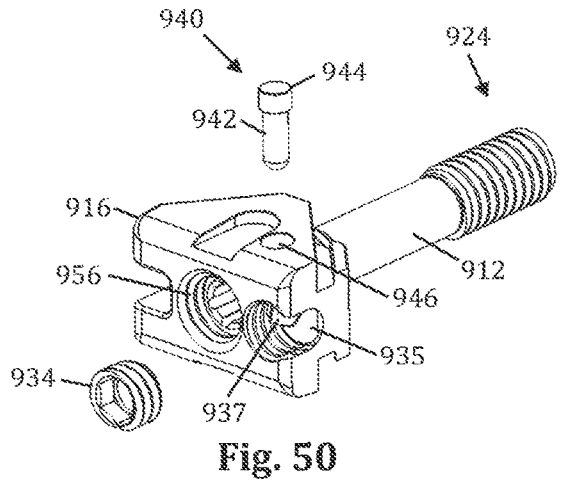
FIG. 50 is a perspective view of an example of a locking element forming part of the expandable fusion device of FIG. 49, according to some embodiments.

FIG. 50 illustrates an example of a proximal wedge 916 configured with a locking element 930 of the instant embodiment. By way of example, the locking element 930 of the present embodiment comprises a deflectable pin 940 and a lock screw 934. The proximal wedge 916 is substantially similar to the proximal wedge 16 described above. By way of example, the proximal wedge 916 of the present embodiment includes a threaded aperture 956 for coupling with the actuator 912 and a lock screw aperture 935 adjacent to the threaded aperture 956. The proximal wedge 916 further includes a cross-bore 937 extending transversely through the wedge 916 such that the cross-bore 937 intersects the threaded aperture 956 and the lock screw aperture 935. A pin aperture 946 configured to receive the pin 940 therein extends vertically through the proximal wedge 916 such that the pin 940 when inserted into the pin aperture extends into the intersection of the lock screw aperture 935, cross-bore 937, and threaded aperture 956.

By way of example, the pin 940 includes a shaft 942 and a head 944. Preferably, the circumference of the head 944 is greater than the circumference of the shaft 942. The pin 940 is sized and configured relative to the pin aperture 946 such that the head 944 is flushly received within the pin aperture 946 and the shaft 942 is deflectable within the pin aperture 946.

Figure 51:
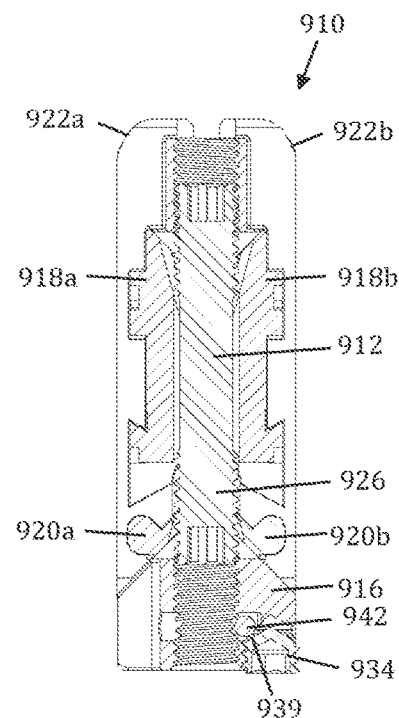
FIGS. 51-53 are sectional views of the expandable fusion device of FIG. 49 in various states of expansion, according to some embodiments.
Figure 52:
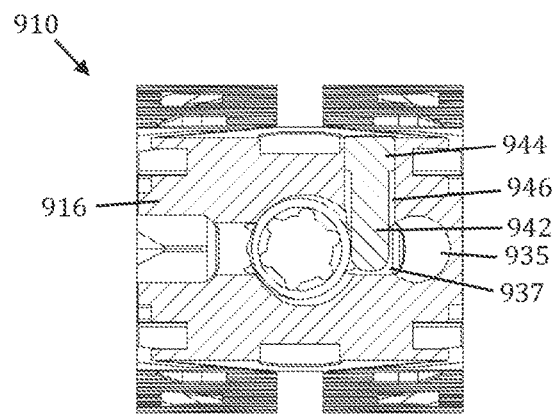
Figure 53:
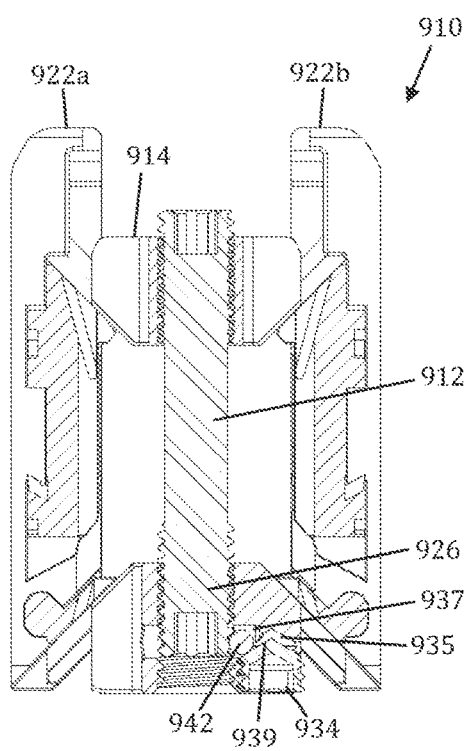

FIGS. 51 and 52 illustrate the expandable fusion device 910 of the present embodiment in a collapsed, unlocked state. FIG. 53 illustrates the expandable fusion device 910 of the present embodiment in an expanded, locked state. Upon completion of the desired expansion, the lock screw 934 is tightened (or introduced and then tightened) within the lock screw aperture 935, which in turn deflects the shaft 942 of the pin 940 medially such that the shaft 942 forcibly contacts the actuator 912 to prevent backout of the actuator 912. By way of example, the lock screw 934 has a tapered nose 939 that enables the application of off-axis lateral force to the pin 940, deflecting or biasing the pin 940 in a medial direction. By way of example, the actuator 912 may have a corresponding locking feature (e.g., groove, series of grooves, serrations, friction surface, etc.) configured to interact with the pin 940 to improve resistance to slippage.

The expandable fusion device 910 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 910.

Figure 54:
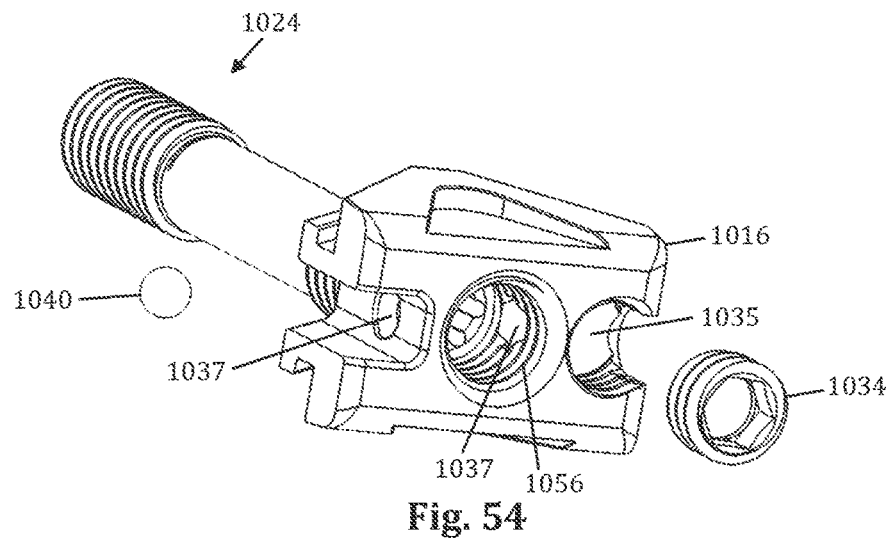
FIG. 54 is a perspective view of another example of a locking element forming part of the expandable fusion device of FIG. 49, according to some embodiments.
Figures 55, 56:
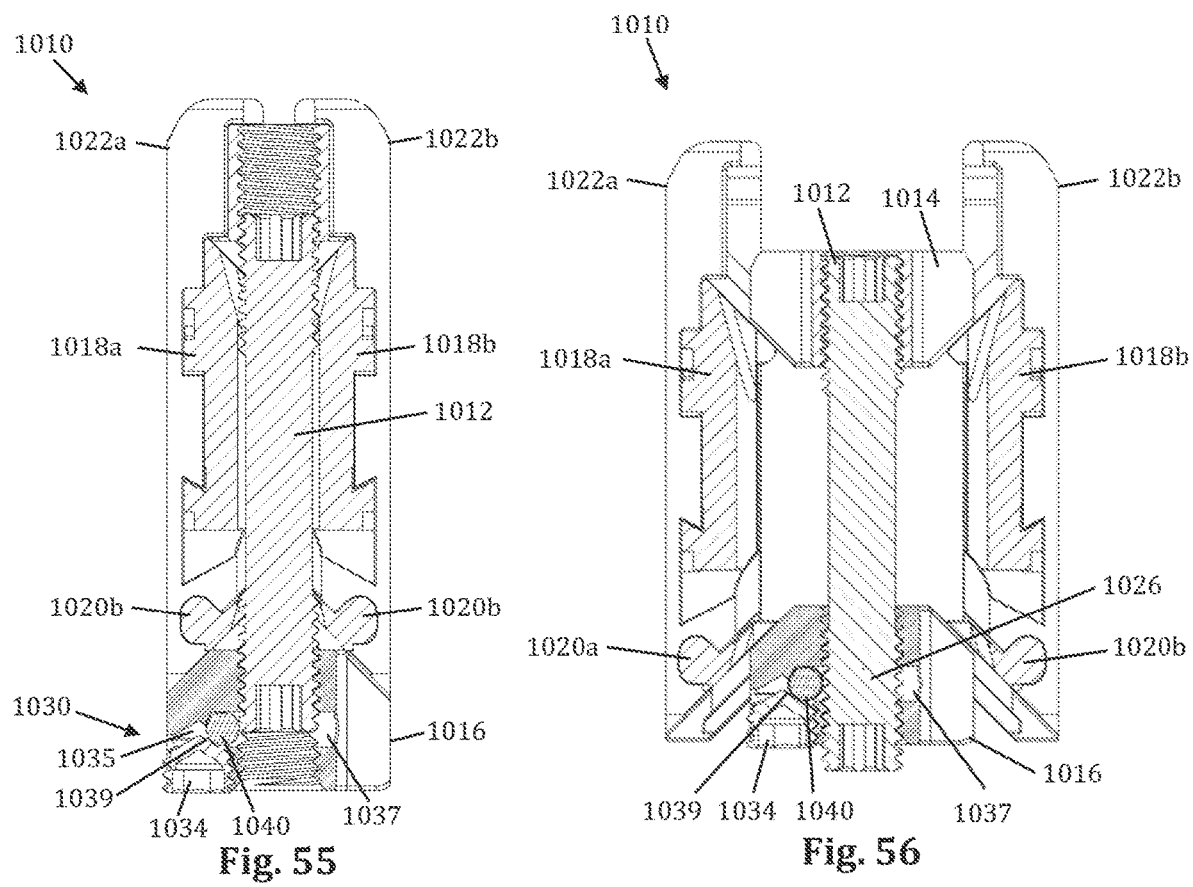
FIGS. 55-56 are sectional views of the expandable fusion device of FIG. 48 in various states of expansion, according to some embodiments.
Figure 57:
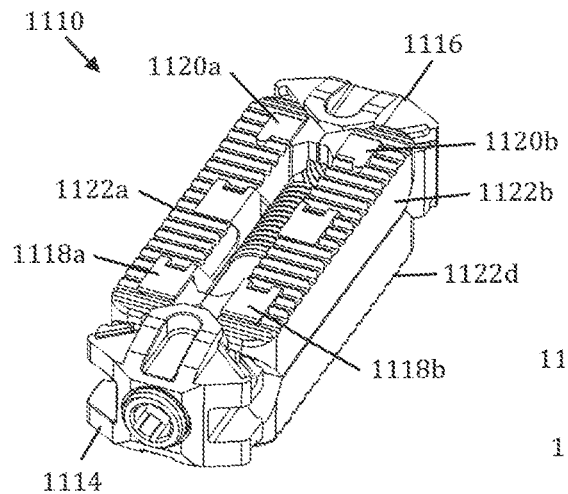
FIG. 57 is a perspective view of another example of an expandable fusion device in a fully collapsed state, according to some embodiments.
Figure 58:
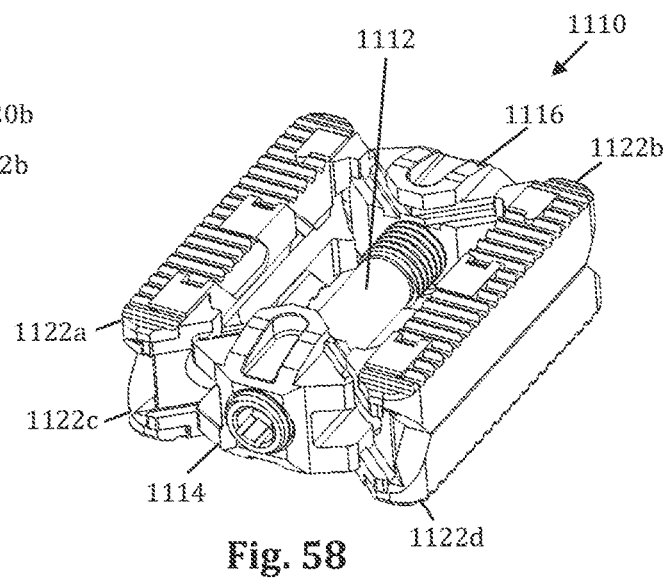
FIG. 58 is a perspective view of the of FIG. 57 in a width-expanded state, according to some embodiments.
Figure 59:
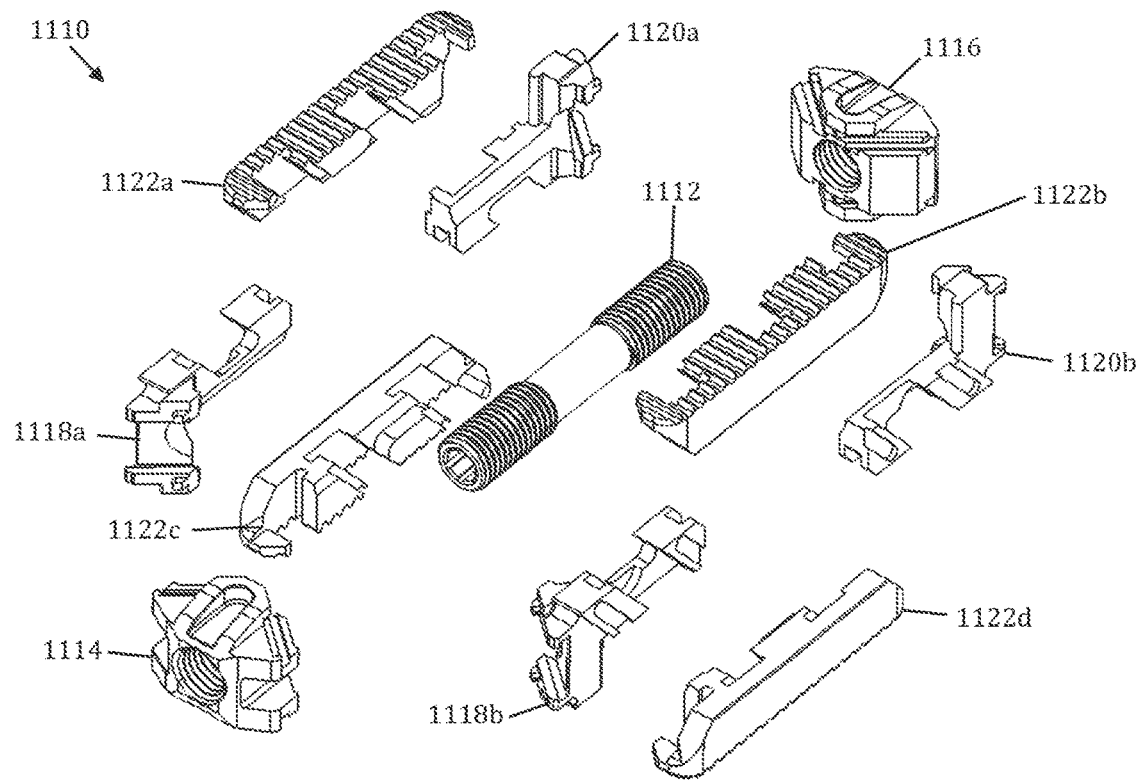
FIG. 59 is an exploded perspective view of the expandable fusion device of FIG. 57, according to some embodiments.

FIGS. 54-56 illustrate an example of an expandable fusion device 1010 for implantation between two adjacent vertebrae according to another embodiment of the disclosure. By way of example only, the expandable fusion device 1010 of the present embodiment includes an actuator 1012, a distal wedge 1014, a proximal wedge 1016, a pair of distal ramps 1018a, 1018b, a pair of proximal ramps 1020a, 1020b, a plurality of endplates 1022a-1022d, and a plurality of guide pins. As with previously-described embodiments, the distal and proximal wedges 1014, 1016 are coupled with the actuator 1012. The distal ramps 1018a, 1018b are slideably coupled with the distal wedge 1014. The proximal ramps 1020a, 1020b are slideably coupled with the proximal wedge 1016. The plurality of endplates 1022a-1022d are slideably coupled with the ramps 1018a, 1018b, 1020a. 1020b. Generally, the expandable fusion device 1010 is substantially similar to expandable fusion device 10 described above, and any/all of the features described above with respect to fusion device 10 (and any other expandable fusion device described herein) may apply to fusion device 1010 unless otherwise noted. By way of example only, the expandable fusion device 1010 is illustrative of a ball detent locking mechanism that may be applied to any expandable fusion device examples described herein, according to some embodiments.

By way of example, the actuator 1012 shown in FIGS. 54-56 is substantially identical to the actuator 10 described above, and comprises a distal end 1024, proximal end 1026, and a longitudinal axis, however the locking mechanism described herein may be applied to any other actuator examples described herein. By way of example, the at least one of the distal end 1024 and proximal end 1026 may be threaded.

FIG. 54 illustrates an example of a proximal wedge 1016 configured with a locking element 1030 of the instant embodiment. By way of example, the locking element 1030 of the present embodiment comprises a ball 1040 and a lock screw 1034. The proximal wedge 1016 is substantially similar to the proximal wedge 16 described above. By way of example, the proximal wedge 1016 of the present embodiment includes a threaded aperture 1056 for coupling with the actuator 1012 and a lock screw aperture 1035 adjacent to the threaded aperture 1056. The proximal wedge 1016 further includes a cross-bore 1037 extending transversely through the wedge 1016 such that the cross-bore 1037 intersects the threaded aperture 1056 and the lock screw aperture 1035. Notably, the intersection between the cross-bore 1037 and the lock screw aperture 1035 comprises an opening large enough to allow only a portion of the ball 1040 to enter the lock screw aperture 1035. This ensures that the lock screw 1034 will be able to contact the ball 1040 and also ensures that the ball 1040 will not fall into the lock screw aperture 1035.

FIG. 55 illustrates the expandable fusion device 1010 of the present embodiment in a collapsed, unlocked state. FIG. 56 illustrates the expandable fusion device 1010 of the present embodiment in an expanded, locked state. Upon completion of the desired expansion, the lock screw 1034 is tightened (or introduced and then tightened) within the lock screw aperture 1035, which in turn deflects the ball 1040 medially such that the ball 1040 forcibly contacts the actuator 1012 to prevent backout of the actuator 1012. By way of example, the lock screw 1034 has a tapered nose 1039 that enables the application of off-axis lateral force to the ball 1040, deflecting or biasing the ball 1040 in a medial direction. By way of example, the actuator 1012 may have a corresponding locking feature (e.g., groove, series of grooves, serrations, friction surface, etc.) configured to interact with the ball 1040 to improve resistance to slippage.

The expandable fusion device 1010 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1010.

FIGS. 57-65 illustrate an example of an expandable fusion device 1110 for implantation between two adjacent vertebrae according to another embodiment of the disclosure. By way of example only, the expandable fusion device 1110 of the present embodiment includes an actuator 1112, a distal wedge 1114, a proximal wedge 1116, a pair of distal ramps 1118a, 1118b, a pair of proximal ramps 1120a, 1120b, a plurality of endplates 1122a-1122d, and (optionally) a plurality of guide pins. As with previously-described embodiments, the distal and proximal wedges 1114, 1116 are coupled with the actuator 1112. The distal ramps 1118a, 1118b are slideably coupled with the distal wedge 1114. The proximal ramps 1120a, 1120b are slideably coupled with the proximal wedge 1116. The plurality of endplates 1122a-1122d are slideably coupled with the ramps 1118a, 1118b, 1120a. 1120b. Generally, the expandable fusion device 1110 is substantially similar to expandable fusion device 10 described above, and any/all of the features described above with respect to fusion device 10 (and any other expandable fusion device described herein) may apply to fusion device 1110 unless otherwise noted. By way of example only, the expandable fusion device 1110 is illustrative of a configuration to reduce spondylolisthesis that may be applied to any expandable fusion device examples described herein, according to some embodiments.

Spondylolisthesis is a spinal ailment that occurs when a vertebral body slips out of alignment, typically in an anterior direction. As will be described, the expandable fusion device 1110 of the present embodiment may help to alleviate spondylolisthesis by laterally shifting the upper endplates 1122a, 1122b relative to the lower endplates 1122c, 1122d during height expansion, using the fusion device 1110 to apply torque to the displaced vertebra.

By way of example only, the distal wedge 1114 may be substantially identical to the proximal wedge 14 described above in relation to device 10. Similarly, the proximal wedge 1116 may be substantially identical to the proximal wedge 16 described above. Alternatively, the distal and proximal wedges 1114 may be identical to one another.

Figure 60:
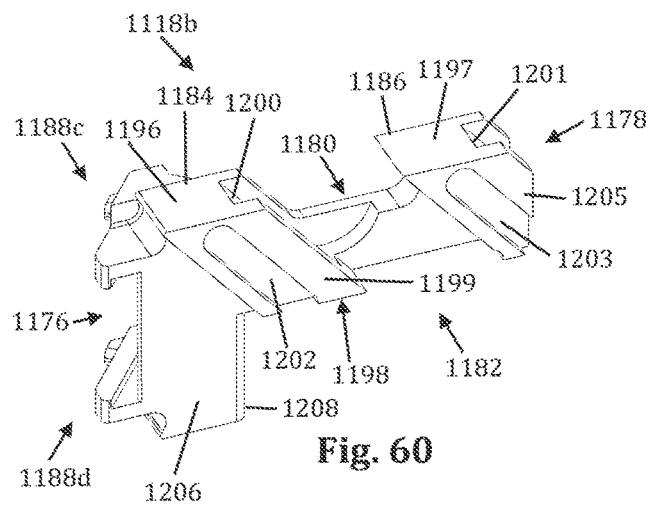
FIGS. 60-61 are perspective views of an example of a distal ramp forming part of the expandable fusion device of FIG. 57, according to some embodiments.
Figure 61:
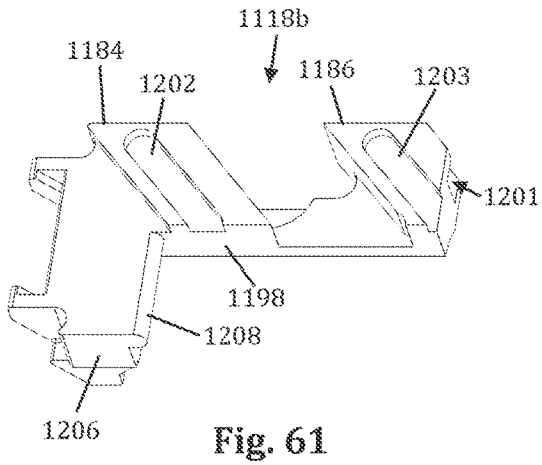

FIGS. 60-61 illustrate an example of a distal ramp 1118b according to the present embodiment. By way of example, the distal ramp 1118b has a distal end 1176, a proximal end 1178, a medial side 1180 (e.g. oriented toward the actuator 1112 in the assembled expandable fusion device 1110), and a lateral side 1182 (e.g. oriented away from the actuator 1112 in the assembled expandable fusion device 1110). Generally, the distal ramp 1118b comprises a first lobe 1184, a second lobe 1186, and a vertical post 1206 that facilitate height expansion of the expandable fusion device 1110. The second distal ramp 1118b may be configured for slideable coupling with the distal wedge 1114 and/or the endplates 1122b, 1122d. The slideable coupling with the wedge 1114 is identical to that described above with respect to fusion device 10.

The first lobe 1184 comprises an inclined structure (e.g. half of a chevron shape of previously described embodiments) having an apex oriented in the proximal direction. The first lobe 1184 includes a top surface 1196, a bottom surface 1198, and a lateral surface 1199. By way of example, the first lobe 1184 has a generally U-shaped cross-sectional shape, however it should be noted that the first lobe 1184 may have any suitable cross-sectional shape including but not limited to (and by way of example only a circle, an oval, an ellipse, a triangle, a square, a T-shape, a V-shape, a regular polygon, an irregular polygon, or an irregular shape, or any combination thereof). The first lobe 1184 further includes a recessed ramp slot 1202 including a translation stop formed within the lateral surface 1199 and configured to slideably receive the one or more guide pins therein to help stabilize the construct during height expansion. The first lobe 1184 further comprises a proximal-facing angled translation surface 1200 configured to slideably engage inclined surface 1152 of endplate 22b to facilitate height expansion.

The second lobe 1186 comprises an inclined structure (e.g. half of a chevron shape of previously described embodiments) having an apex oriented in the proximal direction. The second lobe 1186 includes a top surface 1197, a bottom surface 1198, and a lateral surface 1205. By way of example, the second lobe 1186 has a generally U-shaped cross-sectional shape, however it should be noted that the second lobe 1186 may have any suitable cross-sectional shape including but not limited to (and by way of example only a circle, an oval, an ellipse, a triangle, a square, a T-shape, a V-shape, a regular polygon, an irregular polygon, or an irregular shape, or any combination thereof). The second lobe 1186 further includes a recessed ramp slot 1203 including a translation stop formed within the lateral surface 1205 and configured to slideably receive the one or more guide pins therein to help stabilize the construct during height expansion. The second lobe 1186 further comprises a proximal-facing angled translation surface 1201 configured to slideably engage inclined surface 1156 of endplate 22b to facilitate height expansion.

By way of example, bottom surface 1198 functionally resembles the L-shaped cutaway surface 400 described above (and essentially forms an "L" shape with the vertical post 1206). To wit, the bottom surface 1198 is configured to slideably mate with a corresponding surface on the second proximal ramp 1120b.

By way of example, the distal end 1176 comprises tongue and groove connectors 1188c, 1188d that slideably mate with corresponding tongue and groove connectors on the distal wedge 1114. The distal end 1176 also includes a vertical post 1206 including a vertical protrusion 1208 that are configured to facilitate height expansion.

Figure 62:
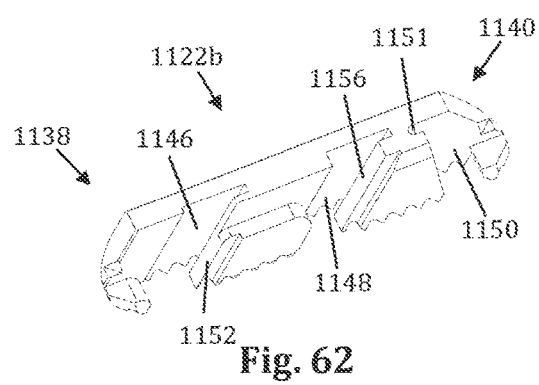
FIG. 62 is a perspective view of an example of an endplate forming part of the expandable fusion device of FIG. 57, according to some embodiments.

By way of example, the various endplates 1122a-1122d are either identical or identical mirror images of one another, and thus only one of the endplates needs to be described in further detail. FIG. 62 illustrate one example of an endplate 1122b according to the present disclosure. By way of example only, the endplate 1122b has a first (e.g. distal) end 1138 and a second (e.g. proximal) end 1140.

The endplate 1122b further comprises a first inclined slot 1146 proximate the first end 1138, a second inclined slot 1148 positioned proximally of the first inclined slot 1146, and a vertical channel 1150 positioned proximate the second end 1140. Optionally, in any embodiment, the slopes or shapes of the inclined slots 1146 and 1148 are equal or differ from each other. The first inclined slot 1146 has an inclined surface 1152 generally transverse to the longitudinal axis of the implant. The first inclined slot 1146 is sized and configured to slideably receive at least a portion of the first lobe 1184 of the second distal ramp 1118b such that the angled translation surface 1200 of the first lobe 1184 is slideably associated with the inclined surface 1152. The second inclined slot 1148 has an inclined surface 1156 generally transverse to the longitudinal axis of the implant. The second inclined slot 1148 is sized and configured to slideably receive at least a portion of the second lobe 1186 of the second distal ramp 1118b such that the angled translation surface 1201 of the second lobe 1186 is slideably associated with the inclined surface 1156. Thus, after width expansion has completed, as the distal wedge 1114 advances the distal ramp 1118b toward the proximal wedge 1116 (and proximal ramp 1120b), the endplate 1122b is vertically displaced in part due to the angular translation along the inclined surface 152 (resulting in height expansion).

The vertical channel 1150 has a size and shape corresponding to the size and shape of the vertical post of the second proximal ramp 1120b, which as will be explained below, is the same or mirrored equivalence of the vertical post 1206 of the distal ramp 1118b, and is configured to facilitate vertical translation of the endplate 1122b relative to the proximal ramp 1120b. The vertical channel 1150 further includes a vertical recess 1151 sized and configured to receive a vertical protrusion 1208 (or its mirrored equivalence). Thus, in the instant embodiment, the lower endplates 1122c, 1122d translate vertically relative to the distal ramps 1118a, 1118b and obliquely relative to the proximal ramps 1120a, 1120b. The upper endplates 1122a, 1122b translate vertically relative to the proximal ramps 1120a, 1120b, and obliquely relative to the distal ramps 1118a, 1118b.

By way of example, at least two of the first distal ramp 1118a, the second distal ramp 1118b, the first proximal ramp 1120a, and the second proximal ramp 1120b are identical. Additionally, at least two of the first distal ramp 1118a, the second distal ramp 1118b, the first proximal ramp 1120a, and the second proximal ramp 1120b have a mirrored equivalence. For example, in the instant embodiment, the first distal ramp 1118a is identical to the second proximal ramp 1120b, the second distal ramp 1118b is identical to the first proximal ramp 1120a, the first and second distal ramps 1118a, 1118b have a mirrored equivalence, and the first and second proximal ramps 1120a, 1120b have a mirrored equivalence. Similarly, by way of example only, at least two of the endplates 1122a, 1122b, 1122c, 1122d are identical, and at least two of the endplates 1122a, 1122b, 1122c, 1122d have a mirrored equivalence.

Figure 63:
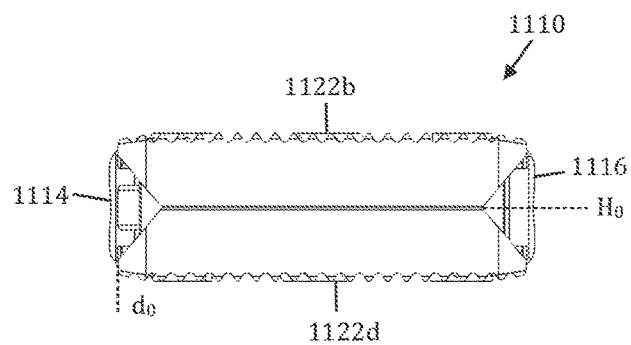
FIGS. 63-65 are plan views of the expandable fusion device of FIG. 57 in various states of expansion, according to some embodiments.
Figure 64:
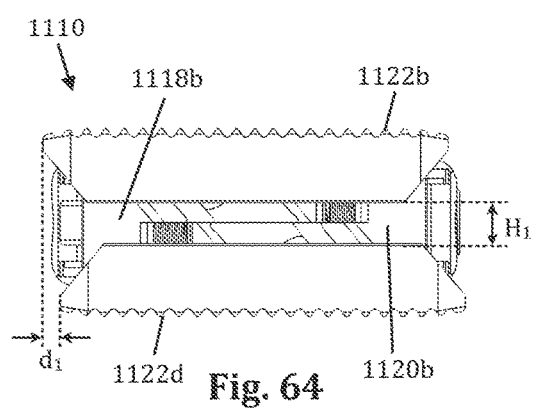
Figure 65:
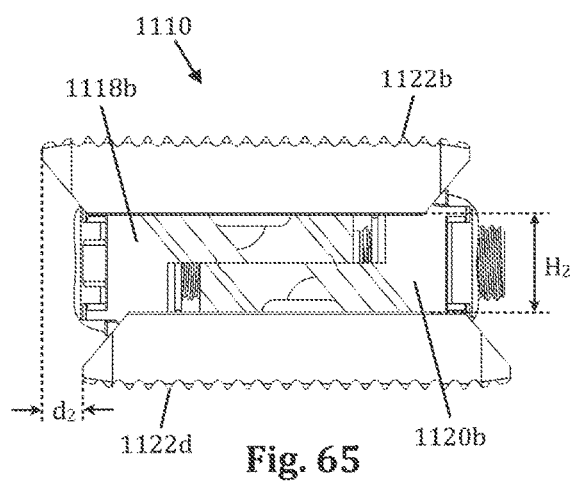

FIGS. 63-65 illustrate the relationship between height expansion and horizontal endplate displacement according to some embodiments. By way of example, FIG. 63 illustrates a fully collapsed implant having a height expansion $H_0$ and a horizontal displacement $d_0$, each of which are essentially zero. FIG. 64 illustrates that after a height expansion $H_1$, a horizontal displacement $d_1$ has occurred. Similarly, FIG. 65 illustrates that a height expansion $H_2$ will result in a horizontal displacement $d_2$. The exact value of horizontal displacement $d_n$ that occurs with respect to a particular height expansion $H_n$ may vary depending upon the angles of the inclined translation surfaces on the ramps and endplates. More acute angles would result in a greater horizontal displacement.

The expandable fusion device 1110 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1110.

FIGS. 66-69 illustrate an example of an expandable fusion device 1210 for implantation between two adjacent vertebrae according to another embodiment of the disclosure. By way of example only, the expandable fusion device 1210 of the present embodiment includes an actuator 1212, a distal wedge 1214, a proximal wedge 1216, a pair of distal ramps 1218a, 1218b, a pair of proximal ramps 1220a, 1220b, a plurality of endplates 1222a-1222d, and a plurality of guide pins (optionally). As with previously-described embodiments, the distal and proximal wedges 1214, 1216 are coupled with the actuator 1212. The distal ramps 1218a, 1218b are slideably coupled with the distal wedge 1214. The proximal ramps 1220a, 1220b are slideably coupled with the proximal wedge 1216. The plurality of endplates 1222a-1222d are slideably coupled with the ramps 1218a, 1218b, 1220a. 1220b. Generally, the expandable fusion device 1210 is substantially similar to expandable fusion device 10 described above, and any/all of the features described above with respect to fusion device 10 (and any other expandable fusion device described herein) may apply to fusion device 1210 unless otherwise noted. By way of example only, the expandable fusion device 1210 is illustrative of a configuration to effect vertebral derotation that may be applied to any expandable fusion device examples described herein, according to some embodiments.

Vertebral rotation is a spinal ailment that occurs when a vertebral body slips rotationally out of alignment, for example in scoliosis patient. As will be described, the expandable fusion device 1210 of the present embodiment may help to effect derotation by horizontally shifting same side upper and lower endplates (e.g. endplates 1222a, 1222c and endplates 1212b, 1212d relative to one another during height expansion, using the fusion device 1210 to apply rotational torque to the displaced vertebra.

In the instant embodiment, the actuator 1212, distal wedge 1214, and proximal wedge 1216 are identical or substantially similar to corresponding parts described in previous embodiments. By way of example, the distal ramps 1218a, 1218b and proximal ramps 1220a, 1220b are identical to one another save for an optional dovetail connector described in further detail below. By way of example, the ramps 1218a, 1218b, 1220a, 1220b are identical in form and function (save for the dovetail connector) to the second distal ramp 1118b described above. Furthermore, since the ramps 1218a, 1218b, 1220a, 1220b are identical, the endplates 1222a, 1222b, 1222c, 1222d are also identical. This reduces the number of different parts needed during assembly. By way of example, the endplates 1222a, 1222b, 1222c, 1222d are identical to endplate 1122b described above.

Figure 66:
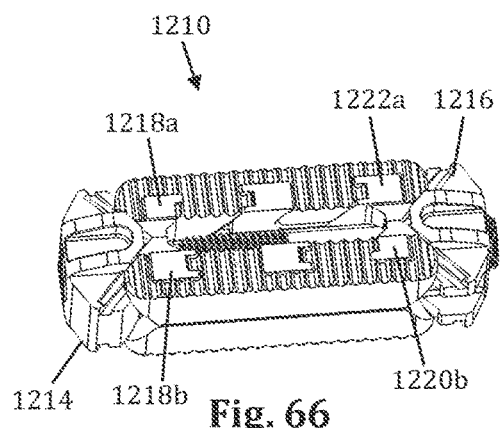
FIG. 66 is a perspective view of another example of an expandable fusion device in a fully collapsed state, according to some embodiments.
Figure 67:
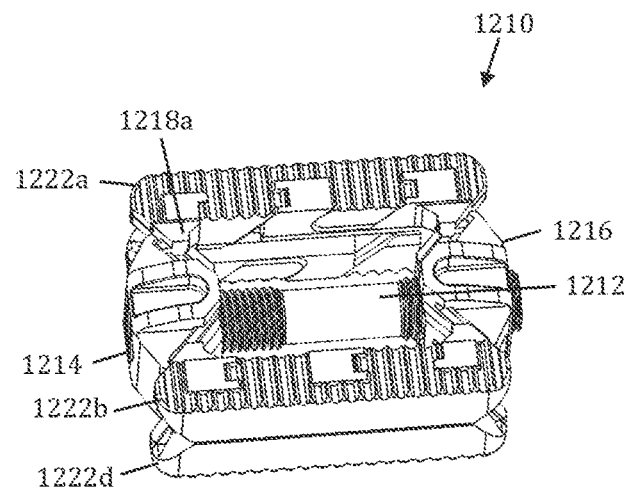
FIG. 67 is a perspective view of the expandable fusion device of FIG. 66 in a width-expanded state, according to some embodiments.
Figure 68:
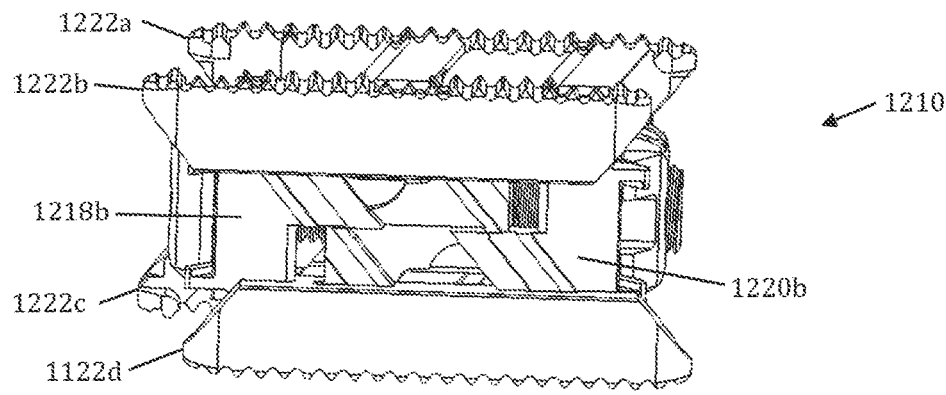
FIG. 68 is a perspective view of the expandable fusion device of FIG. 66 in a fully expanded state, according to some embodiments.

By way of example, FIG. 66 depicts the expandable fusion device 1210 of the instant in a fully collapsed state. FIG. 67 shows the expandable fusion device 1210 in a fully width-expanded state. At this point the endplates 1222a, 1222b, 1222c, 1222d are not horizontally displaced. FIG. 68 illustrates the expandable fusion device 1210 in a fully width and height expanded state. As can be seen, the first upper endplate 1222a and second lower endplate 1222d have shifted in a proximal direction, and the second upper endplate 1222b and first lower endplate 1222c have shifted in a distal direction.

Figure 69:
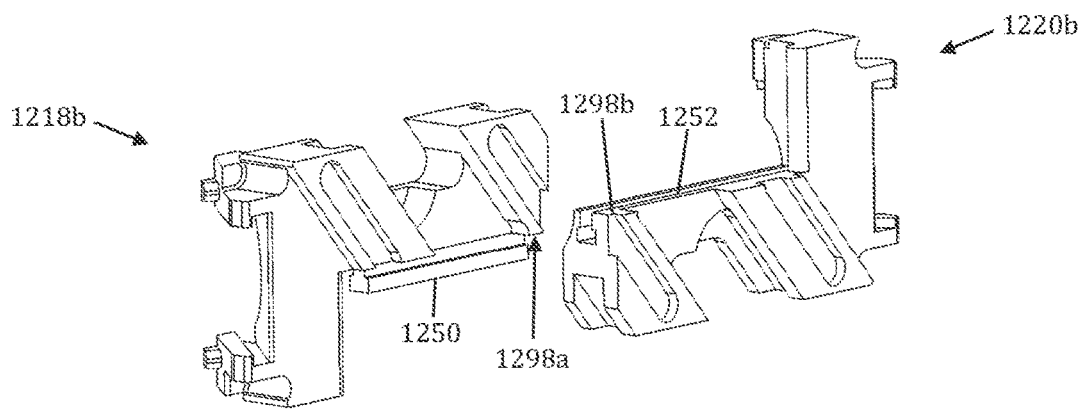
FIG. 69 is a perspective view of an example of proximal and distal ramps forming part of the expandable fusion device of FIG. 66, according to some embodiments.

FIG. 69 illustrates an example of second distal and proximal ramps 1218b, 1220b that have been provided with a dovetail connector to ensure that the expandable fusion device 1210 maintains its structural integrity amid the torsion forces applied to the vertebra (and counter-torsion forces applied to the device 1210 by the vertebra). In the instant embodiment, the distal ramp 1218b includes an elongated dovetail flange 1250 extending along the smooth bottom surface 1298a. The proximal ramp 1220b includes a complementary dovetail channel 1252 formed within the bottom surface 1298b. The elongated dovetail flange 1250 is slideably associated with the dovetail channel 1252 allowing axial translation but preventing other relative movement between the distal and proximal ramps 1218b, 1220b (e.g. rotational movement, etc.).

The expandable fusion device 1210 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1210.

FIGS. 70-75 illustrate an example of an expandable fusion device 1310 for implantation between two adjacent vertebrae according to another embodiment of the disclosure. By way of example only, the expandable fusion device 1310 of the present embodiment includes an actuator 1312, a distal wedge 1314, a proximal wedge 1316, a pair of distal ramps 1318a, 1318b, a pair of proximal ramps 1320a, 1320b, a plurality of endplates 1322a-1322d, and a plurality of guide pins 1323. As with previously-described embodiments, the distal and proximal wedges 1314, 1316 are coupled with the actuator 1312. The distal ramps 1318a, 1318b are slideably coupled with the distal wedge 1314. The proximal ramps 1320a, 1320b are slideably coupled with the proximal wedge 1316. The plurality of endplates 1322a-1322d are slideably coupled with the ramps 1318a, 1318b, 1320a, 1320b. Generally, the expandable fusion device 1310 is substantially similar to expandable fusion device 10 described above, and any/all of the features described above with respect to fusion device 10 (and any other expandable fusion device described herein) may apply to fusion device 1310 unless otherwise noted. By way of example only, the expandable fusion device 1310 is illustrative of one example of a width stabilizer that may be applied to any expandable fusion device examples described herein, according to some embodiments.

Figure 73:
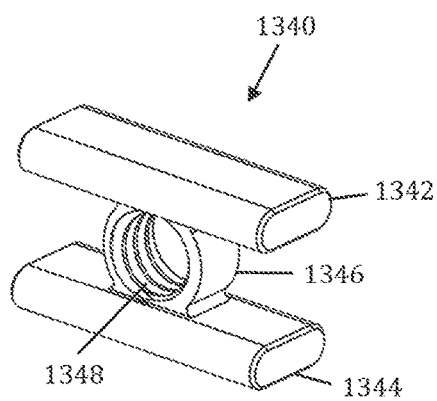
FIG. 73 is a perspective view of an example of a width stabilizer forming part of the expandable fusion device of FIG. 71, according to some embodiments.

Referring first to FIG. 73, one example of a width stabilizer 1340 is shown. By way of example only, the width stabilizer 1340 of the present example comprises a first crossbar 1342 vertically separated from a second crossbar 1344 by an engagement element 1346. The first and second crossbars 1344 may have any cross-sectional shape that ensures the endplates 1322a-1322d remain generally parallel to one another during width expansion, including but not limited to elliptical, rectangular, trapezoidal, polygonal, and the like. The engagement element 1346 may comprise any structural element capable of registering the width stabilizer 1340 to the actuator 1312. By way of example only, the engagement element 1346 of the present embodiment comprises a ring member having a threaded aperture 1348 extending therethrough. The threaded aperture 1348 is sized and configured to allow passage of the actuator 1312 therethrough.

Figure 70:
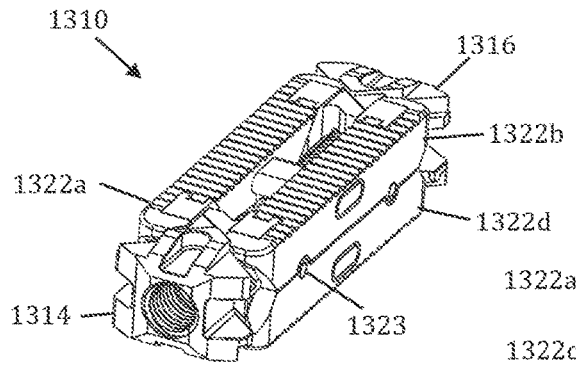
FIG. 70 is a perspective view of another example of an expandable fusion device in a fully collapsed state, according to some embodiments.
Figure 71:
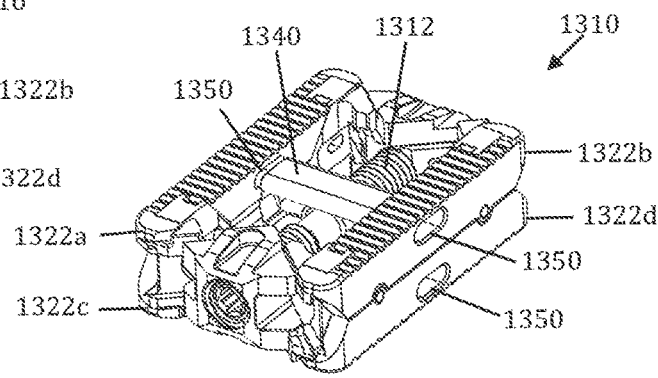
FIG. 71 is a perspective view of the expandable fusion device of FIG. 70 in a width-expanded state, according to some embodiments.
Figure 72:
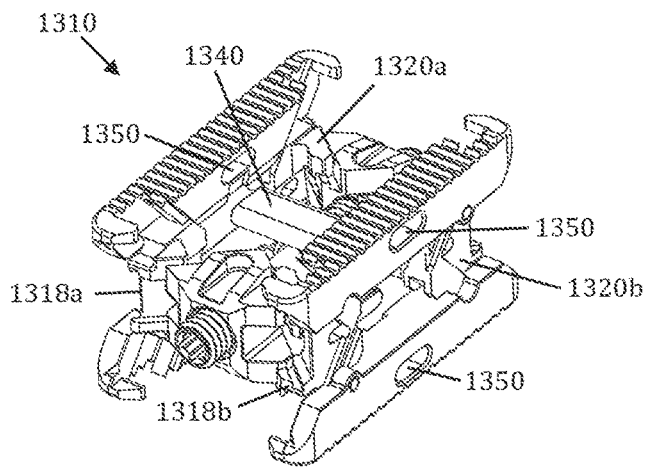
FIG. 72 is a perspective view of the expandable fusion device of FIG. 70 in a fully expanded state, according to some embodiments.
Figure 74:
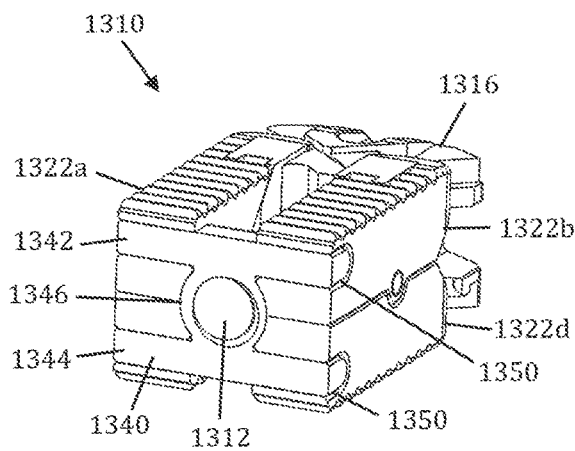
FIGS. 74-75 are sectional views of the expandable fusion device of FIG. 70 in various states of expansion, according to some embodiments.
Figure 75:
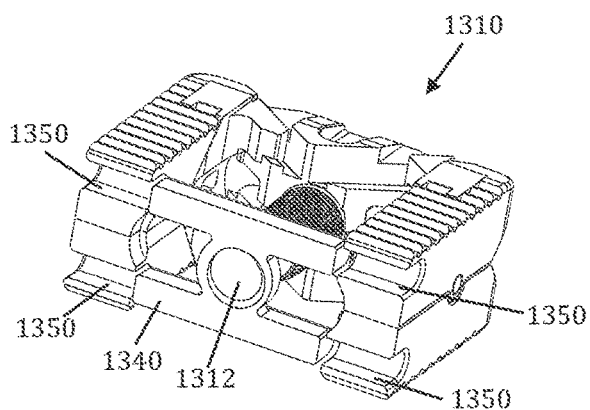
Figure 76:
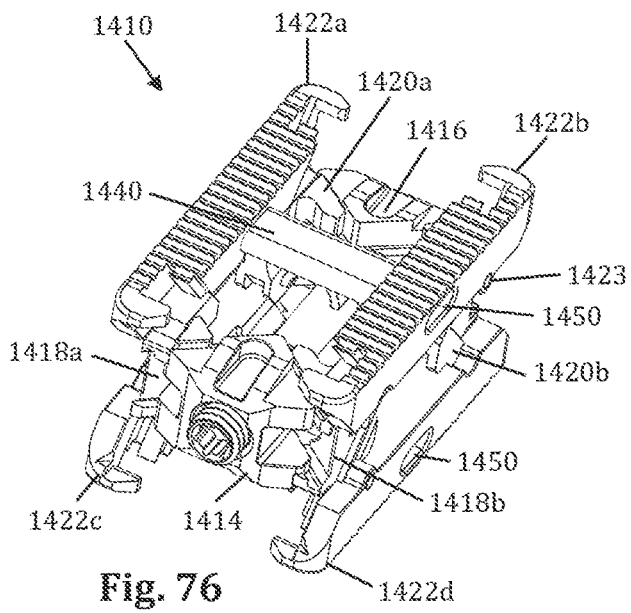
FIG. 76 is a perspective view of another example of an expandable fusion device in a fully expanded state, according to some embodiments.

Referring to FIGS. 70-75, the endplates 1322a-1322d each have a lateral aperture 1350 extending therethrough generally perpendicular to a longitudinal axis of the endplate through which it is formed, the lateral aperture 1350 configured to receive at least a portion of the first or second crossbar 1342, 1344. By way of example, the lateral apertures 1350 are positioned at the midpoints of each endplate, however this position may vary depending on how many width stabilizers are in use and the ramp configuration of the specific embodiment being used. As shown in FIGS. 70 and 74, the lateral apertures 1350 are sized and shaped to snugly receive the crossbars 1342, 1344 therein without allowing for any wiggle motion. This snug interaction maintains the endplates 1322a-1322d in a parallel orientation during width expansion. At the completion of width expansion as shown in FIGS. 71 and 75, the first and second crossbars 1342, 1344 are no longer engaged within the lateral apertures 1350, and height expansion is no longer prohibited (e.g. FIG. 72).

The expandable fusion device 1310 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1310.

FIGS. 76-80 illustrate an example of an expandable fusion device 1410 for implantation between two adjacent vertebrae according to another embodiment of the disclosure. By way of example only, the expandable fusion device 1410 of the present embodiment includes an actuator 1412, a distal wedge 1414, a proximal wedge 1416, a pair of distal ramps 1418a, 1418b, a pair of proximal ramps 1420a, 1420b, a plurality of endplates 1422a-1422d, and a plurality of guide pins 1423. As with previously-described embodiments, the distal and proximal wedges 1414, 1416 are coupled with the actuator 1412. The distal ramps 1418a, 1418*b* are slideably coupled with the distal wedge 1414. The proximal ramps 1420*a*, 1420*b* are slideably coupled with the proximal wedge 1416. The plurality of endplates 1422*a*-1422*d* are slideably coupled with the ramps 1418*a*, 1418*b*, 1420*a*. 1420*b*. Generally, the expandable fusion device 1410 is substantially similar to expandable fusion device 10 described above, and any/all of the features described above with respect to fusion device 10 (and any other expandable fusion device described herein) may apply to fusion device 1410 unless otherwise noted. By way of example only, the expandable fusion device 1410 is illustrative of another example of a width stabilizer that may be applied to any expandable fusion device examples described herein, according to some embodiments.

Figure 77:
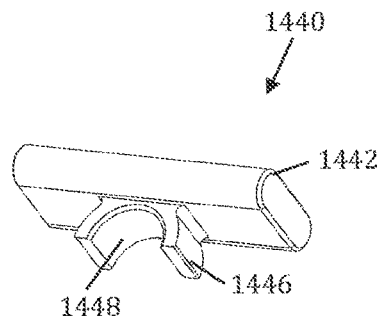
FIG. 77 is a perspective view of an example of a width stabilizer forming part of the expandable fusion device of FIG. 76, according to some embodiments.

Referring first to FIG. 77, one example of a width stabilizer 1440 is shown. By way of example only, the width stabilizer 1440 of the present example comprises a crossbar 1442 and an engagement element 1446. The crossbar 1442 may have any cross-sectional shape that ensures the endplates 1422*a*-1422*d* remain generally parallel to one another during width expansion, including but not limited to elliptical, rectangular, trapezoidal, polygonal, and the like. The engagement element 1446 may comprise any structural element capable of registering the width stabilizer 1440 to the actuator 1412. By way of example only, the engagement element 1446 of the present embodiment comprises a half ring member having an arcuate surface 1448 configured to engage the actuator 1412.

Figure 78:
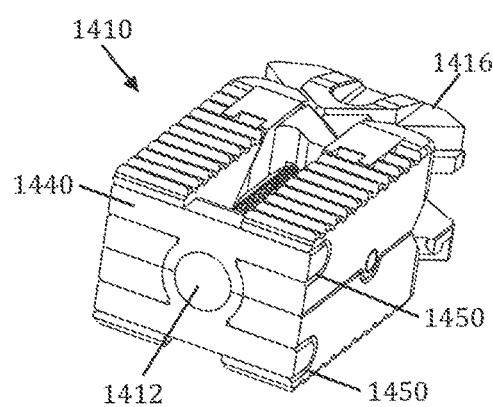
FIGS. 78-80 are sectional views of the expandable fusion device of FIG. 76 in various states of expansion, according to some embodiments.
Figure 79:
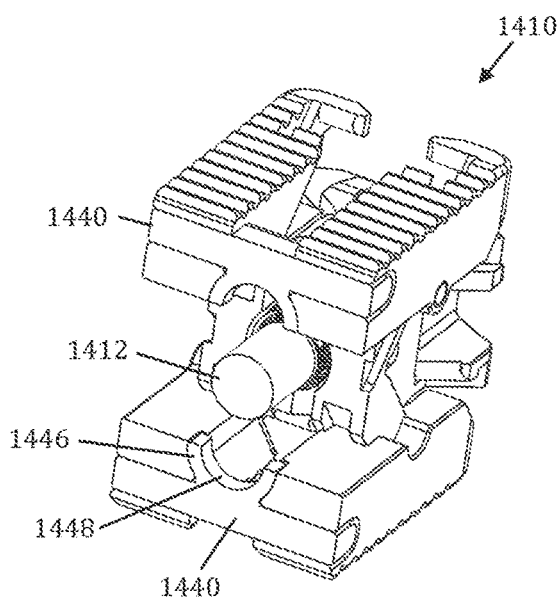
Figure 80:
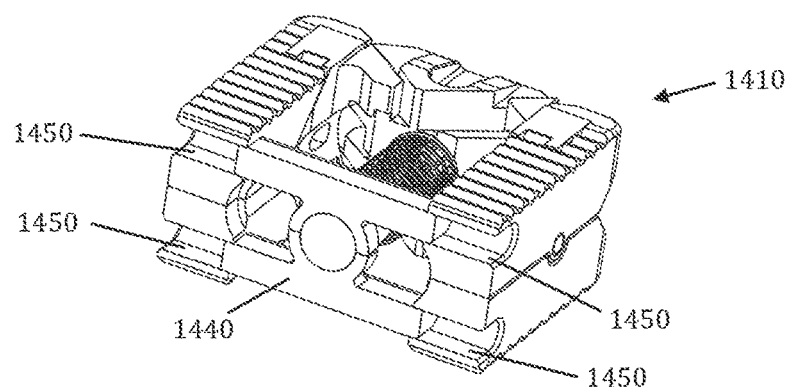

Referring to FIGS. 76-80, the endplates 1422*a*-1422*d* each have a lateral aperture 1450 extending therethrough generally perpendicular relative to a longitudinal axis of the endplate through which it is formed, the lateral aperture 1450 configured to receive at least a portion of the crossbar 1442. By way of example, the lateral apertures 1450 are positioned at the midpoint of each endplate, however this position may vary depending on how many width stabilizers are in use per endplate and the ramp configuration of the specific embodiment being used. Because the width stabilizer 1440 is a single crossbar, a pair of width stabilizers 1440 is used in the current embodiment to force the endplates to remain parallel during width expansion. As shown in FIGS. 78-79, the lateral apertures 1450 are sized and shaped to snugly receive the crossbar 1442 therein without allowing for any wiggle motion. This snug interaction maintains the endplates 1422*a*-1422*d* in a parallel orientation during width expansion. The width stabilizers 1440 of the current example do not inhibit height expansion at any time (see e.g. FIG. 79) because they are not attached to the actuator 1412 as in device 1310 of the previous embodiment. Thus, as shown in FIG. 80, at least a portion of the crossbar 1442 may remain engaged within the lateral apertures 1450 even after completion of width expansion.

The expandable fusion device 1410 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1410.

FIGS. 81-84 illustrate an example of an expandable fusion device 1510 for implantation between two adjacent vertebrae according to another embodiment of the disclosure. By way of example only, the expandable fusion device 1510 of the present embodiment includes an actuator 1512, a distal wedge 1514, a proximal wedge 1516, a pair of distal ramps 1518*a*, 1518*b*, a pair of proximal ramps 1520*a*, 1520*b*, a plurality of endplates 1522*a*-1522*d*, and a (optionally) plurality of guide pins. As with previously-described embodiments, the distal and proximal wedges 1514, 1516 are coupled with the actuator 1512. The distal ramps 1518*a*, 1518*b* are slideably coupled with the distal wedge 1514. The proximal ramps 1520*a*, 1520*b* are slideably coupled with the proximal wedge 1516. The plurality of endplates 1522*a*-1522*d* are slideably coupled with the ramps 1518*a*, 1518*b*, 1520*a*. 1520*b*. Generally, the expandable fusion device 1510 is substantially similar to expandable fusion device 10 described above, and any/all of the features described above with respect to fusion device 10 (and any other expandable fusion device described herein) may apply to fusion device 1510 unless otherwise noted. By way of example only, the expandable fusion device 1510 is illustrative of another example of a width stabilizer that may be applied to any expandable fusion device examples described herein, according to some embodiments.

Figure 84:
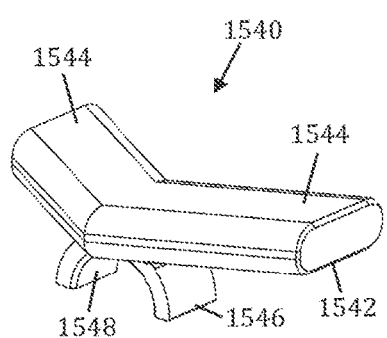
FIG. 84 is a perspective view of an example of a width stabilizer forming part of the expandable fusion device of FIG. 84, according to some embodiments.
Figure 85:
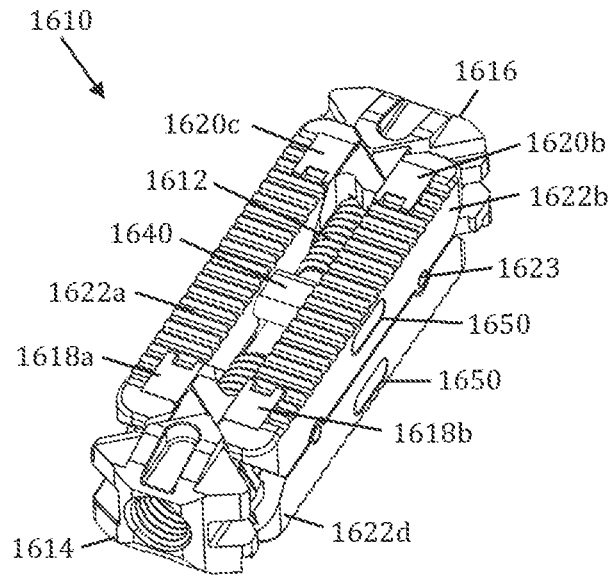
FIG. 85 is a perspective view of another example of an expandable fusion device in a fully collapsed state, according to some embodiments.

Referring first to FIG. 84, one example of a width stabilizer 1540 is shown. By way of example only, the width stabilizer 1540 of the present example comprises a crossbar 1542 and an engagement element 1546. The crossbar 1542 may have any cross-sectional shape that ensures the endplates 1522*a*-1522*d* remain generally parallel to one another during width expansion, including but not limited to elliptical, rectangular, trapezoidal, polygonal, and the like. By way of example, the crossbar 1542 has a generally chevron shape with its apex in the distal direction, and comprises a pair of angled struts 1544. The angled struts 1544 allow the strut components and engagement element 1546 to be centered between the endplates in embodiments with a ramp structure that would preclude straight struts at the midline. Additionally, the angled struts 1544 keep the struts 1544 from disengaging from the lateral apertures 1550 during height expansion. The engagement element 1546 may comprise any structural element capable of registering the width stabilizer 1540 to the actuator 1512. By way of example only, the engagement element 1546 of the present embodiment comprises a half ring member having an arcuate surface 1548 configured to engage the actuator 1512.

Figure 81:
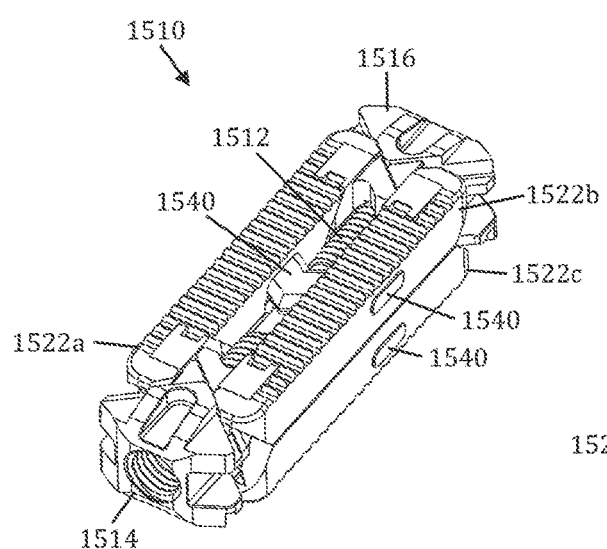
FIG. 81 is a perspective view of another example of an expandable fusion device in a fully collapsed state, according to some embodiments.
Figure 82:
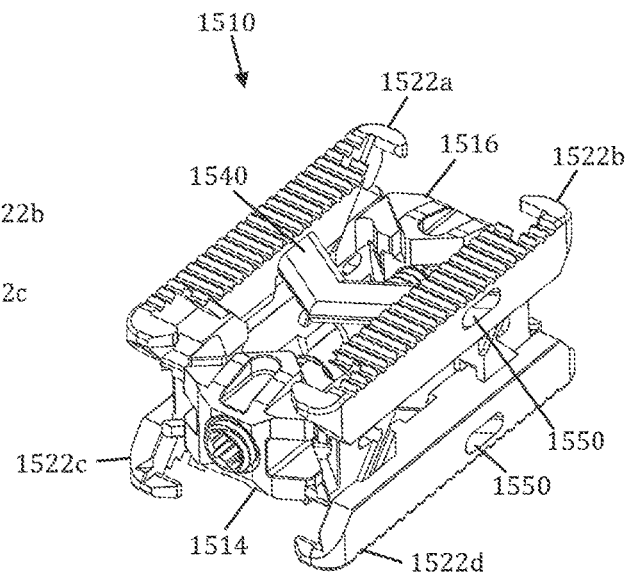
FIG. 82 is a perspective view of the expandable fusion device of FIG. 81 in a fully expanded state, according to some embodiments.
Figure 83:
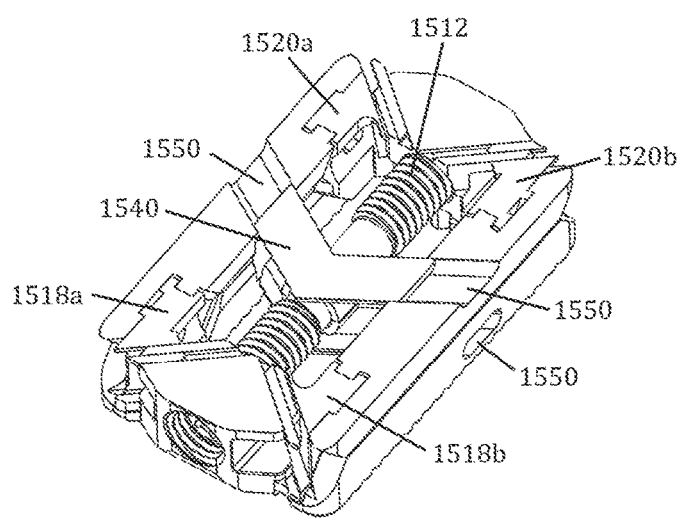
FIG. 83 is a perspective view of the expandable fusion device of FIG. 81 without the endplates in a width-expanded state, according to some embodiments.

Referring to FIGS. 81-84, the endplates 1522*a*-1522*d* each have a lateral aperture 1550 extending therethrough at an oblique angle relative to a longitudinal axis of the endplate through which it is formed, the lateral aperture 1550 configured to receive at least a portion of the crossbar 1542 (e.g. FIG. 83). By way of example, the lateral apertures 1550 are positioned proximal of the midpoint of each endplate but angled toward the centerline of the device 1510, however this position may vary depending on how many width stabilizers are in use per endplate and the ramp configuration of the specific embodiment being used. Because the width stabilizer 1540 is a single crossbar, a pair of width stabilizers 1540 is used in the current embodiment to force the endplates to remain parallel during width expansion. As shown in FIGS. 81 and 83, the lateral apertures 1550 are sized and shaped to snugly receive the crossbar 1542 therein without allowing for any wiggle motion. This snug interaction maintains the endplates 1522*a*-1522*d* in a parallel orientation during width expansion. The width stabilizers 1540 of the current example do not inhibit height expansion at any time because they are not attached to the actuator 1512 as in device 1310 above. Thus, as shown in FIG. 83, at least a portion of the crossbar 1542 may remain engaged within the lateral apertures 1550 even after completion of width expansion.

The expandable fusion device 1510 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1510.

FIGS. 85-88 illustrate an example of an expandable fusion device 1610 for implantation between two adjacent vertebrae according to another embodiment of the disclosure. By way of example only, the expandable fusion device 1610 of the present embodiment includes an actuator 1612, a distal wedge 1614, a proximal wedge 1616, a pair of distal ramps 1618*a*, 1618*b*, a pair of proximal ramps 1620*a*, 1620*b*, a plurality of endplates 1622*a*-1622*d*, and a plurality of guide pins 1623. As with previously-described embodiments, the distal and proximal wedges 1614, 1616 are coupled with the actuator 1612. The distal ramps 1618*a*, 1618*b* are slideably coupled with the distal wedge 1614. The proximal ramps 1620*a*, 1620*b* are slideably coupled with the proximal wedge 1616. The plurality of endplates 1622*a*-1622*d* are slideably coupled with the ramps 1618*a*, 1618*b*, 1620*a*. 1620*b*. Generally, the expandable fusion device 1610 is substantially similar to expandable fusion device 10 described above, and any/all of the features described above with respect to fusion device 10 (and any other expandable fusion device described herein) may apply to fusion device 1610 unless otherwise noted. By way of example only, the expandable fusion device 1610 is illustrative of another example of a width stabilizer that may be applied to any expandable fusion device examples described herein, according to some embodiments.

Figure 86:
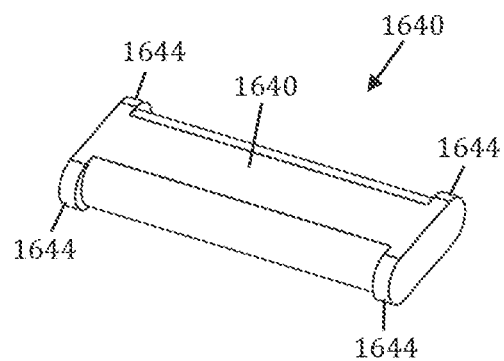
FIG. 86 is a perspective view of an example of a width stabilizer forming part of the expandable fusion device of FIG. 85, according to some embodiments.
Figure 87:
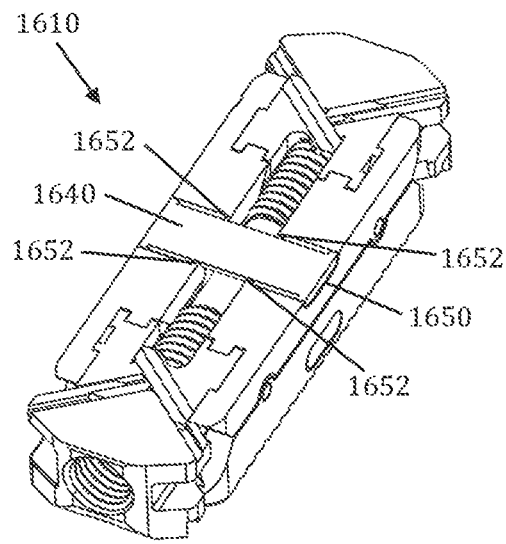
FIGS. 87-88 are perspective views of the expandable fusion device of FIG. 85 in various states of expansion with the endplates removed, according to some embodiments.
Figure 88:
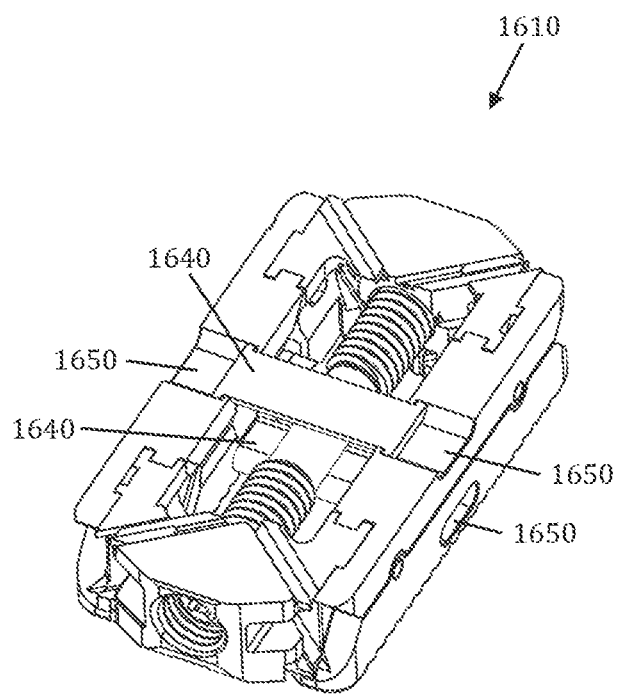
Figure 89:
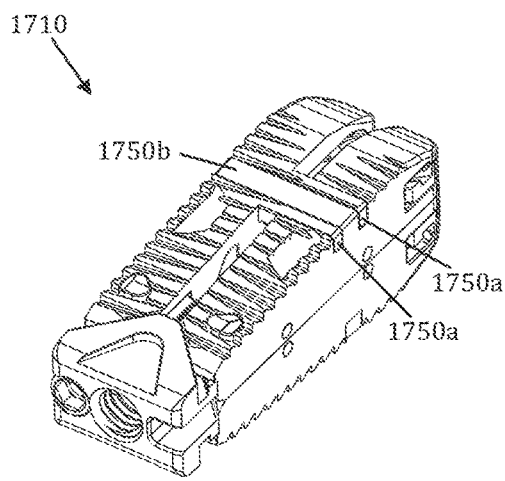
FIG. 89 is a perspective view of another example of an expandable fusion device in a fully collapsed state, according to some embodiments.
Figure 90:
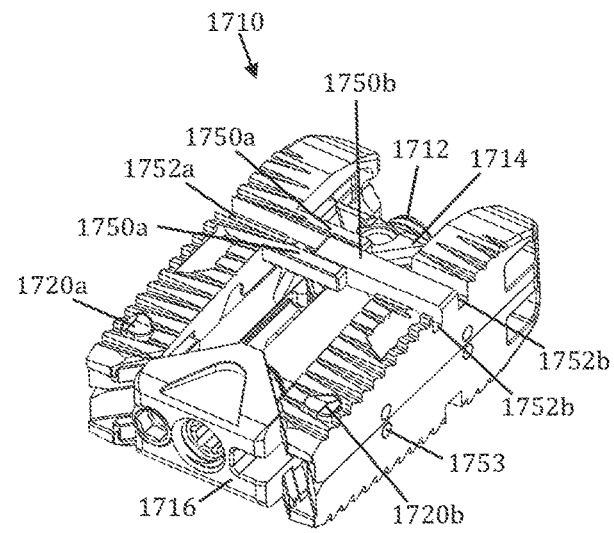
FIG. 90 is a perspective view of the expandable fusion device of FIG. 89 in a width-expanded state, according to some embodiments.
Figure 91:
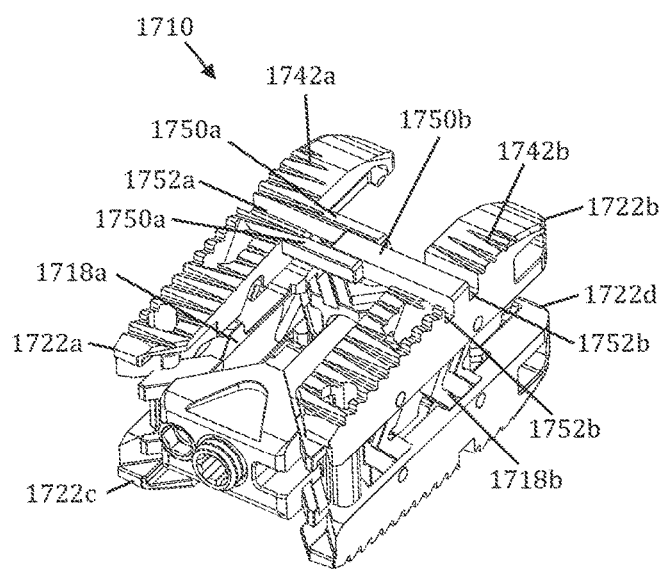
FIG. 91 is a perspective view of the expandable fusion device of FIG. 89 in a fully expanded state, according to some embodiments.

Referring first to FIG. 86, one example of a width stabilizer 1640 is shown. By way of example only, the width stabilizer 1640 of the present example comprises a single linear crossbar 1642 having a pair of lateral flanges 1644 positioned at either end of the crossbar 1642. The crossbar 1642 may have any cross-sectional shape that ensures the endplates 1622*a*-1622*d* remain generally parallel to one another during width expansion, including but not limited to elliptical, rectangular, trapezoidal, polygonal, and the like.

Referring to FIGS. 85-88, the endplates 1622*a*-1622*d* each have a lateral aperture 1650 extending therethrough generally perpendicular relative to a longitudinal axis of the endplate through which it is formed, the lateral aperture 1650 configured to receive at least a portion of the crossbar 1642. The medial opening of the aperture 1650 includes a translation stop 1652 that interacts with the flanges 1644 to prevent the crossbar 1642 from exiting the aperture 1650. The translation stop 1642 not only prevents disassembly but also functions to limit width expansion. To enable insertion of the crossbar 1642 into the lateral apertures 1650 (e.g. past the translation stops 1652), one or more of the flanges 1644 may be formed after assembly for example by swaging the ends of the crossbar 1642, or by pressing, welding, or otherwise attaching the flanges 1644 to the ends of the crossbar 1642. Alternatively, at least one of the lateral flanges 1644 may be at least partially deflectable to enable insertion of the crossbar 1642 into the lateral apertures 1650 of the endplates 1622*a*-1622*d* during assembly of the expandable fusion device 1610. By way of example, the lateral apertures 1650 are positioned at the midpoint of each endplate, however this position may vary depending on how many width stabilizers are in use per endplate and the ramp configuration of the specific embodiment being used. Because the width stabilizer 1640 is a single crossbar, a pair of width stabilizers 1640 is used in the current embodiment to force the endplates to remain parallel during width expansion. The lateral apertures 1450 are sized and shaped to snugly receive the crossbar 1642 therein without allowing for any wiggle motion. This snug interaction maintains the endplates 1622*a*-1622*d* in a parallel orientation during width expansion. The width stabilizers 1640 of the current example do not inhibit height expansion at any time because they are not attached to the actuator 1612 as in device 1310 above.

The expandable fusion device 1610 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1610.

FIGS. 89-99 illustrate an example of an expandable fusion device 1710 for implantation between two adjacent vertebrae according to another embodiment of the disclosure. By way of example only, the expandable fusion device 1710 of the present embodiment includes an actuator 1712, a distal wedge 1714, a proximal wedge 1716, a pair of distal ramps 1718*a*, 1718*b*, a pair of proximal ramps 1720*a*, 1720*b*, a plurality of endplates 1722*a*-1722*d*, and a plurality of guide pins 1723. As with previously-described embodiments, the distal and proximal wedges 1714, 1716 are coupled with the actuator 1712. The distal ramps 1718*a*, 1718*b* are slideably coupled with the distal wedge 1714. The proximal ramps 1720*a*, 1720*b* are slideably coupled with the proximal wedge 1716. The plurality of endplates 1722*a*-1722*d* are slideably coupled with the ramps 1718*a*, 1718*b*, 1720*a*. 1720*b*. Generally, the expandable fusion device 1710 is substantially similar to expandable fusion device 10 described above, and any/all of the features described above with respect to fusion device 10 (and any other expandable fusion device described herein) may apply to fusion device 1710 unless otherwise noted. By way of example only, the expandable fusion device 1710 is illustrative of a width stabilizer that may be applied to any expandable fusion device examples described herein, according to some embodiments.

By way of example only, the width stabilizer 1750 of the present example comprises a plurality of interdigitated protrusions 1750 extending medially from one endplate to nest in grooves 1752 on another endplate. For example, FIGS. 89-91 and 93-94 illustrate an expandable fusion device 1710 having a single protrusion 1750*b* formed in the outer contact surface 1742 of the second upper endplate 1722*b* and extending medially toward the first upper endplate 1722*a*. The single protrusion 1750*b* is received within a complementary groove 1752*a* formed in the outer contact surface 1742 of the first upper endplate 1722*a*, enabling single-axis translation of the protrusion 1750*b* within the groove 1752*a*. Simultaneously, the first upper endplate 1722*a* has a pair of protrusions 1750*a* extending medially toward the second upper endplate 1722*b*. The protrusions 1750*a* are received within complementary grooves 1752*b* formed in the outer contact surface 1742 of the second upper endplate 1722*b*, enabling single-axis translation of the protrusions 1750*a* within the grooves 1752*b*. The protrusions 1750*a* extend on either side of the protrusion 1750*b* and are in flush slideable contact with the protrusion 1752*b*. The grooves 1752*b* are located on either side of the protrusion 1750*b* on the second upper endplate 1722*b*. The nesting of the protrusions 1750 within the grooves 1752 as well as the flush contact between protrusions maintains the endplates in a parallel orientation during width expansion. In some embodiments, the interdigitating protrusions 1750 and, optionally, the complementary grooves 1752 are present only on one pair of endplates (the upper pair or the lower pair) and not the other in order to (among other things) maximize the volume of fusion mass.

Figure 92:
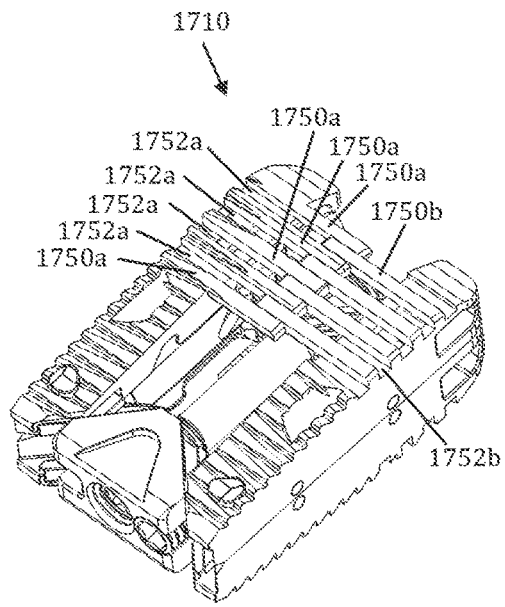
FIG. 92 is a perspective view of the expandable fusion device of FIG. 89 shown with an alternative example of a width stabilizer, according to some embodiments.
Figure 93:
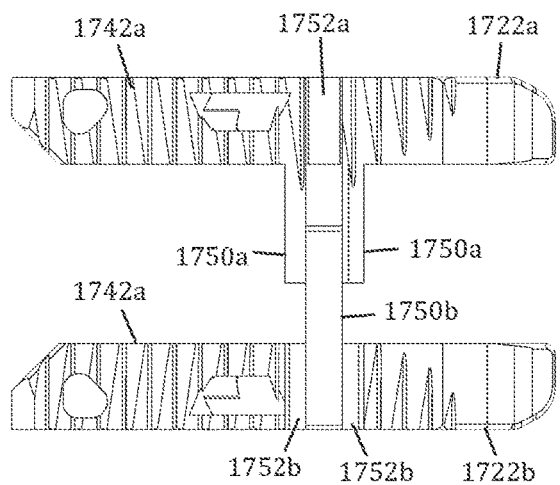
FIGS. 93-94 are top plan and perspective views, respectively, of an upper endplate assembly forming part of the expandable fusion device of FIG. 89, according to some embodiments.
Figure 94:
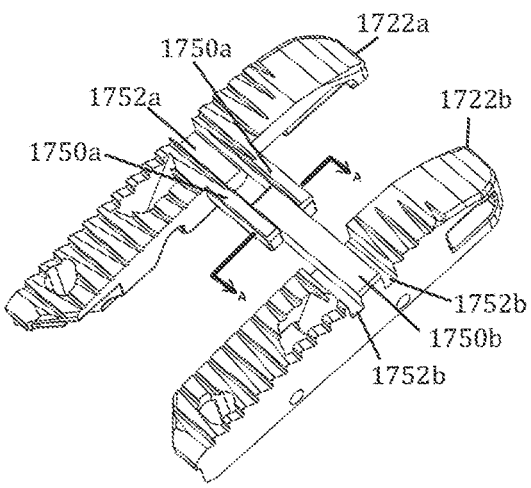

According to the present embodiment, the expandable fusion implant 1710 may be provided with any number of interdigitated protrusions 1750 without departing from the scope of the disclosure. For example, FIG. 92 illustrates an example of an expandable fusion implant 1710 having more than one protrusion 1750 extending from each endplate 1722a, 1722b. By way of example only, the expandable fusion implant 1710 of FIG. 92 includes five protrusions 1750a extending from the first upper endplate 1722a interdigitated with four protrusions 1752b extending from the second upper endplate 1722b. Accordingly, the first upper endplate 1722a includes four complementary grooves 1752a and the second upper endplate 1722b includes five complementary grooves 1752b.

Figure 95:
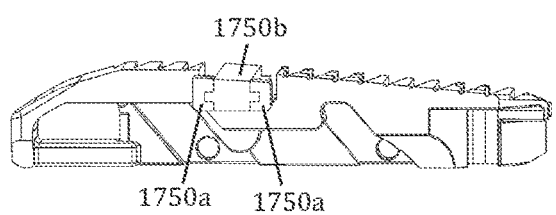
FIGS. 95-99 are sectional views of the upper endplate assembly of FIG. 93 depicting various examples of width stabilizers, according to some embodiments.
Figure 96:
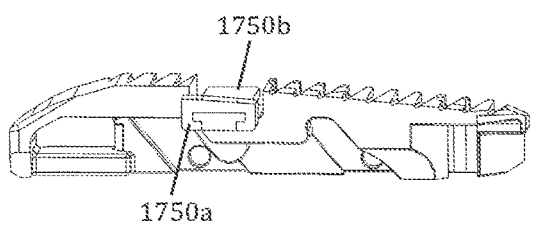
Figure 97:
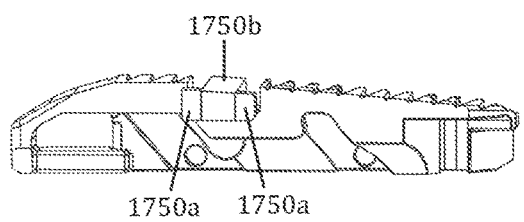
Figure 98:
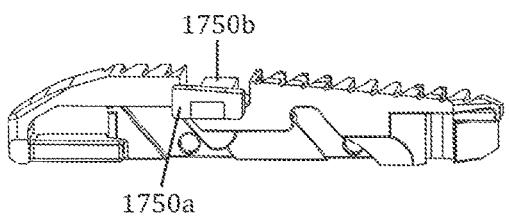
Figure 99:
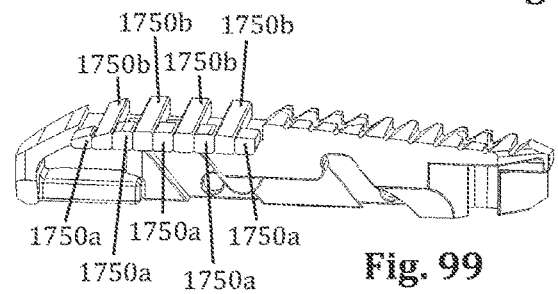

The protrusions 1750 and grooves 1752 may have any cross-sectional shape that ensures the endplates 1722a-1722d remain generally parallel to one another during width expansion, including but not limited to square, rectangular, trapezoidal, polygonal, and the like. Additionally, the protrusions 1750 and grooves 1752 may have a dovetail engagement. FIGS. 95-99 illustrate several examples of protrusion interaction. By way of example only, FIG. 95 illustrates an embodiment in which the protrusion 1750b has a "+" shaped dovetail and protrusions 1750a have corresponding elongated recesses to receive the dovetail. FIG. 96 illustrates an example embodiment in which the protrusion 1750b has a "T" shaped dovetail and protrusions 1750a have corresponding elongated recesses to receive the dovetail. FIG. 97 illustrates the example of FIGS. 89-91 and 93-94 in which the protrusions 1750a and 1750b are simply interdigitated. FIG. 98 illustrates an example embodiment in which the protrusions 1750a include a bridge 1754 that captures protrusion 1750b therein. FIG. 99 shows interdigitation of the embodiment of FIG. 92.

The expandable fusion device 1710 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1710.

FIGS. 100-105 illustrate an example of an expandable fusion device 1810 for implantation between two adjacent vertebrae according to another embodiment of the disclosure. By way of example only, the expandable fusion device 1810 of the present embodiment includes an actuator 1812, a distal wedge 1814, a proximal wedge 1816, a pair of identical distal ramps 1818a, 1818b, a pair of identical proximal ramps 1820a, 1820b, a plurality of endplates 1822a-1822d, and a plurality of optional guide pins 1823. As with previously-described embodiments, the distal and proximal wedges 1814, 1816 are coupled with the actuator 1812. The distal ramps 1818a, 1818b are slideably coupled with the distal wedge 1814. The proximal ramps 1820a, 1820b are slideably coupled with the proximal wedge 1816. The plurality of endplates 1822a-1822d are slideably coupled with the ramps 1818a, 1818b, 1820a, 1820b. Generally, the expandable fusion device 1810 is substantially similar to expandable fusion device 10 described above, and any/all of the features described above with respect to fusion device 10 (and any other expandable fusion device described herein) may apply to fusion device 1810 unless otherwise noted. By way of example only, the expandable fusion device 1810 is illustrative of an expandable fusion device that expands in width and then has lordotic expansion that may be applied to any expandable fusion device examples described herein, according to some embodiments.

By way of example, the actuator 1812, distal wedge 1814, and proximal wedge 1816 may be identical or substantially similar to corresponding elements disclosed herein with respect to other embodiments.

Figure 103:
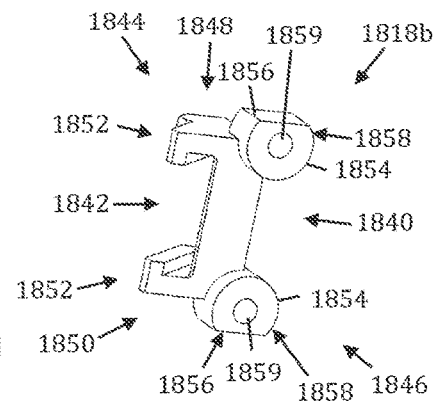
FIG. 103 is a perspective view of an example of a distal ramp forming part of the expandable fusion device of FIG. 100, according to some embodiments.

FIG. 103 illustrates an example of a distal ramp 1818b according to the present example embodiment. By way of example only, the distal ramp 1818b has a proximal end 1840, distal end 1842, medial side 1844, lateral side 1846, upper portion 1848, and lower portion 1850. The distal side of the upper and lower portions 1848, 1850 each have a tongue and groove connector 1852 configured to slideably interact with the corresponding tongue and groove connectors on the distal wedge 1814 as described above. The upper and lower portions 1848, 1850 each have a translation member 1854 positioned on a proximal-lateral corner of the distal ramp 1818b. By way of example only, the translation members 1854 are each generally circular with a generally planar outer facing surface 1856 and an arcuate translation surface 1858. The generally planar outer facing surfaces 1856 are configured to nest within first apertures 1894 on the endplates 1822 when the expandable fusion device 1810 is in the fully collapsed state (e.g. to minimize the height dimension of the collapsed implant for insertion). The translation surface 1856 is configured to slideably engage the angled slot 1886 of the endplate (e.g. endplate 1822b), and furthermore translates along the angled slot 1886 during lordosis expansion. Optionally, at least one of the translation members 1854 may have a guide pin aperture 1859 for receiving a guide pin 1823 therein. The guide pin functions as a lordosis-expansion limiting member as it will stop lordosis expansion when the guide pin 1823 reaches the end of the ramp slot 1888.

Figure 104:
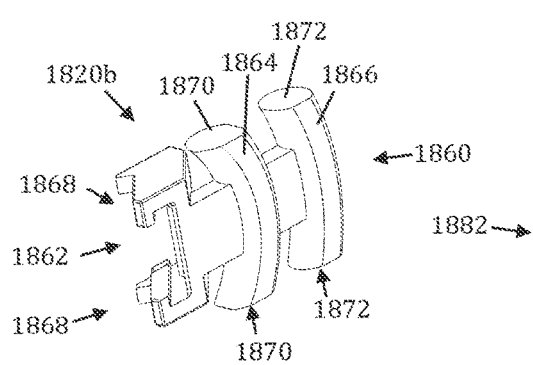
FIG. 104 is a perspective view of an example of a proximal ramp forming part of the expandable fusion device of FIG. 100, according to some embodiments.

FIG. 104 illustrates an example of a proximal ramp 1820b according to the present example embodiment. By way of example only, the proximal ramp 1820b has a distal end 1860 and a proximal end 1862. The proximal ramp 1820b further includes at least one (e.g. first) arc ramp 1864, and optionally a second (or more) arc ramp 1866 (shown by way of example only) positioned distally of the first arc ramp 1864. The arc ramps 1864, 1868 are curved along concentric arcs having a center point in the proximal direction. The arc ramps 1864, 1868 are configured to slideably mate with first and second arc channels 1890, 1892, respectively, of the corresponding endplates 1822 (e.g. endplates 1822b, 1822d). By way of example, the arc ramps 1864, 1868 essentially function as pivot guides during lordosis expansion, but also help hold the expansion angle in place once lordosis expansion is complete. Each arc ramp 1864, 1868 has a pair of outer facing planar surfaces 1870, 1872, respectively, that are configured to nest within first apertures 1896, 1898 on the endplates 1822, respectively, when the expandable fusion device 1810 is in the fully collapsed state (e.g. to minimize the height dimension of the collapsed implant for insertion). The proximal end 1862 includes a pair of tongue and groove connectors 1868 configured to slideably interact with the corresponding tongue and groove connectors on the proximal wedge 1816 as described above.

Figure 100:
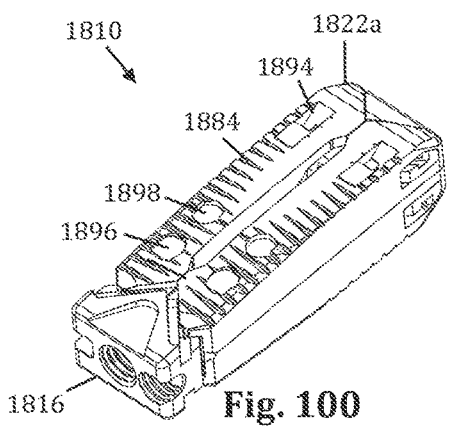
FIG. 100 is a perspective view of another example of an expandable fusion device in a fully collapsed state, according to some embodiments.
Figure 101:
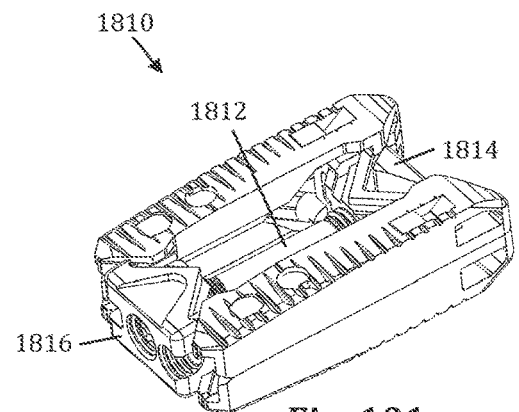
FIG. 101 is a perspective view of the expandable fusion device of FIG. 100 in a width-expanded state, according to some embodiments.
Figure 102:
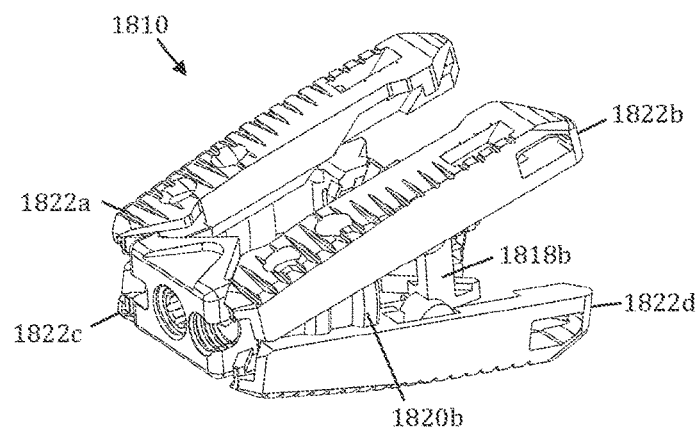
FIG. 102 is a perspective view of the expandable fusion device of FIG. 100 in a fully expanded state, according to some embodiments.
Figure 105:
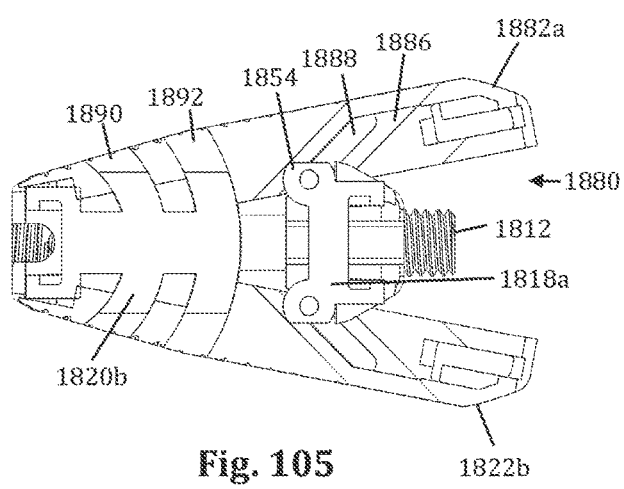
FIG. 105 is a sectional view of the expandable fusion device of FIG. 102, according to some embodiments.

With specific reference to FIGS. 100 & 105, the relevant endplate structure will now be described. By way of example, endplate 1822a will be described, but since each endplate is either identical (e.g. 1822d) to or a mirrored equivalence of (e.g. endplates 1822*b*, 1822*c*) endplate 1822*a*, it should be understood that the described elements are present on each endplate without reservation. By way of example only, the endplate 1822*a* has a distal end 1880, a proximal end 1882, and an outer vertebral contact surface 1884. An angled slot 1886 is formed in the distal portion of endplate 1822*a*, intersecting the outer contact surface 1884 (e.g. at aperture 1894) and angling proximally therefrom. The angled slot 1886 is configured to slideably receive the translation member 1854 of the distal ramp 1818*a* therein to facilitate lordosis expansion. The angled slot 1886 may further include an optional ramp slot 1888 to slideably receive guide pin 1823. The proximal portion of the endplate 1822*a* includes at least one arc channel 1890 (depending on the number of arc ramps as described above), and in the instant example, a second arc channel 1892. The arc channels are oriented in concentric arcs having a center point in a proximal direction, and each intersect the outer contact surface 1884 at an aperture (e.g. apertures 1896, 1898). The arc channels 1890, 1892 are configured to slideably mate with first and second arc ramps 1864, 1866, respectively, of the corresponding proximal ramps 1820*a*, 1820*b* as described above. Thus the arcs of the arc channels 1890, 1892, are equal to the arcs of the respective arc ramps 1864, 1866.

In operation, first width expansion proceeds substantially as described above with respect to previous embodiments. That is, the actuator 1812 is turned a select number of actuations until some width expansion is reached and the endplate disengages from the distal wedge 1814. Once the disengagement occurs, further rotation of the actuator 1812 results in the distal ramps 1818*a*, 1818*b* translating along the respective angled slots in the endplates, increasing at least one of the width, height, and lordosis angle in the process. In other words, actuation of the drive feature in for a first number of actuations in the first actuation direction results in at least some width expansion. Actuation of the drive feature by a second number of actuations beyond the first number of actuations in the first actuation direction then increases at least one of width, height, and lordotic angle.

The expandable fusion device 1810 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1810.

FIGS. 106-113 illustrate an example of an expandable fusion device 1910 for implantation between two adjacent vertebrae according to another embodiment of the disclosure. By way of example only, the expandable fusion device 1910 of the present embodiment includes an actuator 1912, a distal wedge 1914, a proximal wedge 1916, a pair of distal ramps 1918*a*, 1918*b*, a pair of proximal ramps 1920*a*, 1920*b*, a plurality of endplates 1922*a*-1922*d*, and optionally a plurality of guide pins. As with previously-described embodiments, the distal and proximal wedges 1914, 1916 are coupled with the actuator 1912. The distal ramps 1918*a*, 1918*b* are slideably coupled with the distal wedge 1914. The proximal ramps 1920*a*, 1920*b* are slideably coupled with the proximal wedge 1916. The plurality of endplates 1922*a*-1922*d* are slideably coupled with the ramps 1918*a*, 1918*b*, 1920*a*. 1920*b*. Generally, the expandable fusion device 1910 is substantially similar to expandable fusion device 10 described above, and any/all of the features described above with respect to fusion device 10 (and any other expandable fusion device described herein) may apply to fusion device 1910 unless otherwise noted. By way of example only, the expandable fusion device 1910 is illustrative of a lateral lordotic expansion mechanism that may be applied to any expandable fusion device examples described herein, according to some embodiments. By way of example only, the expandable fusion device 1910 of the present embodiment has a posterior side 1936 and an anterior side 1934.

Figure 110:
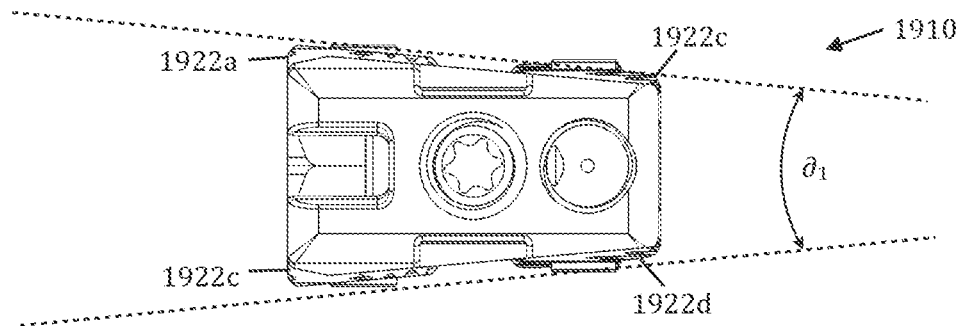
FIGS. 110-113 are a plan views of the expandable fusion device of FIG. 106 in various states of expansion, according to some embodiments.
Figure 111:
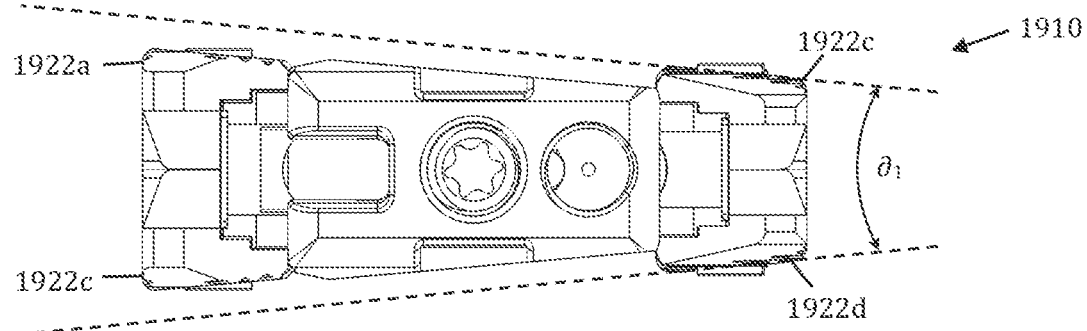
Figure 112:
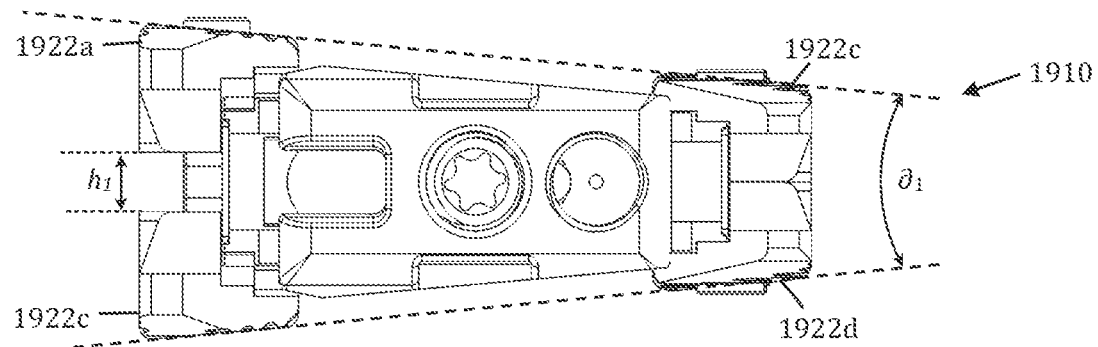
Figure 113:
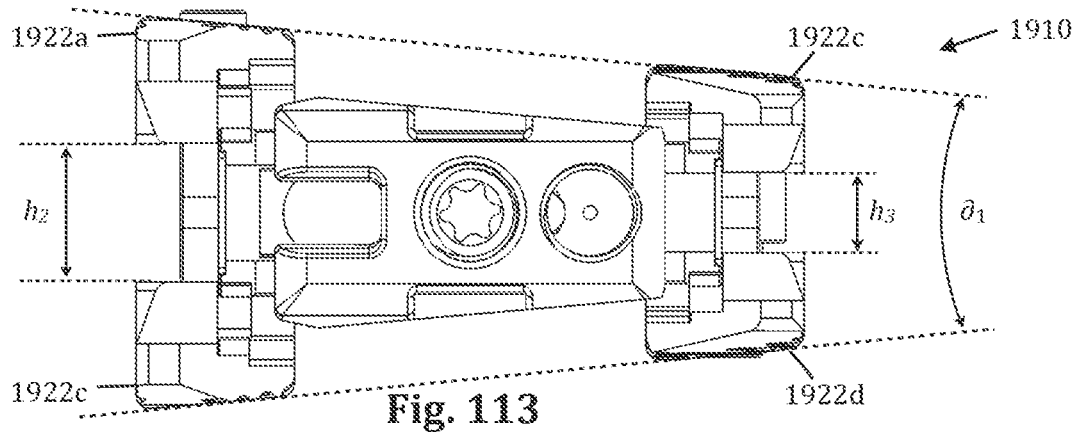
Figure 114:
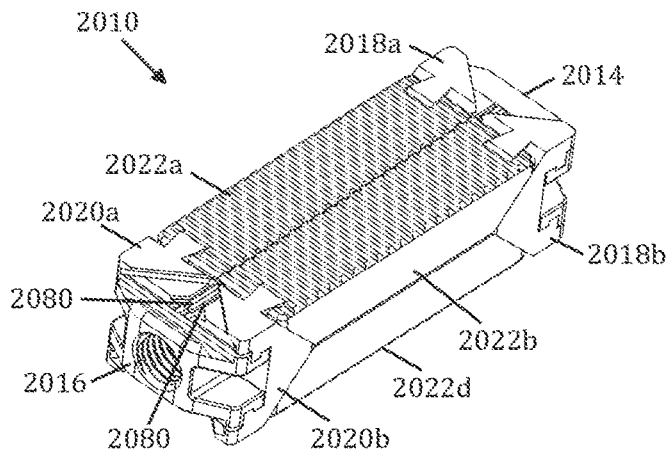
FIG. 114 is a perspective view of another example of an expandable fusion device in a fully collapsed state, according to some embodiments.
Figure 115:
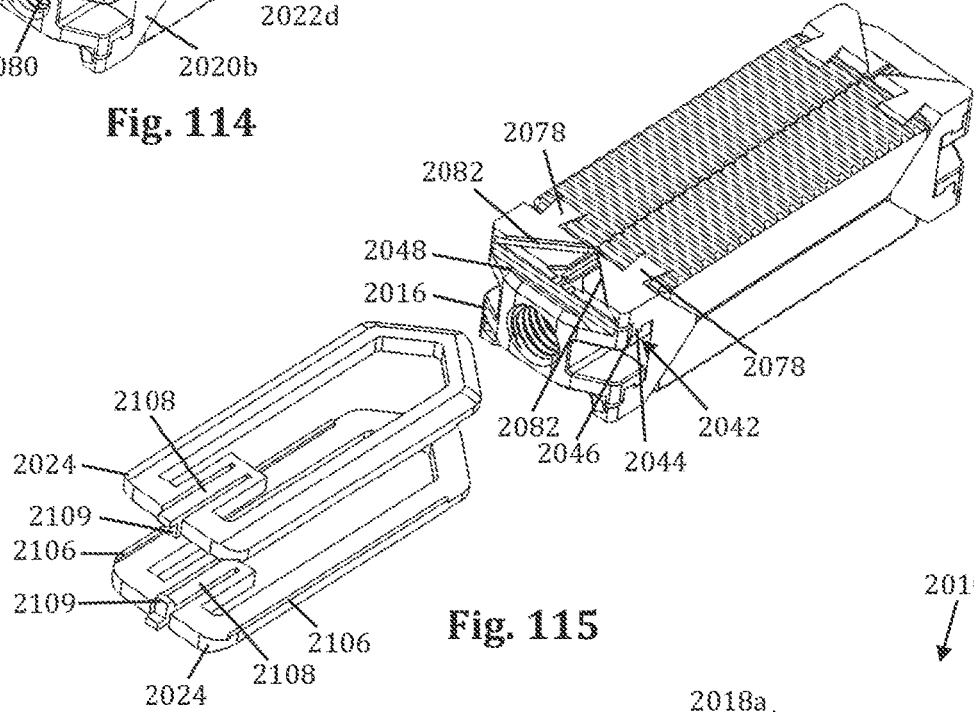
FIGS. 115-118 are perspective views of the expandable fusion device in FIG. 114 in various states of expansion, according to some embodiments.
Figure 116:
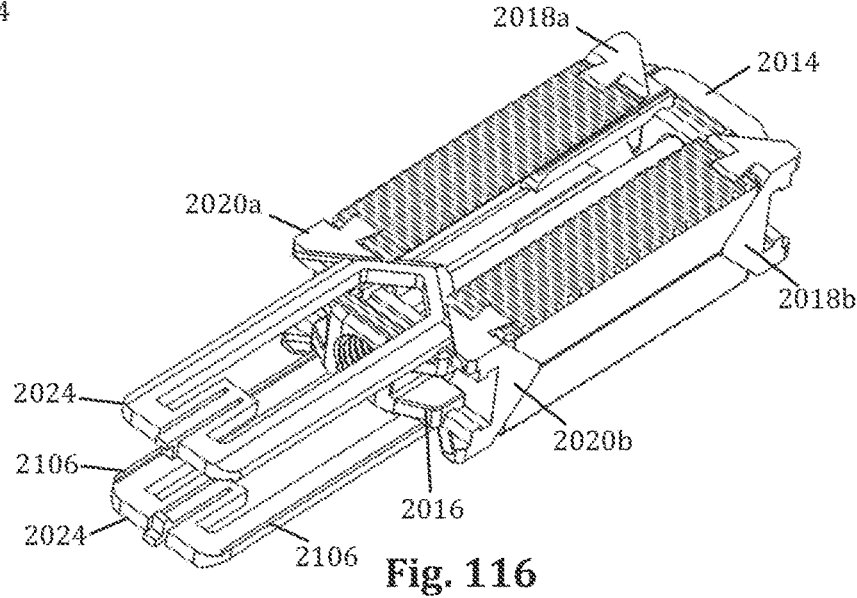
Figure 117:
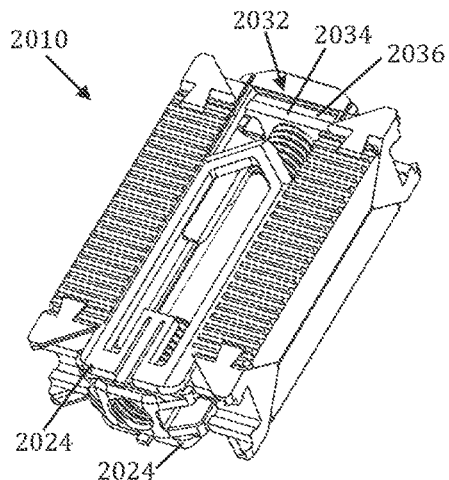
Figure 118:
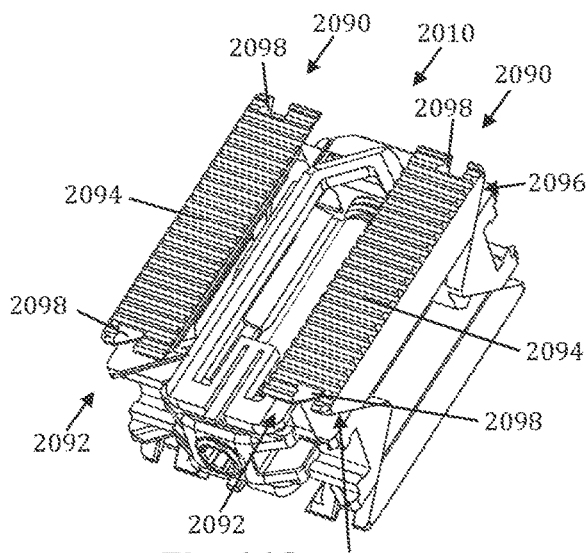
Figure 119:
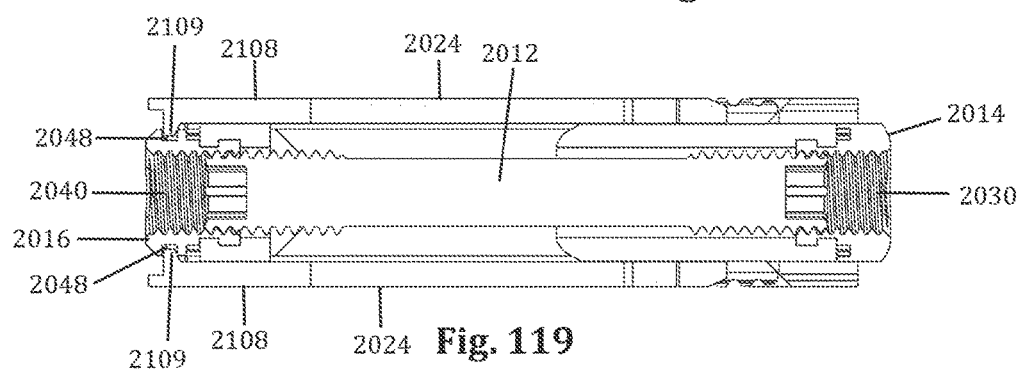
FIGS. 119-120 are sectional views of the expandable fusion device of FIG. 114, according to some embodiments.
Figure 120:
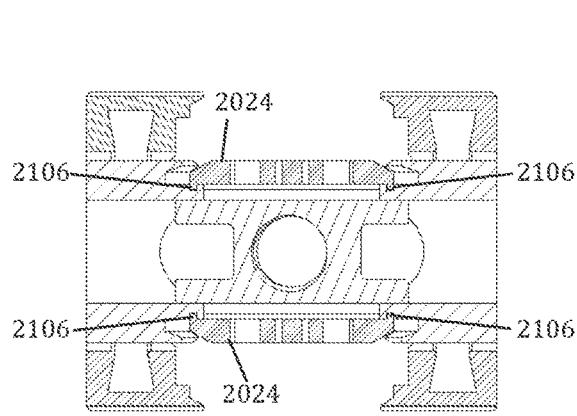
Figure 121:
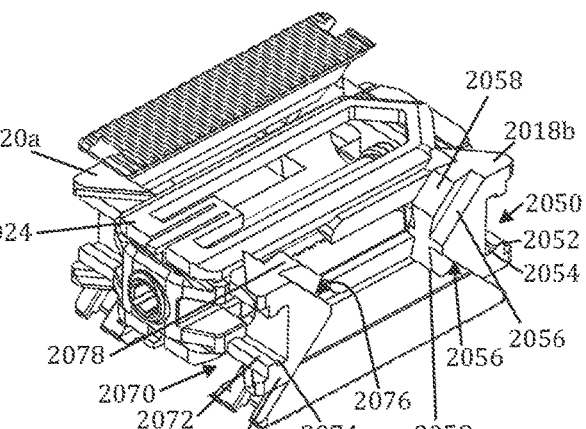
FIG. 121 is a perspective view of the expandable fusion device of FIG. 114 with an endplate removed, according to some embodiments.
Figure 122:
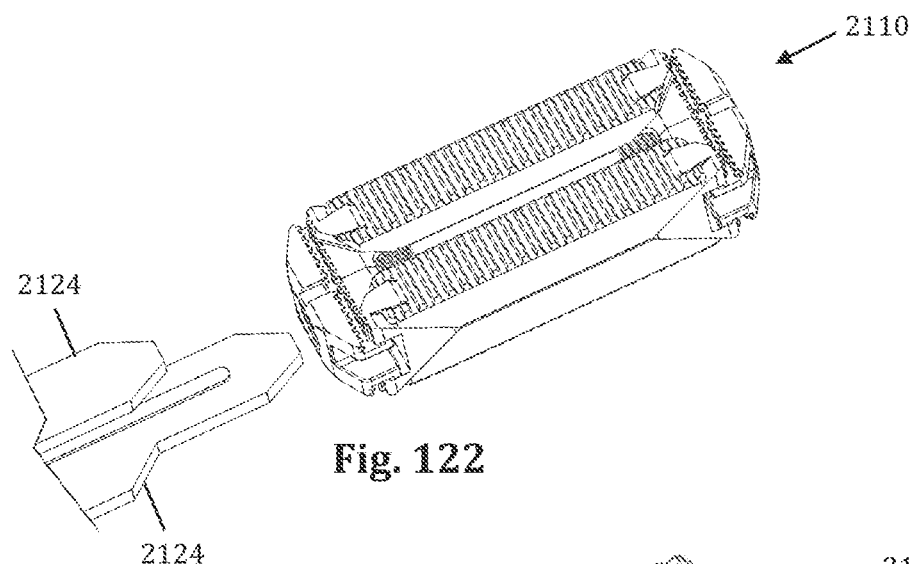
FIG. 122 is a perspective view of another example of an expandable fusion device in a fully collapsed state, according to some embodiments.
Figure 123:
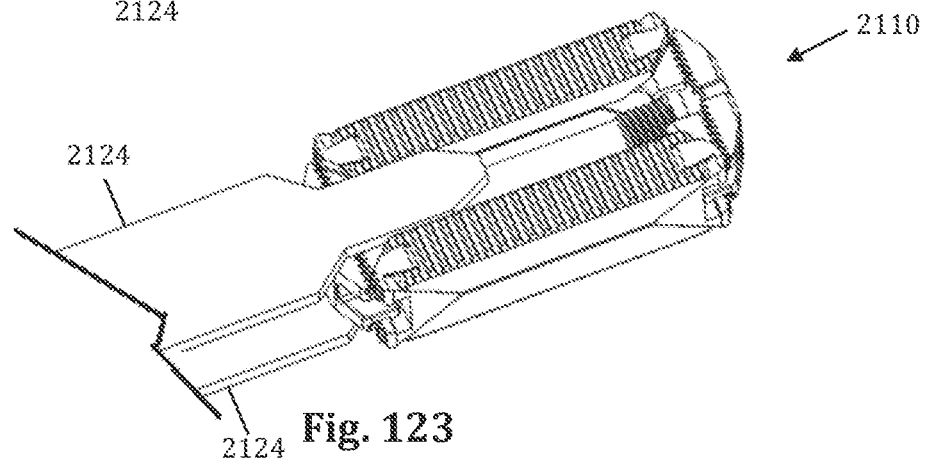
Figure 124:
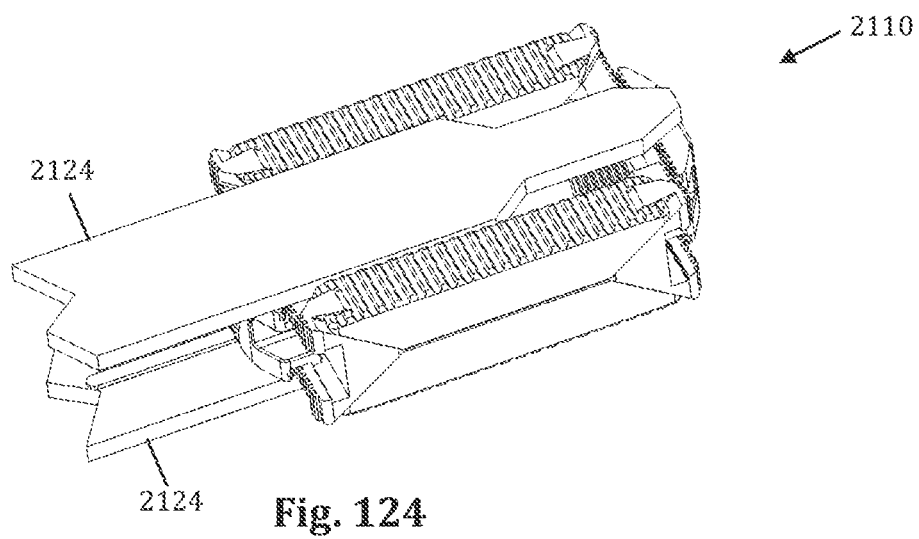

The expandable fusion implant 1910 is configured to have a preselected lateral lordotic angle when in the fully collapsed position such that when the device 1910 is initially inserted into the intervertebral space, the lordotic angle $\partial 1$ of the implant matches the lordosis of the spine at the surgical target site (e.g. FIG. 110). Also, it should be noted that the outer contact surfaces of the upper endplates 1922*a*, 1922*b*, and the outer contact surfaces of the lower endplates 1922*c*, 1922*d*, may be generally coplanar in a plane defined by the lordotic angle $\partial 1$. This is accomplished by having a posterior endplate pair (e.g. endplates 1922*b*, 1922*d*) that are each thicker than the anterior endplate pair (e.g. endplates 1922*a*, 1922*c*) so that the posterior side of the implant may have a greater height dimension than the anterior side. A challenge that occurs with expandable implants, however, is that during width expansion, as the posterior endplates move away from the anterior endplates, the lordotic angle of the implant decreases and the relevant outer contact surfaces are no longer coplanar (e.g. FIG. 111). Subsequent height expansion will not fix the problem if the endplates increase in height at the same rate. To solve this problem, expandable fusion device 1910 of the present example is configured to delay the height expansion of the anterior pair of endplates (e.g. 1922*b*, 1922*c*) until the posterior pair of endplates (e.g. 1922*b*, 1922*d*) has expanded in height (h1) enough to re-establish the desired lordotic angle $\partial 1$ (e.g. FIG. 112) and bring the outer contact surfaces of the upper and lower endplate pairs into alignment. Once this occurs, the anterior pair of endplates 1922*a*, 1922*c* expand in height at the same rate as the posterior endplates 1922*b*, 1922*d*, and still maintain the desired lordotic angle $\partial 1$. Thus the maximum height expansion (h2) of the posterior endplates 1922*c*, 1922*d* will be greater than the maximum height expansion (h3) of the anterior endplates 1922*a*, 1922*c* (e.g. FIG. 113).

By way of example, the actuator 1912, distal wedge 1914, proximal wedge 1916, distal ramps 1918*a*, 1918*b*, and proximal ramps 1920*a*, 1920*b* may be identical or substantially similar to corresponding elements disclosed herein with respect to other embodiments, and therefore their specific structure will not be described unless necessary.

By way of example, the endplates comprise posterior endplates 1922*c*, 1922*d*, and anterior endplates 1922*a*, 1922*c*. Endplate 1922*a* will be described herein as representative of the anterior endplates, as endplate 1922*c* is identical or a mirrored equivalent and has the same elements as endplate 1922*a*. By way of example, the first anterior endplate 1922*a* has a distal end 1930, a proximal end 1932, an outer facing contact surface 1937*a* and a plurality of angled slots (not shown, but same or similar as previously described) that interact with inclined surfaces on the distal and proximal ramps 1918*a*, 1920*a* (not shown, but same or similar as previously described) to facilitate height expansion in the same manner as described previously with respect to other embodiments. By way of example only, in the instant embodiment the plurality of angled slots comprises a first distal angled slot that intersects with the outer facing contact surface 1937*a* at a first distal aperture 1946*a*, a second distal angled slot that intersects with the outer facing contact surface 1937*a* at a first distal aperture 1948*a*, a first proximal angled slot that intersects with the outer facing contact surface 1937*a* at a first proximal aperture 1950*a*, and a second proximal angled slot that intersects with the outer facing contact surface 1937*a* at a second proximal aperture 1952*a*. Prior to height expansion (regardless of width expansion), the relevant portions of the distal ramp 1918*a* (e.g. the first and second lobes) flushly contact the angled surfaces of the endplate 1922*a* so that height expansion may begin as soon as the endplate 1922*a* dissociates from the wedges 1914, 1916.

By way of example, endplate 1922*b* will be described herein as representative of the posterior endplates, as endplate 1922*d* is identical or a mirrored equivalent and has the same elements as endplate 1922*b*. By way of example the first posterior endplate 1922*b* has a distal end 1930, a proximal end 1932, an outer facing contact surface 1937*b* and a plurality of angled slots (not shown, but same or similar as previously described) that interact with inclined surfaces on the distal and proximal ramps 1918*b*, 1920*b* (not shown, but same or similar as previously described) to facilitate height expansion in the same manner as described previously with respect to other embodiments. By way of example only, in the instant embodiment the plurality of angled slots comprises a first distal angled slot that intersects with the outer facing contact surface 1937*b* at a first distal aperture 1946*b*, a second distal angled slot that intersects with the outer facing contact surface 1937*b* at a first distal aperture 1948*b*, a first proximal angled slot that intersects with the outer facing contact surface 1937*b* at a first proximal aperture 1950*b*, and a second proximal angled slot that intersects with the outer facing contact surface 1937*b* at a second proximal aperture 1952*b*. Prior to height expansion (regardless of width expansion), the relevant portions of the distal ramp 1918*a* (e.g. the first and second lobes) are spaced apart from the angled surfaces of the endplate 1922*b* by a gap 1954 so that height expansion may be delayed until the endplate 1922*a* reaches a sufficient height to restore the lordotic angle of the device 1910. Because of the gap 1954, the anterior ramps 1918*b*, 1920*b* are able to translate at the same rate as the posterior ramps 1918*a*, 1920*a*, but the ramps must traverse the gap 1954 before the inclined surfaces on the ramps engage the inclined surfaces of the endplates. Once that happens, height expansion of the posterior side 1936 occurs.

Due to the elongated nature of the endplates in a lateral expandable fusion device, it may desirable to have a vertical stabilization feature to ensure the middle of the implant aligned during expansion. By way of example, FIG. 109 illustrates one example of first and second vertical stabilizers 1960, 1970 for use with the expandable fusion device 1910 of the present embodiment. By way of example, the first vertical stabilizer 1960 comprises a post 1962 associated with the upper posterior endplate 1922*a* that extends vertically toward the lower posterior endplate 1922*c* such that it is received within a vertical channel 1964 formed within the endplate 1922*c*. By way of example only, the post 1962 is immovably associated with the endplate 1922*a* (e.g. integrally formed, press-fit or otherwise secured within a corresponding recess, etc.) and slideably associated with the channel 1964. The post 1962 and corresponding channel 1964 may have any cross-sectional shape capable of maintaining alignment, including but not limited to circular, oval, elliptical, square, polygonal, irregular, etc. In some embodiments, the location of the post 1962 an channel 1964 may be reversed such that the post 1962 is provided on the lower posterior endplate 1922*c* and the corresponding channel is formed within the upper posterior endplate 1922*a*. Furthermore, although shown as having one vertical stabilizer 1960 on the posterior side, it should be understood that the expandable fusion device 1910 may have any number of vertical stabilizers without departing from the scope of the disclosure.

By way of example, the second vertical stabilizer 1970 comprises a post 1972 associated with the lower anterior endplate 1922*d* that extends from a recess 1974 formed within the lower anterior endplate 1922*d* vertically toward the upper anterior endplate 1922*b*. The second vertical stabilizer 1970 further comprises a sleeve 1976 associated with the upper anterior endplate 1922*b*, the sleeve having an elongated side(s) 1978 and a channel 1980 configured to slideably receive the post 1972 therein. By way of example only, the post 1972 is immovably associated with the endplate 1922*d* (e.g. integrally formed, press-fit or otherwise secured within a corresponding recess, etc.). Similarly, the sleeve 1976 is immovably associated with the endplate 1922*b* (e.g. integrally formed, press-fit or otherwise secured within a corresponding recess, etc.). The elongated sides 1978 are sized and configured to engage the recess 1974 surrounding the post 1972. The sleeve 1976 functions to extend the length of the channel 1980 to ensure that the post 1972 does not dissociate from the channel 1980 during vertical expansion. By way of example, the post 1972 and corresponding channel 1980 may have any complimentary cross-sectional shape capable of maintaining alignment, including but not limited to circular, oval, elliptical, square, polygonal, irregular, etc. Similarly, the sleeve 1976 and corresponding recess 1974 may have any complimentary cross-sectional shape capable of maintaining alignment, including but not limited to circular, oval, elliptical, square, polygonal, irregular, etc. Furthermore, although shown as having one vertical stabilizer 1970 on the anterior side, it should be understood that the expandable fusion device 1910 may have any number of vertical stabilizers without departing from the scope of the disclosure.

In operation, first width expansion proceeds substantially as described above with respect to previous embodiments. That is, the actuator 1912 is turned a select number of actuations until at least some width expansion (and in some embodiments—exclusively width expansion) is reached and the endplate disengages from the distal wedge 1914. Once the disengagement occurs, further rotation of the actuator 1912 then increases at least one of width, height, and lordotic angle. It is further envisioned, that in other embodiments, the first number of actuations of the actuator 1912 may result in at least some height expansion (and in some embodiments—exclusively height expansion), whereas further rotation of the actuator 1912 then increases at least one of width, height, and lordotic angle.

The expandable fusion device 1910 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1910.

FIGS. 114-121 illustrate an example of an expandable fusion device 2010 for implantation between two adjacent vertebrae according to another embodiment of the disclosure. By way of example only, the expandable fusion device 2010 of the present embodiment includes an actuator 2012, a distal wedge 2014, a proximal wedge 2016, a pair of distal ramps 2018*a*, 2018*b*, a pair of proximal ramps 2020*a*, 2020*b*, a plurality of endplates 2022*a*-2022*d*, and a plurality (but at least one) of expansion shims 2024. As with previously-described embodiments, the distal and proximal wedges 2014, 2016 are coupled with the actuator 2012. The distal ramps 2018a, 2018b are slideably coupled with the distal wedge 2014. The proximal ramps 2020a, 2020b are slideably coupled with the proximal wedge 2016. The plurality of endplates 2022a-2022d are slideably coupled with the ramps 2018a, 2018b, 2020a. 2020b. By way of example only, the expandable fusion device 2010 is illustrative of an independent width expansion mechanism that may be applied to any expandable fusion device examples described herein, according to some embodiments. Generally, width expansion is achieved by manually inserting a pair of expansion shims 2024 corresponding to the desired width expansion between the proximal ramps 2020a, 2020b, which forces the endplates 2012a-2012d and the distal ramps 2018a, 2018b laterally apart. Height expansion is achieved by turning the actuator 2012, which causes the wedges 2014, 2016 to advance toward one another. This in turn causes distal ramps 2018a, 2018b to move toward the proximal ramps 2020a, 2020b, which causes the upper and lower endplate pairs to be displaced vertically. Width expansion and height expansion occur independently of one another, and one is not necessarily a prerequisite for the other. In some embodiments, the width expansion shims 2024 may exert width-expanding forces onto the endplates, and not the ramps. In some embodiments, the width expansion shims 2024 may exert width-expanding forces onto the ramps, and not the endplates. In some embodiments, the shims 2024 may exert width-expanding forces onto the upper pair of endplates and/or the lower pair of endplates, as well as dove-tail into such pairs of endplates to prevent further width expansion, such that each shim would then also be detained in at least one of the endplates against back-out and would travel up and down with its respective pair of endplates during height expansion and height collapse.

By way of example only, the actuator 2012 is identical or substantially similar to actuator 12 described above, and therefore its specific structure will not be described unless necessary.

By way of example, the distal wedge 2014 may be a generally rectangular member having a central threaded aperture 2030 configured to threadedly receive the threaded distal end of the actuator 2012 therein. The top and bottom sides each include a transverse tongue and groove connector 2032 for configured to slideably mate with a corresponding tongue and groove connector on the distal ramps 2018a, 2018b. By way of example, the tongue and groove connector 2032 comprises a transverse ridge 2034 and a transverse slot 2036, each extending at least substantially the width of the proximal side of the distal wedge 2014.

The proximal wedge 2016 may be a generally rectangular member having a central threaded aperture 2040 configured to threadedly receive the threaded proximal end of the actuator 2012 therein. The top and bottom sides each include a transverse tongue and groove connector 2042 for configured to slideably mate with a corresponding tongue and groove connector on the proximal ramps 2020a, 2020b. By way of example, the tongue and groove connector 2042 comprises a transverse ridge 2044 and a transverse slot 2046, each extending at least substantially the width of the distal side of the proximal wedge 2016. The top and bottom sides each include a second transverse slot 2048 on the proximal side of the proximal wedge 2016, the second transverse slot 2048 configured to receive flange 2109 of the shims 2024 therein.

By way of example only, the distal ramps 2018a, 2018b each include a pair of distal facing transverse tongue and groove connectors 2050 including a transverse ridge 2052 and a transverse slot 2054, the tongue and groove connectors 2050 configured to mate with the tongue and groove connectors 2032 of the distal wedge 2014 to provide a secure interface between the distal wedge 2014 and the distal ramps 2018a, 2018b. The distal ramps 2018a, 2018b each include a pair of proximal-facing inclined surfaces 2056 which interact with the distal angled surfaces 2096 of the endplates 2022a-2022d. Dovetail protrusions 2058 slideably mate with the dovetail slots 2098 at the distal end of the endplates to register the distal ends of the endplates to the distal ramps 2018a, 2018b. The distal ramps 2018a, 2018b may further each include a medial tongue and groove connector 2060 extending parallel to the longitudinal axis of the device 2010 and configured to engage the elongated lips 2106 of the expansion shims 2024 to guide the shims 2024 as they are being inserted.

By way of example only, the proximal ramps 2020a, 2020b each include a pair of distal facing transverse tongue and groove connectors 2070 including a transverse ridge 2072 and a transverse slot 2074, the tongue and groove connectors 2070 configured to mate with the tongue and groove connectors 2042 of the proximal wedge 2016 to provide a secure interface between the proximal wedge 2016 and the proximal ramps 2020a, 2020b. The proximal ramps 2020a, 2020b each include a pair of distal-facing inclined surfaces 2076 which interact with the proximal angled surfaces 2096 of the endplates 2022a-2022d. Dovetail protrusions 2078 slideably mate with the dovetail slots 2098 at the proximal end of the endplates to register the proximal ends of the endplates to the proximal ramps 2020a, 2020b. The proximal ramps 2020a, 2020b may further each include a medial tongue and groove connector 2080 extending parallel to the longitudinal axis of the device 2010 and configured to engage the elongated lips 2106 of the expansion shims 2024 to guide the shims 2024 as they are being inserted. The proximal ramps 2020a, 2020b further each include inwardly angled guide surfaces 2082 at the medial-proximal corner to engage with the tapered distal end 2102 of the expansion shims 2024 to force the ramps 2020a, 2020b apart during shim 2024 insertion to effect width expansion.

By way of example only, the endplates 2022a-2022d each include a distal end 2090, proximal end 2092, and an outer vertebral contact surface 2094. Each distal end 2090 includes a distal-facing inclined surface 2096 configured to slideably mate with the inclined surfaces 2056 of the distal ramps 2018a, 2018b to facilitate height expansion. Each distal end 2090 further includes a dovetail slot 2098 configured to slideably mate with the dovetail protrusions 2058 on the distal ramps 2018a, 2018b to register the distal ends of the endplates to the distal ramps 2018a, 2018b. Each proximal end 2092 includes a proximal-facing inclined surface 2096 configured to slideably mate with the inclined surfaces 2076 of the proximal ramps 2020a, 2020b to facilitate height expansion. Each proximal end 2092 further includes a dovetail slot 2098 configured to slideably mate with the dovetail protrusions 2078 on the proximal ramps 2020a, 2020b to register the proximal ends of the endplates to the proximal ramps 2020a, 2020b.

By way of example only, the expansion shims 2024 each include a proximal end 2100, tapered distal end 2102, and parallel sides 2104 (though it is envisioned that in other embodiments, the shims may be stepped and comprise 2 or more pairs of parallel sides forming 2 or more areas of different shim width). The parallel sides 2104 each include an elongated lip 2106 extending toward the actuator 2012 and configured to mate with the longitudinal tongue and groove connectors 2060, 2080 to maintain alignment during insertion. Optionally, the mating tongue and groove connectors may be on the endplates instead of the ramps. The proximal end 2100 includes a deflectable pall 2108 including a vertical flange 2109 at the proximal end of the pall 2108. When the expansion shim 2024 becomes fully inserted into the device 2010, the vertical flange 2109 will snap into the second transverse slot 2048 of the proximal wedge 2016, locking the shim 2024 and therefore the width expansion into place.

The expandable fusion device 2010 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 2010.

FIGS. 122-133 illustrate an example of an expandable fusion device 2110 for implantation between two adjacent vertebrae according to another embodiment of the disclosure. By way of example only, the expandable fusion device 2110 of the present embodiment includes an actuator 2112, a distal wedge 2114, a proximal wedge 2116, a pair of distal ramps 2118a, 2118b, a pair of proximal ramps 2120a, 2120b, and a plurality of endplates 2122a-2122d. As with previously-described embodiments, the distal and proximal wedges 2114, 2116 are coupled with the actuator 2112. The distal ramps 2118a, 2118b are slideably coupled with the distal wedge 2114. The proximal ramps 2120a, 2120b are slideably coupled with the proximal wedge 2116. The plurality of endplates 2122a-2122d are slideably coupled with the ramps 2118a, 2118b, 2120a, 2120b. Generally, the expandable fusion device 2110 is substantially similar to expandable fusion device 2010 described above, and any/all of the features described above with respect to fusion device 2010 (and any other expandable fusion device described herein) may apply to fusion device 2110 unless otherwise noted. By way of example only, the expandable fusion device 2110 is illustrative of an independent width expansion mechanism that may be applied to any expandable fusion device examples described herein, according to some embodiments. Generally, width expansion is achieved by manually inserting a pair of expansion shims 2124 corresponding to the desired width expansion between the proximal ramps 2120a, 2120b, which forces the endplates 2112a-2112d and the distal ramps 2118a, 2118b laterally apart. The shims 2124 are removed and width expansion is locked in place by interlocking crenellations on the wedges 2114, 2116 and ramps 2118a, 2118b, 2120a, 2120b. Height expansion is achieved by turning the actuator 2112, which causes the wedges 2114, 2116 to advance toward one another. This in turn causes distal ramps 2118a, 2118b to move toward the proximal ramps 2120a, 2120b, which causes the upper and lower endplate pairs to be displaced vertically. Width expansion and height expansion occur independently of one another, and one is not necessarily a prerequisite for the other. In an embodiment, the shims 2124 possess at least one longitudinal fin intended to mate with at least one (e.g. centrally) located groove/channel (best seen on FIG. 129 or 130) on the at least proximal and optionally on the distal wedges. Once the fin on the shim is slidably engaged with the channel on a wedge, this articulation prevents the shim from translating in the plane transverse to the long axis of the shim allowing for uneven width expansion (left vs. right—seen in FIGS. 131-133). In some embodiments, the shims 2124 may exert width-expanding force onto the upper pair of endplates and/or the lower pair of endplates. In some embodiments, the width expansion shims 2124 may exert width-expanding forces onto the endplates, and not the ramps. In some embodiments, the width expansion shims 2124 may exert width-expanding forces onto the ramps, and not the endplates.

By way of example only, the actuator 2112 is identical or substantially similar to actuator 12 described above, and therefore its specific structure will not be described unless necessary. Similarly, the particular structure that enables height expansion on the distal and proximal ramps 2118a, 2118b, 2120a, 2120b (e.g. inclined surfaces, dovetail protrusions, etc.) is identical to the corresponding structure on the distal and proximal ramps 2018a, 2018b, 2020a, 2020b described above. Furthermore, the endplates 2122a-2122d are identical in structure and function to the endplates 2022a-2022b described above and thus won't be described in detail with respect to the present embodiment.

By way of example, the distal wedge 2114 may be a generally rectangular member having a central threaded aperture 2130 configured to threadedly receive the threaded distal end of the actuator 2112 therein. The top and bottom sides each include a transverse tongue and groove connector 2132 for configured to slideably mate with a corresponding tongue and groove connector on the distal ramps 2118a, 2118b. By way of example, the tongue and groove connector 2132 comprises a transverse ridge 2134 and a transverse slot 2136, each extending at least substantially the width of the proximal side of the distal wedge 2114. Notably, the distal wall of the transverse slot 2136 includes a plurality of crenellations 2138 configured to mate with complementary crenellations 2156 provided on the distal ramps 2118a, 2118b to selectively lock width expansion at a desired width, as will be explained below.

By way of example, the proximal wedge 2116 may be a generally rectangular member having a central threaded aperture 2140 configured to threadedly receive the threaded distal end of the actuator 2112 therein. The top and bottom sides each include a transverse tongue and groove connector 2142 for configured to slideably mate with a corresponding tongue and groove connector on the proximal ramps 2120a, 2120b. By way of example, the tongue and groove connector 2142 comprises a transverse ridge 2144 and a transverse slot 2146, each extending at least substantially the width of the proximal side of the proximal wedge 2116. Notably, the proximal wall of the transverse slot 2146 includes a plurality of crenellations 2148 configured to mate with complementary crenellations 2166 provided on the proximal ramps 2120a, 2120b to selectively lock width expansion at a desired width, as will be explained below.

By way of example only, the distal ramps 2118a, 2118b each include a pair of distal facing transverse tongue and groove connectors 2150 including a transverse ridge 2152 and a transverse slot 2154, the tongue and groove connectors 2150 configured to mate with the tongue and groove connectors 2132 of the distal wedge 2114 to provide a secure interface between the distal wedge 2114 and the distal ramps 2118a, 2118b. Notably, the distal-facing surface of the transverse ridge 2152 includes a plurality of crenellations 2156 configured to mate with complementary crenellations 2138 distal wedge 2114 to selectively lock width expansion at a desired width, as will be explained below. The distal ramps 2118a, 2118b further each include inwardly angled guide surfaces 2158 at the medial-distal corner to engage with the tapered distal end of the expansion shims 2124 to force the ramps 2118a, 2118b apart during shim 2124 insertion to effect width expansion. This is possible because the expandable fusion device 2110 of the present embodiment is symmetrical in several planes and the terms "proximal" and "distal" are relative terms used for the purpose of illustration only and both of the proximal and distal ends may in operation serve as the leading or trailing end.

By way of example only, the proximal ramps 2120a, 2120b each include a pair of distal facing transverse tongue and groove connectors 2160 including a transverse ridge 2162 and a transverse slot 2164, the tongue and groove connectors 2160 configured to mate with the tongue and groove connectors 2142 of the proximal wedge 2116 to provide a secure interface between the proximal wedge 2116 and the proximal ramps 2120a, 2120b. Notably, the proximal-facing surface of the transverse ridge 2162 includes a plurality of crenellations 2166 configured to mate with complementary crenellations 2148 on the proximal wedge 2116 to selectively lock width expansion at a desired width, as will be explained below. The proximal ramps 2120a, 2120b further each include inwardly angled guide surfaces 2168 at the medial-proximal corner to engage with the tapered distal end of the expansion shims 2124 to force the ramps 2120a, 2120b apart during shim 2124 insertion to effect width expansion.

Figure 129:
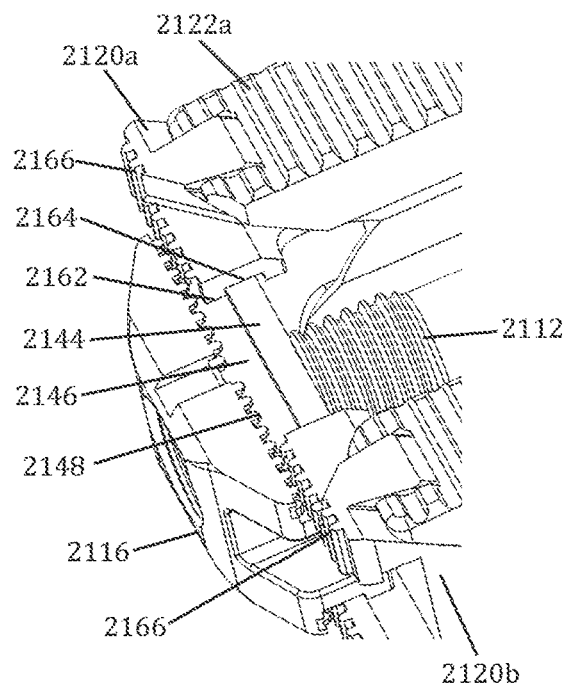
FIGS. 129-130 are perspective views of a proximal end of the expandable fusion device of FIG. 122, according to some embodiments.
Figure 130:
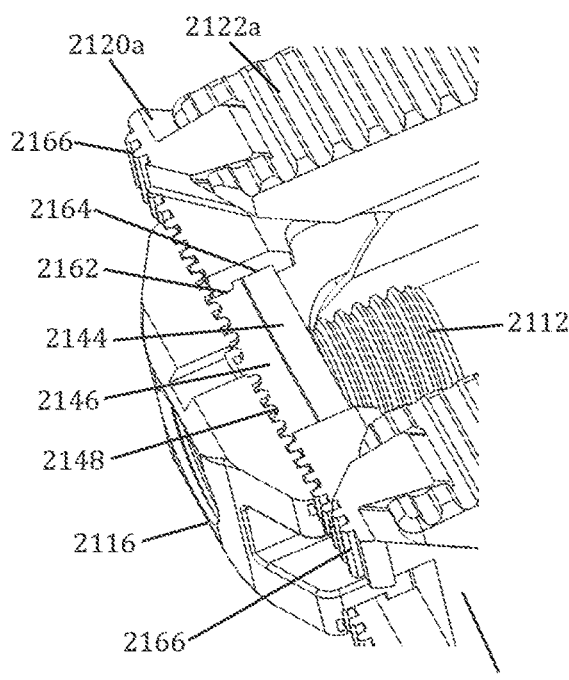

Referring now to FIGS. 129-130, it should be noted that the transverse slot 2146 of the proximal wedge is wider than the ridge 2162 of the first and second proximal ramps 2120a, 2120b and the transverse slots 2164 of the first and second proximal ramps 2120a, 2120b are wider than the ridge 2144 of the proximal wedge 2116 to maintain the crenellations in an unlocked state thereby enabling translation of the proximal ramps 2120a, 2120b to effect width expansion, as shown by way of example in FIG. 129. Similarly, the transverse slot 2136 of the distal wedge is wider than the ridge 2152 of the first and second distal ramps 2118a, 2118b and the transverse slots 2154 of the first and second distal ramps 2118a, 2118b are wider than the ridge 2134 of the distal wedge 2114 to maintain the crenellations in an unlocked state thereby enabling translation of the distal ramps 2118a, 2118b to effect width expansion. Initial rotation of the actuator 2112 causes the distal and proximal wedges 2114, 2116 to be pulled towards the respective distal and proximal ramps 2118a, 2118b, 2120a, 2120b, thereby causing the respective crenellations to interlock, as shown in FIG. 130, which locks in the expanded width of the device 2110. Continued rotation of the actuator 2112 causes height expansion without changing the width.

Figure 131:
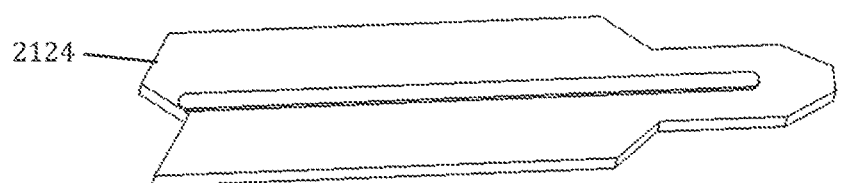
FIGS. 131-133 are perspective views of several examples of shims for use with the expandable fusion device of FIG. 122, according to some embodiments.
Figure 132:
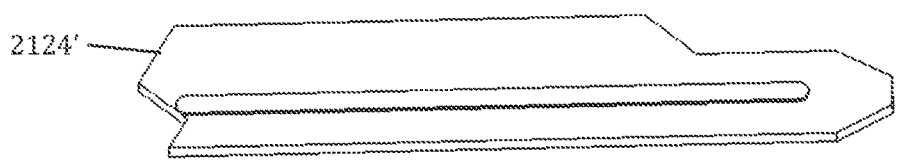
Figure 133:
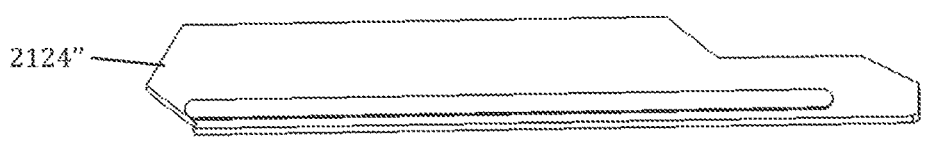
Figure 134:
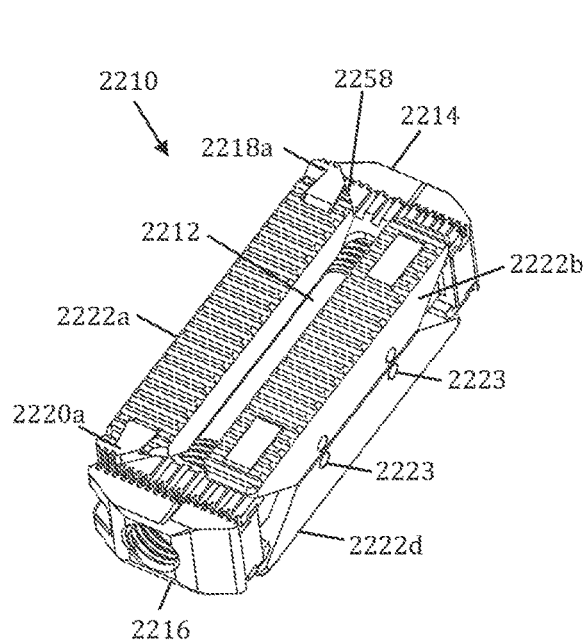
FIG. 134 is a perspective view of another example of an expandable fusion device in a fully collapsed state, according to some embodiments.
Figure 135:
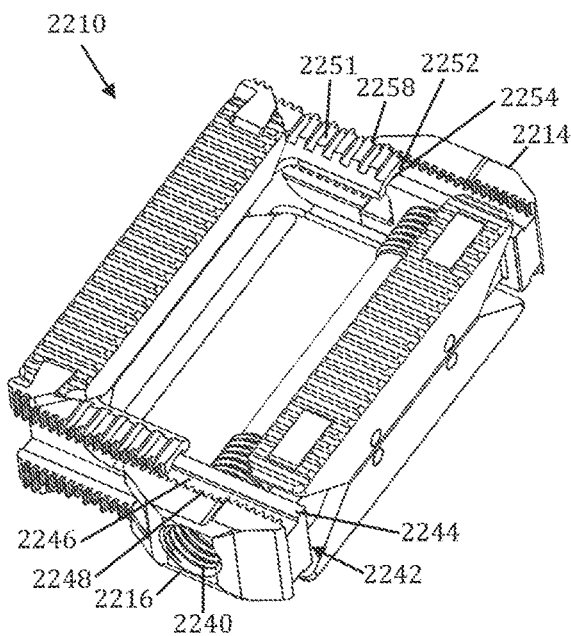
FIG. 135 is a perspective view of the expandable fusion device of FIG. 134 in a width expanded state, according to some embodiments.
Figure 136:
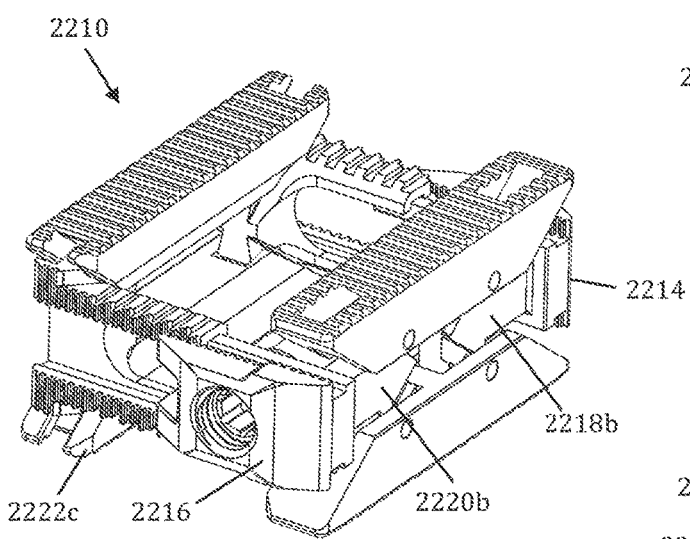
FIG. 136 is a perspective view of the expandable fusion device of FIG. 134 in a fully expanded state, according to some embodiments.

The use of crenellations enables the expanded width of the device 2110 to be locked in place in any configuration. Thus, the specific width footprint may be customized based on the size and configuration of the shims 2124 selected for the procedure. For example, FIGS. 131-133 illustrate several examples of shims 2124 that may be used with the instant example embodiment. For example, FIG. 131 illustrates an example of a shim 2124 that if used would cause symmetric bilateral expansion. FIG. 132 illustrates an example of a shim 2124' that if used would cause biased expansion. FIG. 133 illustrates an example of a shim 2124" that if used would cause unilateral expansion.

The expandable fusion device 2110 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 2110.

FIGS. 134-140 illustrate an example of an expandable fusion device 2210 for implantation between two adjacent vertebrae according to another embodiment of the disclosure. By way of example only, the expandable fusion device 2210 of the present embodiment includes an actuator 2212, a distal wedge 2214, a proximal wedge 2216, a pair of distal ramps 2218a, 2218b, a pair of proximal ramps 2220a, 2220b, a plurality of endplates 2222a-2222d, and a plurality of guide pins 2223. As with previously-described embodiments, the distal and proximal wedges 2214, 2216 are threadedly coupled with the actuator 2212. The distal ramp 2218a is slideably coupled with the distal wedge 2214, while distal ramp 2218b is integrally formed with (or otherwise immovably attached) to the distal wedge 2214. The proximal ramp 2220a is slideably coupled with the proximal wedge 2216, while the proximal ramp 2220b is integrally formed with (or otherwise immovably attached) the proximal wedge 2216. The plurality of endplates 2222a-2222d are slideably coupled with the ramps 2218a, 2218b, 2220a. 2220b. Generally, the expandable fusion device 2210 is substantially similar to expandable fusion device 2110 described above, and any/all of the features described above with respect to fusion device 2110 (and any other expandable fusion device described herein) may apply to fusion device 2210 unless otherwise noted. By way of example only, the expandable fusion device 2210 is illustrative of independent unidirectional width expansion mechanism that may be applied to any expandable fusion device examples described herein, according to some embodiments. Generally, width expansion is achieved by manually inserting a pair of expansion shims (not shown) corresponding to the desired width expansion between the proximal wedge 2116 and proximal ramp 2120a, which forces the endplates 2112a-2112d and the distal structure laterally apart. The shims are removed and width expansion is locked in place by interlocking crenellations on the wedges 2214, 2216 and ramps 2218a, 2220a. Height expansion is achieved by turning the actuator 2212, which causes the wedges 2214, 2216 to advance toward one another. This in turn causes distal ramps 2218a, 2218b to move toward the proximal ramps 2220a, 2220b, which causes the upper and lower endplate pairs to be displaced vertically. Width expansion and height expansion occur independently of one another, and one is not necessarily a prerequisite for the other.

By way of example only, the actuator 2112 is identical or substantially similar to actuator 12 described above, and therefore its specific structure will not be described unless necessary. Similarly, the particular structure that enables height expansion on the distal and proximal ramps 2218a, 2220a (e.g. inclined surfaces, dovetail protrusions, etc.) is identical to the corresponding structure on the distal and proximal ramps 2018a, 2020a, described above. Furthermore, the endplates 2122a-2122d are identical (or substantially similar) in structure and function to the endplates 2022a-2022b (and/or other embodiments) described above and thus won't be described in detail with respect to the present embodiment.

Figure 137:
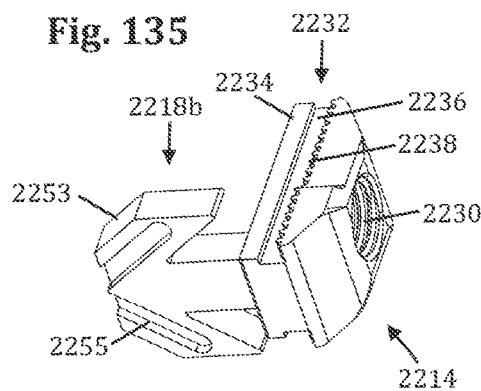
FIGS. 137-138 are perspective views of a wedge forming part of the expandable fusion device of FIG. 134, according to some embodiments.
Figure 138:
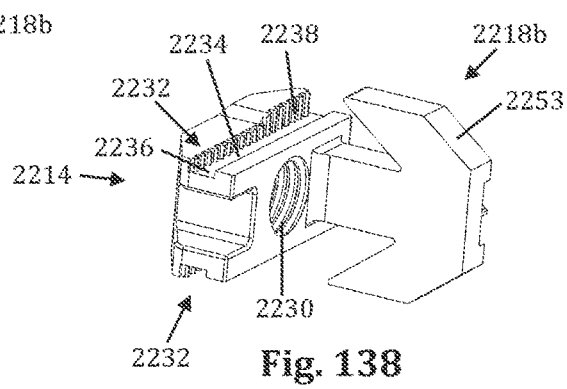

FIGS. 137-138 illustrate an example of a distal wedge 2214 of the present embodiment. By way of example, the distal wedge 2214 may be a generally rectangular member having a central threaded aperture 2230 configured to threadedly receive the threaded distal end of the actuator 2212 therein. The top and bottom sides each include a transverse tongue and groove connector 2232 for configured to slideably mate with a corresponding tongue and groove connector on the distal ramp 2118a. By way of example, the tongue and groove connector 2232 comprises a transverse ridge 2234 and a transverse slot 2236, each extending at least substantially the width of the proximal side of the distal wedge 2214. Notably, the distal wall of the transverse slot 2236 includes a plurality of crenellations 2238 configured to mate with complementary crenellations 2256 provided on the distal ramps 2118a to selectively lock width expansion at a desired width, as will be explained below.

By way of example, the proximal wedge 2216 may be a generally rectangular member having a central threaded aperture 2240 configured to threadedly receive the threaded distal end of the actuator 2212 therein. The top and bottom sides each include a transverse tongue and groove connector 2242 for configured to slideably mate with a corresponding tongue and groove connector on the proximal ramp 2220a. By way of example, the tongue and groove connector 2242 comprises a transverse ridge 2244 and a transverse slot 2246, each extending at least substantially the width of the proximal side of the proximal wedge 2216. Notably, the proximal wall of the transverse slot 2246 includes a plurality of crenellations 2248 configured to mate with complementary crenellations 2266 provided on the proximal ramps 2220a to selectively lock width expansion at a desired width, as will be explained below.

By way of example only, the first distal ramp 2218a comprises a pair of elongated medial extensions 2251 that function to increase the maximum width expansion distance. The first distal ramp 2218a includes a pair of distal facing transverse tongue and groove connectors 2250 extending the length of the medial extensions 2251 and including a transverse ridge 2252 and a transverse slot 2254, the tongue and groove connectors 2250 configured to mate with the tongue and groove connectors 2232 of the distal wedge 2214 to provide a secure interface between the distal wedge 2214 and the distal ramp 2218a. Notably, the distal-facing surface of the transverse ridge 2252 includes a plurality of crenellations 2256 configured to mate with complementary crenellations 2238 distal wedge 2214 to selectively lock width expansion at a desired width. In an initial collapsed state, when the proximal and distal wedges are forced apart by the actuator the mating crenellations are forced apart (or "unclutched") allowing for the width expansion to take place. Once the actuator is actuated and the wedges are drawn toward each other, the at least one pair of crenellations engages and interdigitates, causing any further width expansion and/or collapse to be locked/inhibited. The distal ramp 2218a further includes inwardly angled guide surfaces 2258 to engage with tapered distal end of expansion shims (not shown) to laterally displace the ramp 2218a during shim insertion to effect width expansion. This is possible because the expandable fusion device 2210 of the present embodiment is symmetrical in several planes and the terms "proximal" and "distal" are relative terms used for the purpose of illustration only and both of the proximal and distal ends may in operation serve as the leading or trailing end.

In the present embodiment, the second distal ramp 2218b is integrally formed with the distal wedge 2214, as shown in FIGS. 137-138. By way of example, the second distal ramp 2218b comprises a truncated chevron shaped ramp including inclined translation surfaces 2253 that interact with inclined surfaces on the endplates 2222b, 2222d (in a manner as taught throughout this disclosure) and optional ramp slots 2255 (to receive guide pins 2223).

By way of example only, the first proximal ramp 2220a comprises a pair of elongated medial extensions 2261 that function to increase the maximum width expansion distance. The first proximal ramp 2220a includes a pair of distal facing transverse tongue and groove connectors 2260 extending the length of the medial extensions 2261 and including a transverse ridge 2262 and a transverse slot 2264, the tongue and groove connectors 2260 configured to mate with the tongue and groove connectors 2242 of the proximal wedge 2216 to provide a secure interface between the proximal wedge 2216 and the proximal ramp 2220a. Notably, the proximal-facing surface of the transverse ridge 2262 includes a plurality of crenellations 2266 configured to mate with complementary crenellations 2248 on the proximal wedge 2216 to selectively lock width expansion at a desired width. The proximal ramps 2220a further each include inwardly angled guide surfaces 2268 to engage with a tapered distal end of an expansion shims 2224 to laterally displace the ramp 2220a during shim insertion to effect width expansion. Similar to the second distal ramp 2218b described above, the second proximal ramp 2220b is integrally formed with the proximal wedge 2216. By way of example, the second distal ramp 2218b comprises a truncated chevron shaped ramp including inclined translation surfaces that interact with inclined surfaces on the endplates 2222b, 2222d (in a manner as taught throughout this disclosure) and optional ramp slots (to receive guide pins 2223).

Figure 139:
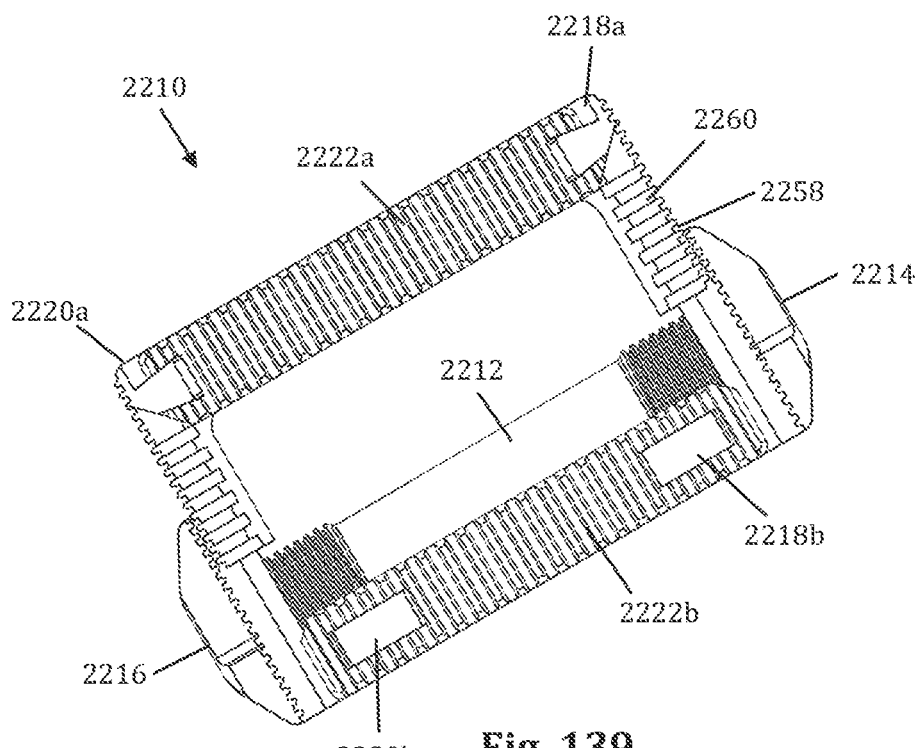
FIGS. 139-140 are top plan views of the expandable fusion device of FIG. 134 in a width expanded state, according to some embodiments.
Figure 140:
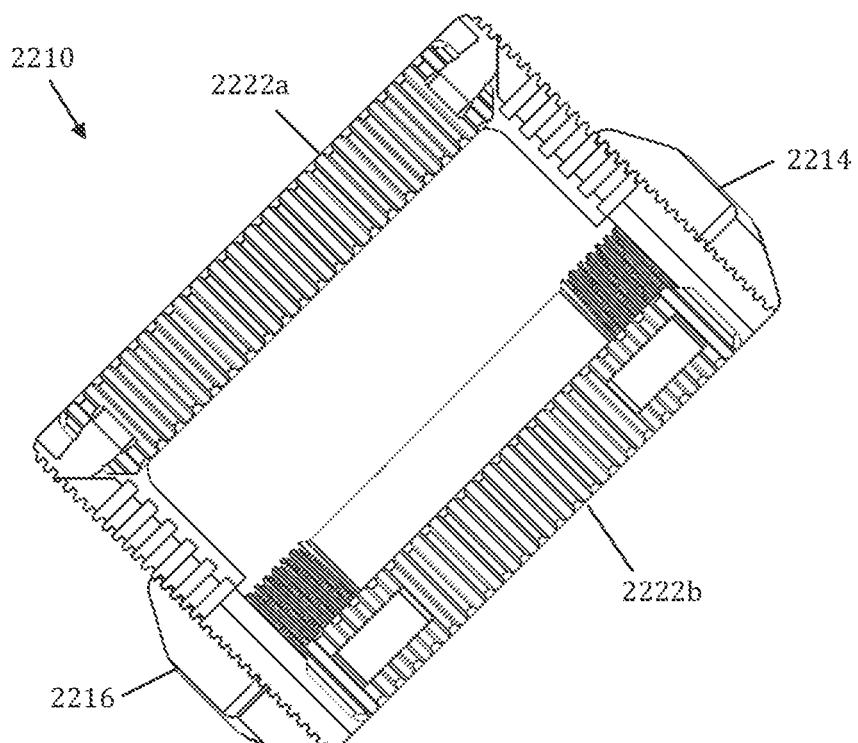

As with the previous embodiment, it should be noted that the transverse slot 2246 of the proximal wedge 2216 is wider than the ridge 2262 of the first proximal ramp 2220a, and the transverse slots 2264 of the first proximal ramp 2220a is wider than the ridge 2244 of the proximal wedge 2216 to maintain the crenellations in an unlocked state thereby enabling translation of the proximal ramp 2220a to effect width expansion, as shown by way of example in FIG. 138. Similarly, the transverse slot 2236 of the distal wedge 2214 is wider than the ridge 2252 of the first distal ramp 2218a and the transverse slots 2254 of the first distal ramp 2218a is wider than the ridge 2234 of the distal wedge 2214 to maintain the crenellations in an unlocked state thereby enabling translation of the distal ramps 2218a to effect width expansion. Initial rotation of the actuator 2212 causes the distal and proximal wedges 2214, 2216 to be pulled towards the respective distal and proximal ramps 2218a, 2220a, thereby causing the respective crenellations to interlock, as shown in FIG. 139, which locks in the expanded width of the device 2210. Continued rotation of the actuator 2212 causes height expansion without changing the width.

The use of crenellations enables the expanded width of the device 2210 to be locked in place in any configuration. Thus, the specific width footprint may be customized based on the size and configuration of the shims selected for the procedure.

The expandable fusion device 2210 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 2210.

FIGS. 141-145 illustrate an example of an expandable fusion device 2310 for implantation between two adjacent vertebrae according to another embodiment of the disclosure. The expandable fusion device 2310 differs from the previously disclosed embodiments herein in that it is expandable in length, as well as width and height, though it is conceived that in other embodiments, it may additionally also be able to change/expand lordotic angle as taught elsewhere here. As used herein, the "length" is defined as the distance between the proximal-most point of any endplate to the distal-most point of any endplate. By way of example only, the expandable fusion device 2310 of the present embodiment comprises a first expansion unit 2311*a*, a second expansion unit 2311*b*, a first actuator 2312, and a second actuator 2313. The first actuator is operable to expand the expansion units 2311*a*, 2311*b* in width and height. The second actuator 2313 is operable to adjust the length of the expandable fusion device 2310.

By way of example, the first expansion unit 2311*a* may be substantially similar to one or more of the example expandable fusion device embodiments disclosed herein, for example expandable fusion device 10 described above. By way of example only, the first expansion unit 2311*a* comprises a proximal wedge 2314, a medial wedge 2316, a pair of proximal ramps 2318, a pair of medial ramps 2320, and a plurality of endplates 2322. As with previously-described embodiments, the proximal ramps 2318 are slideably coupled with the proximal wedge 2314. The medial ramps 2320, are slideably coupled with the medial wedge 2316. The plurality of endplates 2322 are slideably coupled with the ramps 2318, 2320. Generally, the expandable fusion device 2310 is substantially similar to expandable fusion device 10 described above, and any/all of the features described above with respect to fusion device 10 (and any other expandable fusion device described herein) may apply to fusion device 2310 unless otherwise noted. Notably, the mechanics of width and height expansion of expansion unit 2311*a* with respect to the structure and interactions between the proximal wedge 2314, medial wedge 2316 (which is essentially a distal wedge for width and height expansion of the expansion unit 2311*a*), ramps 2318, 2320, and endplates 2322 is identical to the structure and interactions of the corresponding elements of expandable fusion device 10 described above, and therefore the details of the width and height expansion component of the expansion unit 2311 will not described further here.

By way of example, the second expansion unit 2311*b* may be substantially similar to one or more of the example expandable fusion device embodiments disclosed herein, for example expandable fusion device 10 described above. By way of example only, the second expansion unit 2311*b* comprises a distal wedge 2315, a medial wedge 2317, a pair of distal ramps 2319, a pair of medial ramps 2321, and a plurality of endplates 2323. As with previously-described embodiments, the distal ramps 2318 are slideably coupled with the distal wedge 2315. The medial ramps 2321, are slideably coupled with the medial wedge 2317. The plurality of endplates 2323 are slideably coupled with the ramps 2319, 2321. Notably, the mechanics of width and height expansion of expansion unit 2311*b* with respect to the structure and interactions between the distal wedge 2315, medial wedge 2317 (which is essentially a proximal wedge for width and height expansion of the expansion unit 2311*b*), ramps 2319, 2321, and endplates 2323 is identical to the structure and interactions of the corresponding elements of expandable fusion device 10 described above, and therefore the details of the width and height expansion component of the expansion unit 2311*b* will not be described further here.

The first actuator 2312 is substantially similar (but greater in length) to the actuator 12 described above, and comprises a cylindrically shaped elongate shaft having a first thread feature at a distal end and a second thread feature at a proximal end. The thread features are separated by a non-threaded segment disposed between the distal and proximal ends. At least one of the distal and proximal ends includes a drive feature 2324 configured to engage with a driver instrument (not shown) to operate the actuator. The first and second thread features each comprise a thread disposed externally around the shaft of the actuator 2312. By way of example, the first thread feature and the second thread feature have opposing threading directions. The proximal end of the first actuator 2312 is configured to engage the threaded aperture of the proximal wedge 2314, and the distal end of the first actuator 2312 is configured to engage the threaded aperture of the distal wedge.

The second actuator 2313 comprises a cylindrically shaped elongate shaft having a first thread feature 2326 at a proximal end and a second thread feature 2327 at a distal end. The thread features are separated by a turnbuckle 2328 positioned on the shaft, for example at or near the midpoint of the shaft. The turnbuckle 2328 comprises a shaped or textured region that provides a engagement point for an instrument (e.g. wrench) to effect rotation of the actuator 2313. The first and second thread features each comprise a thread disposed externally around the shaft of the actuator 2313. By way of example, the first thread feature 2326 and the second thread feature 2327 have opposing threading directions.

The medial wedges 2316, 2317 are identical or mirror equivalents, and so only the medial wedge 2316 will be described herein, but it should be understood that all features described in relation to the medial wedge 2316 also apply to the medial wedge 2317. As previously mentioned, the specific elements of the medial wedge 2316 that facilitate width and/or height expansion of the first expansion unit 2311*a* will also not be described in further detail, as they are the same or substantially similar to the corresponding elements on (for example) the proximal wedge 16 or the expandable fusion device 10 described above. By way of example only, the medial wedge 2316 comprises a non-threaded central aperture 2330 configured to allow unobstructed passage of the first actuator 2312 therethrough. The medial wedge 2316 further includes at least one threaded passage 2332 positioned on the side of the central aperture 2330, configured to receive the proximal portion of the second actuator 2313 (having the first thread feature 2326) therein. The corresponding feature on the medial wedge 2317 is configured to receive the distal portion of the second actuator 2313 (having the second thread feature 2327) therein. The medial wedge 2316 further includes medial cutout portions 2334 that function to create space for a wrench or other suitable actuating instrument (not shown) to engage the turnbuckle 2328 of the second actuator 2313.

Figure 141:
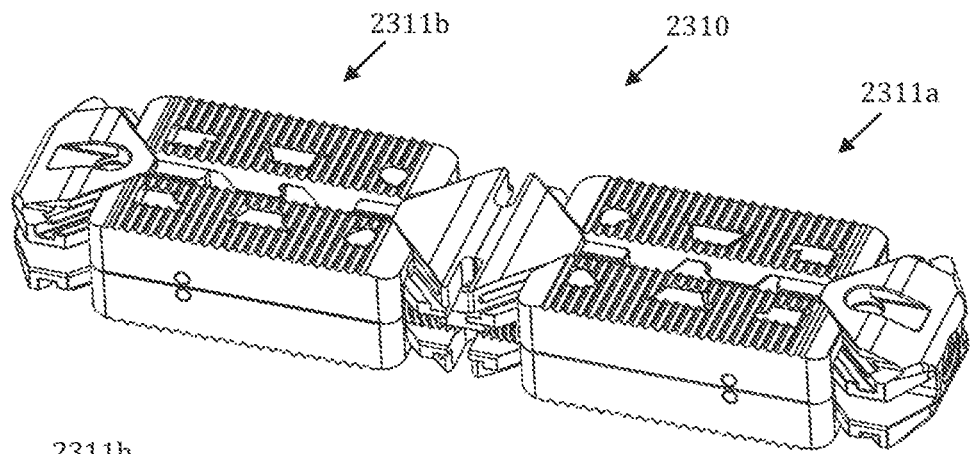
FIGS. 141-145 are perspective views of another example of an expandable fusion device according to some embodiments
Figure 142:
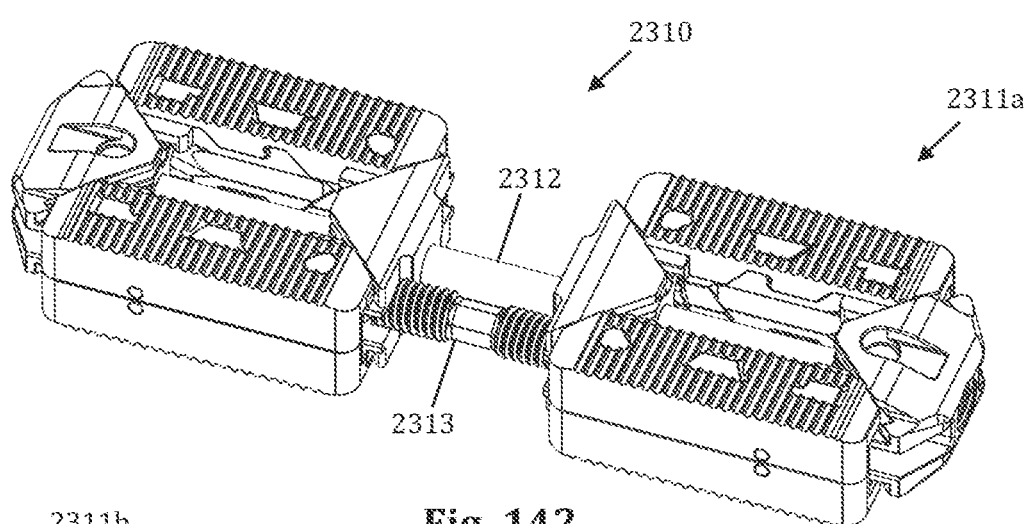
Figure 143:
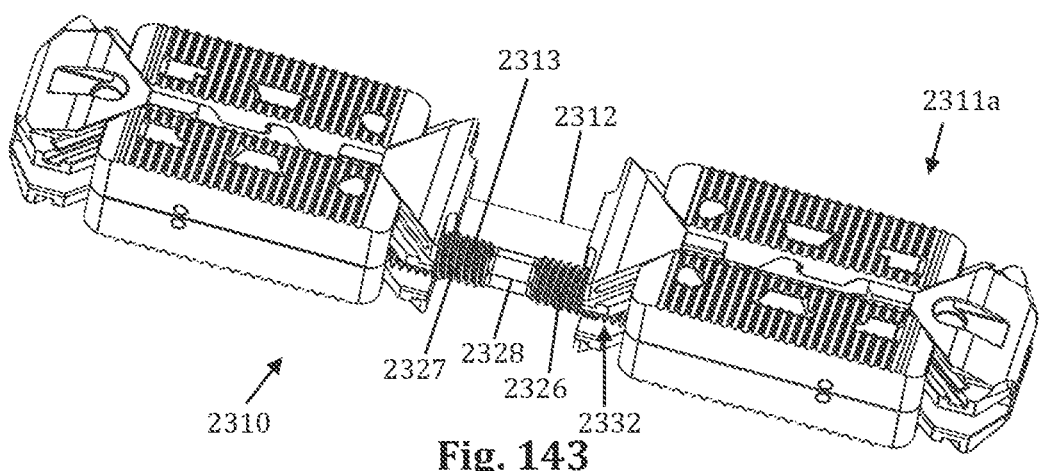
Figure 144:
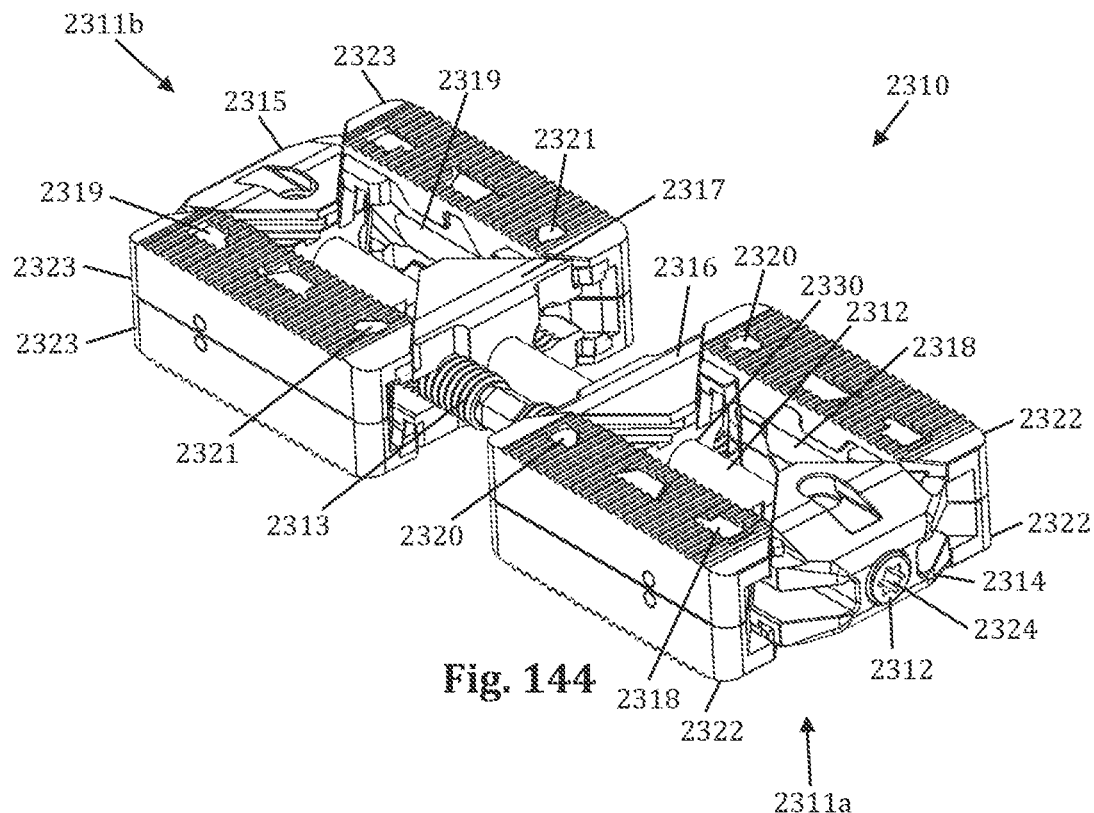
Figure 145:
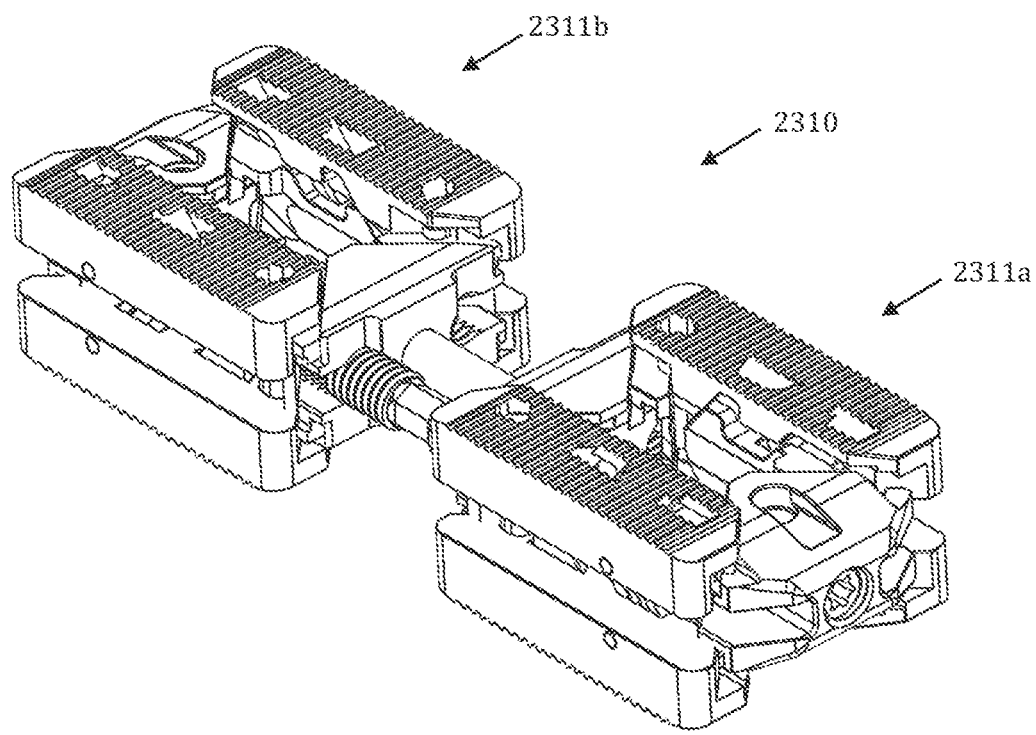

FIG. 141 illustrates the expandable fusion device 2310 of the present embodiment in an initial, fully collapsed configuration. FIG. 143 illustrates the expandable fusion device 2310 in a length expanded state. To get to this state requires a two-step process. The first step is to adjust the distance between the medial wedges 2316, 2317. Once this distance has been set, the second step is to then adjust the distance between the proximal and distal wedges 2314, 2315. To adjust the distance between the medial wedges 2316, 2317, a wrench or other suitable instrument is engaged with the turnbuckle 2328 to rotate the second actuator 2313. This causes the medial wedges 2316, 2317 to translate away from one another due to the threaded interactions between the second actuator 2313 and the medial wedges 2316, 2317, creating a distance between the medial wedges 2316, 2317 that ultimately represents the amount of length expansion of the expandable fusion device 2310, as shown in FIG. 142. However, because the proximal and distal wedges 2314, 2315 don't move during this process (or move less than the medial wedges 2416, 2417), translation of the medial wedges 2316, 2317 at first causes width expansion of the first and second expandable units 2311a, 2311b instead of length expansion. Thus, after the distance between the medial wedges 2316, 2317 has been set, the first actuator 2312 may be rotated counterclockwise (for example) to translate the proximal and distal wedges 2314, 2315 away from one another, thereby returning the width to the original state and realizing the fully expanded length, as shown in FIG. 143 (e.g. expandable fusion device 2310 now expanded in length, but collapsed in width and height). This step is important to ensure proper location of the endplates 2322, 2323 within the intervertebral space. At this point, the first actuator 2312 may be rotated (e.g. clockwise) to effect width expansion (e.g. FIG. 144) and height expansion (e.g. FIG. 145) in the manner described above.

The expandable fusion device 2310 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 2310.

FIGS. 146-151 illustrate an example of an expandable fusion device 2410 for implantation between two adjacent vertebrae according to another embodiment of the disclosure. The expandable fusion device 2410 is similar to device 2310 described above in that it is expandable in length, as well as width and height. As used herein, the "length" is defined as the distance between the proximal-most point of any endplate to the distal-most point of any endplate. By way of example only, the expandable fusion device 2410 of the present embodiment comprises a first expansion unit 2411a, a second expansion unit 2411b, a first actuator 2412, and a second actuator 2413. The first actuator is operable to expand the expansion units 2411a, 2411b in width and height. The second actuator 2413 is operable to adjust the length of the expandable fusion device 2410.

By way of example, the first expansion unit 2411a may be substantially similar to one or more of the example expandable fusion device embodiments disclosed herein, for example expandable fusion device 10 described above. By way of example only, the first expansion unit 2411a comprises a proximal wedge 2414, a medial wedge 2416, a pair of proximal ramps 2418, a pair of medial ramps 2420, and a plurality of endplates 2422. As with previously-described embodiments, the proximal ramps 2418 are slideably coupled with the proximal wedge 2414. The medial ramps 2420, are slideably coupled with the medial wedge 2416. The plurality of endplates 2422 are slideably coupled with the ramps 2418, 2420. In the current embodiment, the locations of the ramps 2418, 2420 have been shifted to the lateral edges of the endplates 2422 to make the second actuator 2413 accessible from either the proximal or distal ends of the device 2410 (see, e.g. FIGS. 149-151). Generally, the expandable fusion device 2410 is substantially similar to expandable fusion device 10 described above, and any/all of the features described above with respect to fusion device 10 (and any other expandable fusion device described herein) may apply to fusion device 2410 unless otherwise noted. Notably, the mechanics of width and height expansion of expansion unit 2411a with respect to the structure and interactions between the proximal wedge 2414, medial wedge 2416 (which is essentially a distal wedge for width and height expansion of the expansion unit 2411a), ramps 2418, 2420, and endplates 2422 is identical to the structure and interactions of the corresponding elements of expandable fusion device 10 described above, and therefore the details of the width and height expansion component of the expansion unit 2411 will not described further here.

By way of example, the second expansion unit 2411b may be substantially similar to one or more of the example expandable fusion device embodiments disclosed herein, for example expandable fusion device 10 described above. By way of example only, the second expansion unit 2411b comprises a distal wedge 2415, a medial wedge 2417, a pair of distal ramps 2419, a pair of medial ramps 2421, and a plurality of endplates 2423. As with previously-described embodiments, the distal ramps 2418 are slideably coupled with the distal wedge 2415. The medial ramps 2421, are slideably coupled with the medial wedge 2417. The plurality of endplates 2423 are slideably coupled with the ramps 2419, 2421. In the current embodiment, the locations of the ramps 2419, 2421 have been shifted to the lateral edges of the endplates 2423 to make the second actuator 2413 accessible from either the proximal or distal ends of the device 2410. Notably, the mechanics of width and height expansion of expansion unit 2411b with respect to the structure and interactions between the distal wedge 2415, medial wedge 2417 (which is essentially a proximal wedge for width and height expansion of the expansion unit 2411b), ramps 2419, 2421, and endplates 2423 is identical to the structure and interactions of the corresponding elements of expandable fusion device 10 described above, and therefore the details of the width and height expansion component of the expansion unit 2411b will not be described further here.

The first actuator 2412 is substantially similar (but greater in length) to the actuator 12 described above, and comprises a cylindrically shaped elongate shaft having a first thread feature at a distal end and a second thread feature at a proximal end. The thread features are separated by a non-threaded segment disposed between the distal and proximal ends. At least one of the distal and proximal ends includes a drive feature 2424 configured to engage with a driver instrument (not shown) to operate the actuator. The first and second thread features each comprise a thread disposed externally around the shaft of the actuator 2412. By way of example, the first thread feature and the second thread feature have opposing threading directions. The proximal end of the first actuator 2412 is configured to engage the threaded aperture of the proximal wedge 2414, and the distal end of the first actuator 2412 is configured to engage the threaded aperture of the distal wedge.

The second actuator 2413 comprises a cylindrically shaped elongate shaft having a first thread feature 2426 at a proximal end and a second thread feature 2427 at a distal end. The thread features are separated by a non-threaded segment 2428 positioned on the shaft, for example at or near the midpoint of the shaft. At least one of the distal and proximal ends includes a drive feature 2425 configured to engage with a driver instrument (not shown) to operate the second actuator 2413. The first and second thread features each comprise a thread disposed externally around the shaft of the actuator 2413. By way of example, the first thread feature 2426 and the second thread feature 2427 have opposing threading directions.

Figure 149:
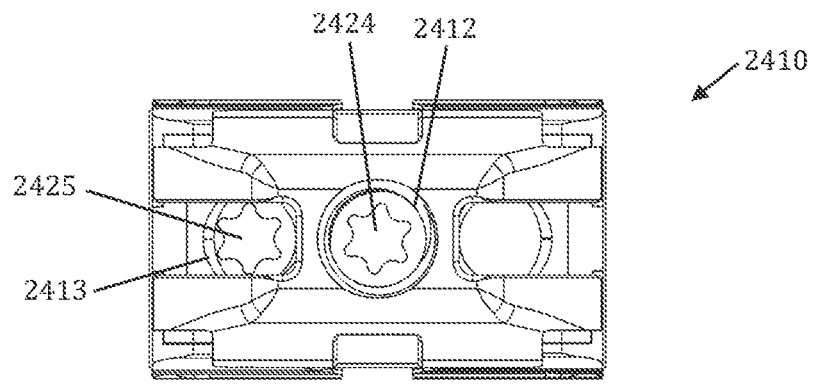
FIGS. 149-151 are end plan views of the expandable fusion device of FIG. 146, according to some embodiments.
Figure 150:
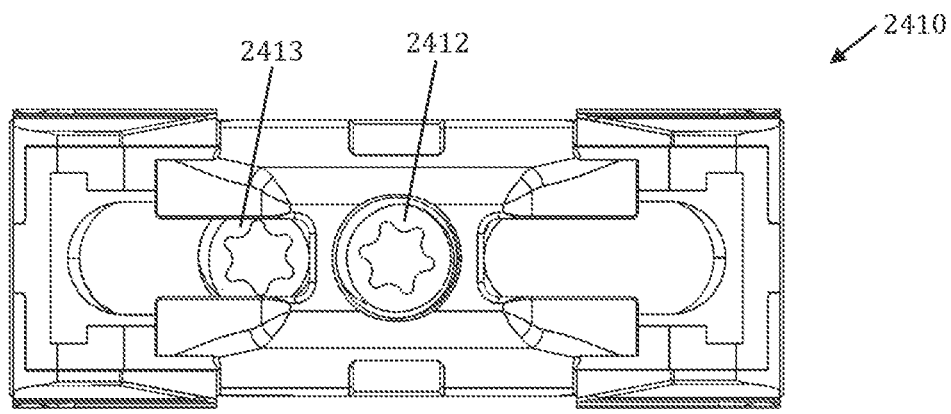
Figure 151:
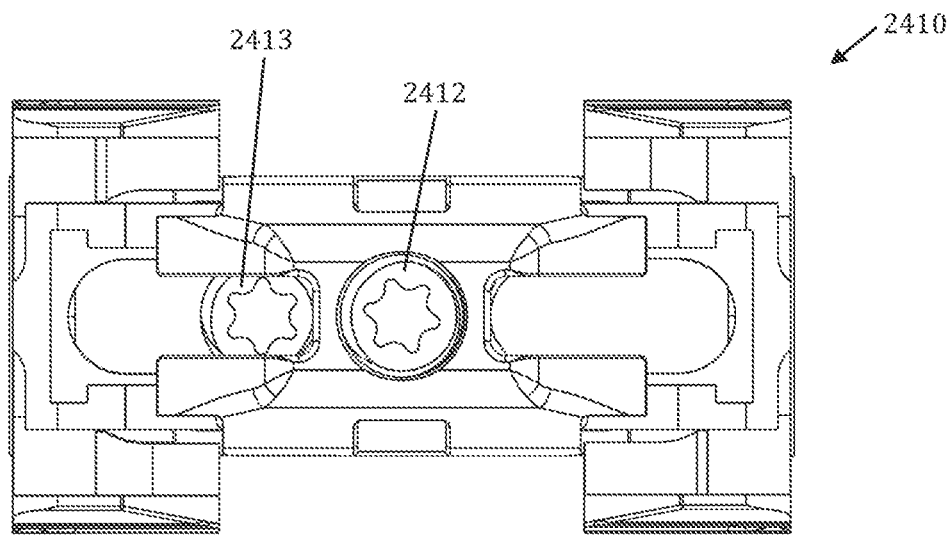

The medial wedges 2416, 2417 are identical or mirror equivalents, and so only the medial wedge 2416 will be described herein, but it should be understood that all features described in relation to the medial wedge 2416 also apply to the medial wedge 2417. As previously mentioned, the specific elements of the medial wedge 2416 that facilitate width and/or height expansion of the first expansion unit 2411*a* will also not be described in further detail, as they are the same or substantially similar to the corresponding elements on (for example) the proximal wedge 16 or the expandable fusion device 10 described above. By way of example only, the medial wedge 2416 comprises a non-threaded central aperture 2430 configured to allow unobstructed passage of the first actuator 2412 therethrough. The medial wedge 2416 further includes at least one threaded passage 2432 positioned on the side of the central aperture 2430, configured to receive the proximal portion of the second actuator 2413 (having the first thread feature 2426) therein. The corresponding feature on the medial wedge 2417 is configured to receive the distal portion of the second actuator 2413 (having the second thread feature 2427) therein. As shown in FIGS. 149-151, the second actuator 2413 is accessible from the proximal and/or distal ends of the expandable fusion device 2410. As a result, the length, width, and height may be adjusted intraoperatively while the expandable fusion device 2410 is in the disc space.

Figure 146:
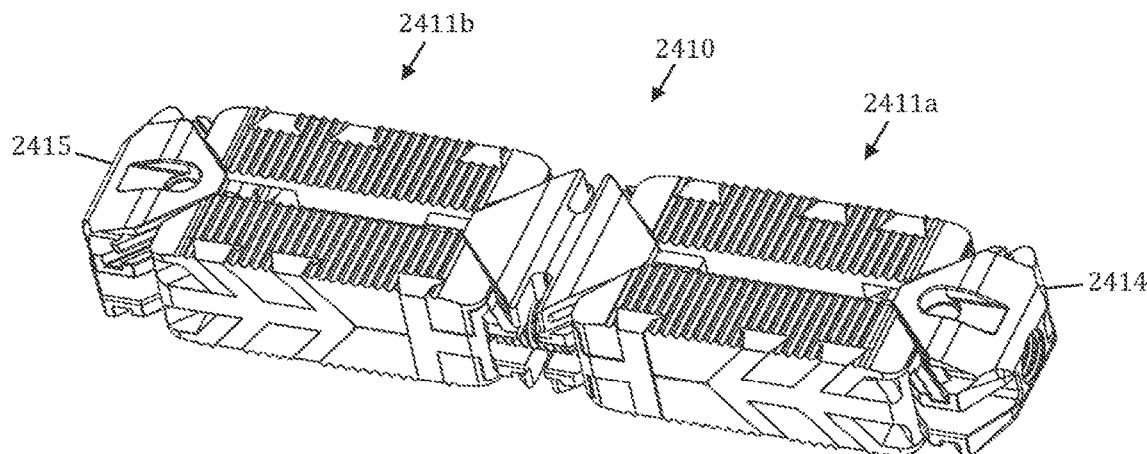
FIGS. 146-148 are perspective views of another example of an expandable fusion device, according to some embodiments.
Figure 147:
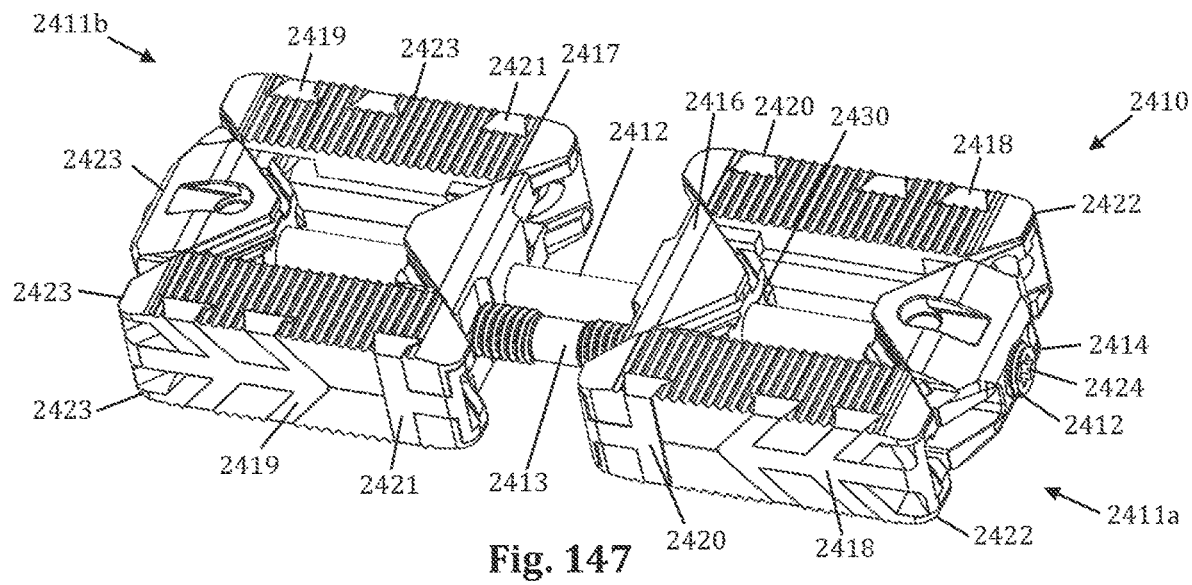
Figure 148:
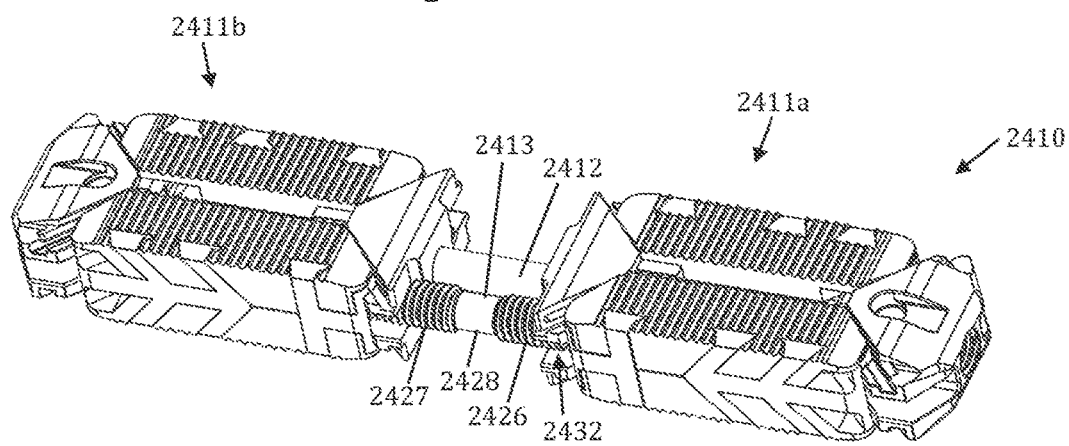

FIG. 146 illustrates the expandable fusion device 2410 of the present embodiment in an initial, fully collapsed configuration. FIG. 148 illustrates the expandable fusion device 2410 in a length expanded state. To get to this state requires a two-step process. The first step is to adjust the distance between the medial wedges 2416, 2417. Once this distance has been set, the second step is to then adjust the distance between the proximal and distal wedges 2414, 2415. To adjust the distance between the medial wedges 2416, 2417, a driver instrument is inserted through the proximal wedge 2414 (or distal wedge 2415) and engaged with the drive feature 2428 of the second actuator 2413 to rotate the second actuator 2413. This causes the medial wedges 2416, 2417 to translate away from one another due to the threaded interactions between the second actuator 2413 and the medial wedges 2416, 2417, creating a distance between the medial wedges 2416, 2417 that ultimately represents the amount of length expansion of the expandable fusion device 2410, as shown in FIG. 147. However, because the proximal and distal wedges 2414, 2415 don't move during this process (or move less than the medial wedges 2416, 2417), translation of the medial wedges 2416, 2417 at first causes width expansion of the first and second expandable units 2411*a*, 2411*b* instead of length expansion. Thus, after the distance between the medial wedges 2416, 2417 has been set, the first actuator 2412 may be rotated counterclockwise (for example) to translate the proximal and distal wedges 2414, 2415 away from one another, thereby returning the width to the original state and realizing the fully expanded length, as shown in FIGS. 148 and 149 (e.g. expandable fusion device 2410 now expanded in length, but collapsed in width and height). This step is important to ensure proper location of the endplates 2422, 2423 within the intervertebral space. At this point, the first actuator 2412 may be rotated (e.g. clockwise) to effect width expansion (e.g. FIG. 150) and height expansion (e.g. FIG. 151) in the manner described above.

The expandable fusion device 2410 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 2410.

Figure 152:
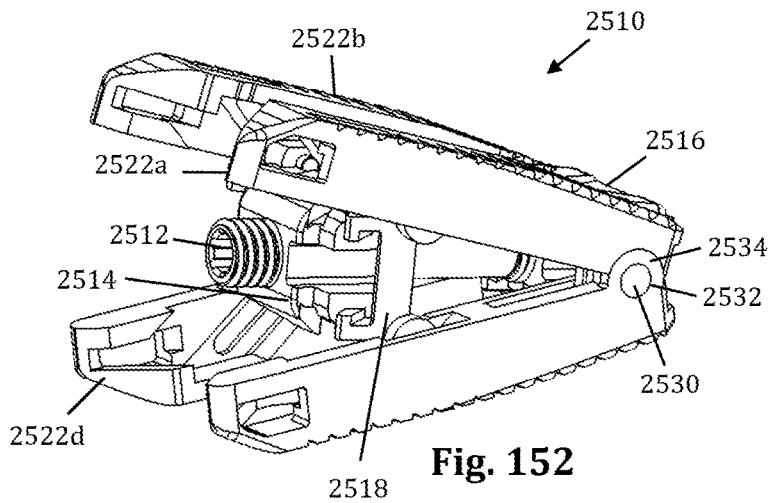
FIG. 152 is a perspective view of another example of an expandable fusion device configured for lordotic expansion in a fully expanded state, according to some embodiments.
Figure 153:
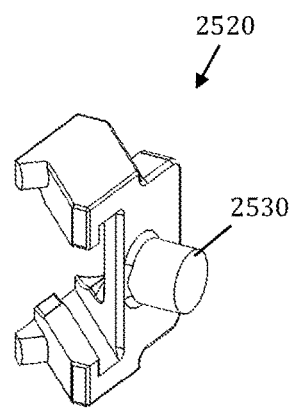
FIG. 153 is a perspective view of an example of a proximal ramp forming part of the expandable fusion device of FIG. 152, according to some embodiments.

FIGS. 152-153 illustrate an example of an expandable fusion device 2510 for implantation between two adjacent vertebrae according to another embodiment of the disclosure. By way of example only, the expandable fusion device 2510 of the present embodiment includes an actuator 2512, a distal wedge 2514, a proximal wedge 2516, a pair of identical distal ramps 2518, a pair of identical proximal ramps 1820, a plurality of endplates 1822*a*-1822*d*, and a plurality of optional guide pins. As with previously-described embodiments, the distal and proximal wedges 2514, 2516 are coupled with the actuator 2512. The distal ramps 2518 are slideably coupled with the distal wedge 2514. The proximal ramps 2520 are slideably coupled with the proximal wedge 2516. The plurality of endplates 2522*a*-2522*d* are slideably coupled with the ramps 2518, 2520. Generally, the expandable fusion device 2510 is substantially similar to expandable fusion device 1810 described above (FIGS. 100-105), and any/all of the features described above with respect to fusion device 1810 (and any other expandable fusion device described herein) may apply to fusion device 2510 unless otherwise noted. By way of example only, the expandable fusion device 2510 is illustrative of an expandable fusion device that expands in width, height, and lordotic expansion that may be applied to any expandable fusion device examples described herein, according to some embodiments.

By way of example, the actuator 2512, distal wedge 2514, and proximal wedge 2516 may be identical or substantially similar to corresponding elements disclosed herein with respect to other embodiments.

FIG. 153 illustrates an example of a proximal ramp 2520 according to the present example embodiment. By way of example only, the proximal ramp 2520 of the present embodiment is substantially similar to the proximal ramp 1820 of device 1810, but instead having of one or more arc ramps (e.g. arc ramps 1864, 1866 above) to support lordotic expansion, the proximal ramp 2520 of the present embodiment has a lateral facing cylindrical boss 2530 configured to be received within boss apertures 2532 on the proximal end of each of the endplates 2522*a*-2522*d* such that the endplates 2522*a*-2522*d* are pivotally mated with the proximal ramp 2520. In a single boss embodiment, the endplates 2522*a*-2522*d* may be configured with nesting protrusions 2234 in which the boss apertures 2532 are formed. The ends of the bosses may be swaged or otherwise detained within the boss apertures 2532.

In operation, first width expansion proceeds substantially as described above with respect to previous embodiments. That is, the actuator 2512 is turned a select number of actuations until at least some width expansion (an in some embodiments—exclusively width expansion) is reached and the endplate disengages from the distal wedge 2514. Once the disengagement occurs, further rotation of the actuator 2512 results in the distal ramps 2518 translating along the respective angled slots in the endplates and the endplates pivoting about the cylindrical boss 2530, increasing at least one of the width, height, and lordosis angle in the process. In other words, actuation of the drive feature in for a first number of actuations in the first actuation direction results in width expansion. Actuation of the drive feature by a second number of actuations beyond the first number of actuations in the first actuation direction then increases at least one of width, lordotic angle and, in some embodiments—height. In other embodiments, the first number of actuations of the actuator 2512 may result in at least some height expansion (and in some embodiments—exclusively height expansion), whereas further rotation of the actuator 1912 then increases at least one of width, height, and lordotic angle.

The expandable fusion device 2510 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 2510.

Figure 154:
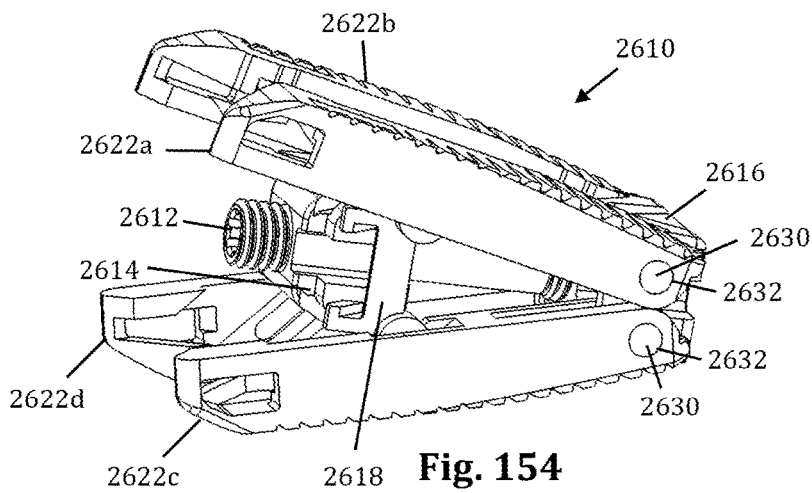
FIG. 154 is a perspective view of another example of an expandable fusion device configured for lordotic expansion in a fully expanded state, according to some embodiments.
Figure 155:
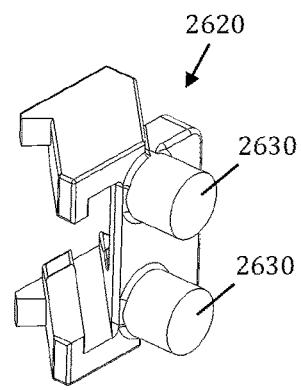
FIG. 155 is a perspective view of an example of a proximal ramp forming part of the expandable fusion device of FIG. 154, according to some embodiments; and, FIG. 156 is a perspective view of another example of an expandable fusion device configured for transverse lordotic expansion in a fully expanded state, according to some embodiments.

FIGS. 154-155 illustrate an example of an expandable fusion device 2610 for implantation between two adjacent vertebrae according to another embodiment of the disclosure. By way of example only, the expandable fusion device 2610 of the present embodiment includes an actuator 2612, a distal wedge 2614, a proximal wedge 2616, a pair of identical distal ramps 2618, a pair of identical proximal ramps 1820, a plurality of endplates 1822a-1822d, and a plurality of optional guide pins. As with previously-described embodiments, the distal and proximal wedges 2614, 2616 are coupled with the actuator 2612. The distal ramps 2618 are slideably coupled with the distal wedge 2614. The proximal ramps 2620 are slideably coupled with the proximal wedge 2616. The plurality of endplates 2622a-2622d are slideably coupled with the ramps 2618, 2620. Generally, the expandable fusion device 2610 is substantially similar to expandable fusion device 1810 described above (FIGS. 100-105), and any/all of the features described above with respect to fusion device 1810 (and any other expandable fusion device described herein) may apply to fusion device 2610 unless otherwise noted. By way of example only, the expandable fusion device 2610 is illustrative of an expandable fusion device that expands in width, height, and lordotic expansion that may be applied to any expandable fusion device examples described herein, according to some embodiments.

By way of example, the actuator 2612, distal wedge 2614, and proximal wedge 2616 may be identical or substantially similar to corresponding elements disclosed herein with respect to other embodiments.

FIG. 155 illustrates an example of a proximal ramp 2620 according to the present example embodiment. By way of example only, the proximal ramp 2620 of the present embodiment is substantially similar to the proximal ramp 1820 of device 1810, but instead having of one or more arc ramps (e.g. arc ramps 1864, 1866 above) to effect lordotic expansion, the proximal ramp 2620 of the present embodiment has a pair of lateral facing cylindrical bosses 2630 configured to be received within boss apertures 2632 on the proximal end of each of the endplates 2622a-2622d such that the endplates 2622a-2622d are pivotally mated with the proximal ramp 2620. The ends of the bosses may be swaged or otherwise detained within the boss apertures 2632.

In operation, first width expansion proceeds substantially as described above with respect to previous embodiments. That is, the actuator 2612 is turned a select number of actuations until maximum width expansion is reached and the endplate disengages from the distal wedge 2614. Once the disengagement occurs, further rotation of the actuator 2612 results in the distal ramps 2618 translating along the respective angled slots in the endplates and each endplate pivoting about a different cylindrical boss 2630, increasing at least one of the width, height, and lordosis angle in the process. In other words, actuation of the drive feature in for a first number of actuations in the first actuation direction results in width expansion. Actuation of the drive feature by a second number of actuations beyond the first number of actuations in the first actuation direction then increases at least one of width, height, and lordotic angle. In other embodiments, the first number of actuations of the actuator 2512 may result in at least some height expansion (and in some embodiments—exclusively height expansion), whereas further rotation of the actuator 1912 then increases at least one of width, height, and lordotic angle.

The expandable fusion device 2610 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 2610.

Figure 156:
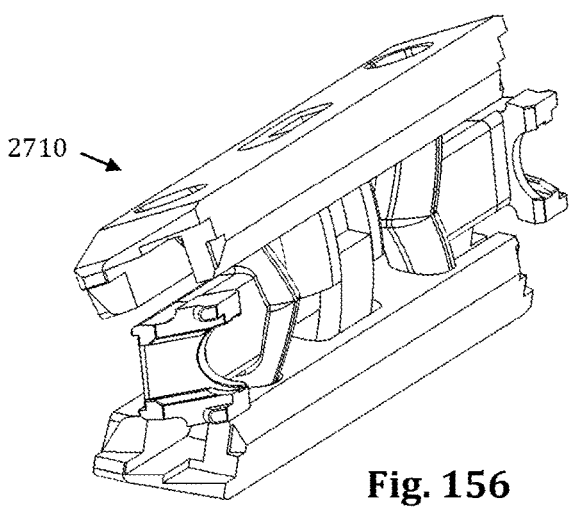

FIG. 156 illustrates an example of an expandable fusion device 2710 for implantation between two adjacent vertebrae according to another embodiment of the disclosure. By way of example only, the expandable fusion device 2710 is illustrative of an expandable fusion device that expands in width, height, and transverse lordotic expansion that may be applied to any expandable fusion device examples described herein, according to some embodiments.

In this embodiment, the ramps are curved in the plane transverse to the long axis of the device, in turn allowing the endplates to lordose in the plane transverse to the long axis. Optionally, the endplates may be kept aligned with a telescoping stabilizer slide having substantially the same curvature as the ramps in the same transverse plane.

The teachings contained herein include descriptions that are merely exemplary in nature and are in no way intended to limit the teachings, their applications, or uses. While directed generally towards embodiments of the expandable fusion device and method for its implantation between two adjacent lumbar vertebrae using a lateral, posterior and transforaminal approaches to spine, it should be appreciated that similar mechanisms and arrangements of the same are also used in treatment of cervical, thoracic and sacral spine segments, utilizing other surgical approaches including but not limited to transpedicular, transiliac, anterior and anterior-lateral approaches and configured to interface with respective anatomies and approach angles. Similarly, while the teachings are directed generally towards embodiments of the expandable fusion device which might include, for example, a drive system having an actuator drawing wedges together to cause expansion, perhaps in combination with a spacer system that is independent of the drive system, it should be appreciated that in other embodiments the same functionality can be achieved through actuator forcing the wedges apart, or perhaps the spacer or spacers can be any suitable object, of any shape size or configuration that can separate structural components in a manner similar, or substantially similar, to the teachings set-forth herein.

Unless otherwise defined, all technical terms used herein are intended to have the same meaning as commonly understood by one of ordinary skill in the art to which this disclosure belongs. The singular forms "a," "an," and "the" include plural references unless the context clearly dictates otherwise. Any reference to "or" herein is intended to encompass "and/or" unless otherwise stated. The term "about" can be used to refer to a variance around the stated amount that is near the stated amount by 10%, 9%, 8%, 7%, 6%, 5%, 4%, 3%, 2%, or 1%, including amounts or ranges therein in amount of 0.1%. The term "longitudinal axis" can be used to refer to a theoretical axis in space comprising an axis of revolving symmetry of an object. The term "slidably coupled" can be used to refer to a relationship between two or more components whereby the components share at least one degree of freedom. The term "external width" can be used to refer to the width between the outermost surfaces of an object. The term "external distance" can be used to refer to the distance between the outermost surfaces of an object. The term "apex" can be used to refer to the maximum value of a distance, measurement, or parameter. The term "thread feature" can be used to refer to one or more helical or spiral protrusions or recesses capable of acting as, or coupling with another thread feature.

Moreover, it should be appreciated that the devices taught herein are expandable, which means that they can also be collapsible in some embodiments. One of the benefits is that each of the embodiments can have a collapsed configuration for insertion into a target space through a small surgical corridor which can be, for example, an intervertebral space. As such, they have an expanded configuration for expansion in the target space to serve as a scaffolding to support surrounding tissue which can be, for example, the tissue surrounding an intervertebral space, as well as bone graft material in a spinal fusion procedure. In some embodiments, the devices can be designed to expand in the cephalocaudal direction only, "cephalocaudal" expansion, also referred to as "craniocaudal" expansion and, perhaps, "vertical" expansion. In some embodiments, the devices can be designed to expand in the transverse direction only, "transverse" expansion, also referred to as "lateral" expansion. That is, one of skill will appreciate that the designs can be designed to include, and thus to operate with, only one of the expansions systems described herein. That is, this teaching is expressly intended to represent unilaterally expandable device, cephalocaudally expandable only, and transversely expandable only, in which one of skill can use any one of the expansion systems taught herein to expand the endplates of the devices either laterally only or vertically only. The embodiments that are illustrated and described in most detail, however, are the devices that include both of the expansion systems taught herein, a concerted design that includes the drive system and the spacer system, in which each system is designed to work independent of the other in a single device to obtain the improvements, and address the problems in the art, at least as set-forth herein.

Moreover, the methods, devices, and systems taught herein can be used on any subject for experimental purposes, or for medical treatments, for example. The terms "subject" and "patient" can be used interchangeably in some embodiments and can be used to refer to an animal such as a mammal including, but not limited to, non-primates such as, for example, a cow, pig, horse, cat, dog; and primates such as, for example, a monkey or a human. As such, the terms "subject" and "patient" can also be applied to non-human biologic applications including, but not limited to, veterinary, companion animals, commercial livestock, and the like.

Moreover, terms of degree are used herein to provide relative relationships between the position and/or movements of components of the systems taught herein. For example, the phrase "at least substantially" can be used to refer to an approximation, perhaps relevant to an amount, position, or function one amount, position, or function relative to another. For example, an axis that is at least substantially parallel to another axis can be used to refer to an orientation that is intended, for all practical purposes to be parallel, but it is understood that this is just a convenient reference and that there can be variations due to stresses internal to the system and imperfections in the devices and systems. Likewise, the phrase "at least substantially parallel", "at least substantially on a plane", or "at least substantially coincident", for example, can each refer to a type of an orientation or movement that is intended, for all practical purposes, to be on or near, for example, an axis or a plane, or a point, as the case may be, as a convenient measure of the orientation or movement without having to suffer the hard definition, the ultimate measure, unless otherwise defined is known to one of skill as just a convenient reference, allowing variance until there are variations due to stresses internal to the system and imperfections in the devices and systems that affect the operation of the methods, devices and systems to the point that they are no longer of use and, in some embodiments, to the point of being non-functional. In some embodiments, the term "at least substantially parallel", "at least substantially on a plane", or "at least substantially coincident", for example, can be described as any deviation from "0°" (meaning "parallel" or "on the plane, in some embodiments), such as a deviation from the parallel or plane in an amount of about 1°, about 2°, about 3°, about 4°, about 5°, or any range or amount therein in increments of 0.1° with respect to angular deviations, and in an amount of about 1 mm, about 2 mm, about 3 mm, about 4 mm, about 5 mm, or any range or amount therein in increments of 0.1 mm, with respect to distance deviations.

I claim:

1. An expandable fusion device, comprising:
an interdigitated endplate system, including
a separable upper endplate assembly having a first endplate and a second endplate, the first endplate having a first plurality of protrusions and the second endplate having a second plurality of protrusions;
a separable lower endplate assembly having a third endplate and a fourth endplate, the third endplate having a third plurality of protrusions and the fourth endplate having a fourth plurality of protrusions;
a transverse expansion assembly to (i) expand the distance between the first endplate and second endplate of the upper endplate assembly and (ii) expand the distance between the third endplate and the fourth endplate of the lower endplate assembly, the transverse expansion assembly includes a wedge assembly that comprises a distal wedge and a proximal wedge that are drawn toward each other a first distance in a first step by applying a first force to the wedges through an actuator; and
a cephalocaudal expansion assembly configured to expand the distance between the upper endplate assembly and the lower endplate assembly, the cephalocaudal expansion assembly includes a ramp assembly comprising a distal ramp and a proximal ramp that are drawn toward each other in a second step by applying a second force to the ramps through the wedges by using the actuator to draw the distal wedge and proximal wedge toward each other a second distance;
wherein,
the first plurality of protrusions are interdigitated with the second plurality of protrusions to telescope upon lateral expansion;
the third plurality of protrusions are interdigitated with the fourth plurality of protrusions to telescope upon lateral expansion;
the interdigitated endplate system distributes the area over which the device contacts the upper and lower vertebral endplates; and,
the device is configured for transverse expansion to occur before cephalocaudal expansion.

2. The expandable fusion device of claim 1, wherein
the first plurality of protrusions extend medially from the first endplate to nest in grooves on the second endplate; and,
the third plurality of protrusions extend medially from the third endplate to nest in grooves on the fourth endplate.

3. The expandable fusion device of claim 1, wherein the first endplate, the second endplate, the third endplate, and the fourth endplate are each comprised of a rigid beam having a longitudinal axis.

4. The expandable fusion device of claim 1, wherein the ramp assembly comprises a first distal ramp, a second distal ramp, a first proximal ramp, and a second proximal ramp.

5. The expandable fusion device of claim 1, wherein at least one of the second endplate and the fourth endplate is larger than at least one of the first endplate and the third endplate.

6. The expandable fusion device of claim 1, the device further comprising the actuator, wherein the actuator is threaded.

7. The expandable fusion device of claim 1, wherein the device further comprises an expansion lock.

8. A method of fusing an intervertebral space of a subject, comprising,
inserting the device of claim 1 into an intervertebral space of the subject with an inserter tool; and,
performing cephalocaudal expansion and transverse expansion of the device.

9. A method of fusing an intervertebral space of a subject, comprising,
inserting the device of claim 2 into an intervertebral space of the subject with an inserter tool; and,
performing cephalocaudal expansion and transverse expansion of the device.

10. A method of fusing an intervertebral space of a subject, comprising,
inserting the device of claim 3 into an intervertebral space of the subject with an inserter tool; and,
performing cephalocaudal expansion and transverse expansion of the device.

11. A method of fusing an intervertebral space of a subject, comprising,
inserting the device of claim 4 into an intervertebral space of the subject with an inserter tool; and,
performing cephalocaudal expansion and transverse expansion of the device.

12. An expandable fusion device that is expandable in length, the device comprising: the expandable device of claim 1 coupled in series to a second expandable device.

13. A method of at least inhibiting subsidence of an intervertebral implant in a subject, the method comprising:
selecting the device of claim 1;
inserting the device in the intervertebral space; and,
expanding the device laterally and vertically;
wherein, the interdigitating protrusions slidably translate upon the lateral expansion to provide the larger footprint to distribute forces applied to the upper vertebral endplate and the lower vertebral endplate across the larger footprint upon the vertical expansion.

14. The method of claim 13, wherein
the first plurality of protrusions extend medially from the first endplate to nest in grooves on the second endplate; and,
the third plurality of protrusions extend medially from the third endplate to nest in grooves on the fourth endplate.

15. The expandable fusion device of claim 1, wherein
each of the first plurality of protrusions has a mating surface on the second endplate, wherein the mating surface is a recess; and,
each of the third plurality of protrusions has a mating surface on the fourth endplate, wherein the mating surface is a recess.

16. The expandable fusion device of claim 1, wherein
each of the first plurality of protrusions has a mating surface on the second endplate, wherein the mating surface is a channel; and,
each of the third plurality of protrusions has a mating surface on the fourth endplate, wherein the mating surface is a channel.

17. The expandable fusion device of claim 1, wherein
each of the first plurality of protrusions has a mating surface on the second endplate, wherein the mating surface is a port; and,
each of the third plurality of protrusions has a mating surface on the fourth endplate, wherein the mating surface is a port.

18. The expandable fusion device of claim 1, wherein
the first plurality of protrusions and the second plurality of protrusions slidably translate with a tongue-in-groove configuration to provide additional rigidity to the upper endplate assembly upon the lateral expansion; and,
the third plurality of protrusions and the fourth plurality of protrusions slidably translate with a tongue-in-groove configuration to provide additional rigidity to the lower endplate assembly upon the lateral expansion.

* * * * *